US012799137B2

(12) United States Patent
Sawano et al.

(10) Patent No.: US 12,799,137 B2
(45) Date of Patent: Nov. 17, 2026

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO., LTD., Tokyo (JP)

(72) Inventors: Shota Sawano, Tokyo (JP); Keiichi Yasukawa, Tokyo (JP); Takushi Shiomi, Tokyo (JP); Kazuki Terada, Tokyo (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 1055 days.

(21) Appl. No.: 17/766,051

(22) PCT Filed: Sep. 30, 2020

(86) PCT No.: PCT/JP2020/037282

§ 371 (c)(1),
(2) Date: Apr. 1, 2022

(87) PCT Pub. No.: WO2021/066059

PCT Pub. Date: Apr. 8, 2021

(65) Prior Publication Data

US 2022/0388991 A1 Dec. 8, 2022

(30) Foreign Application Priority Data

Oct. 1, 2019 (JP) ................................ 2019-181497
Aug. 24, 2020 (JP) ................................ 2020-141105

(51) Int. Cl.
*C07D 519/00* (2006.01)
*C07D 211/82* (2006.01)
(Continued)

(52) U.S. Cl.
CPC .......... *C07D 519/00* (2013.01); *C07D 211/82* (2013.01); *C07D 403/14* (2013.01);
(Continued)

(58) Field of Classification Search
CPC ................ C07D 519/00; C07D 211/82; C07D 403/14; C07D 491/048; C07D 493/04;
(Continued)

(56) References Cited

U.S. PATENT DOCUMENTS

2014/0175419 A1 6/2014 Nakano et al.
2014/0183486 A1 7/2014 Nakano et al.
(Continued)

FOREIGN PATENT DOCUMENTS

CN 105073709 A 11/2015
CN 105209434 A 12/2015
(Continued)

OTHER PUBLICATIONS

Hundemer, F. et al., (2019). Acceptor derivatization of the 4czipn tadf system: color tuning and introduction of functional groups. ChemistryOpen, 8(12), 1413-1420. (Year: 2019).*
(Continued)

*Primary Examiner* — Dawn L Garrett
(74) *Attorney, Agent, or Firm* — Oblon, McClelland, Maier & Neustadt, L.L.P.

(57) ABSTRACT

A compound is represented by a formula (1) below. D is a group represented by a formula (11), (12) or (13) below; at least one D is a group represented by the formula (12) or (13); at least one R is a substituent; and a sum of the number of R serving as a substituent and the number of a group represented by the formula (12) or (13) is 3 or 4.
(Continued)

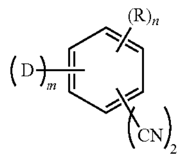

(1)

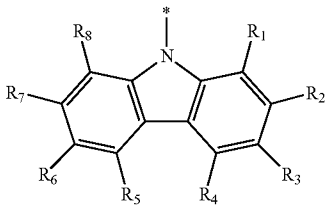

(11)

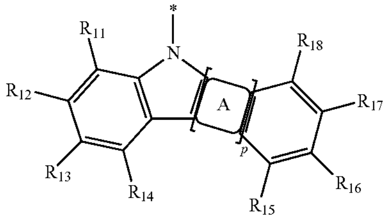

(12)

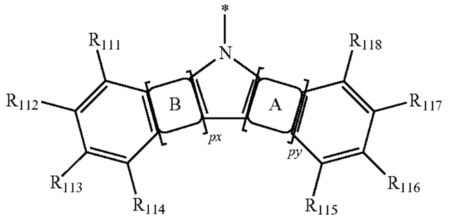

(13)

22 Claims, 6 Drawing Sheets

(51) Int. Cl.

| | |
|---|---|
| ***C07D 403/14*** | (2006.01) |
| ***C07D 491/048*** | (2006.01) |
| ***C07D 493/04*** | (2006.01) |
| ***C07D 495/04*** | (2006.01) |
| ***C07F 5/02*** | (2006.01) |
| ***H10K 50/11*** | (2023.01) |
| ***H10K 50/125*** | (2023.01) |
| ***H10K 85/30*** | (2023.01) |
| ***H10K 85/60*** | (2023.01) |
| ***H10K 101/40*** | (2023.01) |

(52) U.S. Cl.

CPC ....... *C07D 491/048* (2013.01); *C07D 493/04* (2013.01); *C07D 495/04* (2013.01); *C07F 5/027* (2013.01); *H10K 50/11* (2023.02); *H10K 50/125* (2023.02); *H10K 85/322* (2023.02); *H10K 85/615* (2023.02); *H10K 85/622* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *C07B 2200/05* (2013.01); *H10K 2101/40* (2023.02)

(58) Field of Classification Search

CPC ....... C07D 495/04; C07F 5/027; H10K 50/11; H10K 51/125; H10K 85/322; H10K 85/615; H10K 85/622; H10K 85/652; H10K 85/654; H10K 85/657; H10K 85/6572; H10K 85/6574; H10K 85/6576; H10K 2101/40; H10K 85/626; C07B 2200/05; C09K 11/06; C09K 2211/1007; C09K 2211/1011; C09K 2211/1029; C09K 2211/1033; C09K 2211/1037; C09K 2211/1088; C09K 2211/1092

See application file for complete search history.

(56) References Cited

U.S. PATENT DOCUMENTS

| | | | |
|---|---|---|---|
| 2016/0046563 | A1 | 2/2016 | Stoessel et al. |
| 2016/0130225 | A1 | 5/2016 | Tasaki et al. |
| 2016/0172599 | A1 | 6/2016 | Ogiwara et al. |
| 2017/0186974 | A1 | 6/2017 | Jung et al. |
| 2017/0313650 | A1 | 11/2017 | Stoessel et al. |
| 2018/0053901 | A1 | 2/2018 | Yoshida et al. |
| 2020/0119287 | A1 * | 4/2020 | Aguilera-Iparraguirre .................. C09K 11/06 |
| 2020/0148639 | A1 | 5/2020 | Tasaki et al. |
| 2020/0358005 | A1 | 11/2020 | Parham et al. |
| 2020/0407315 | A1 | 12/2020 | Tasaki et al. |
| 2022/0363637 | A1 | 11/2022 | Tasaki et al. |
| 2023/0322673 | A1 | 10/2023 | Tasaki et al. |

FOREIGN PATENT DOCUMENTS

| | | | |
|---|---|---|---|
| CN | 107431136 | A | 12/2017 |
| CN | 109912494 | A | 6/2019 |
| CN | 109912495 | A | 6/2019 |
| CN | 111051283 | A | 4/2020 |
| JP | 2015-213155 | A | 11/2015 |
| JP | 2016-516084 | A | 6/2016 |
| WO | WO 2012/153780 | A1 | 11/2012 |
| WO | WO 2013/038650 | A1 | 3/2013 |
| WO | WO 2014/208698 | A1 | 12/2014 |
| WO | WO 2018/216799 | A1 | 11/2018 |
| WO | WO 2018/237389 | A1 | 12/2018 |
| WO | WO 2019/081391 | A1 | 5/2019 |
| WO | WO 2019/107932 | A1 | 6/2019 |
| WO | WO 2019/107933 | A1 | 6/2019 |
| WO | WO 2019/107934 | A1 | 6/2019 |
| WO | WO 2019/190235 | A1 | 10/2019 |
| WO | WO 2019/195104 | A1 | 10/2019 |
| WO | WO 2020/085765 | A1 | 4/2020 |

OTHER PUBLICATIONS

International Preliminary Report on Patentability & Written Opinion issued Apr. 5, 2022 in PCT/JP2020/037282 filed on Sep. 30, 2020, 6 pages (Submitting English Translation Only).

International Search Report issued Dec. 8, 2020 in PCT/JP2020/037282 filed Sep. 30, 2020, 3 pages.

Adachi, C., "Device Physics of Organic Semiconductors", Kodansha, 2012, pp. 1-10 and pp. 261-268 (with English Translation).

Uoyama, H., et al., "Highly efficient organic light-emitting diodes from delayed fluorescence", Nature, vol. 492, 2012, pp. 234-238, 7 total pages.

Lee, H., et al., "Management of thermally activated delayed fluorescence using a secondary electron accepting unit in thermally activated delayed fluorescent emitters", Journal of Materials Chemistry C, vol. 7, 2019, pp. 6465-6474.

Combined Chinese Office Action and Search Report issued on Oct. 20, 2023 in Chinese Patent Application No. 202080068066.8, 16 pages.

* cited by examiner

COMPOUND, MATERIAL FOR ORGANIC ELECTROLUMINESCENT ELEMENT, ORGANIC ELECTROLUMINESCENT ELEMENT, AND ELECTRONIC DEVICE

CROSS-REFERENCE TO RELATED APPLICATIONS

The present application is a 35 U.S.C. § 371 national stage application of International patent application PCT/JP2020/037282, filed Sep. 30, 2020, which is based on and claims the benefit of priority to Japanese Application No. 2019-181497, filed Oct. 1, 2019 and Japanese Application No. 2020-141105, filed Aug. 24, 2020. The entire contents of these applications are incorporated herein by reference.

TECHNICAL FIELD

The present invention relates to a compound, an organic-electroluminescence-device material, an organic electroluminescence device, and an electronic device.

BACKGROUND ART

When a voltage is applied to an organic electroluminescence device (hereinafter, occasionally referred to as an organic EL device), holes are injected from an anode and electrons are injected from a cathode into an emitting layer. The injected holes and electrons are recombined in the emitting layer to form excitons. Specifically, according to the electron spin statistics theory, singlet excitons and triplet excitons are generated at a ratio of 25%:75%.

A fluorescent organic EL device using light emission from singlet excitons has been applied to a full-color display such as a mobile phone and a television set, but an internal quantum efficiency is said to be at a limit of 25%. Accordingly, studies has been made to improve a performance of the organic EL device.

For instance, it is expected that the organic EL device emits light more efficiently using triplet excitons in addition to singlet excitons. In view of the above, a highly efficient fluorescent organic EL device using thermally activated delayed fluorescence (hereinafter, sometimes simply referred to as "delayed fluorescence") has been proposed and studied.

A TADF (Thermally Activated Delayed Fluorescence) mechanism uses such a phenomenon that inverse intersystem crossing from triplet excitons to singlet excitons thermally occurs when a material having a small energy difference (ΔST) between singlet energy level and triplet energy level is used. Thermally activated delayed fluorescence is explained in "Yuki Hando-tai no Debaisu Bussei (Device Physics of Organic Semiconductors)" (edited by ADACHI, Chihaya, published by Kodansha, issued on Apr. 1, 2012, on pages 261-268).

As a compound exhibiting TADF properties (hereinafter also referred to as a TADF compound), for example, a compound in which a donor moiety and an acceptor moiety are bonded in a molecule is known.

Examples of Literatures relating to an organic EL device and a compound used for the organic EL device include Patent Literature 1, Patent Literature 2, Patent Literature 3, Patent Literature 4 and Patent Literature 5.

CITATION LIST

Patent Literature(s)

Patent Literature 1: International Publication No. WO2019/107932

Patent Literature 2: International Publication No. WO2019/107933

Patent Literature 3: International Publication No. WO2019/107934

Patent Literature 4: International Publication No. WO2014/208698

Patent Literature 5: International Publication No. WO2018/237389

SUMMARY OF THE INVENTION

Problems to be Solved by the Invention

In order to improve performance of an electronic device such as a display, an organic EL device has been required to be further improved in performance.

The performance of the organic EL device is evaluable in terms of luminous efficiency. As an element for improving the luminous efficiency, a compound having a high photoluminescence quantum yield (PLQY) is usable. The performance of the organic EL device is also evaluable in terms of how low a drive voltage is.

An object of the invention is to provide a compound having a high PLQY. Another object of the invention is to provide an organic-electroluminescence-device material and an organic electroluminescence device containing a compound having a high PLQY, and an electronic device including the organic electroluminescence device. Still another object of the invention is to provide a high-performance organic EL device and an electronic device including the organic electroluminescence device.

Means for Solving the Problem(s)

According to an aspect of the invention, a compound represented by a formula (1) is provided.

[Formula 1]

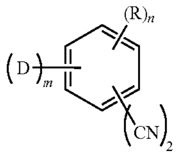

(1)

In the formula (1):

D is a group represented by a formula (11), (12) or (13) below;

at least one D is a group represented by the formula (12) or (13);

m is 1, 2, or 3;

when m is 2 or 3, a plurality of D are mutually the same or different;

R is each independently a hydrogen atom, a halogen atom, or a substituent;

R serving as a substituent is each independently a substituted or unsubstituted aryl group having 6 to 14 ring carbon atoms, a substituted or unsubstituted heteroaryl group having 5 to 14 ring atoms, a substituted or unsubstituted alkyl group having 1 to 6 carbon atoms, a substituted or unsubstituted cycloalkyl group having 3 to 6 ring carbon atoms, a substituted or unsubstituted alkylsilyl group having 3 to 6 carbon atoms, a substituted or unsubstituted arylsilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms;

at least one R is a substituent;

the at least one R serving as a substituent is bonded by a carbon-carbon bond to a benzene ring in the formula (1);

n is 1, 2, or 3;

when n is 2 or 3, a plurality of R are mutually the same or different; and a sum of the number of R serving as a substituent and the number of a group represented by the formula (12) or (13) is 3 or 4.

[Formula 2]

(11)

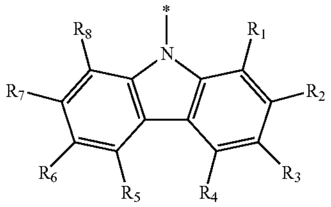

[Formula 3]

(12)

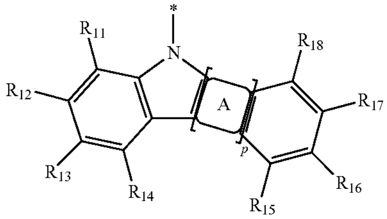

[Formula 4]

(13)

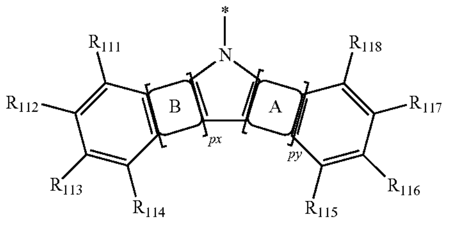

$R_1$ to $R_8$ in the formula (11) are each independently a hydrogen atom, a halogen atom, or a substituent;

$R_{11}$ to $R_{18}$ in the formula (12) are each independently a hydrogen atom, a halogen atom, or a substituent, or at least one combination of a combination of $R_{11}$ and $R_{12}$, a combination of $R_{12}$ and $R_{13}$, a combination of $R_{13}$ and $R_{14}$, a combination of $R_{15}$ and $R_{16}$, a combination of $R_{16}$ and $R_{17}$, or a combination of $R_{17}$ and $R_{18}$ are mutually bonded to form a ring;

$R_{111}$ to $R_{118}$ in the formula (13) are each independently a hydrogen atom, a halogen atom, or a substituent, or at least one combination of a combination of $R_{111}$ and $R_{112}$, a combination of $R_{112}$ and $R_{113}$, a combination of $R_{113}$ and $R_{114}$, a combination of $R_{115}$ and $R_{116}$, a combination of $R_{116}$ and $R_{117}$, or a combination of $R_{117}$ and $R_{118}$ are mutually bonded to form a ring;

$R_1$ to $R_8$ serving as a substituent, $R_{11}$ to $R_{18}$ serving as a substituent, and $R_{111}$ to $R_{118}$ serving as a substituent are each independently a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted cycloalkyl group having 3 to 30 ring carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms;

in the formulae (12) and (13):

A, B and C are each independently a cyclic structure selected from the group consisting of cyclic structures represented by formulae (14), (15) and (16) below;

the cyclic structure A, the cyclic structure B and the cyclic structure C are each fused with adjacent ring(s) at any position(s);

p, px and py are each independently 1, 2, 3, or 4;

when p is 2, 3 or 4, a plurality of cyclic structures A are mutually the same or different;

when px is 2, 3 or 4, a plurality of cyclic structures B are mutually the same or different;

when py is 2, 3 or 4, a plurality of cyclic structures C are mutually the same or different;

at least one D is a group represented by the formula (12) satisfying that p is 2, 3 or 4 and containing, as the cyclic structure A, a cyclic structure selected from the group consisting of cyclic structures represented by formulae (15) and (16) below, or a group represented by the formula (13) satisfying that at least one of px or py is 2, 3 or 4 and containing, as the cyclic structure B or the cyclic structure C, a cyclic structure selected from the group consisting of cyclic structures represented by the formulae (15) and (16); and

* in the formulae (11) to (13) represents a bonding position to a benzene ring in the formula (1).

[Formula 5]

(14)

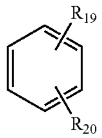

(15)

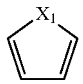

(16)

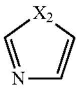

In the formula (14):

$R_{19}$ and $R_{20}$ are each independently a hydrogen atom, a halogen atom, or a substituent, or a combination of $R_{19}$ and $R_{20}$ are mutually bonded to form a ring;

in the formulae (15) and (16):

$X_1$ and $X_2$ are each independently $NR_{120}$, a sulfur atom, or an oxygen atom;

$R_{120}$ is a hydrogen atom, a halogen atom, or a substituent; and $R_{19}$, $R_{20}$ and $R_{120}$ serving as a substituent each independently represent the same as $R_1$ to $R_8$ serving as a substituent.

According to another aspect of the invention, an organic-electroluminescence-device material containing the compound according to the above aspect of the invention is provided.

According to still another aspect of the invention, there is provided an organic electroluminescence device including: an anode; a cathode; and an organic layer, in which the organic layer contains, as a first compound, the compound according to the above aspect of the invention.

According to a further aspect of the invention, an electronic device including the organic electroluminescence device according to the above aspect of the invention is provided.

According to the above aspect of the invention, a compound having a high PLOY can be provided. According to the above aspect of the invention, an organic-electroluminescence-device material or an organic electroluminescence device containing a compound having a high PLQY can be provided. According to the above aspect of the invention, an electronic device including the organic electroluminescence device can be provided. According to the above aspects of the invention, a high-performance organic EL device and an electronic device including the organic electroluminescence device can also be provided.

BRIEF DESCRIPTION OF DRAWING(S)

FIG. 1 schematically shows a device that measures transient PL.

FIG. 2 shows an example of a decay curve of the transient PL.

FIG. 3 schematically shows an exemplary arrangement of an organic electroluminescence device according to a third exemplary embodiment of the invention.

DESCRIPTION OF EMBODIMENT(S)

First Exemplary Embodiment

Compound

Figure 1:
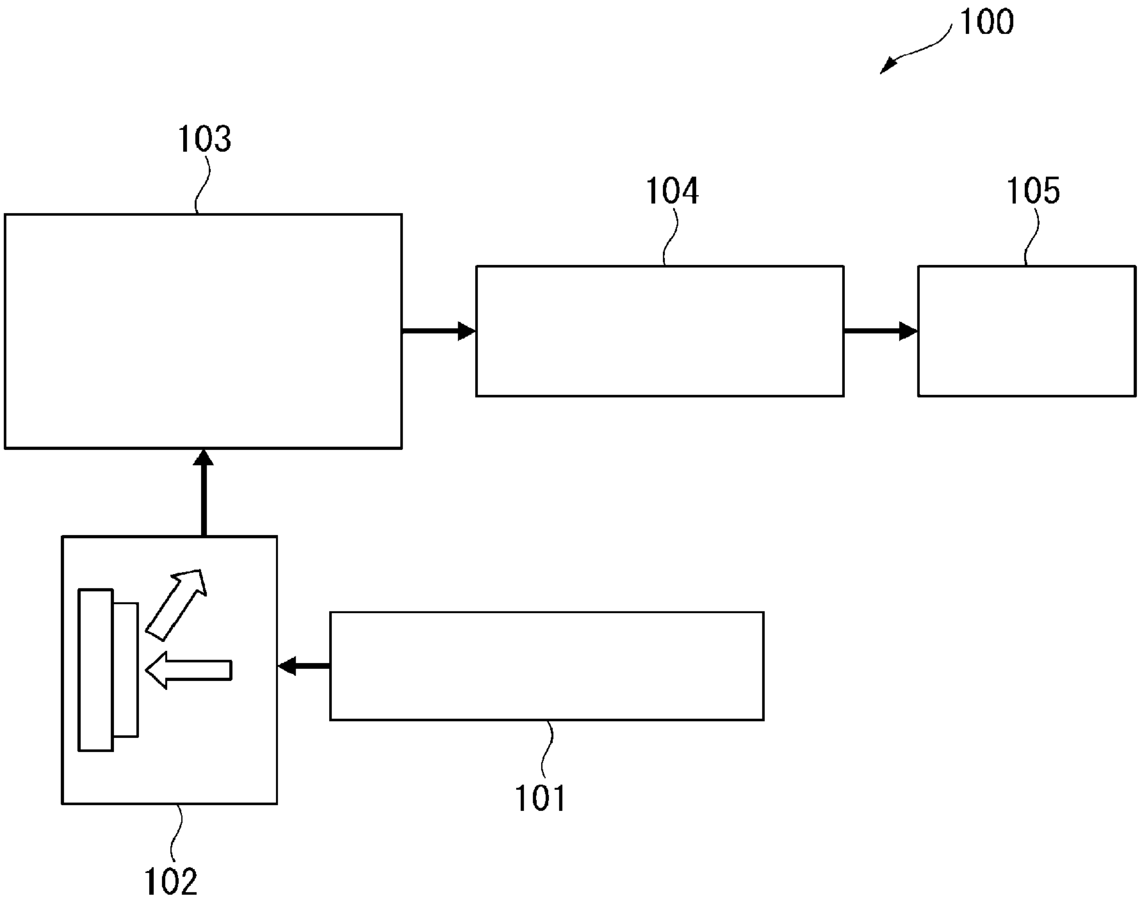

A compound according to a first exemplary embodiment is a compound represented by a formula (1) below.

[Formula 6]

(1)

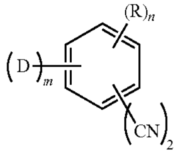

In the formula (1):

D is a group represented by a formula (11), (12) or (13) below;

at least one D is a group represented by the formula (12) or (13);

m is 1, 2, or 3;

when m is 2 or 3, a plurality of D are mutually the same or different;

R is each independently a hydrogen atom, a halogen atom, or a substituent;

R serving as a substituent is each independently a substituted or unsubstituted aryl group having 6 to 14 ring carbon atoms, a substituted or unsubstituted heteroaryl group having 5 to 14 ring atoms, a substituted or unsubstituted alkyl group having 1 to 6 carbon atoms, a substituted or unsubstituted cycloalkyl group having 3 to 6 ring carbon atoms, a substituted or unsubstituted alkylsilyl group having 3 to 6 carbon atoms, a substituted or unsubstituted arylsilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms;

at least one R is a substituent;

the at least one R serving as a substituent is bonded by a carbon-carbon bond to a benzene ring in the formula (1);

n is 1, 2, or 3;

when n is 2 or 3, a plurality of R are mutually the same or different; and a sum of the number of R serving as a substituent and the number of a group represented by the formula (12) or (13) is 3 or 4.

[Formula 7]

(11)

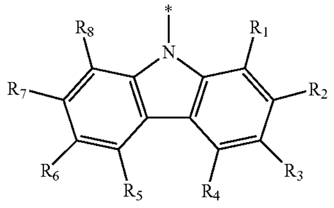

-continued

[Formula 8]

(12)

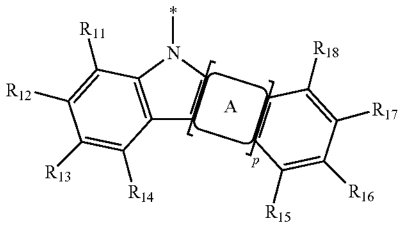

[Formula 9]

(13)

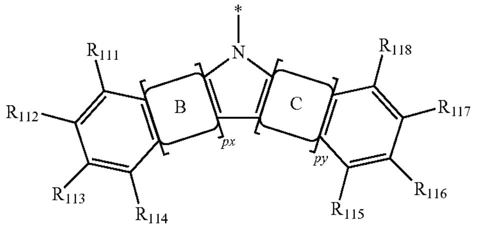

$R_1$ to $R_8$ in the formula (11) are each independently a hydrogen atom, a halogen atom, or a substituent;

$R_{11}$ to $R_{18}$ in the formula (12) are each independently a hydrogen atom, a halogen atom, or a substituent, or at least one combination of a combination of $R_{11}$ and $R_{12}$, a combination of $R_{12}$ and $R_{13}$, a combination of $R_{13}$ and $R_{14}$, a combination of $R_{15}$ and $R_{16}$, a combination of $R_{16}$ and $R_{17}$, or a combination of $R_{17}$ and $R_{18}$ are mutually bonded to form a ring;

$R_{111}$ to $R_{118}$ in the formula (13) are each independently a hydrogen atom, a halogen atom, or a substituent, or at least one combination of a combination of $R_{111}$ and $R_{112}$, a combination of $R_{112}$ and $R_{113}$, a combination of $R_{113}$ and $R_{114}$, a combination of $R_{115}$ and $R_{116}$, a combination of $R_{116}$ and $R_{117}$, or a combination of $R_{117}$ and $R_{118}$ are mutually bonded to form a ring;

$R_1$ to $R_8$ serving as a substituent, $R_{11}$ to $R_{18}$ serving as a substituent, and $R_{111}$ to $R_{118}$ serving as a substituent are each independently a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted cycloalkyl group having 3 to 30 ring carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms;

in the formulae (12) and (13):

A, B and C are each independently a cyclic structure selected from the group consisting of cyclic structures represented by formulae (14), (15) and (16) below;

the cyclic structure A, the cyclic structure B and the cyclic structure C are each fused with adjacent ring(s) at any position(s);

p, px and py are each independently 1, 2, 3, or 4;

when p is 2, 3, or 4, a plurality of cyclic structures A are mutually the same or different;

when px is 2, 3, or 4, a plurality of cyclic structures B are mutually the same or different;

when py is 2, 3, or 4, a plurality of cyclic structures C are mutually the same or different;

at least one D is a group represented by the formula (12) satisfying that p is 2, 3 or 4 and containing, as the cyclic structure A, a cyclic structure selected from the group consisting of cyclic structures represented by formulae (15) and (16) below, or a group represented by the formula (13) satisfying that at least one of px or py is 2, 3 or 4 and containing, as the cyclic structure B or the cyclic structure C, a cyclic structure selected from the group consisting of cyclic structures represented by the formulae (15) and (16); and

* in the formulae (11) to (13) represents a bonding position to a benzene ring in the formula (1).

[Formula10]

(14)

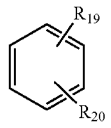

(15)

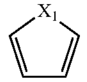

(16)

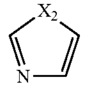

In the formula (14):

$R_{19}$ and $R_{20}$ are each independently a hydrogen atom, a halogen atom, or a substituent, or a combination of $R_{19}$ and $R_{20}$ are mutually bonded to form a ring;

in the formulae (15) and (16):

$X_1$ and $X_2$ are each independently $NR_{120}$, a sulfur atom, or an oxygen atom;

$R_{120}$ is a hydrogen atom, a halogen atom, or a substituent; and $R_{19}$, $R_{20}$ and $R_{120}$ serving as a substituent each independently represent the same as $R_1$ to $R_8$ serving as a substituent.

The compound according to the exemplary embodiment has, in a molecule, at least one of a group $D_A$ or a group $D_B$ as D in the formula (1).

The group $D_A$ is a group represented by the formula (12) satisfying that p is 2, 3 or 4 and containing, as the cyclic structure A, a cyclic structure selected from the group consisting of cyclic structures represented by the formulae (15) and (16). It is preferable that the group $D_A$ satisfies that p is 2, 3 or 4, and contains cyclic structures represented by the formulae (14) and (15) as the cyclic structure A.

The group $D_B$ is a group represented by the formula (13) satisfying that at least one of px or py is 2, 3 or 4 and containing, as the cyclic structure B or the cyclic structure C, a cyclic structure selected from the group consisting of cyclic structures represented by the formulae (15) and (16). It is preferable that the group $D_B$ satisfies that at least one of px or py is 2, 3 or 4, and contains cyclic structures represented by the formulae (14) and (15) as the cyclic structure B or the cyclic structure C.

Further, in the compound according to the exemplary embodiment, a sum ($N_R+N_D$) of the number $N_R$ of R serving as a substituent and the number $N_D$ of the group(s) $D_A$ or the group(s) $D_B$ is 3 or 4.

R serving as a substituent is bonded by a carbon-carbon bond to the benzene ring in the formula (1), which means that a carbon atom among elements of R serving as a substituent is directly bonded to any one of six carbon atoms forming the benzene ring in the formula (1).

In the compound according to the exemplary embodiment, it is preferable that the sum of the number of R serving as a substituent and the number of the group(s) represented by the formula (12) or (13) is 4.

In the compound according to the exemplary embodiment, it is preferable that the sum ($N_R+N_D$) of the number $N_R$ of R serving as a substituent and the number $N_D$ of the group(s) $D_A$ or the group(s) $D_B$ is 4.

The compound represented by the formula (1) is also preferably a compound represented by a formula (110), (120) or (130) below.

[Formula 11]

(110)

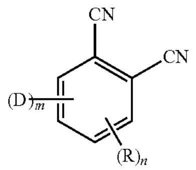

(120)

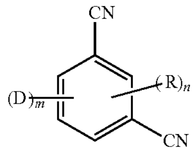

(130)

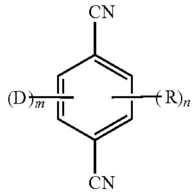

In the formulae (110), (120) and (130): D, m, R and n respectively represent the same as D, m, R and n in the formula (1).

The compound represented by the formula (1) is also preferably a compound selected from the group consisting of compounds represented by formulae (111) to (118) below.

[Formula 12]

(111)

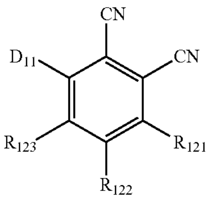

-continued (112)

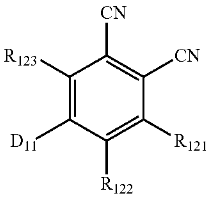

In the formulae (111) and (112):

$D_{11}$ is a group represented by the formula (12) or (13); and $R_{121}$ to $R_{123}$ each independently represent the same as R in the formula (1), at least one of $R_{121}$ to $R_{123}$ is a substituent, and $R_{121}$ to $R_{123}$ serving as a substituent represent the same as R serving as a substituent in the formula (1).

[Formula 13]

(113)

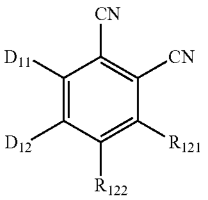

(114)

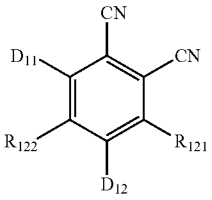

(115)

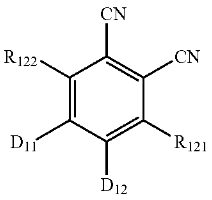

(116)

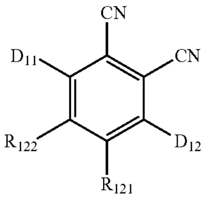

In the formulae (113) to (116):

$D_{11}$ and $D_{12}$ each independently represent the same as D in the formula (1), and at least one of $D_{11}$ or $D_{12}$ is a group represented by the formula (12) or (13); and $R_{121}$ and $R_{122}$ each independently represent the same as R in the formula (1), at least one of $R_{121}$ or $R_{122}$ is a substituent, and $R_{121}$ and $R_{122}$ serving as a substituent represent the same as R serving as a substituent in the formula (1).

[Formula 14]

(117)

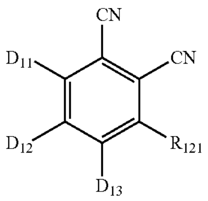

(118)

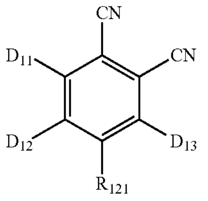

In the formulae (117) and (118):

$D_{11}$ to $D_{13}$ each independently represent the same as D in the formula (1), and at least one of $D_{11}$ to $D_{13}$ is a group represented by the formula (12) or (13); and $R_{121}$ is a substituent, and $R_{121}$ serving as a substituent represents the same as R serving as a substituent in the formula (1).

The compound represented by the formula (1) is also preferably a compound selected from the group consisting of compounds represented by formulae (121) to (129) below.

[Formula 15]

(121)

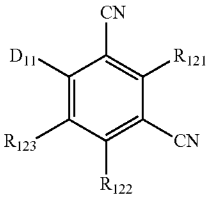

(122)

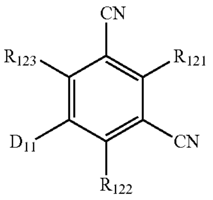

(123)

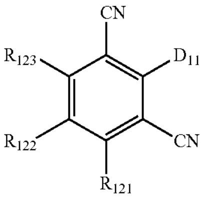

In the formulae (121) to (123):

$D_{11}$ is a group represented by the formula (12) or (13); and $R_{121}$ to $R_{123}$ each independently represent the same as R in the formula (1), at least one of $R_{121}$ to $R_{123}$ is a substituent, and $R_{121}$ to $R_{123}$ serving as a substituent represent the same as R serving as a substituent in the formula (1).

[Formula 16]

(124)

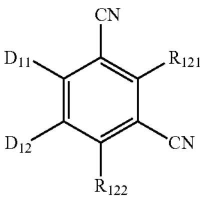

(125)

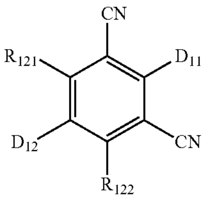

(126)

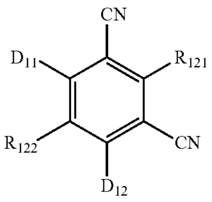

In the formulae (124) to (126):

$D_{11}$ and $D_{12}$ each independently represent the same as D in the formula (1), and at least one of $D_{11}$ or $D_{12}$ is a group represented by the formula (12) or (13); and $R_{121}$ and $R_{122}$ each independently represent the same as R in the formula (1), at least one of $R_{121}$ or $R_{122}$ is a substituent, and $R_{121}$ and $R_{122}$ serving as a substituent represent the same as R serving as a substituent in the formula (1).

[Formula 17]

(127)

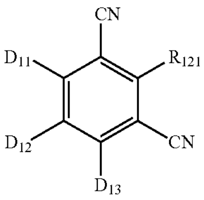

(128)

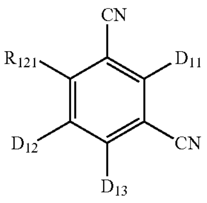

(129)

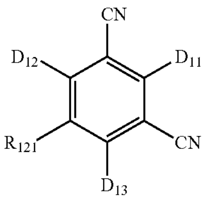

In the formulae (127) to (129):

$D_{11}$ to $D_{13}$ each independently represent the same as D in the formula (1), and at least one of $D_{11}$ to $D_{13}$ is a group represented by the formula (12) or (13); and $R_{121}$ is a substituent, and $R_{121}$ serving as a substituent represents the same as R serving as a substituent in the formula (1).

The compound represented by the formula (1) is also preferably a compound selected from the group consisting of compounds represented by formulae (131) to (135) below.

[Formula 18]

(131)

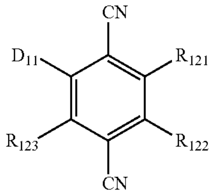

In the formula (131):

$D_{11}$ is a group represented by the formula (12) or (13); and $R_{121}$ to $R_{123}$ each independently represent the same as R in the formula (1), at least one of $R_{121}$ to $R_{123}$ is a substituent, and $R_{121}$ to $R_{123}$ serving as a substituent represent the same as R serving as a substituent in the formula (1).

[Formula 19]

(132)

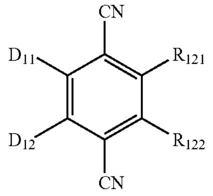

(133)

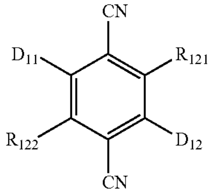

(134)

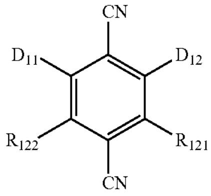

In the formulae (132) to (134):

$D_{11}$ and $D_{12}$ each independently represent the same as D in the formula (1), and at least one of $D_{11}$ or $D_{12}$ is a group represented by the formula (12) or (13); and $R_{121}$ and $R_{122}$ each independently represent the same as R in the formula (1), at least one of $R_{121}$ or $R_{122}$ is a substituent, and $R_{121}$ and $R_{122}$ serving as a substituent represent the same as R serving as a substituent in the formula (1).

[Formula 20]

(135)

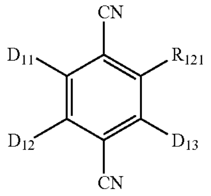

In the formula (135):

$D_{11}$ to $D_{13}$ each independently represent the same as D in the formula (1), and at least one of $D_{11}$ to $D_{13}$ is a group represented by the formula (12) or (13); and $R_{121}$ is a substituent, and $R_{121}$ serving as a substituent represents the same as R serving as a substituent in the formula (1).

It is preferable that: each combination of the combination of $R_{11}$ and $R_{12}$, the combination of $R_{12}$ and $R_{13}$, the combination of $R_{13}$ and $R_{14}$, the combination of $R_{15}$ and $R_{16}$, the combination of $R_{16}$ and $R_{17}$, and the combination of $R_{17}$ and $R_{18}$ in the formula (12) are not mutually bonded; and each combination of the combination of $R_{111}$ and $R_{112}$, the combination of $R_{112}$ and $R_{113}$, the combination of $R_{113}$ and $R_{114}$, the combination of $R_{115}$ and $R_{116}$, the combination of $R_{116}$ and $R_{117}$, and the combination of $R_{117}$ and $R_{118}$ in the formula (13) are not mutually bonded.

In the formula (14), it is preferable that the combination of $R_{19}$ and $R_{20}$ are not mutually bonded.

The compound according to the exemplary embodiment preferably has at least one group represented by the formula (12).

In the formula (12), p is preferably 2, 3, or 4.

In the formula (13), px and py are preferably each independently 2, 3, or 4.

The compound according to the exemplary embodiment preferably has, as D in the formula (1), at least one group $D_A$ represented by the formula (12) satisfying that p is 2, 3 or 4 and containing, as the cyclic structure A, a cyclic structure selected from the group consisting of cyclic structures represented by the formulae (15) and (16).

In the compound according to the exemplary embodiment, the cyclic structure A, the cyclic structure B and the cyclic structure C are preferably each independently a cyclic structure selected from the group consisting of cyclic structures represented by the formulae (14) and (15).

In the compound according to the exemplary embodiment, the group represented by the formula (12) is preferably a group selected from the group consisting of groups represented by formulae (12A), (12B), (12C), (12D), (12E) and (12F) below.

[Formula 21]

(12A)

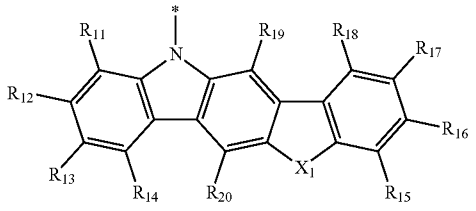

-continued

[Formula 22]

(12B)

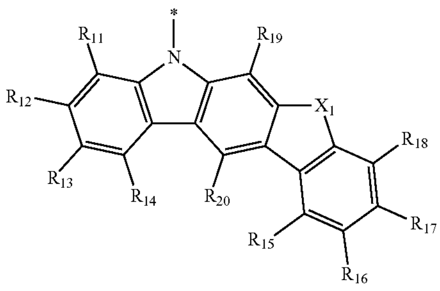

[Formula 23]

(12C)

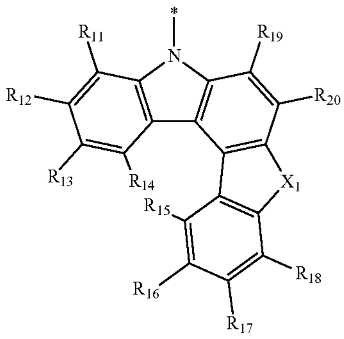

[Formula 24]

(12D)

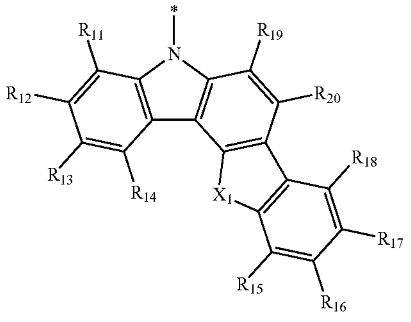

[Formula 25]

(12E)

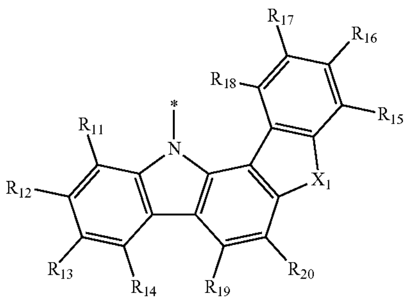

-continued

[Formula 26]

(12F)

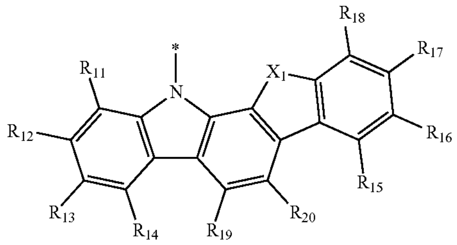

In the formulae (12A), (12B), (12C), (12D), (12E) and (12F):

$R_{11}$ to $R_{18}$ each independently represent the same as $R_{11}$ to $R_{18}$ in the formula (12);

$R_{19}$ and $R_{20}$ each independently represent the same as $R_{19}$ and $R_{20}$ in the formula (14);

$X_1$ represents the same as $X_1$ in the formula (15); and

* in the formulae (12A), (12B), (12C), (12D), (12E) and (12F) represents a bonding position to a benzene ring in the formula (1).

It is preferable that each combination of a combination of $R_{11}$ and $R_{12}$, a combination of $R_{12}$ and $R_{13}$, a combination of $R_{13}$ and $R_{14}$, a combination of $R_{15}$ and $R_{16}$, a combination of $R_{16}$ and $R_{17}$, a combination of $R_{17}$ and $R_{18}$, and a combination of $R_{19}$ and $R_{20}$ in the formulae (12A), (12B), (12C), (12D), (12E) and (12F) are not mutually bonded.

In the compound according to the exemplary embodiment, the group represented by the formula (12) is preferably a group selected from the group consisting of groups represented by the formulae (12A), (12D) and (12F).

In the compound according to the exemplary embodiment, $X_1$ is preferably an oxygen atom or a sulfur atom.

In the compound according to the exemplary embodiment, the group $D_A$ is preferably a group selected from the group consisting of groups represented by the formulae (12A), (12B), (12C), (12D), (12E) and (12F).

The compound according to the exemplary embodiment preferably has, as D in the formula (1), at least one group selected from the group consisting of groups represented by the formulae (12A), (12B), (12C), (12D), (12E) and (12F).

In the compound according to the exemplary embodiment, it is more preferable that D in the formula (1) is at least one group selected from the group consisting of groups represented by the formulae (12A), (12B), (12C), (12D), (12E) and (12F) and having at least one group in which $X_1$ is an oxygen atom or a sulfur atom.

It is preferable that D in the formulae (110), (120) and (130) is each independently a group selected from the group consisting of groups represented by the formulae (12A), (12B), (12C), (12D), (12E) and (12F).

It is preferable that $D_{11}$, $D_{12}$ and $D_{13}$ in the formulae (111) to (118), (121) to (129) and (131) to (135) are each independently a group selected from the group consisting of groups represented by the formulae (12A), (12B), (12C), (12D), (12E) and (12F).

In the compound according to the exemplary embodiment, it is preferable that $R_1$ to $R_8$ serving as a substituent, $R_{11}$ to $R_{18}$ serving as a substituent, and $R_{111}$ to $R_{118}$ serving as a substituent are each independently a substituted or unsubstituted aryl group having 6 to 30 ring carbon atoms, a substituted or unsubstituted alkyl group having 1 to 30 carbon atoms, or a substituted or unsubstituted cycloalkyl group having 3 to 30 ring carbon atoms.

In the compound according to the exemplary embodiment, it is preferable that $R_1$ to $R_8$ serving as a substituent, $R_{11}$ to $R_{18}$ serving as a substituent, and $R_{111}$ to $R_{118}$ serving as a substituent are each independently a substituted or unsubstituted aryl group having 6 to 14 ring carbon atoms, a substituted or unsubstituted alkyl group having 1 to 6 carbon atoms, or a substituted or unsubstituted cycloalkyl group having 3 to 6 ring carbon atoms.

In the compound according to the exemplary embodiment, it is preferable that $R_1$ to $R_8$ serving as a substituent, $R_{11}$ to $R_{18}$ serving as a substituent, and $R_{111}$ to $R_{118}$ serving as a substituent are each independently an unsubstituted aryl group having 6 to 30 ring carbon atoms, an unsubstituted heterocyclic group having 5 to 30 ring atoms, an unsubstituted alkyl group having 1 to 30 carbon atoms, an unsubstituted cycloalkyl group having 3 to 30 ring carbon atoms, an unsubstituted alkylsilyl group having 3 to 30 carbon atoms, an unsubstituted arylsilyl group having 6 to 60 ring carbon atoms, an unsubstituted alkoxy group having 1 to 30 carbon atoms, an unsubstituted aryloxy group having 6 to 30 ring carbon atoms, an unsubstituted alkylamino group having 2 to 30 carbon atoms, an unsubstituted arylamino group having 6 to 60 ring carbon atoms, an unsubstituted alkylthio group having 1 to 30 carbon atoms, or an unsubstituted arylthio group having 6 to 30 ring carbon atoms.

In the compound according to the exemplary embodiment, it is preferable that $R_1$ to $R_8$ serving as a substituent, $R_{11}$ to $R_{18}$ serving as a substituent, and $R_{111}$ to $R_{118}$ serving as a substituent are each independently an unsubstituted aryl group having 6 to 30 ring carbon atoms, an unsubstituted alkyl group having 1 to 30 carbon atoms, or an unsubstituted cycloalkyl group having 3 to 30 ring carbon atoms.

In the compound according to the exemplary embodiment, it is also preferable that $R_1$ to $R_8$, $R_{11}$ to $R_{18}$ and $R_{111}$ to $R_{118}$ are each a hydrogen atom.

In the compound according to the exemplary embodiment, it is preferable that: R is each independently a hydrogen atom, a halogen atom, or a substituent; and R serving as a substituent is each independently a substituted or unsubstituted aryl group having 6 to 14 ring carbon atoms, a substituted or unsubstituted heteroaryl group having 5 to 14 ring atoms, a substituted or unsubstituted alkyl group having 1 to 6 carbon atoms, or a substituted or unsubstituted cycloalkyl group having 3 to 6 ring carbon atoms.

In the compound according to the exemplary embodiment, it is preferable that: R is each independently a hydrogen atom, a halogen atom, or a substituent; and R serving as a substituent is each independently an unsubstituted aryl group having 6 to 14 ring carbon atoms, an unsubstituted heteroaryl group having 5 to 14 ring atoms, an unsubstituted alkyl group having 1 to 6 carbon atoms, an unsubstituted cycloalkyl group having 3 to 6 ring carbon atoms, an unsubstituted alkylsilyl group having 3 to 6 carbon atoms, an unsubstituted arylsilyl group having 3 to 6 carbon atoms, an unsubstituted alkoxy group having 1 to 6 carbon atoms, an unsubstituted aryloxy group having 6 to 14 ring carbon atoms, an unsubstituted alkylamino group having 2 to 12 carbon atoms, an unsubstituted alkylthio group having 1 to 6 carbon atoms, or an unsubstituted arylthio group having 6 to 14 ring carbon atoms.

In the compound according to the exemplary embodiment, it is preferable that: R is each independently a hydrogen atom, a halogen atom, or a substituent; and R serving as a substituent is each independently an unsubstituted aryl group having 6 to 14 ring carbon atoms, an unsubstituted heteroaryl group having 5 to 14 ring atoms, an unsubstituted alkyl group having 1 to 6 carbon atoms, or an unsubstituted cycloalkyl group having 3 to 6 ring carbon atoms.

The compound according to the exemplary embodiment is preferably a delayed fluorescent compound.

Delayed Fluorescence

Delayed fluorescence is explained in "Yuki Hando-tai no Debaisu Bussei (Device Physics of Organic Semiconductors)" (edited by ADACHI, Chihaya, published by Kodansha, on pages 261-268). This document describes that, if an energy difference $\Delta E_{13}$ of a fluorescent material between a singlet state and a triplet state is reducible, a reverse energy transfer from the triplet state to the singlet state, which usually occurs at a low transition probability, would occur at a high efficiency to express thermally activated delayed fluorescence (TADF). Further, a mechanism of generating delayed fluorescence is explained in FIG. 10.38 in the document. The compound according to the exemplary embodiment is preferably a compound exhibiting thermally activated delayed fluorescence generated by such a mechanism.

In general, emission of delayed fluorescence can be confirmed by measuring the transient PL (Photo Luminescence).

The behavior of delayed fluorescence can also be analyzed based on the decay curve obtained from the transient PL measurement. The transient PL measurement is a method of irradiating a sample with a pulse laser to excite the sample, and measuring the decay behavior (transient characteristics) of PL emission after the irradiation is stopped. PL emission in TADF materials is classified into a light emission component from a singlet exciton generated by the first PL excitation and a light emission component from a singlet exciton generated via a triplet exciton. The lifetime of the singlet exciton generated by the first PL excitation is on the order of nanoseconds and is very short. Therefore, light emission from the singlet exciton rapidly attenuates after irradiation with the pulse laser.

On the other hand, the delayed fluorescence is gradually attenuated due to light emission from a singlet exciton generated via a triplet exciton having a long lifetime. As described above, there is a large temporal difference between the light emission from the singlet exciton generated by the first PL excitation and the light emission from the singlet exciton generated via the triplet exciton. Therefore, the luminous intensity derived from delayed fluorescence can be determined.

FIG. 1 shows a schematic diagram of an exemplary device for measuring the transient PL. An exemple of a method of measuring a transient PL using FIG. 1 and an example of behavior analysis of delayed fluorescence will be described.

A transient PL measuring device 100 in FIG. 1 includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device shown in FIG. 1.

The sample housed in the sample chamber 102 is obtained by forming a thin film, in which a matrix material is doped with a doping material at a concentration of 12 mass %, on the quartz substrate.

The thin film sample housed in the sample chamber 102 is irradiated with the pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was prepared as described above from a reference compound H1 as the matrix material and a reference compound D1 as the doping material and was measured in terms of the transient PL.

[Formula 27]

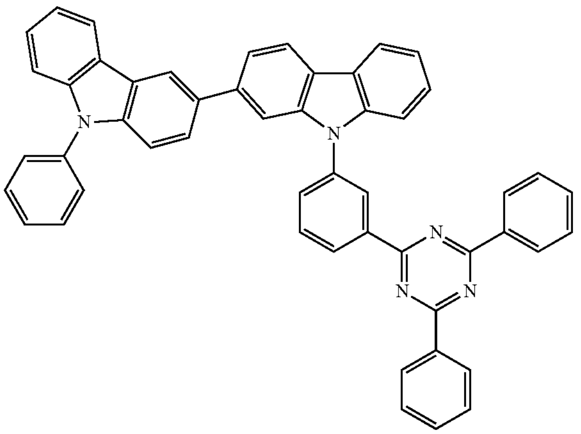

Reference Compound H1

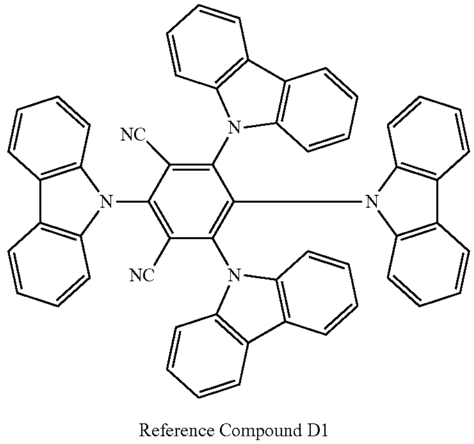

Reference Compound D1

Herein, the decay curve was analyzed with respect to the above thin film sample A and a thin film sample B. The thin film sample B was manufactured in the same manner as described above from a reference compound H2 as the matrix material and the reference compound D1 as the doping material.

Figure 2:
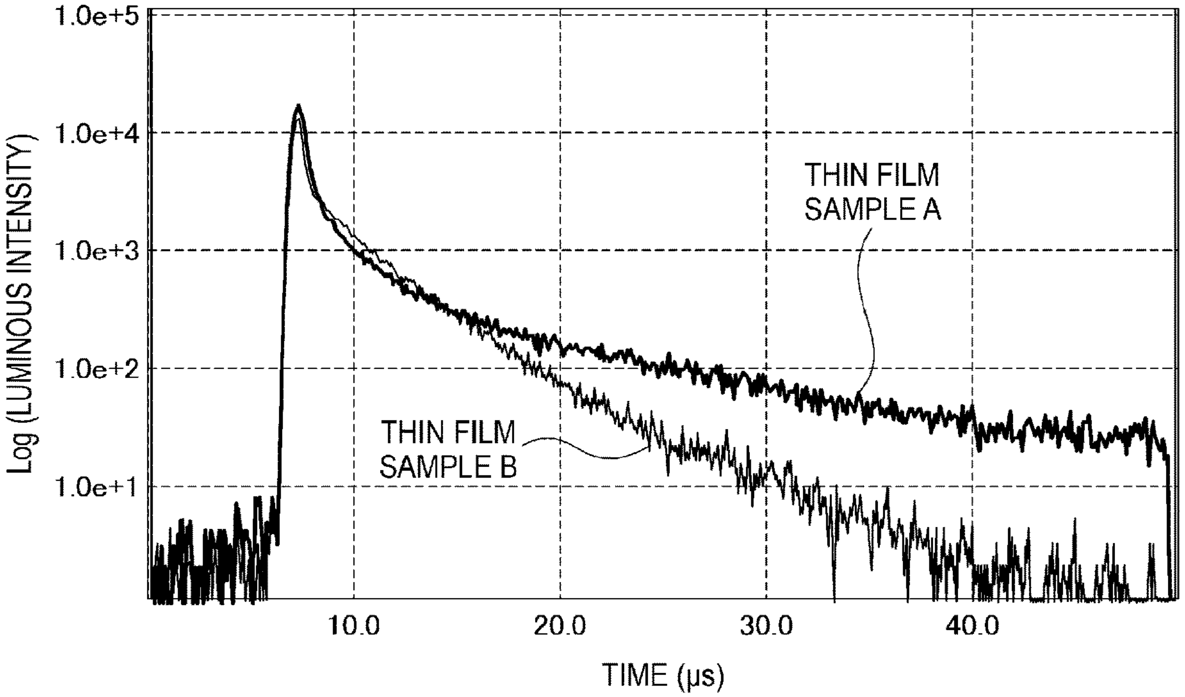

FIG. 2 shows decay curves obtained from the transient PL obtained by measuring the thin film samples A and B.

[Formula 28]

Reference Compound H2

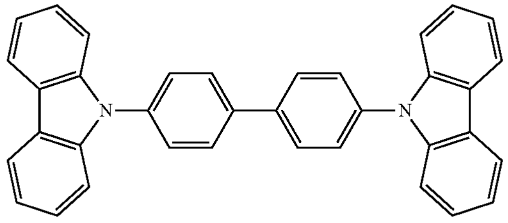

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

Specifically, Prompt emission and Delay emission are present as emission from the delayed fluorescent material. Prompt emission is observed promptly when the excited state is achieved by exciting the compound of the exemplary embodiment with a pulse beam (i.e., a beam emitted from a pulse laser) having a wavelength absorbable by the delayed fluorescent material. Delay emission is observed not promptly when the excited state is achieved but after the excited state is achieved.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 1.

Further, a sample manufactured according to a method shown below is used for measuring delayed fluorescence of the compound according to the exemplary embodiment. For instance, the compound according to the exemplary embodiment is dissolved in toluene to prepare a dilute solution with an absorbance of 0.05 or less at the excitation wavelength to eliminate the contribution of self-absorption. In order to prevent quenching due to oxygen, the sample solution is frozen and degassed and then sealed in a cell with a lid under an argon atmosphere to obtain an oxygen-free sample solution saturated with argon.

The fluorescence spectrum of the sample solution is measured with a spectrofluorometer FP-8600 (manufactured by JASCO Corporation), and the fluorescence spectrum of a 9,10-diphenylanthracene ethanol solution is measured under the same conditions. Using the fluorescence area intensities of both spectra, the total fluorescence quantum yield is calculated by an equation (1) in Morris et al. J. Phys. Chem. 80 (1976) 969.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 1.

In the exemplary embodiment, provided that an amount of Prompt emission of a measurement target compound is denoted by $X_P$ and an amount of Delay emission thereof is denoted by $X_D$, a value of $X_D/X_P$ is preferably 0.05 or more.

The amounts of Prompt emission and Delay emission and a ratio of the amounts thereof in compounds other than the compound according to the exemplary embodiment herein are measured in the same manner as those of the compound according to the exemplary embodiment.

ΔST

In the exemplary embodiment, a difference ($S_1-T_{177K}$) between the lowest singlet energy $S_1$ and an energy gap $T_{77K}$ at 77K is defined as ΔST.

A difference ΔST(M1) between the lowest singlet energy $S_1$(M1) of the compound according to the exemplary embodiment and an energy gap $T_{77K}$(M1) at 77K of the compound according to the exemplary embodiment is preferably less than 0.3 eV, more preferably less than 0.2 eV, further preferably less than 0.1 eV. That is, ΔST(M1) preferably satisfies a relationship of a numerical formula (Numerical Formula 10), (Numerical Formula 11), (Numerical Formula 12) or (Numerical Formula 13) below.

$$\Delta ST(M1)=S_1(M1)-T_{77K}(M1)<0.3\text{ eV} \quad \text{(Numerical Formula 10)}$$

$$\Delta ST(M1)=S_1(M1)-T_{77K}(M1)<0.2\text{ eV} \quad \text{(Numerical Formula 11)}$$

$$\Delta ST(M1)=S_1(M1)-T_{77K}(M1)<0.1\text{ eV} \quad \text{(Numerical Formula 12)}$$

$$\Delta ST(M1)=S_1(M1)-T_{77K}(M1)<0.01\text{ eV} \quad \text{(Numerical Formula 13)}$$

Relationship between Triplet Energy and Energy Gap at 77K

Here, a relationship between a triplet energy and an energy gap at 77K will be described. In the exemplary embodiment, the energy gap at 77K is different from a typical triplet energy in some aspects.

The triplet energy is measured as follows. First, a solution in which a compound (measurement target) is dissolved in an appropriate solvent is encapsulated in a quartz glass tube to prepare a sample. A phosphorescence spectrum (ordinate axis: phosphorescent luminous intensity, abscissa axis: wavelength) of the sample is measured at a low temperature (77K). A tangent is drawn to the rise of the phosphorescence spectrum close to the short-wavelength region. The triplet energy is calculated by a predetermined conversion equation based on a wavelength value at an intersection of the tangent and the abscissa axis.

Herein, the thermally activated delayed fluorescent compound used in the exemplary embodiment is preferably a compound having a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 μmol/L, and the obtained solution is encapsulated in a quartz cell to provide a measurement sample. A phosphorescence spectrum (ordinate axis: phosphorescent luminous intensity, abscissa axis: wavelength) of the sample is measured at a low temperature (77K). A tangent is drawn to the rise of the phosphorescence spectrum close to the short-wavelength region. An energy amount is calculated by a conversion equation (F1) below based on a wavelength value $\lambda_{edge}$ [nm] at an intersection of the tangent and the abscissa axis and is defined as an energy gap $T_{77K}$ at 77K.

$$\text{Conversion Equation } (F1)\text{: } T_{77K}\ [\text{eV}]=1239.85/\lambda\text{edge}$$

The tangent to the rise of the phosphorescence spectrum close to the short-wavelength region is drawn as follows. While moving on a curve of the phosphorescence spectrum from the short-wavelength region to the local maximum value closest to the short-wavelength region among the local maximum values of the phosphorescence spectrum, a tangent is checked at each point on the curve toward the long-wavelength of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

A local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

Lowest Singlet Energy $S_1$

A method of measuring the lowest singlet energy $S_1$ with use of a solution (occasionally referred to as a solution method) is exemplified by a method below.

A toluene solution of a measurement target compound at a concentration of 10 μmol/L is prepared and put in a quartz cell. An absorption spectrum (ordinate axis: absorption intensity, abscissa axis: wavelength) of the thus-obtained sample is measured at a normal temperature (300K). A tangent is drawn to the fall of the absorption spectrum close to the long-wavelength region, and a wavelength value λedge (nm) at an intersection of the tangent and the abscissa axis is assigned to a conversion equation (F2) below to calculate the lowest singlet energy.

$$\text{Conversion Equation } (F2)\text{: } S_1\ [\text{eV}]=1239.85/\lambda\text{edge}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve fell (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

Manufacturing Method of Compound According to Exemplary Embodiment

The compound according to the exemplary embodiment can be manufactured by application of known substitution reactions and materials depending on a target compound, in accordance with or based on synthesis methods described later in Examples.

Specific Examples of Compound According to Exemplary Embodiment

Examples of the compound according to the exemplary embodiment include the following compounds. It should however be noted that the invention is not limited to the specific examples. In the chemical formulae herein, a deuterium atom is denoted by D and a protium atom is denoted by H or a description for a protium is omitted.

[Formula 29]

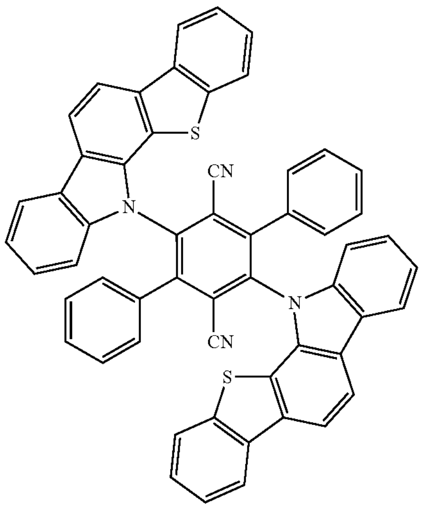

-continued

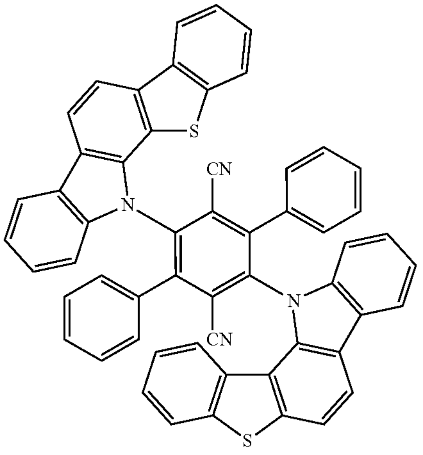

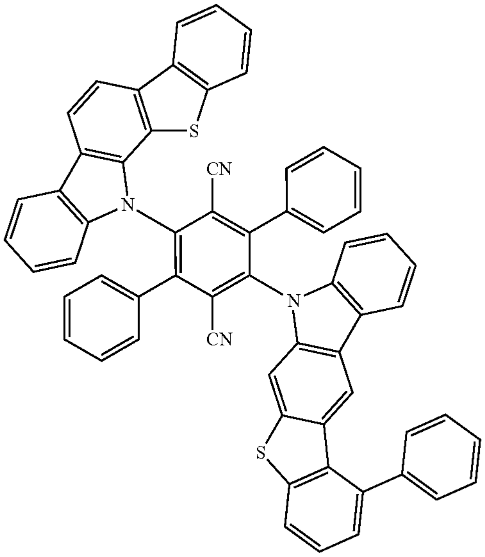

[Formula 30]

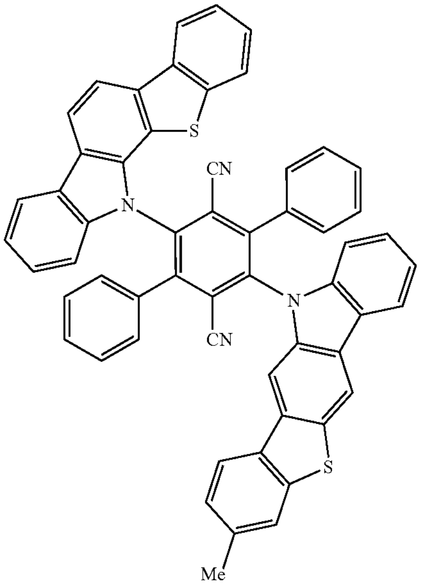

-continued
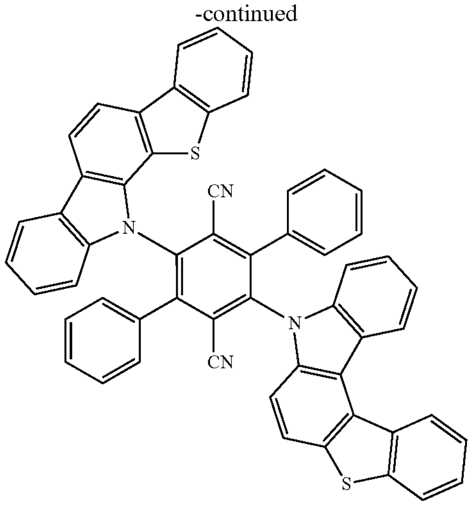
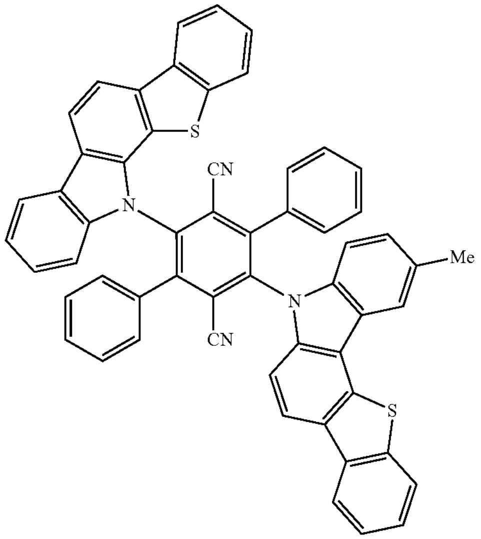
[Formula 31]
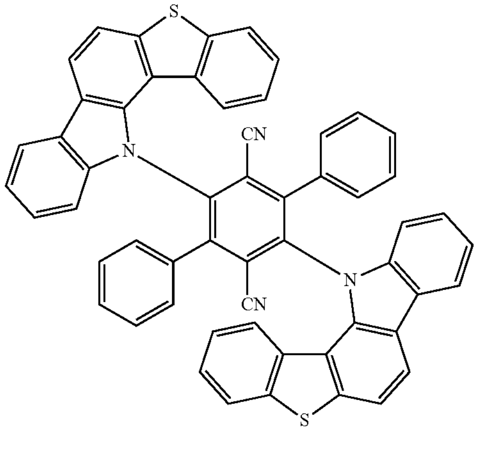
-continued
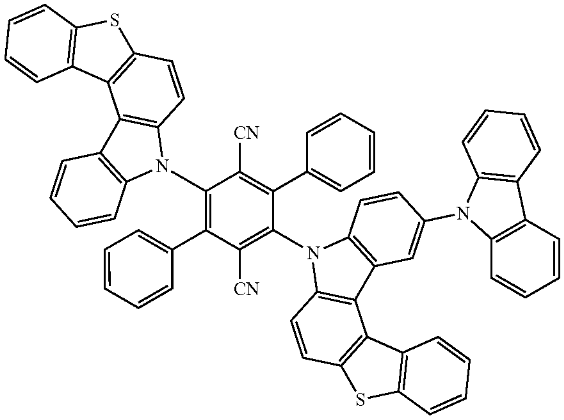
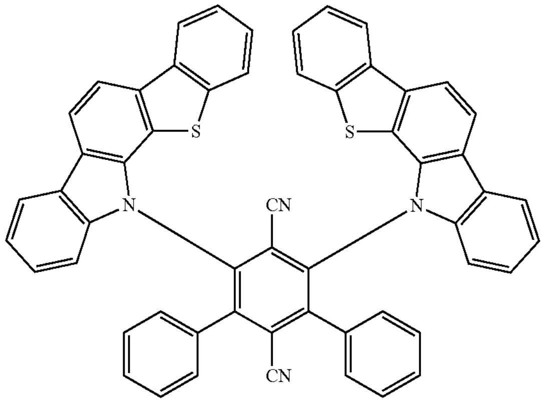
[Formula 32]
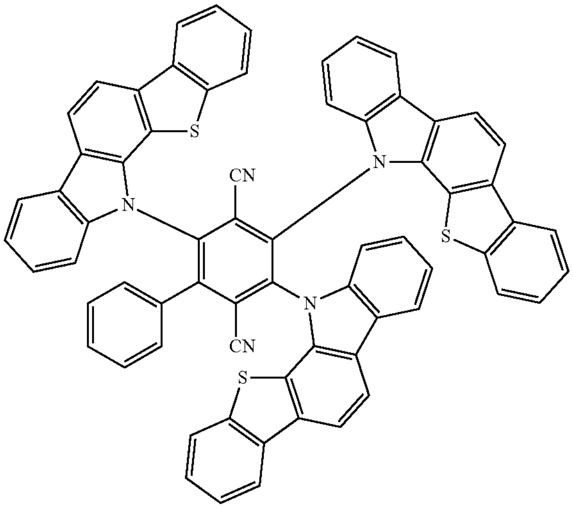

-continued
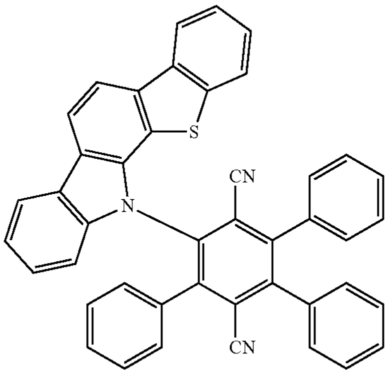
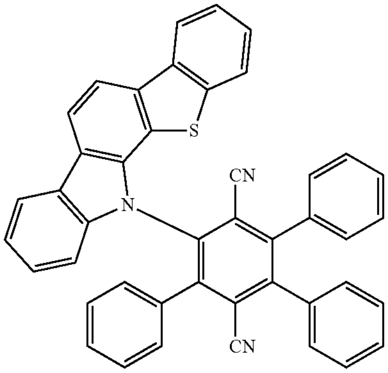
[Formula 33]
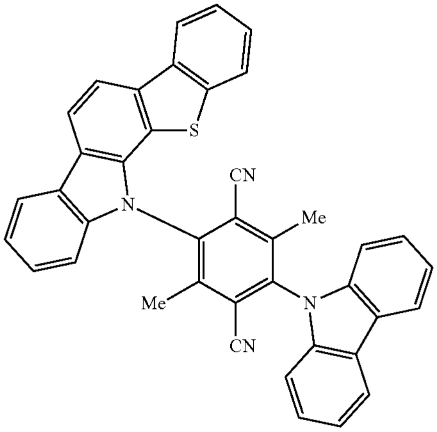
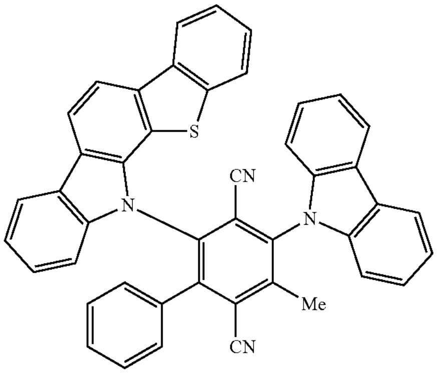
-continued
[Formula 34]
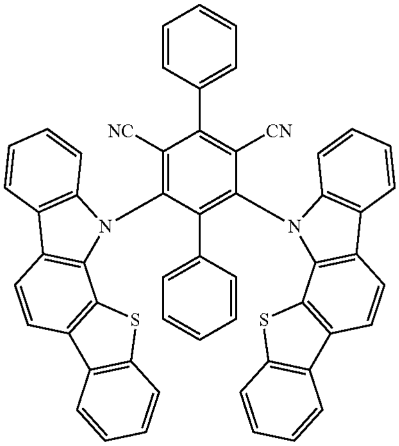
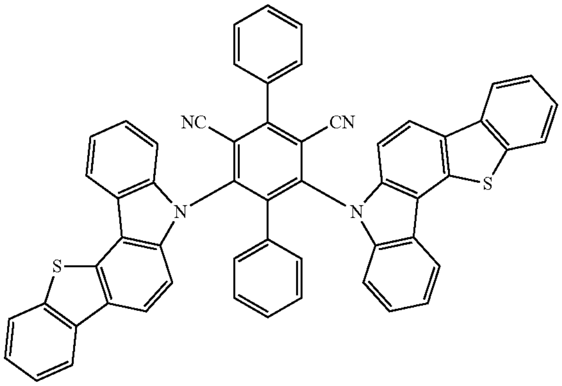
[Formula 35]
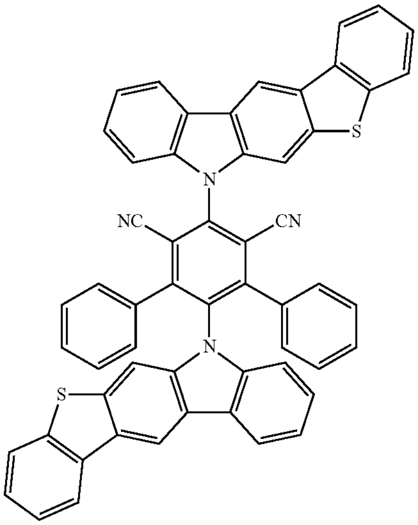

-continued
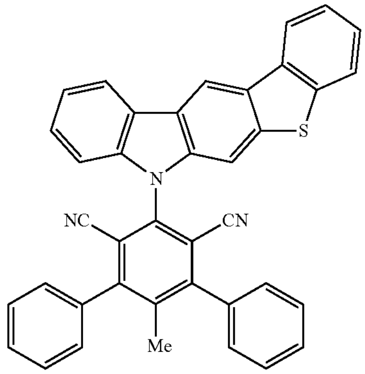
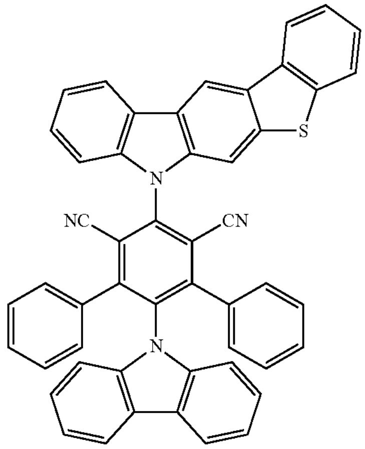
[Formula 36]
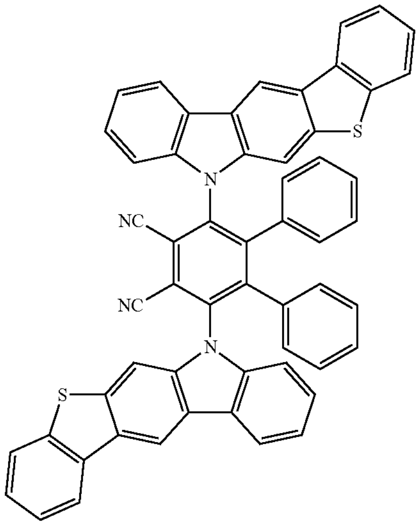
-continued
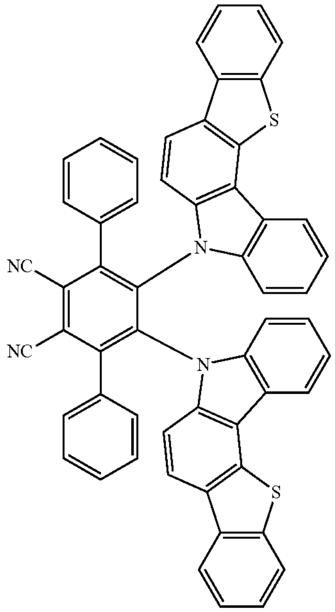
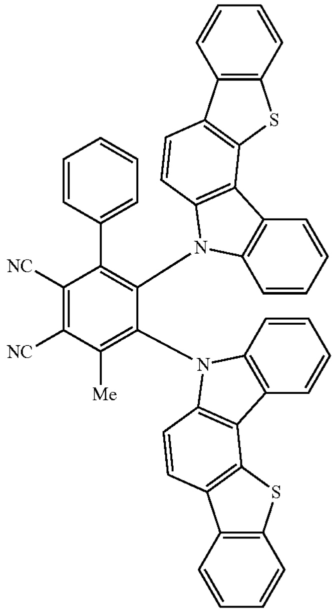

-continued
[Formula 37]
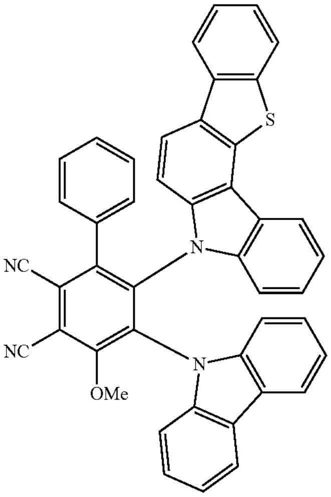
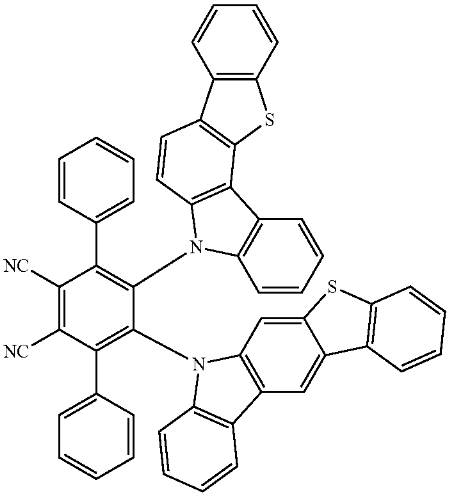
[Formula 38]
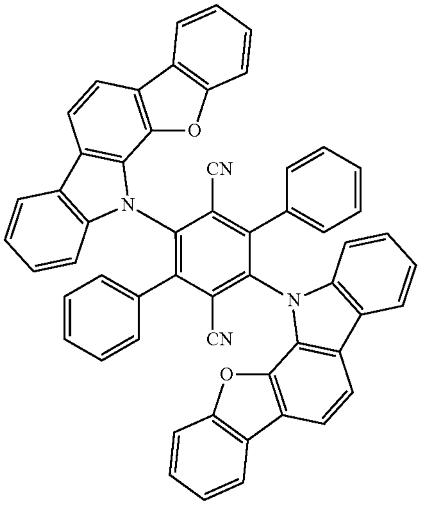
-continued
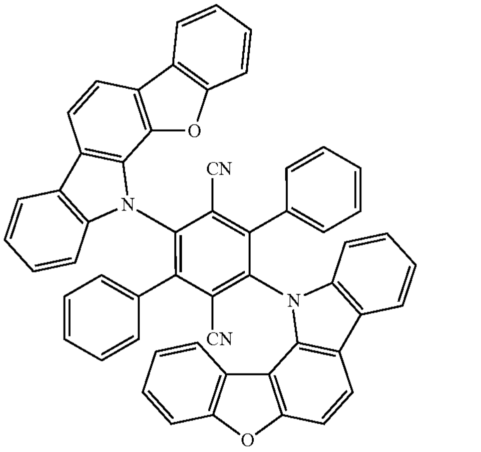
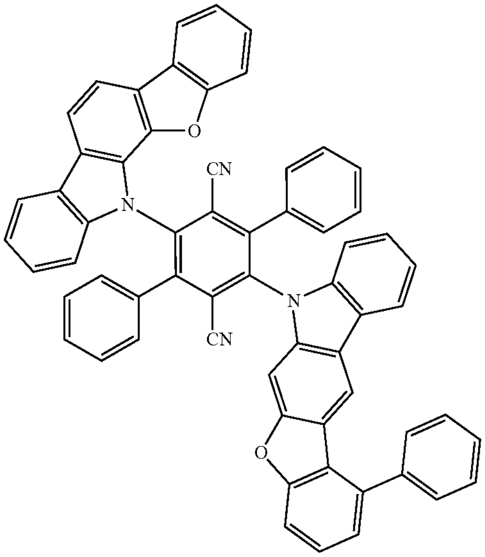
[Formula 39]
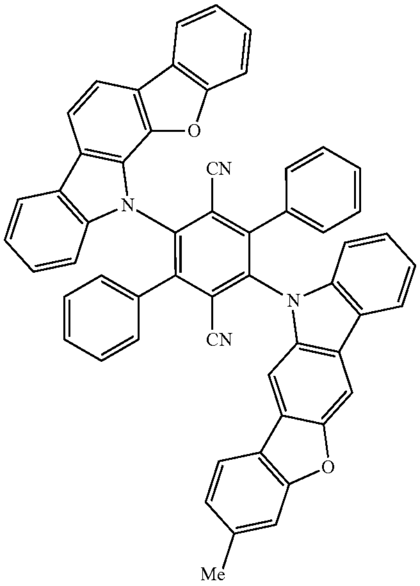

-continued
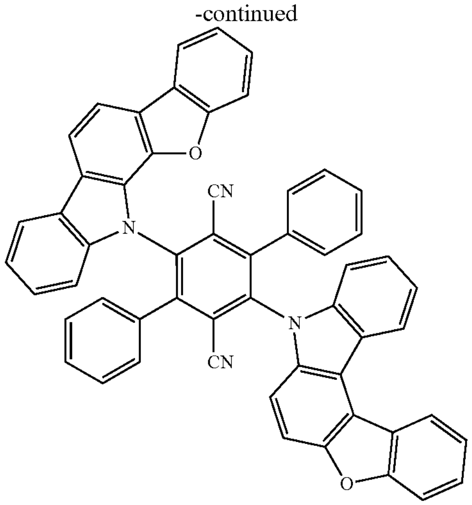
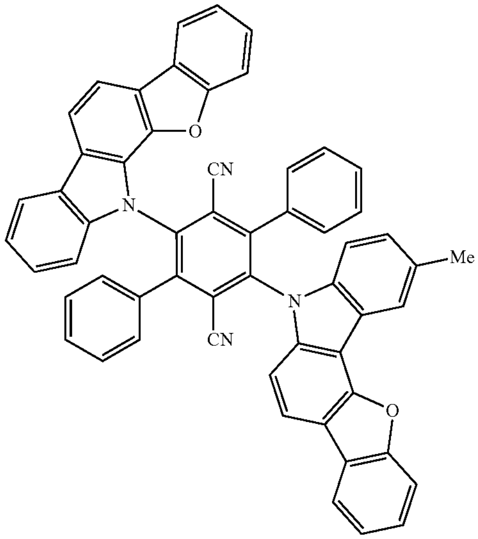
[Formula 40]
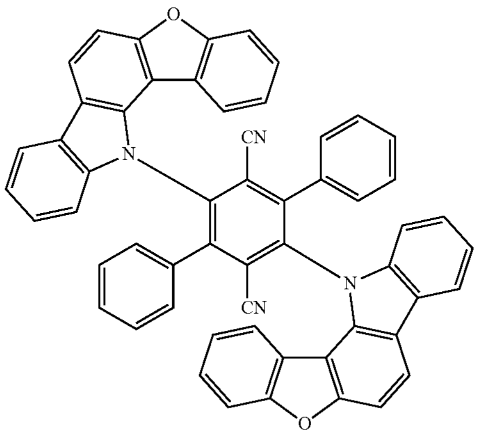
-continued
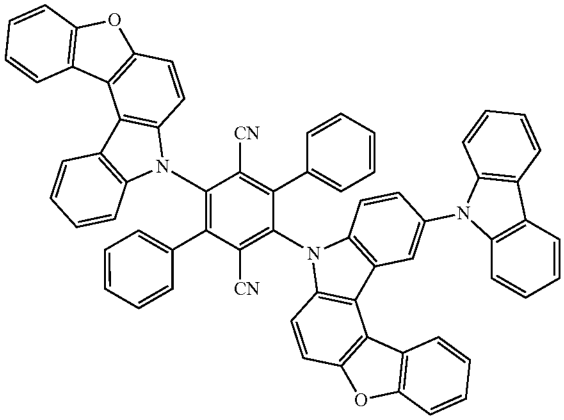
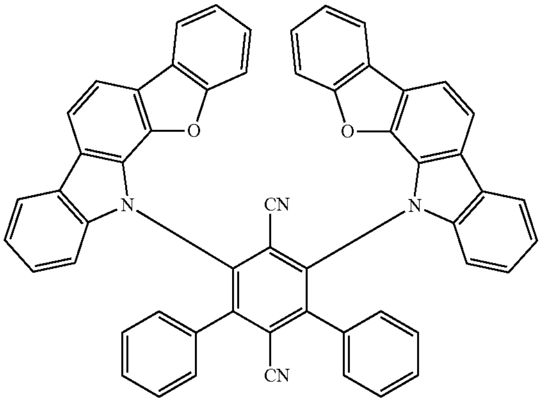
[Formula 41]
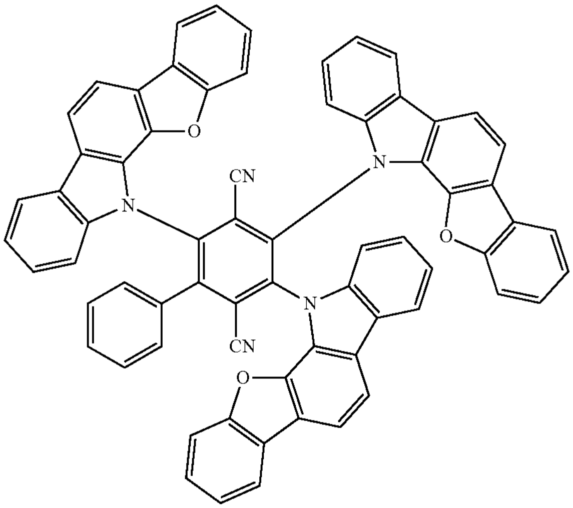

-continued
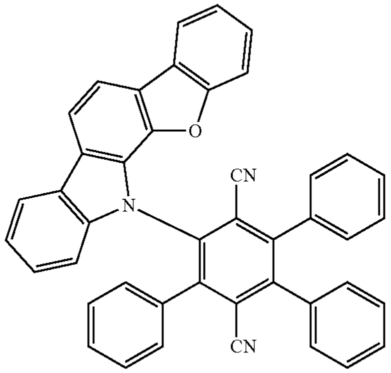
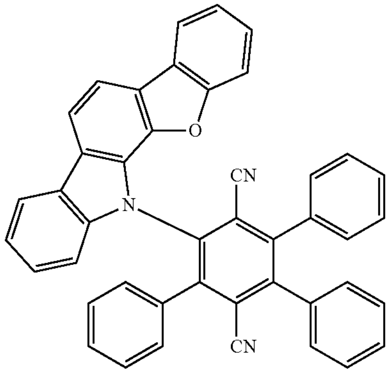
[Formula 42]
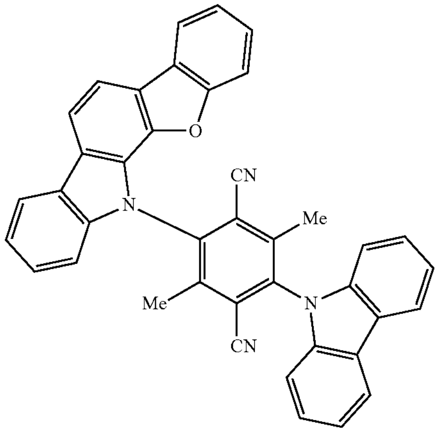
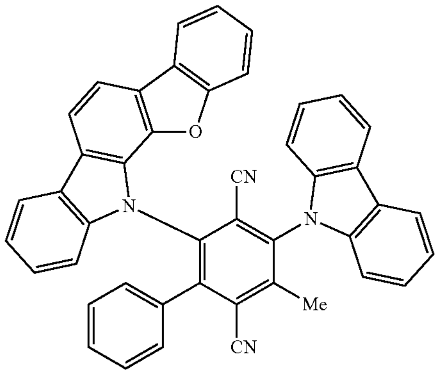
-continued
[Formula 43]
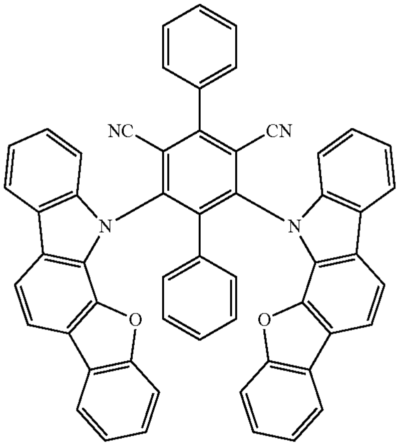
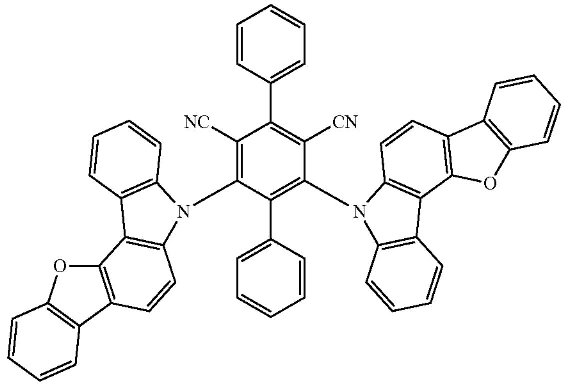
[Formula 44]
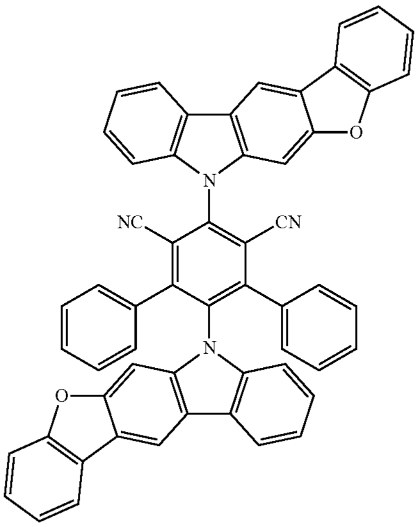

-continued
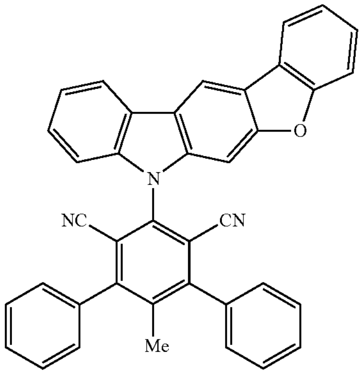
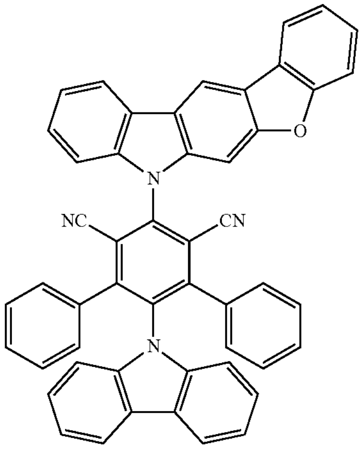
[Formula 45]
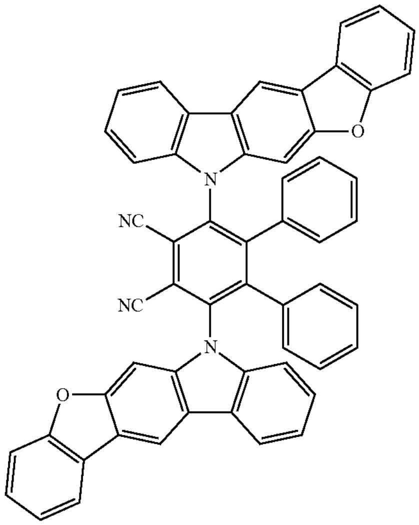
-continued
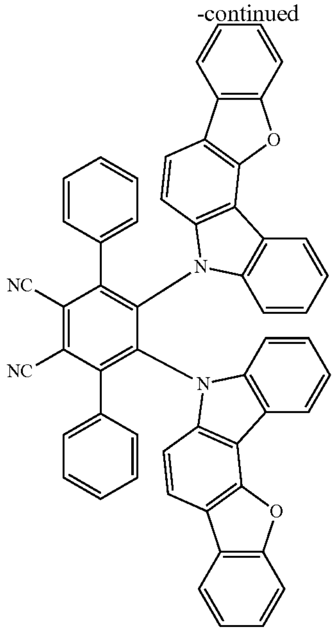
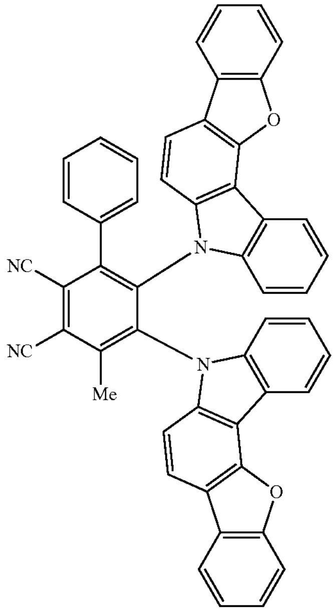

-continued
[Formula 46]
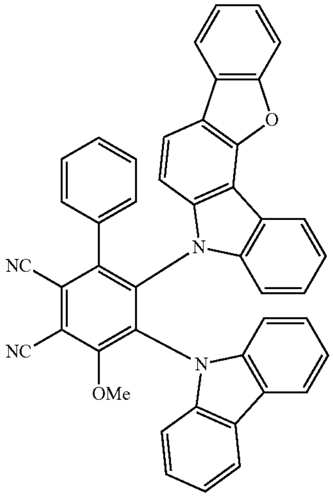
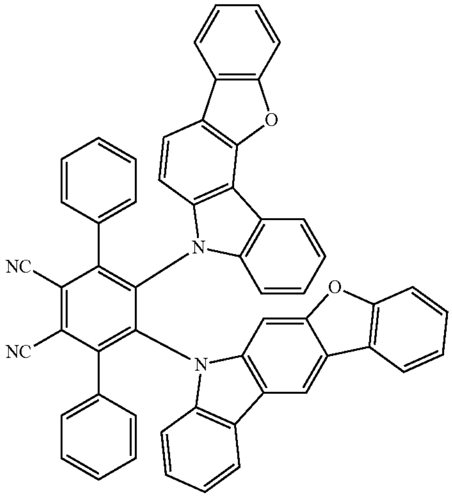
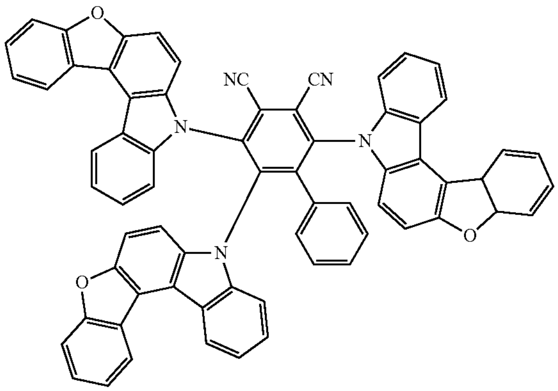
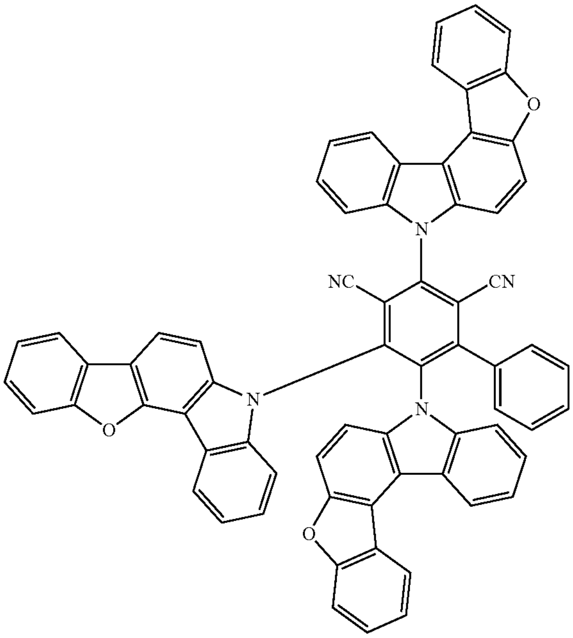
[Formula 47]
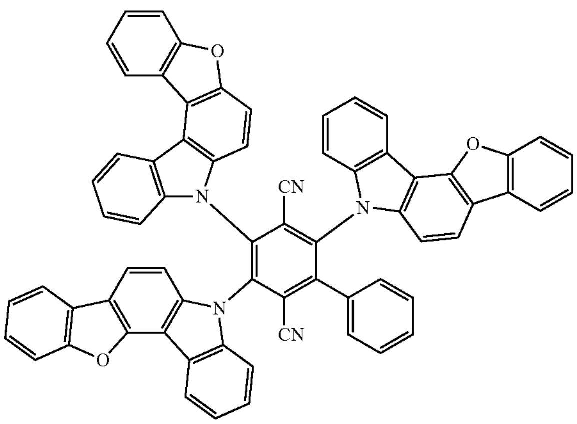
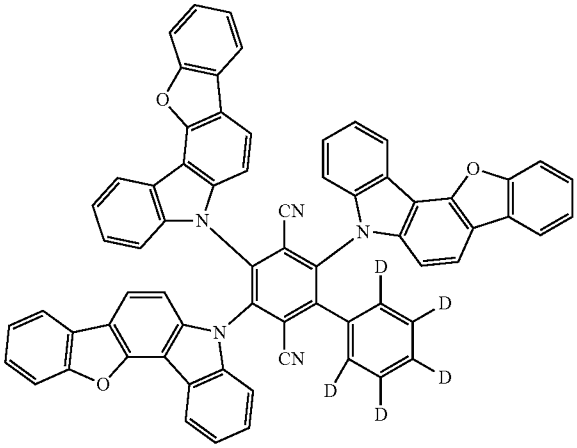

-continued
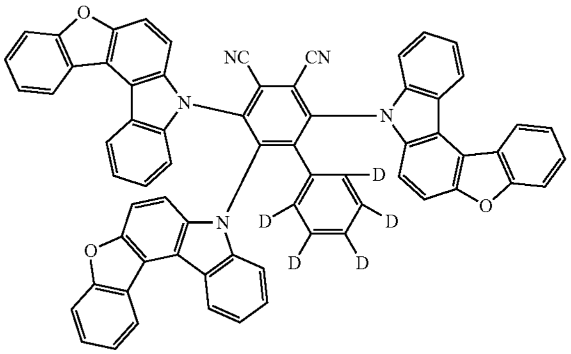
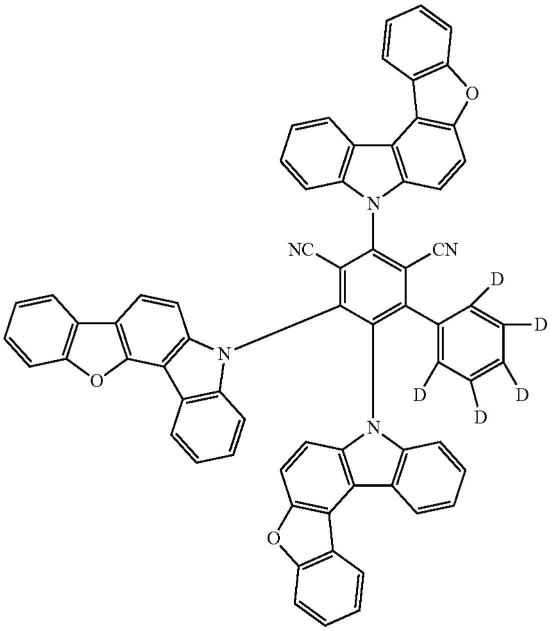
[Formula 48]
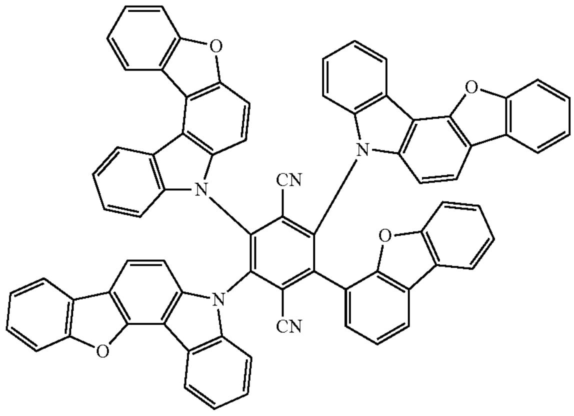
-continued
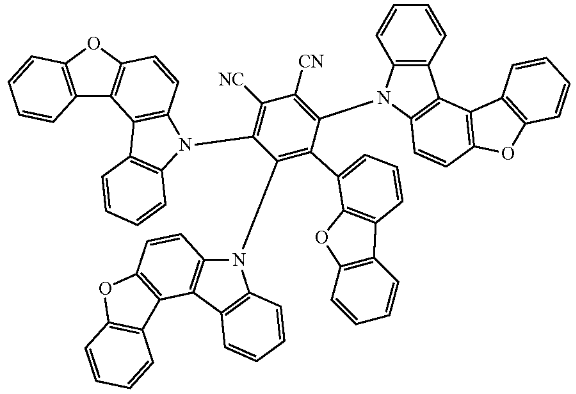
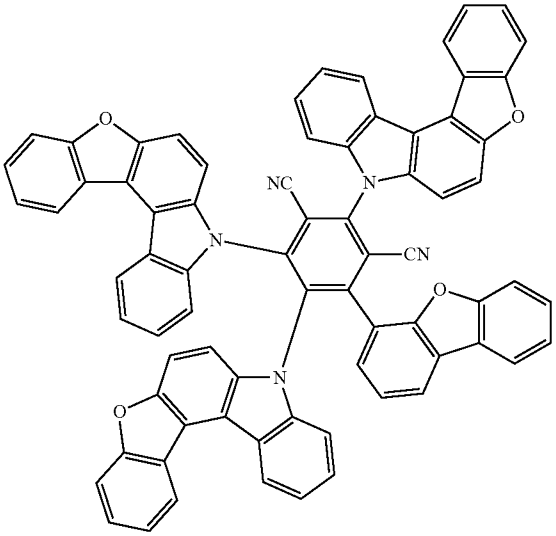
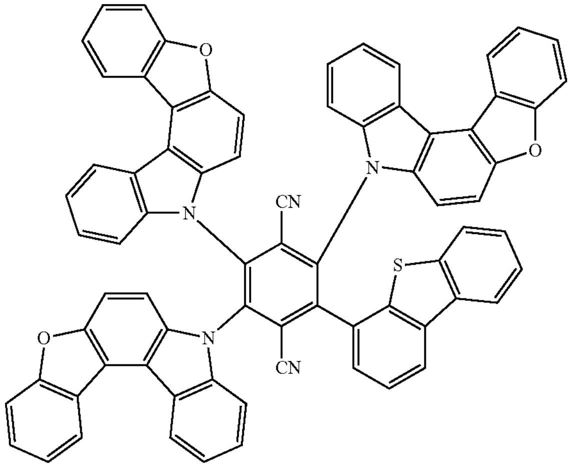

-continued
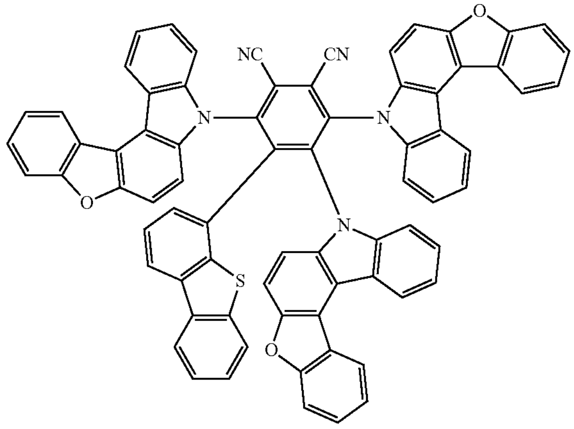
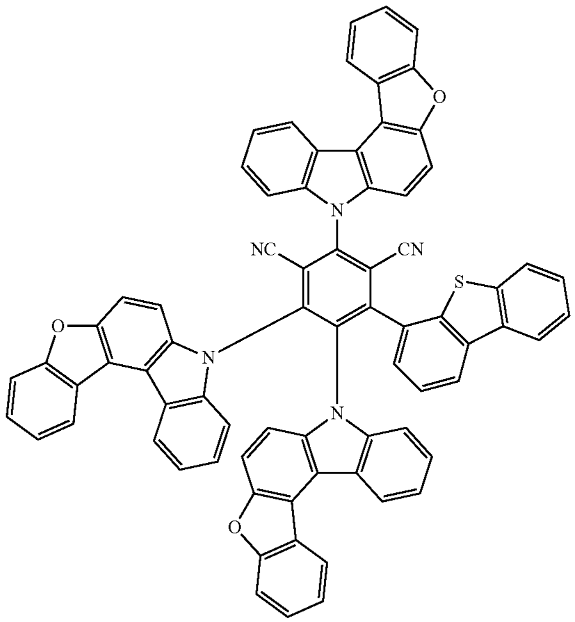
[Formula 49]
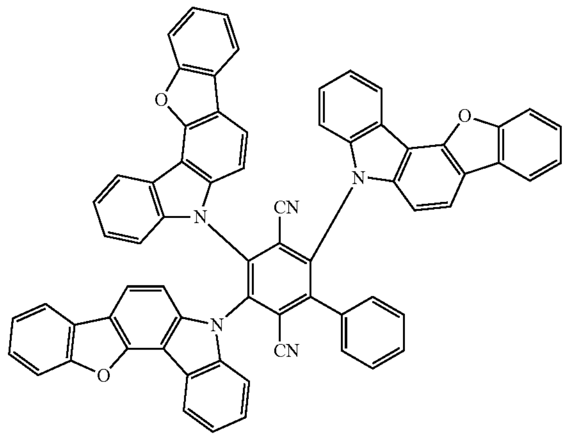
-continued
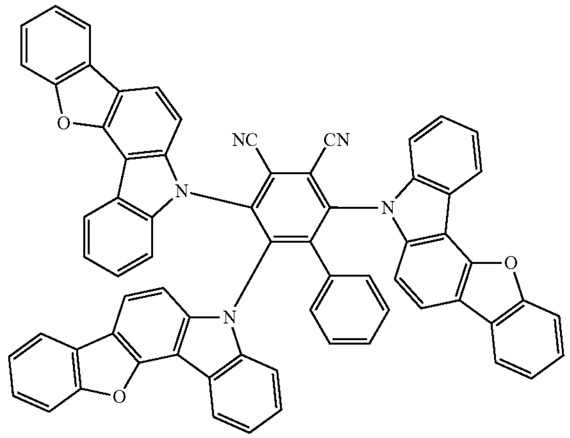
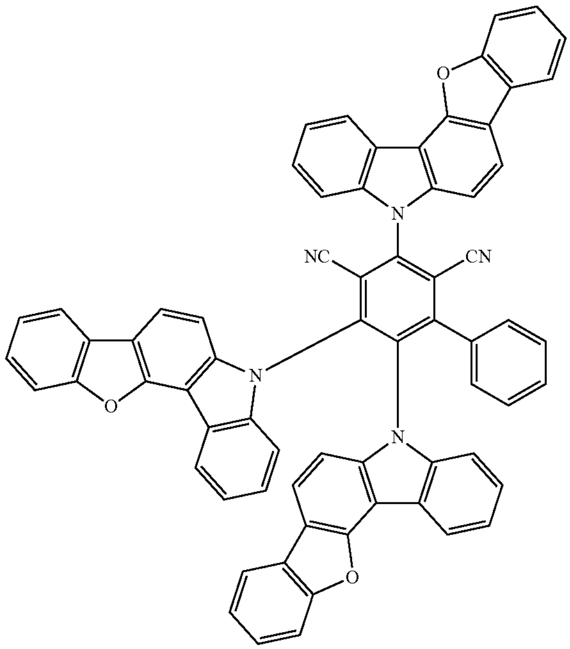
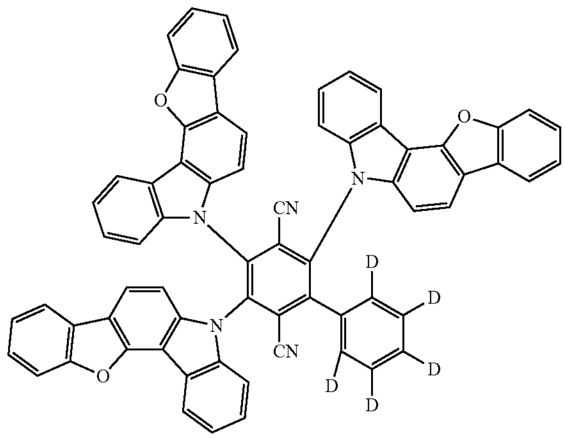

-continued
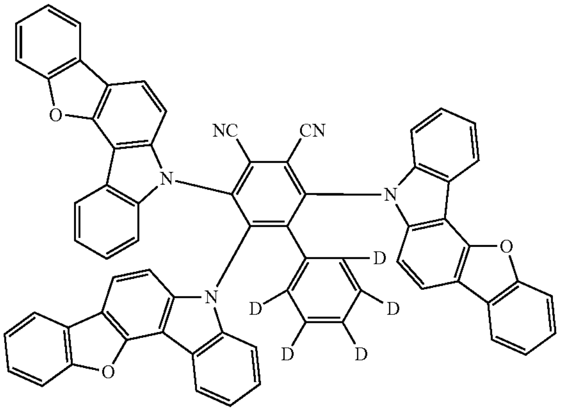
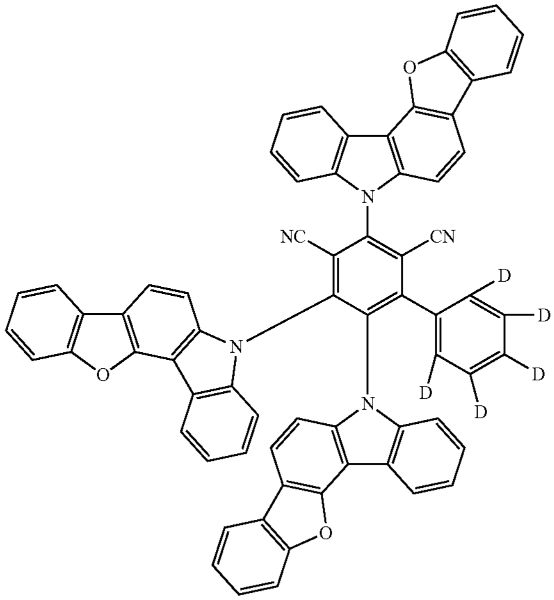
[Formula 50]
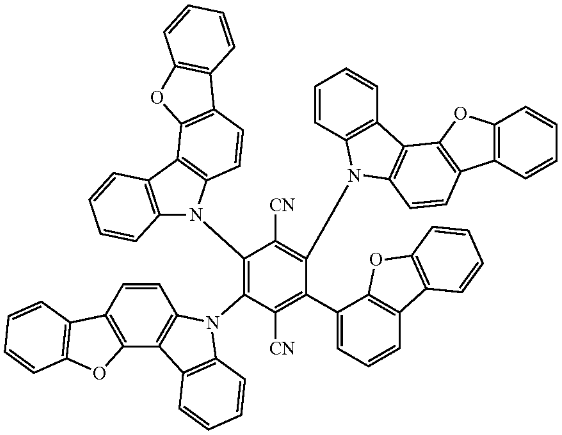
-continued
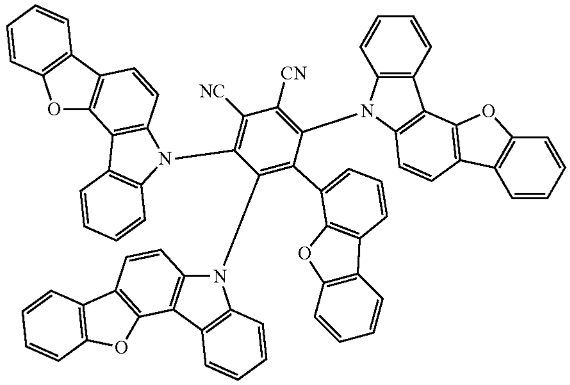
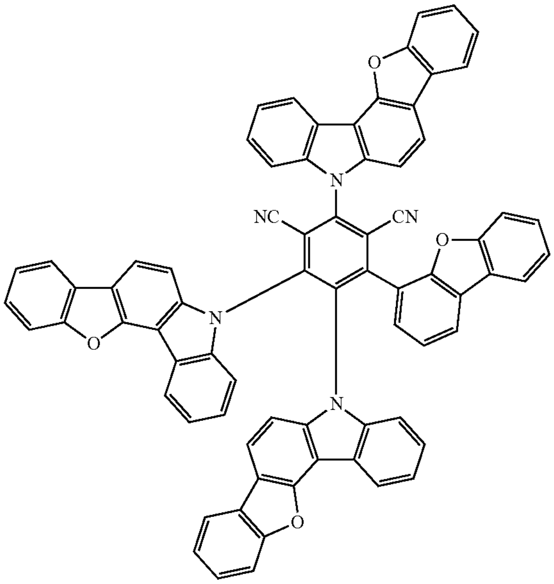
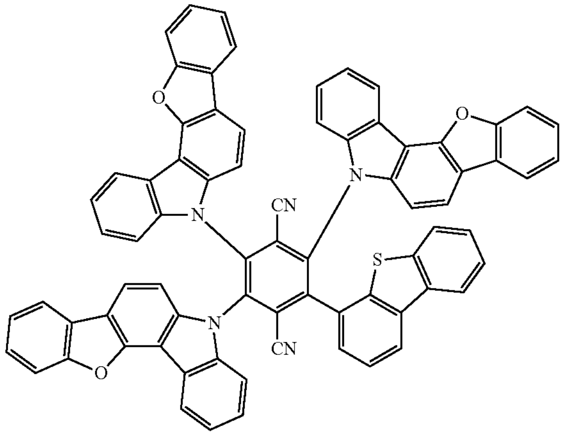

-continued
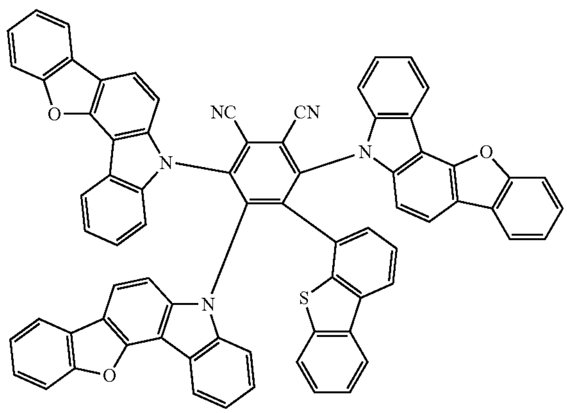
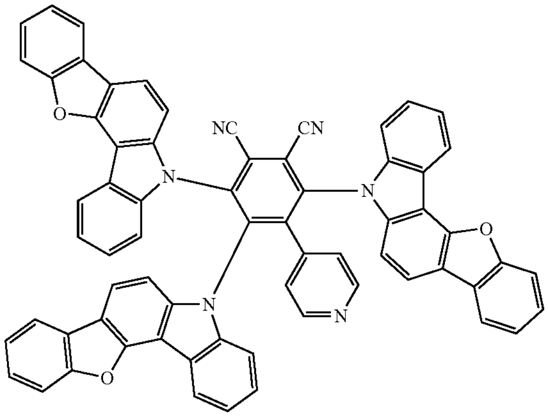
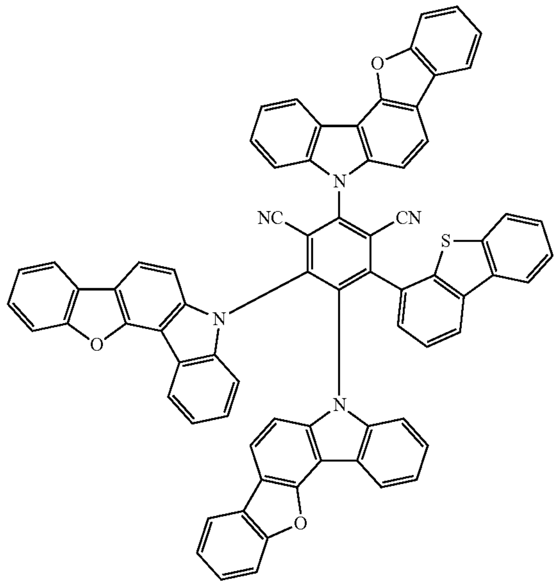
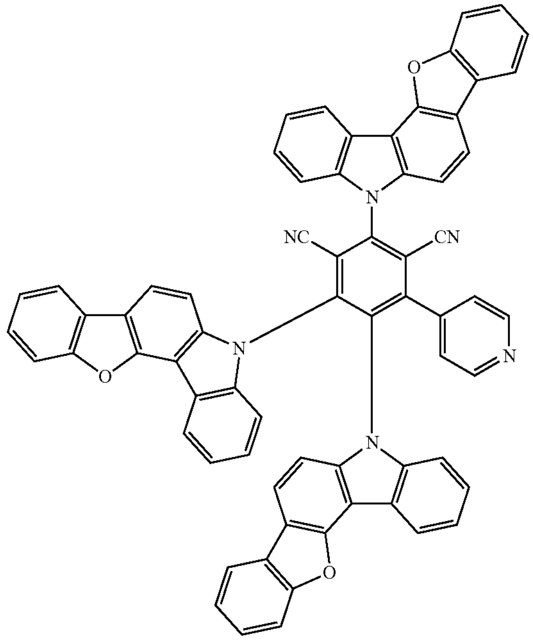
[Formula 51]
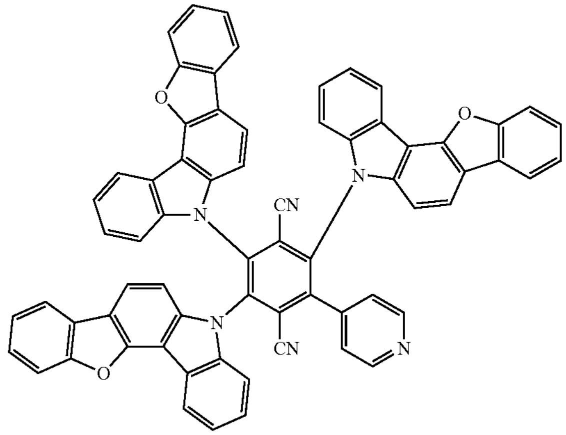
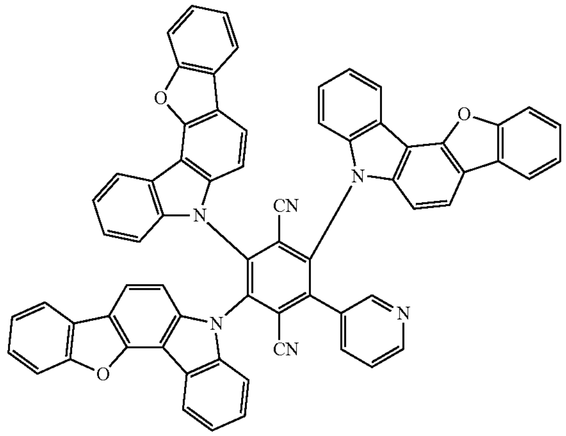

-continued
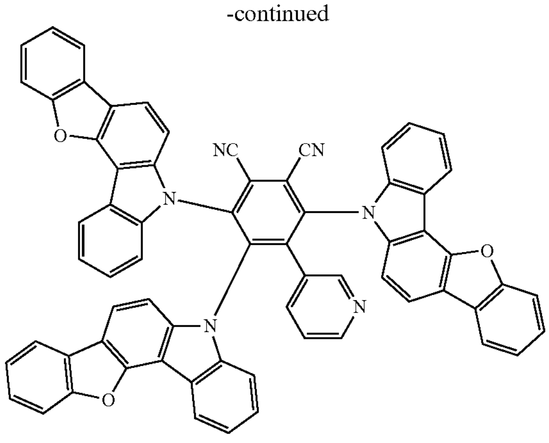
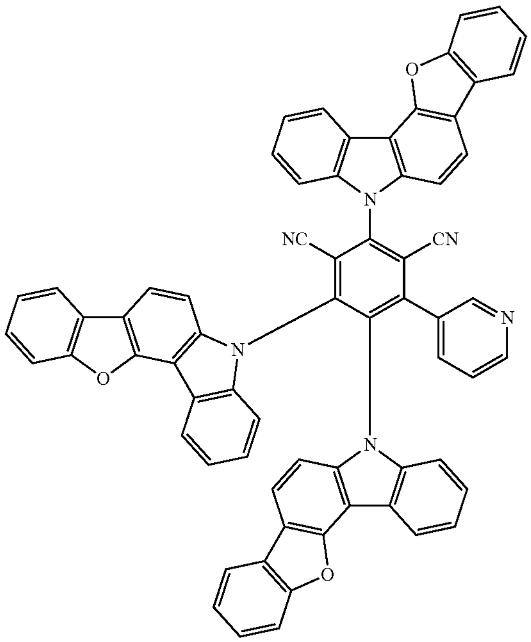
[Formula 52]
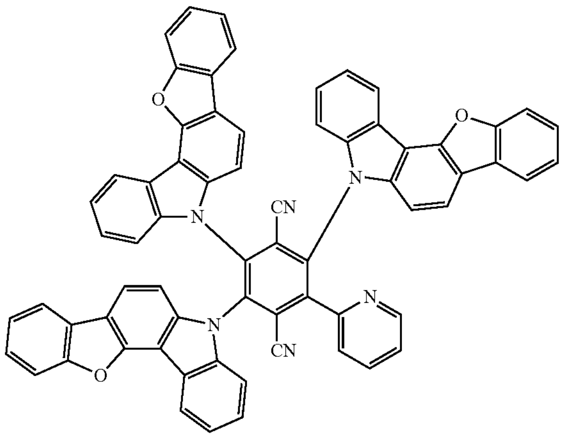
-continued
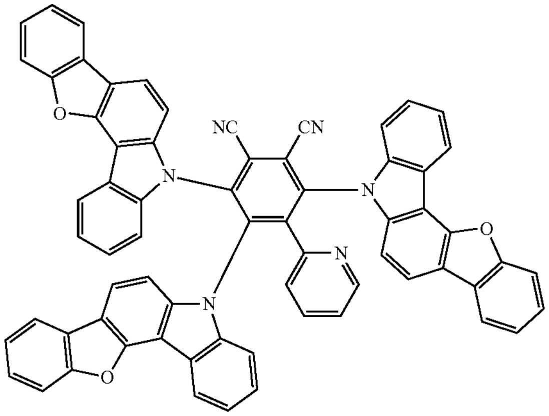
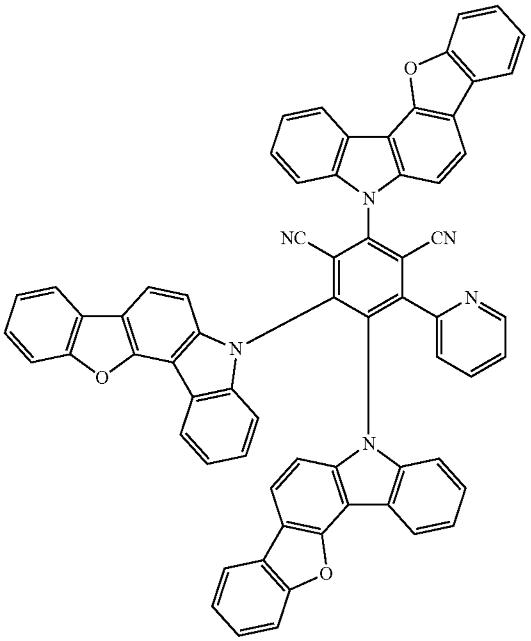
[Formula 53]
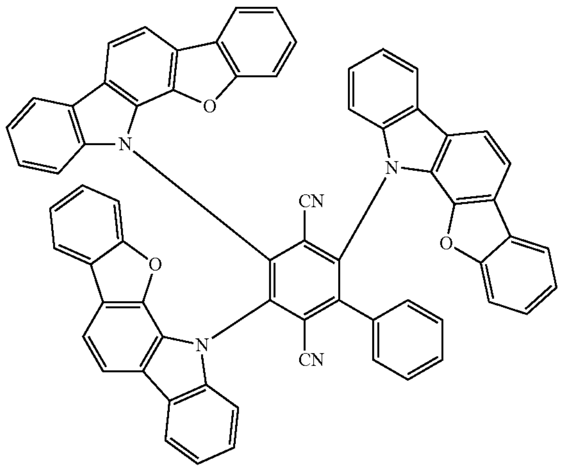

-continued
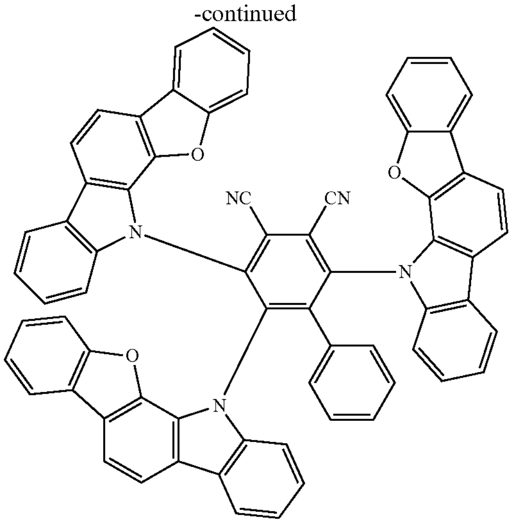
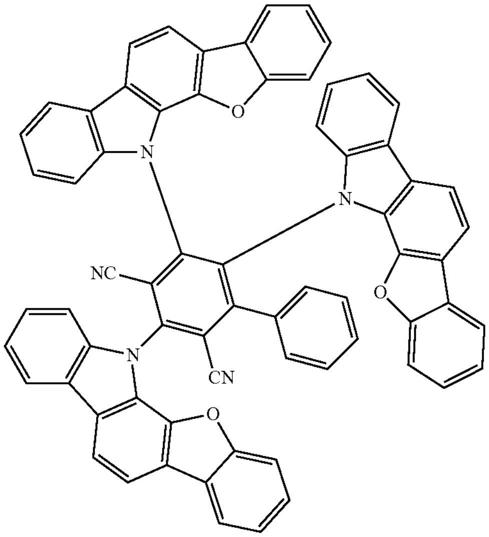
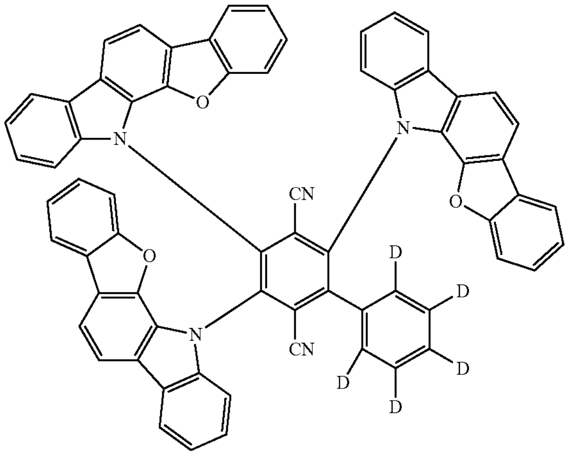
-continued
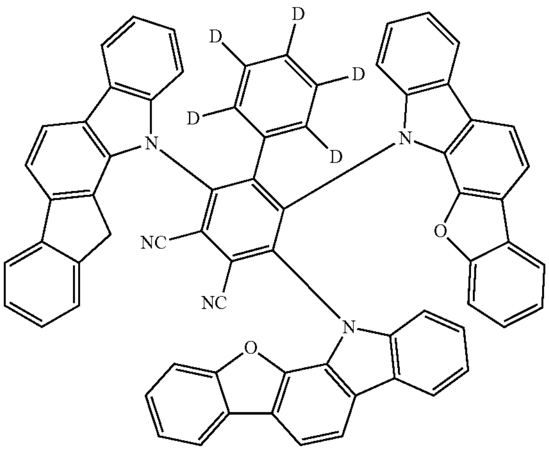
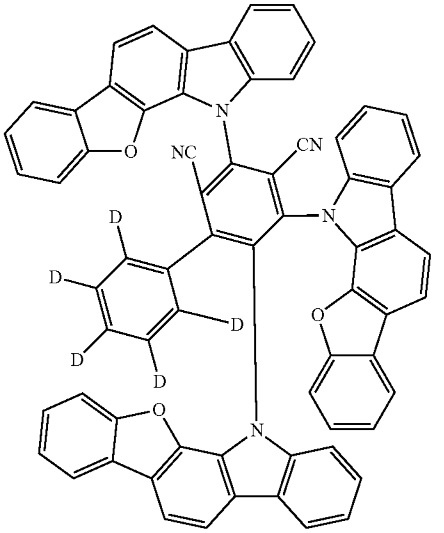
[Formula 54]
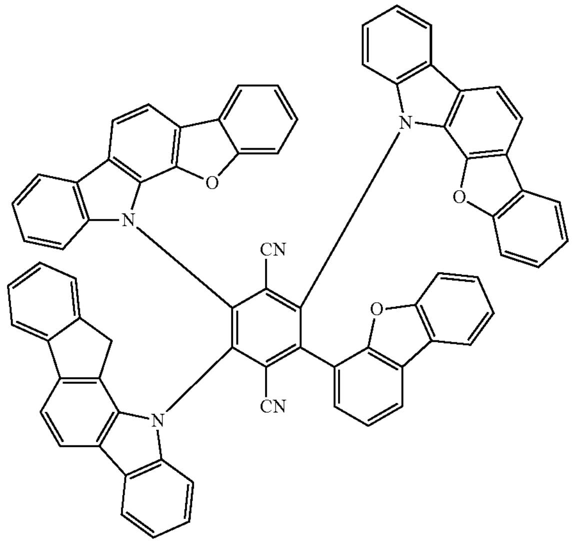

-continued
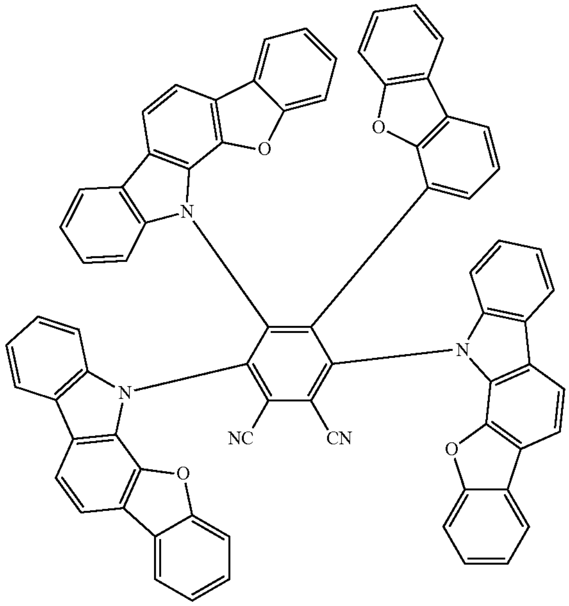
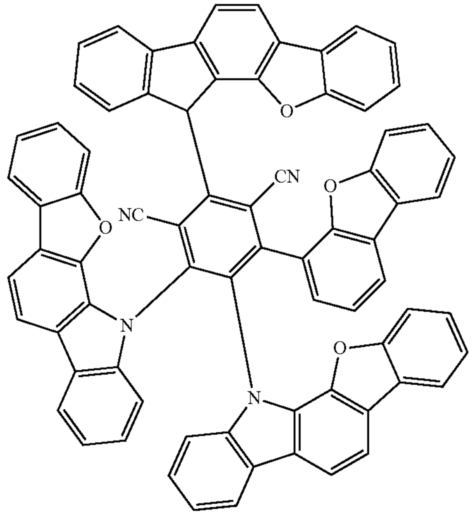
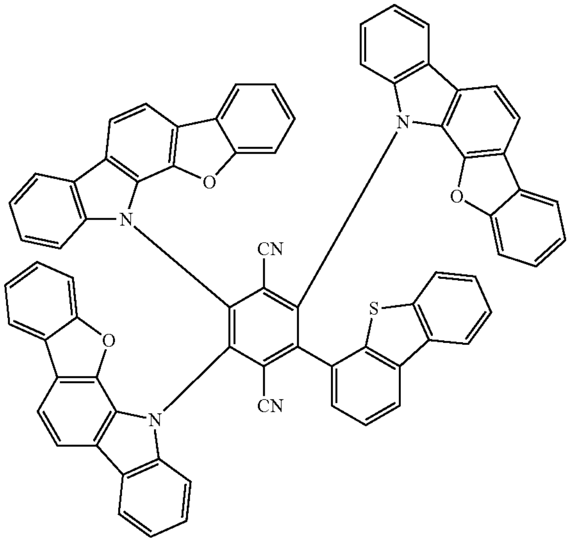
-continued
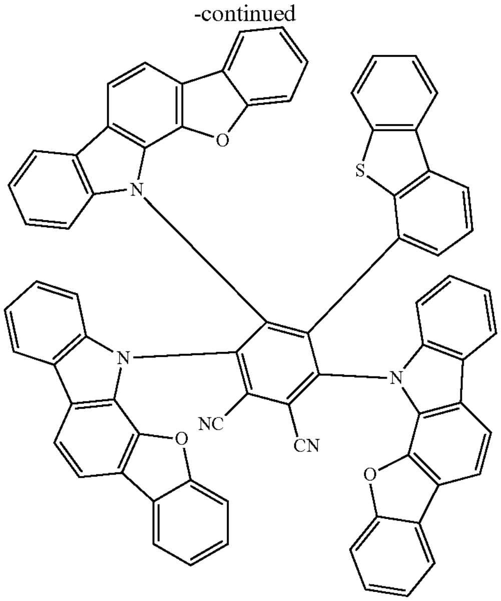
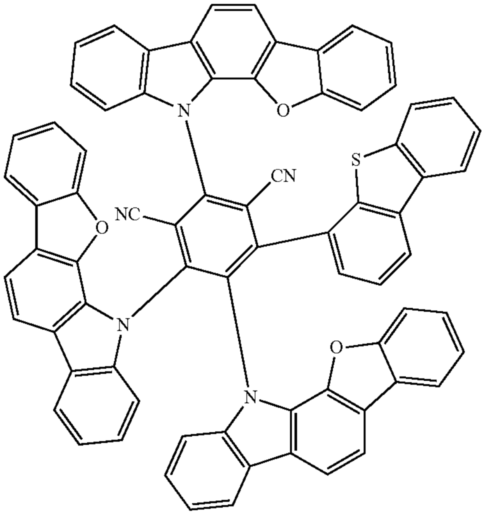
[Formula 55]
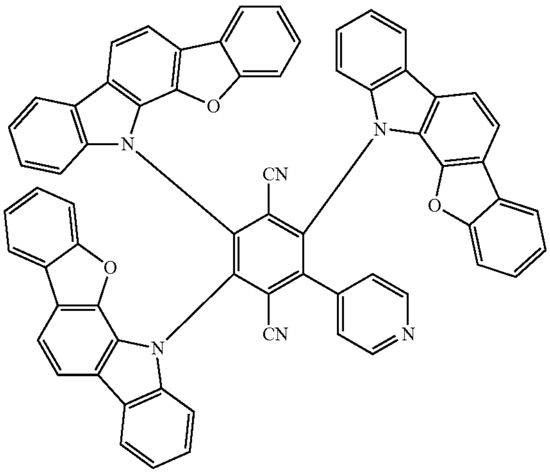

-continued
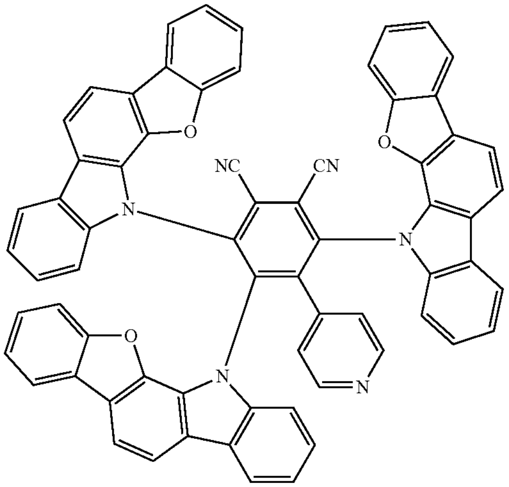
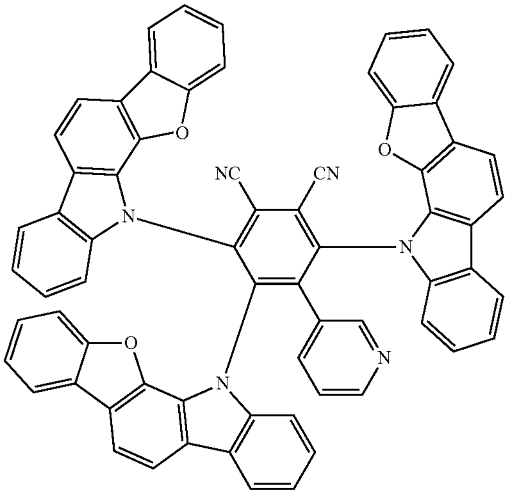
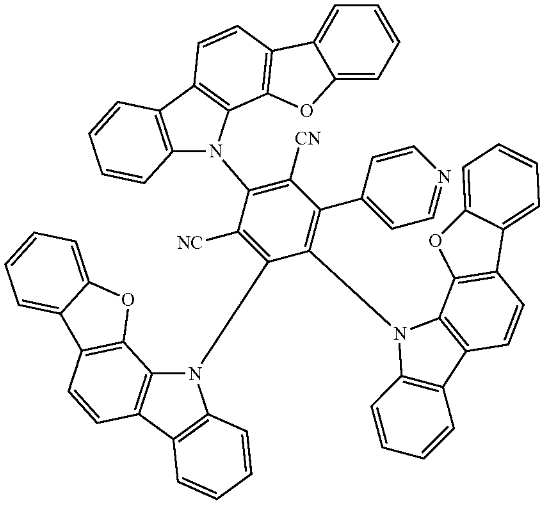
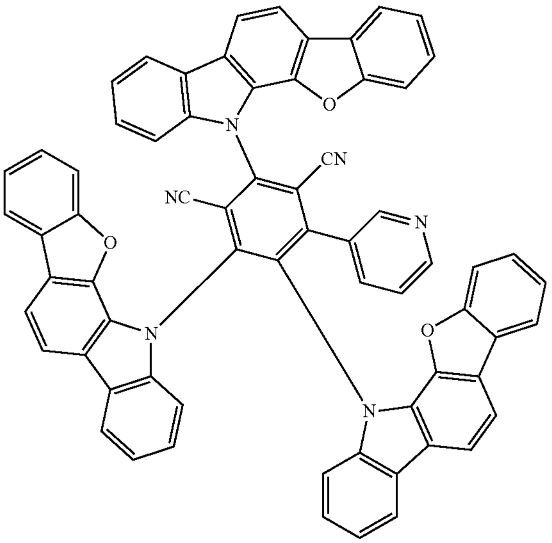
[Formula 56]
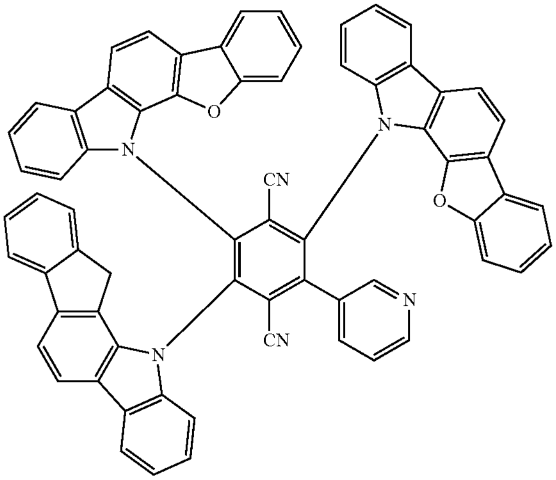
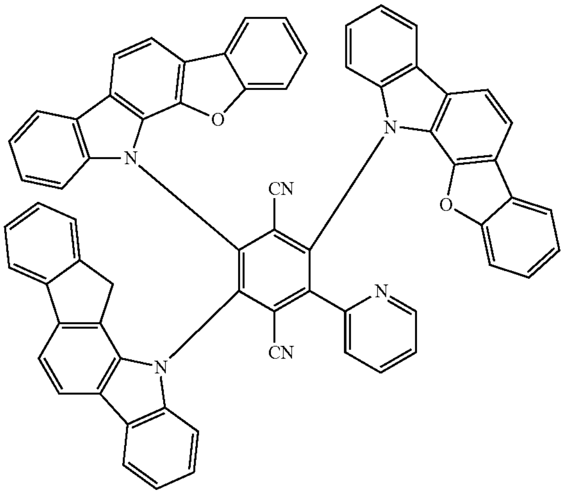
-continued -continued
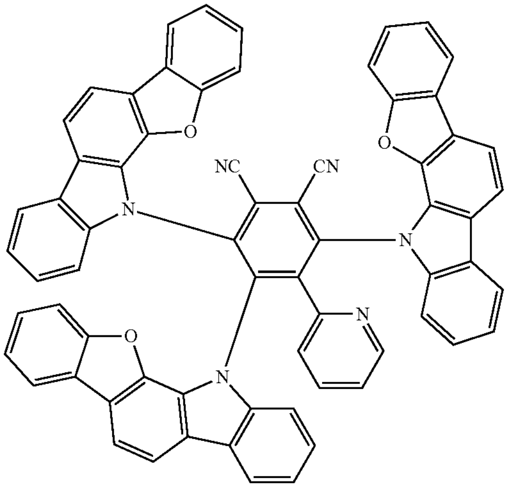
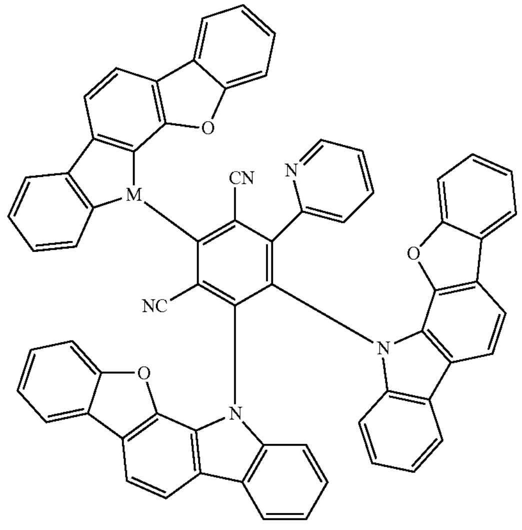
[Formula 57]
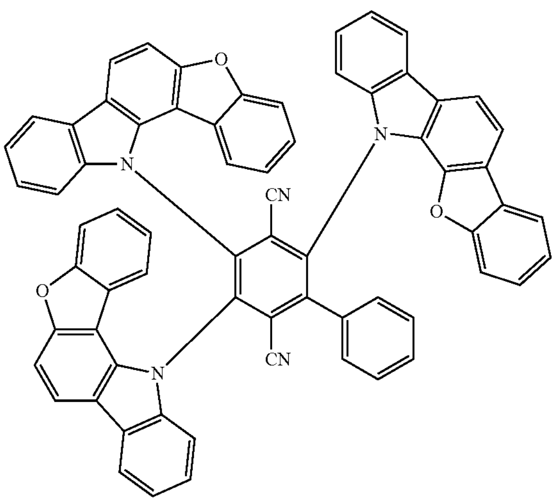
-continued
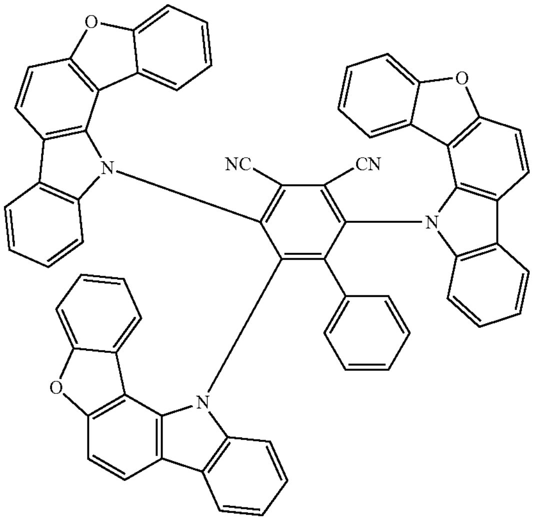
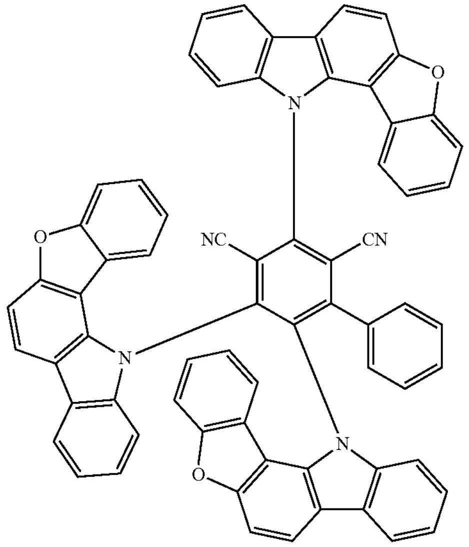
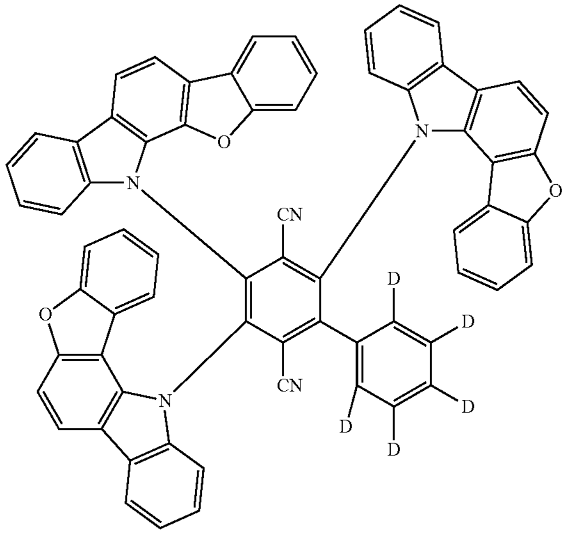

-continued
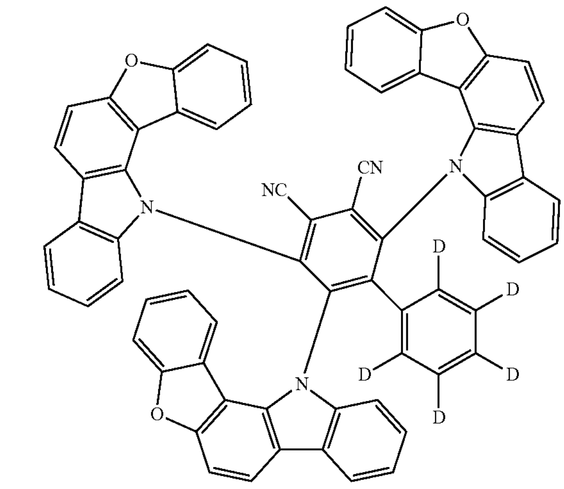
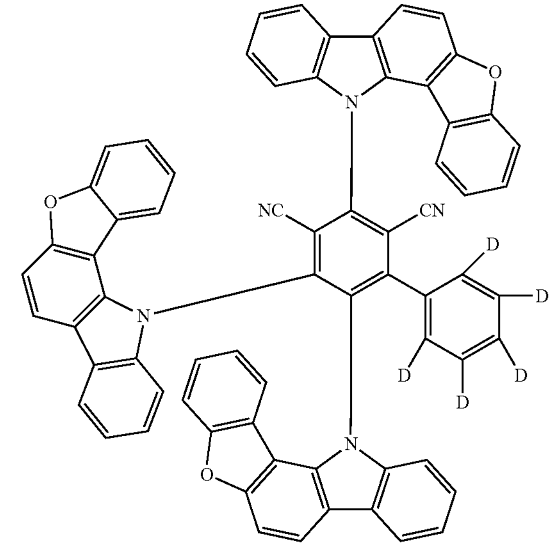
-continued
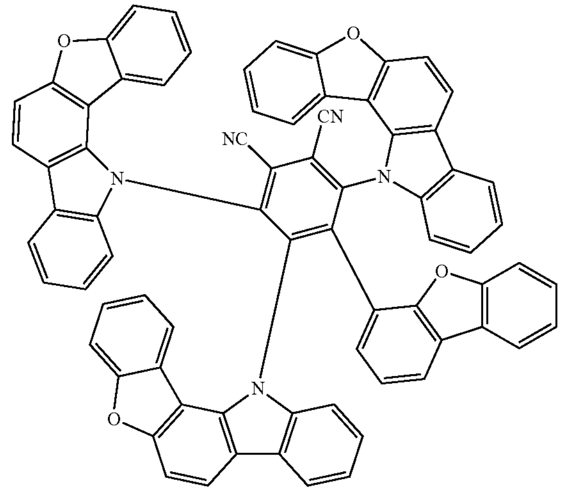
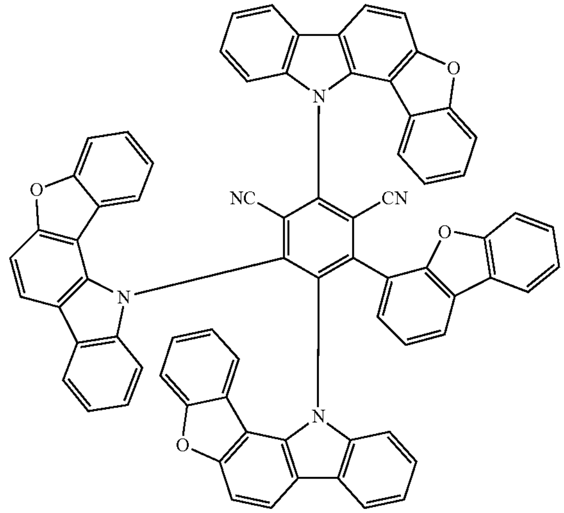 [SMILES: N#Cc1c(-c2cccc3c2oc2ccccc23)c(-n2c3ccccc3c3ccc4oc5ccccc5c4c32)c(-n2c3ccccc3c3ccc4oc5ccccc5c4c32)c(C#N)c1-n1c2ccccc2c2ccc3oc4ccccc4c3c21]
[Formula 58]
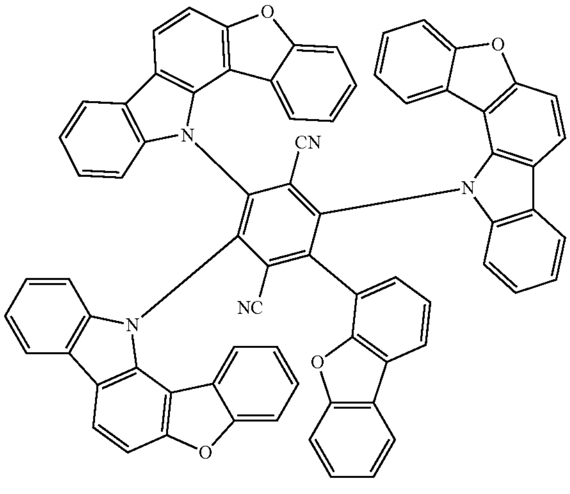
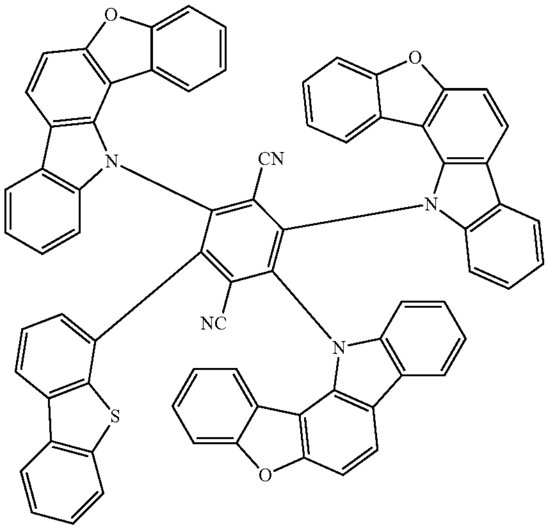

-continued
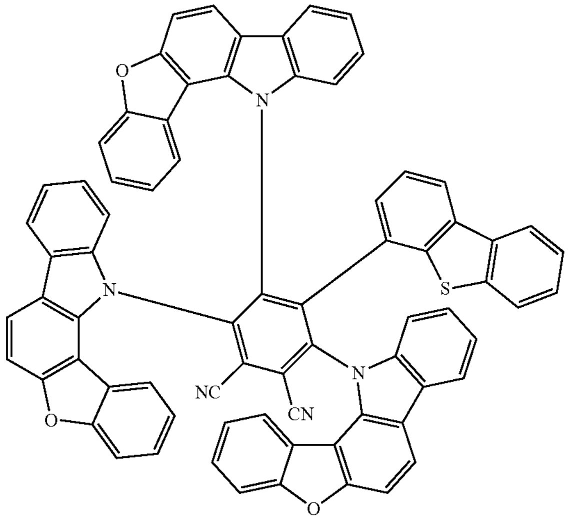
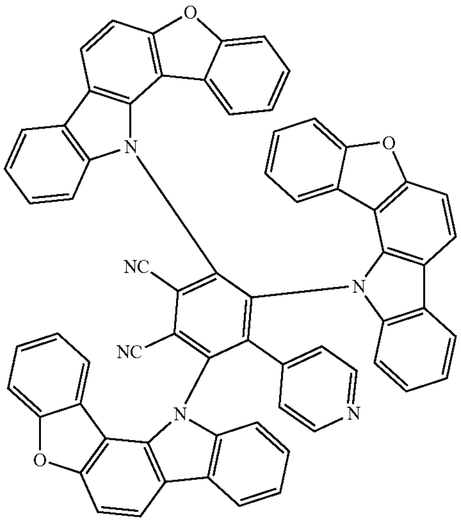
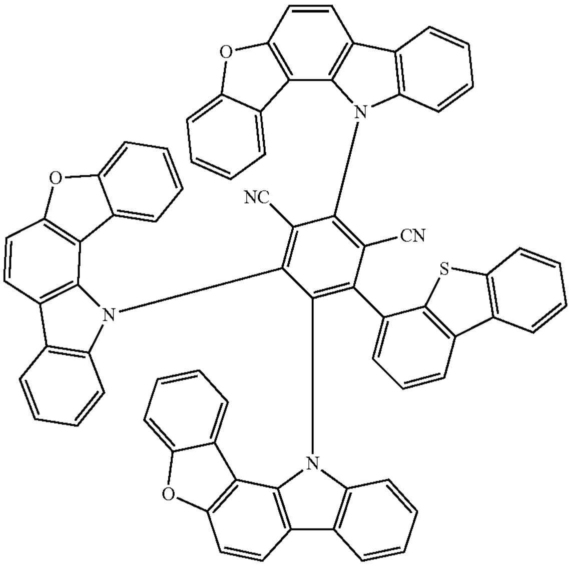 [SMILES: N#Cc1c(-c2cccc3c2sc2ccccc23)c(-n2c3ccccc3c3ccc4oc5ccccc5c4c32)c(-n2c3ccccc3c3ccc4oc5ccccc5c4c32)c(C#N)c1-n1c2ccccc2c2ccc3oc4ccccc4c3c21]
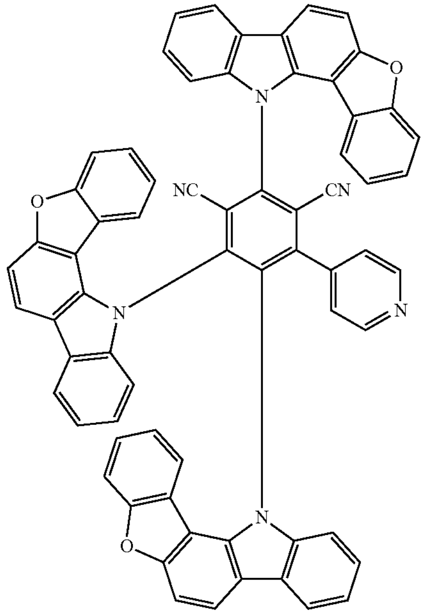
[Formula 59]
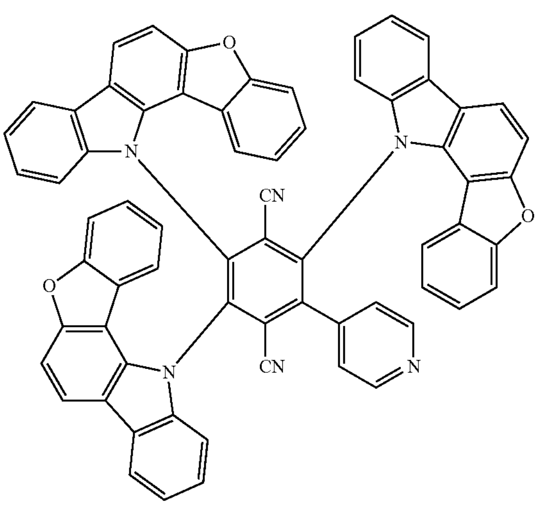
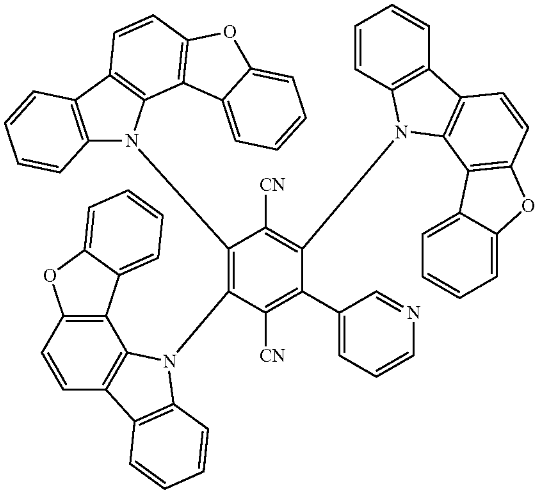

-continued
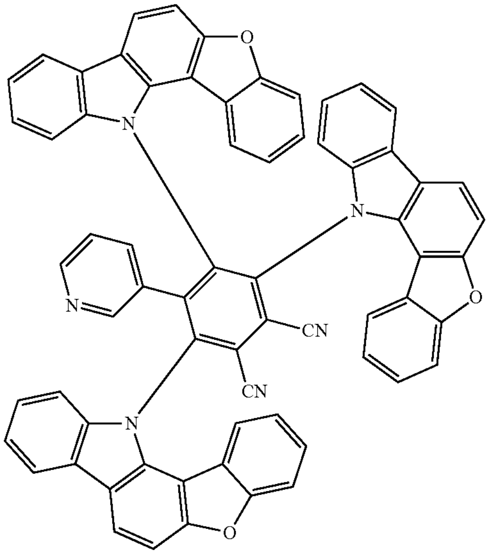
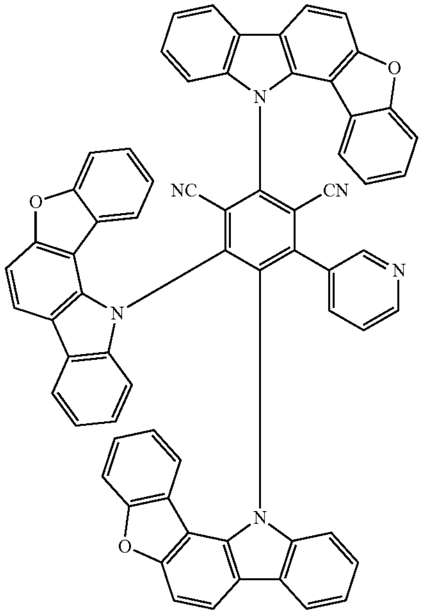
[Formula 60]
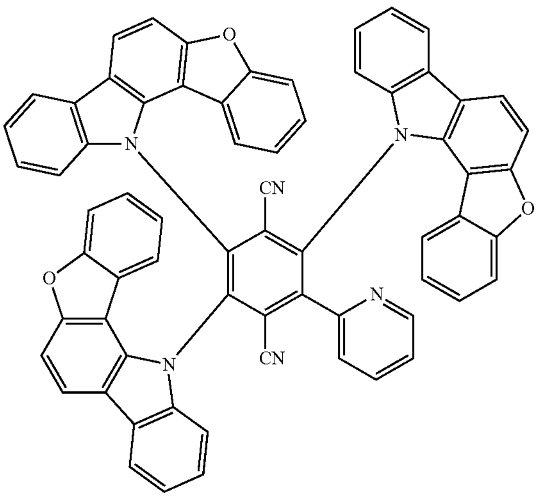
-continued
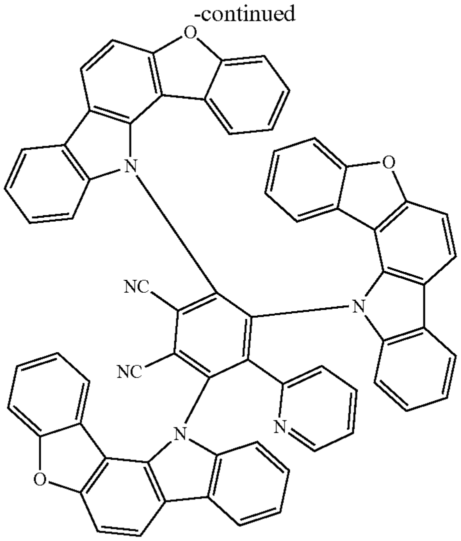
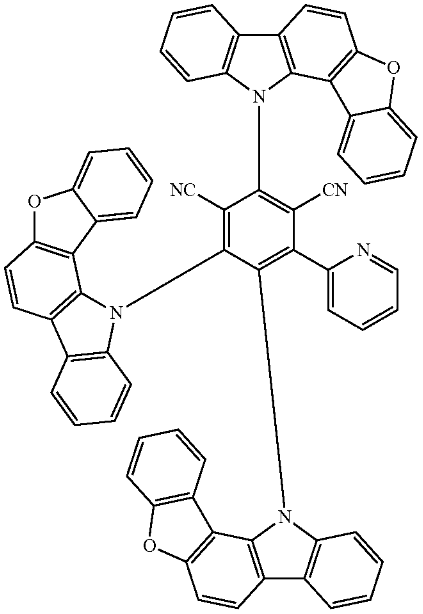
[Formula 61]
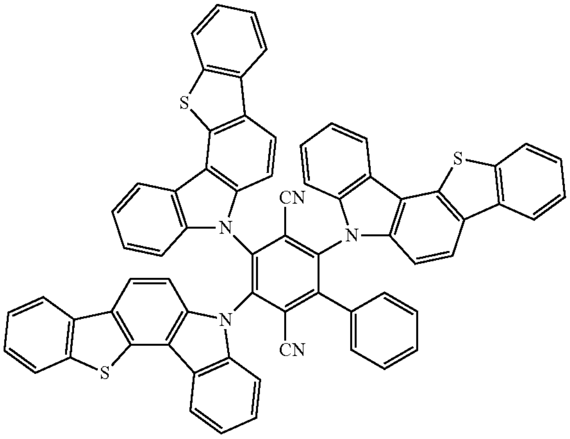

-continued
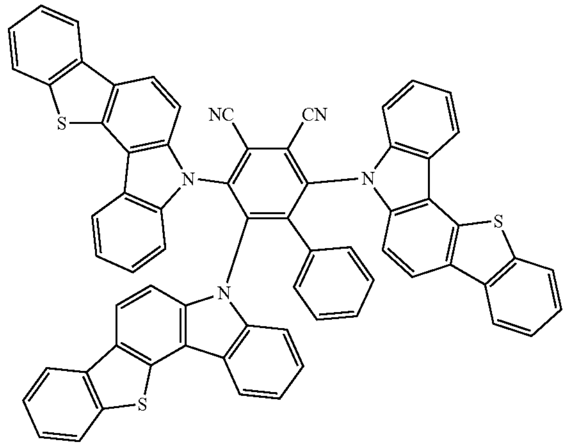
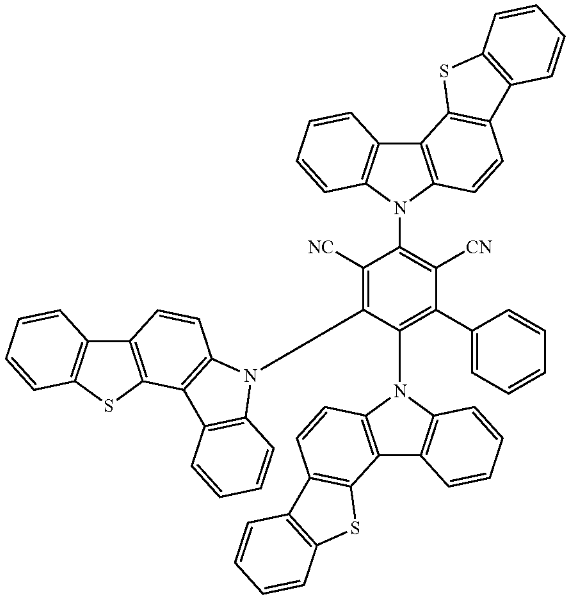
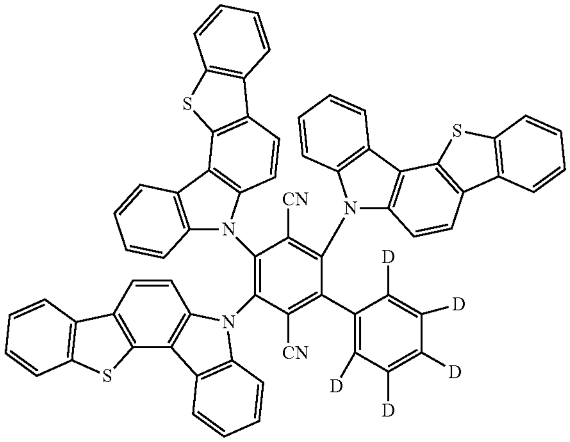
-continued
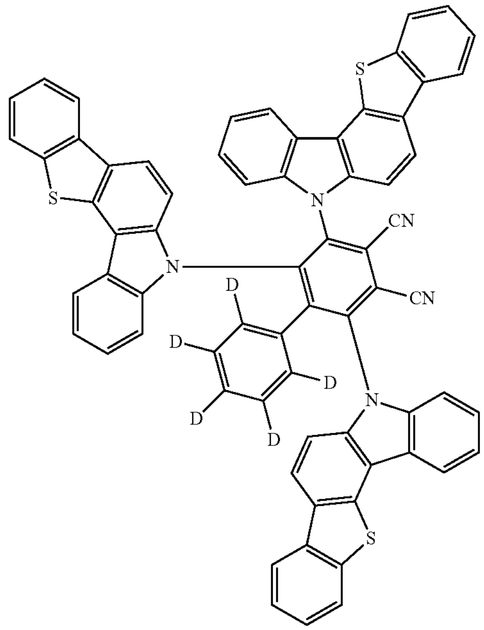
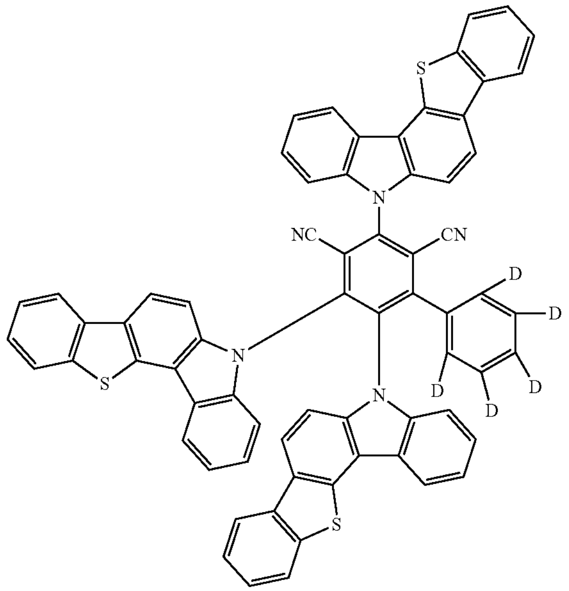
[Formula 62]
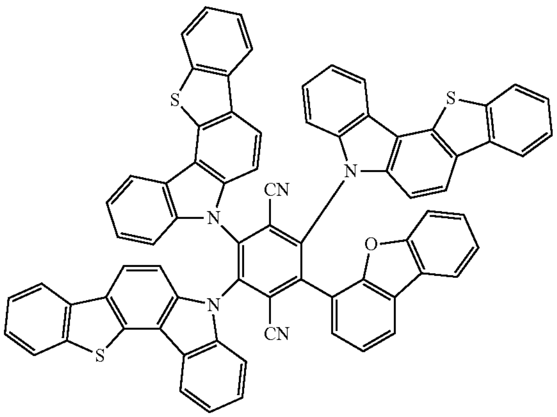

-continued
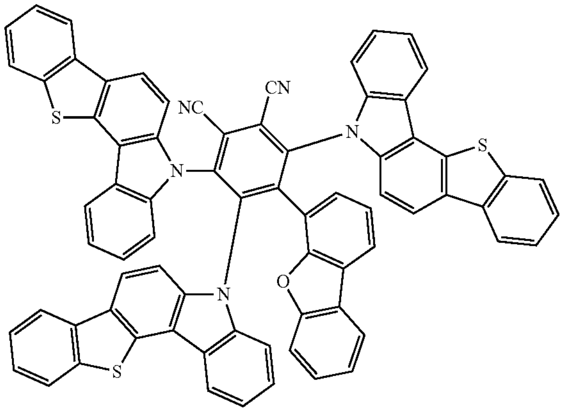
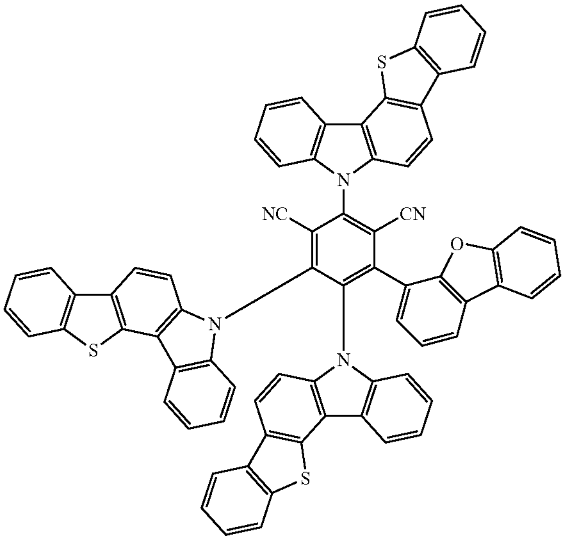
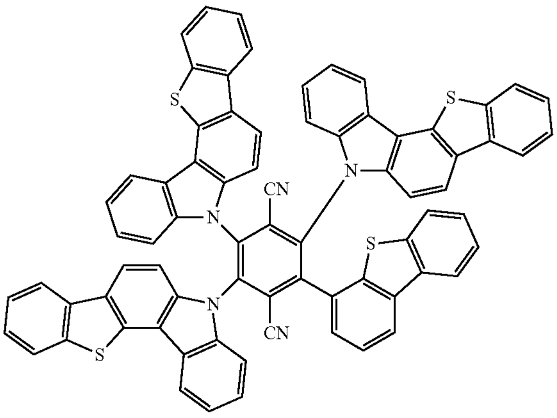
-continued
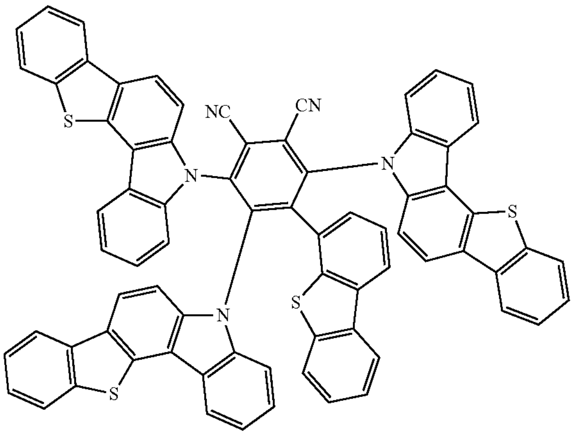
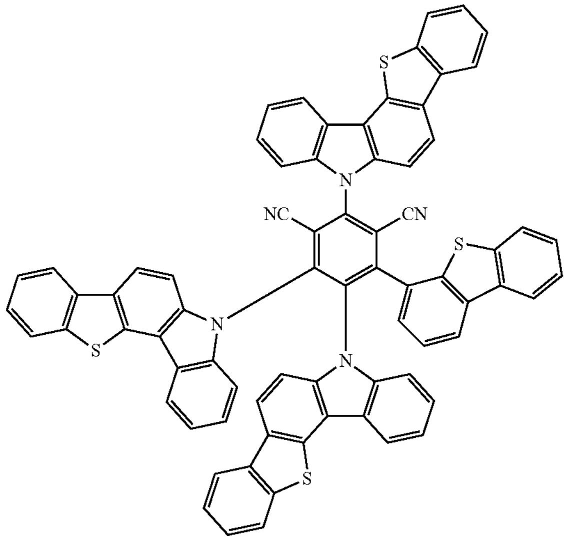
[Formula 63]
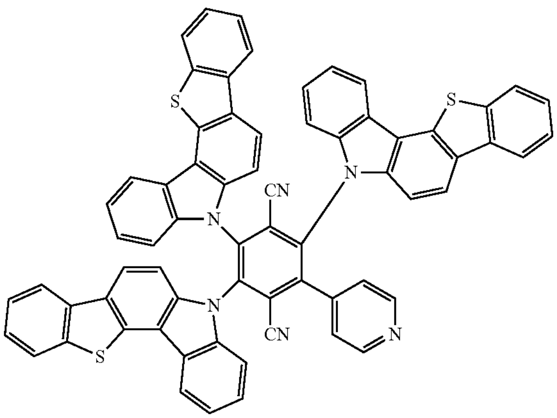

-continued
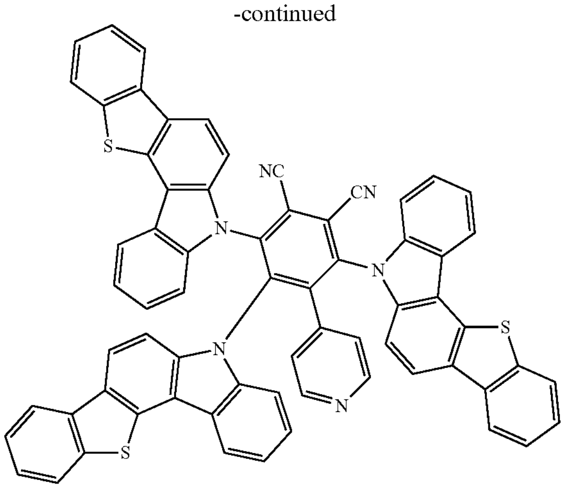
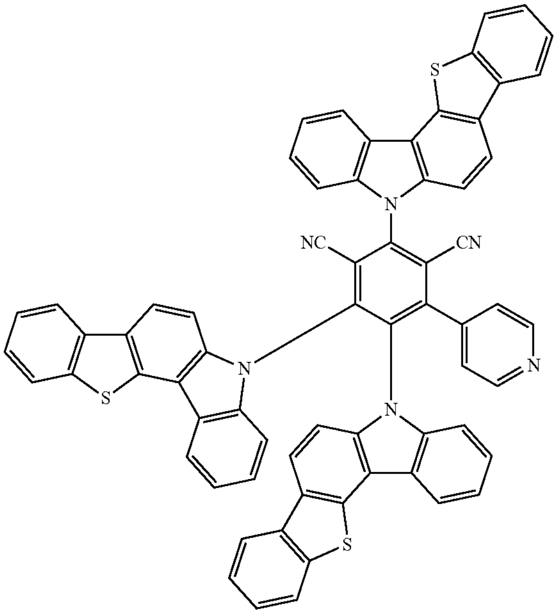
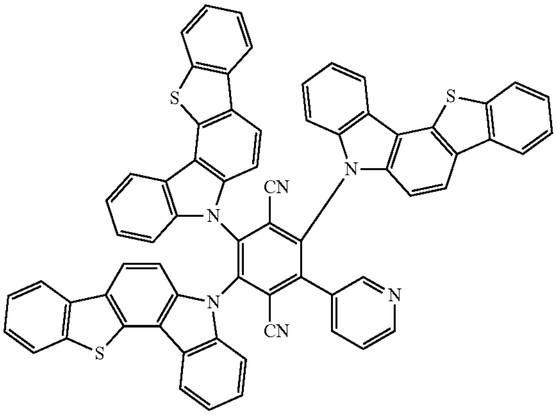
-continued
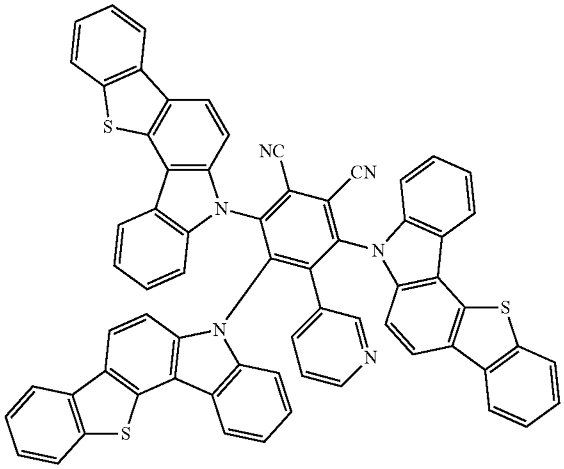
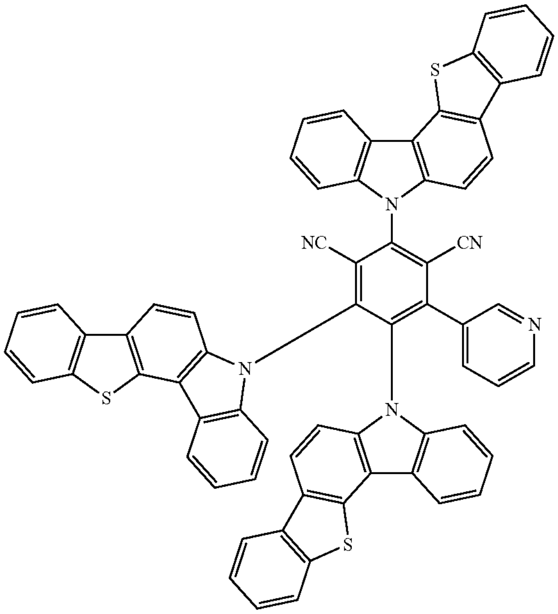
[Formula 64]
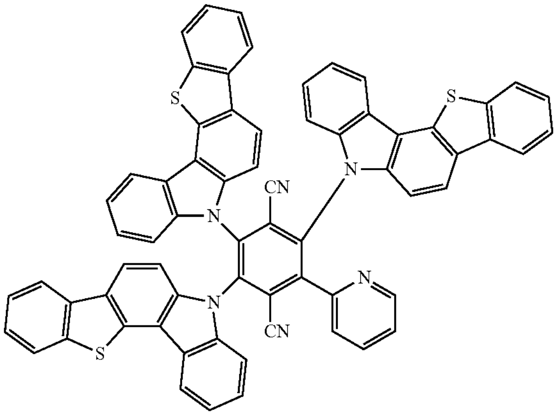

-continued
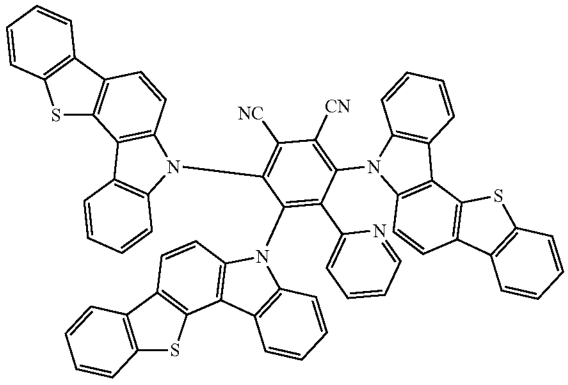
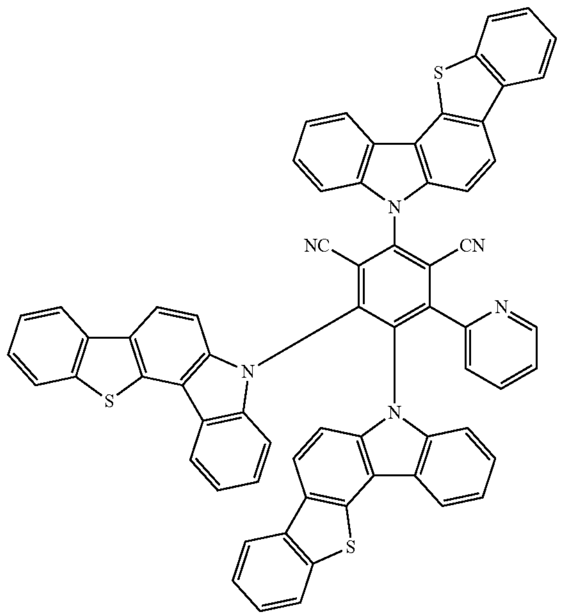
[Formula 65]
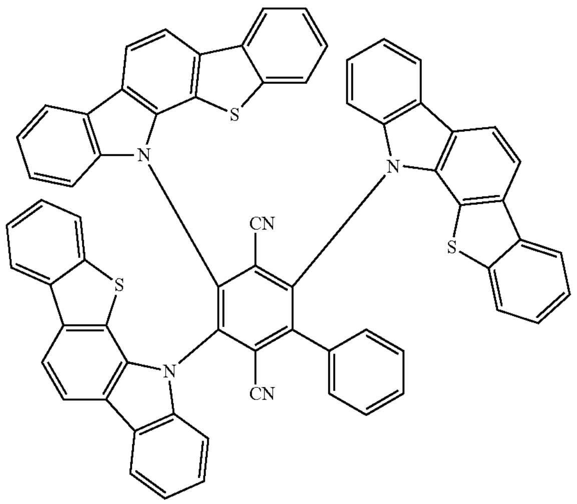
-continued
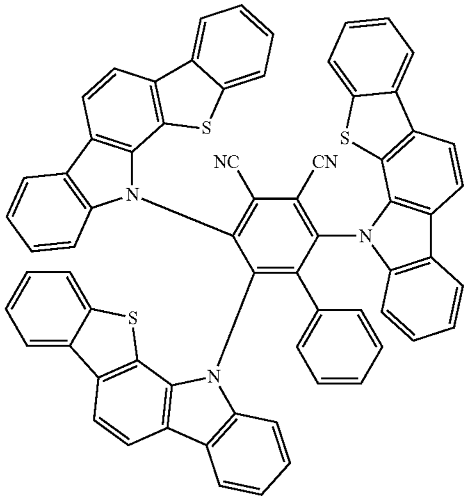
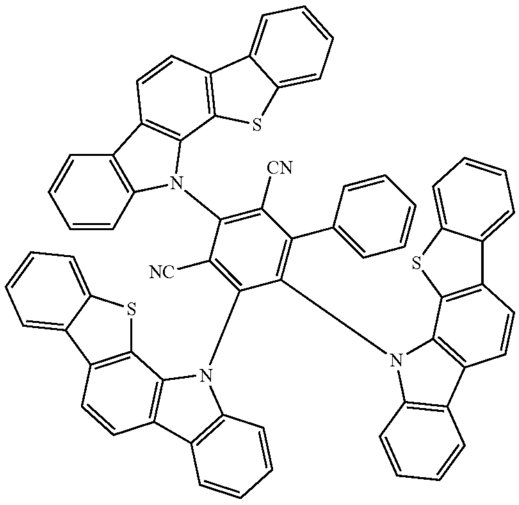
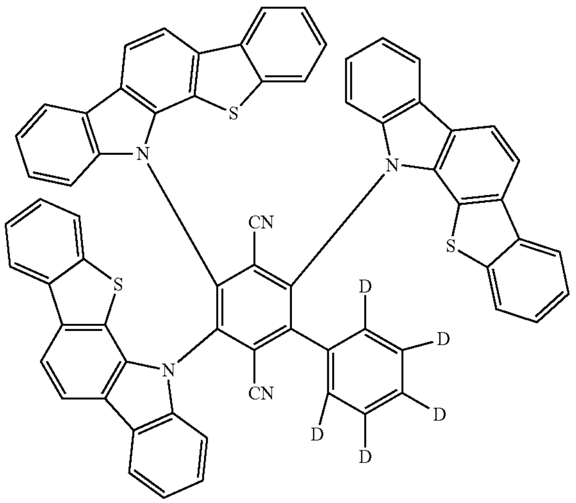

-continued
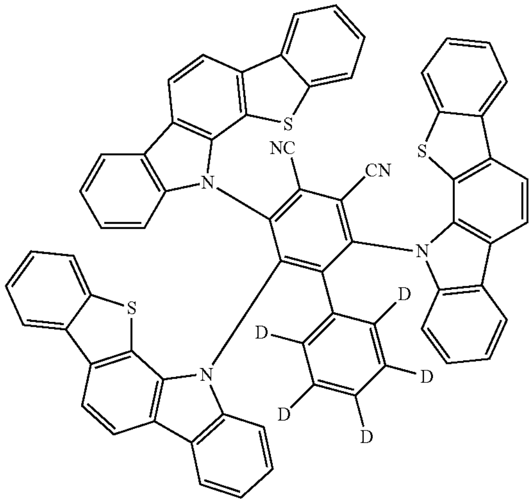
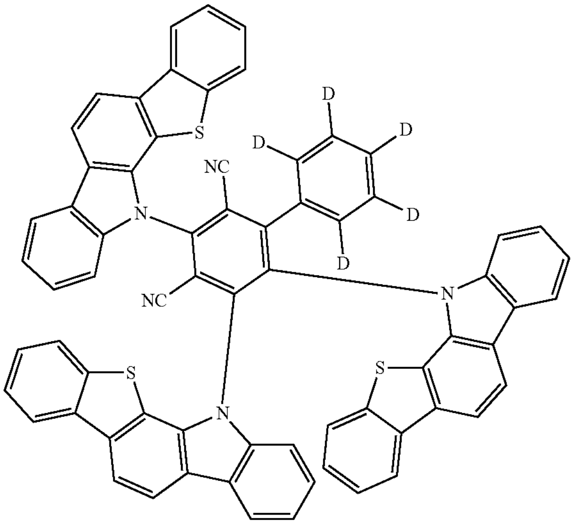
[Formula 66]
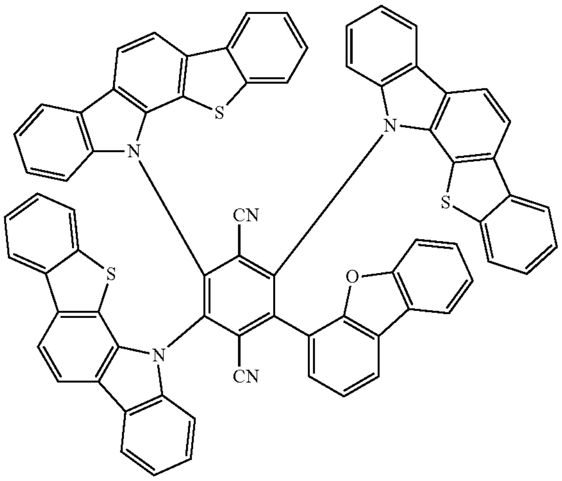
-continued
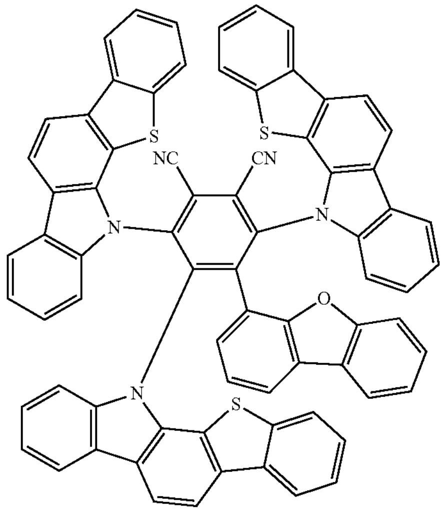
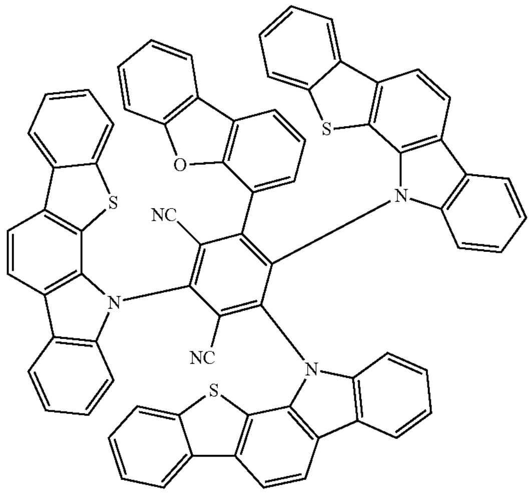
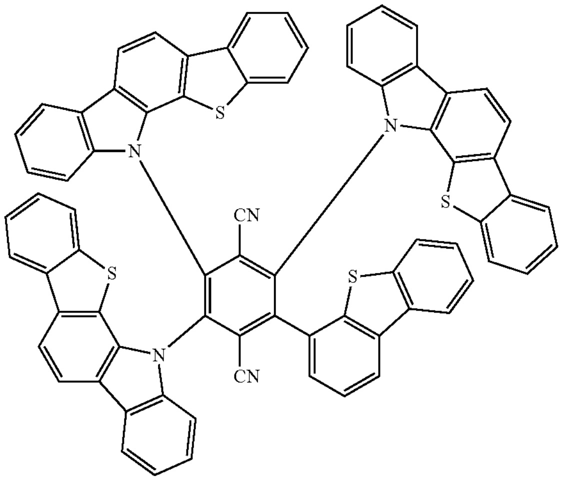

-continued
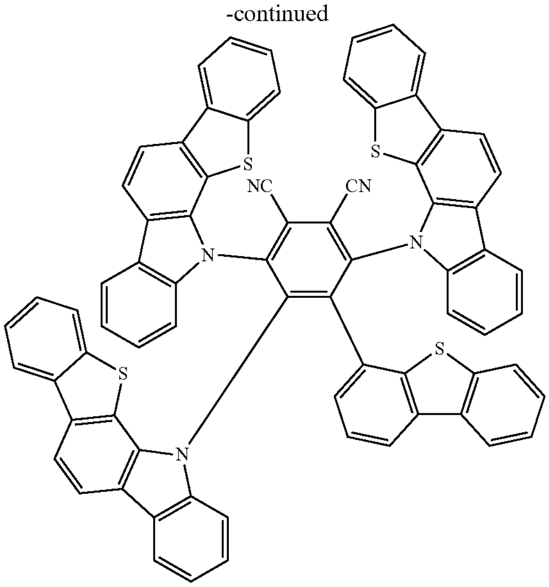
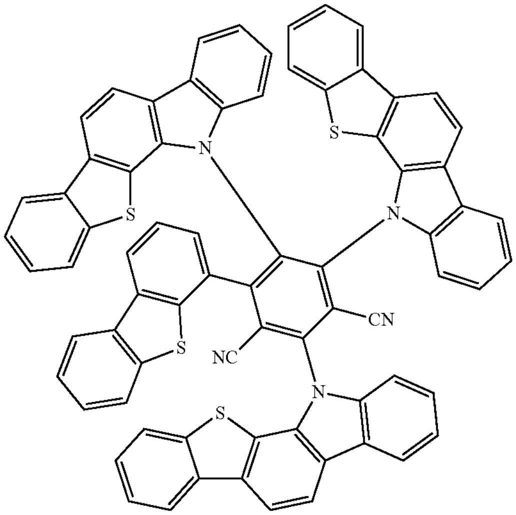
[Formula 67]
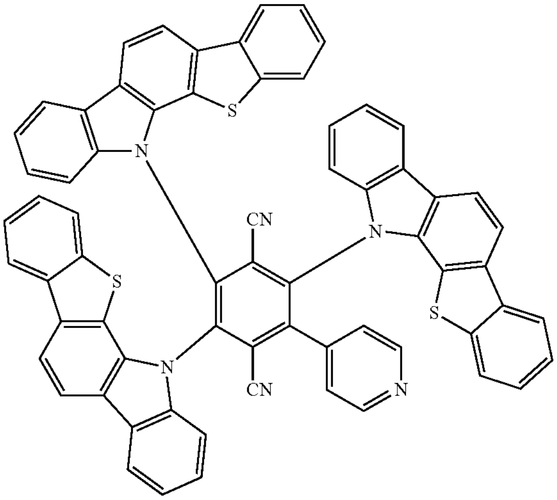
-continued
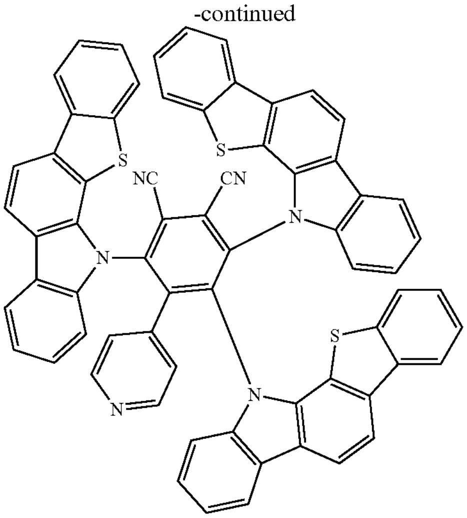
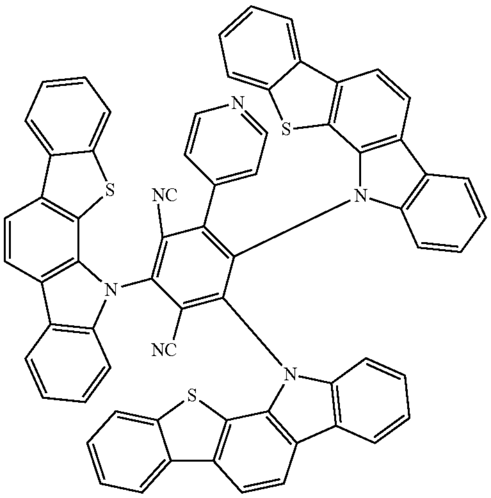
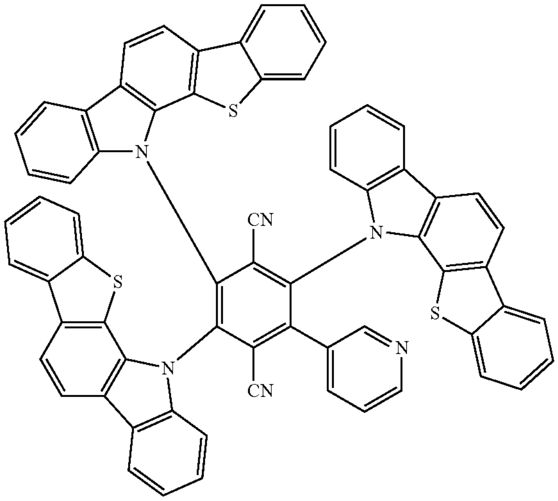

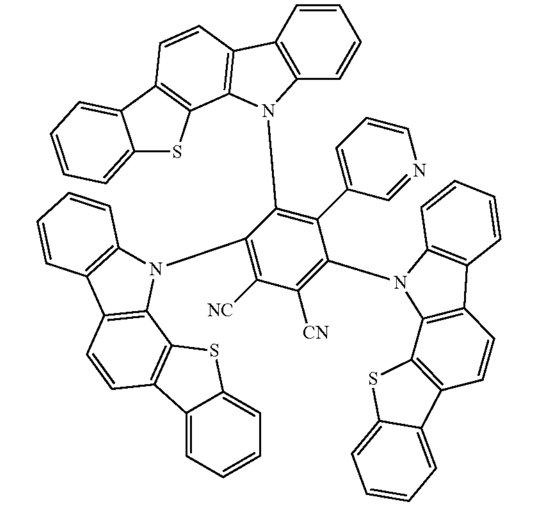
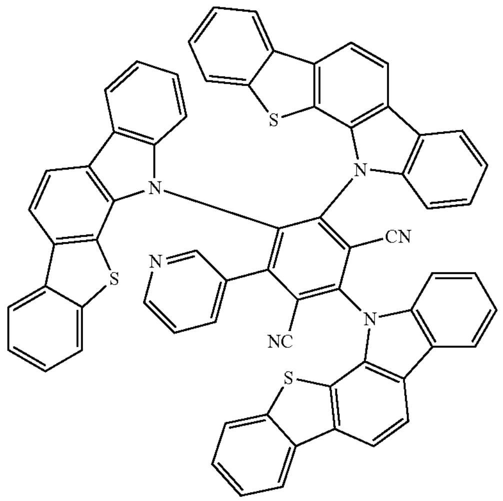
[Formula 68]
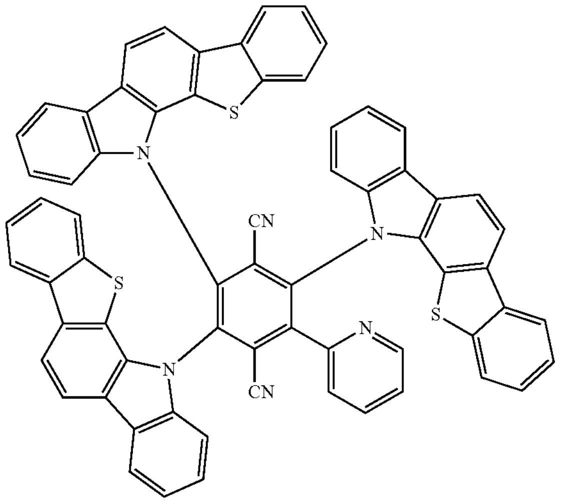
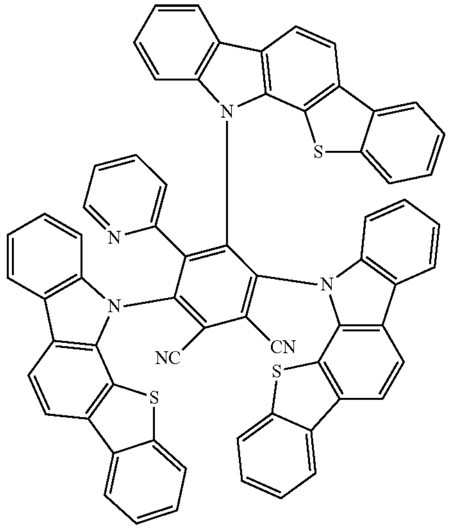
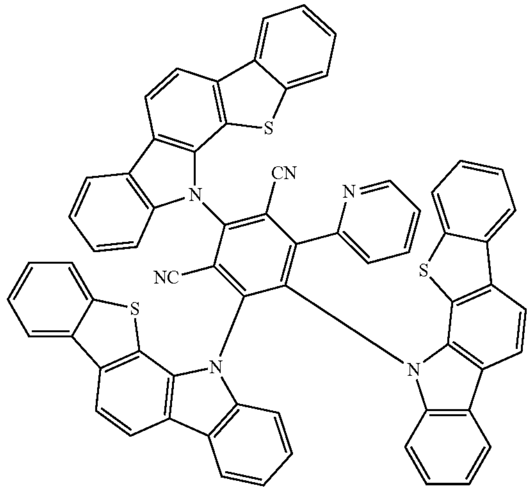
[Formula 69]
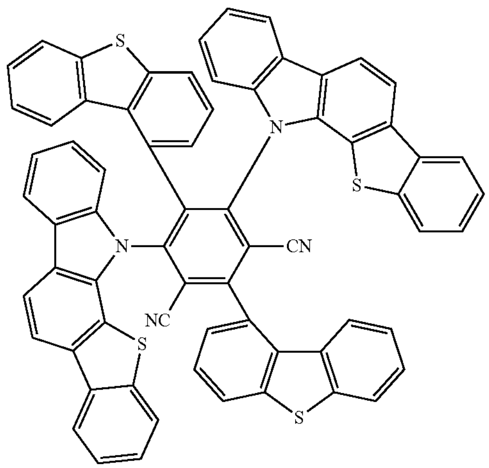

-continued
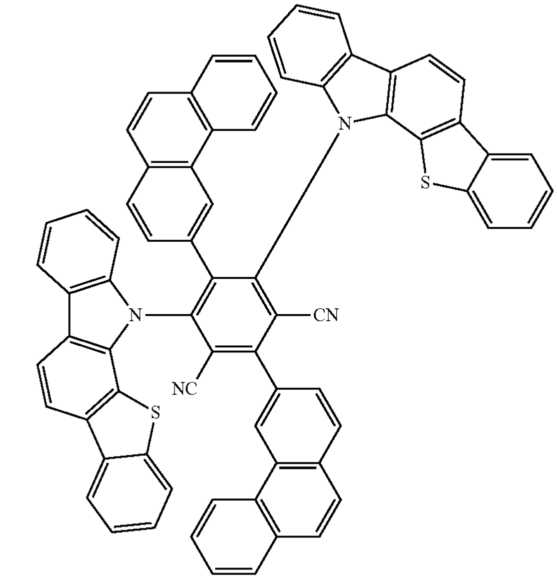
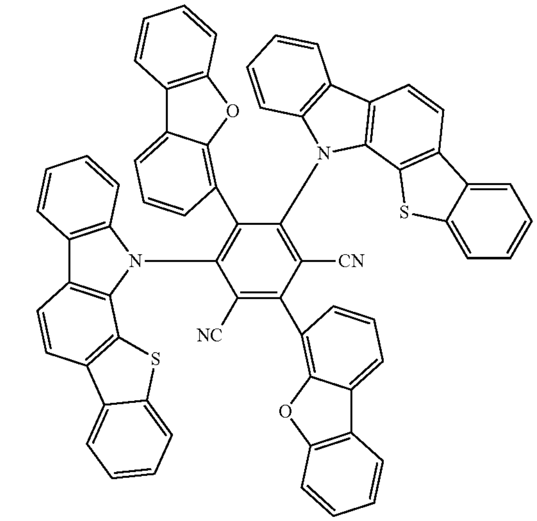
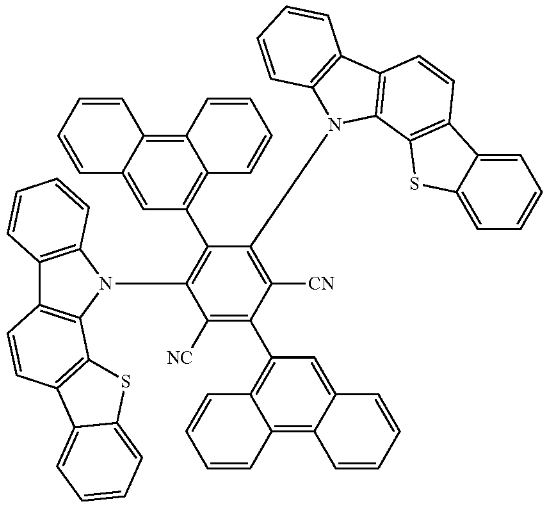
-continued
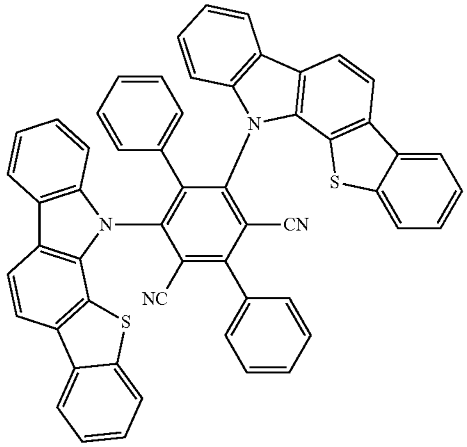
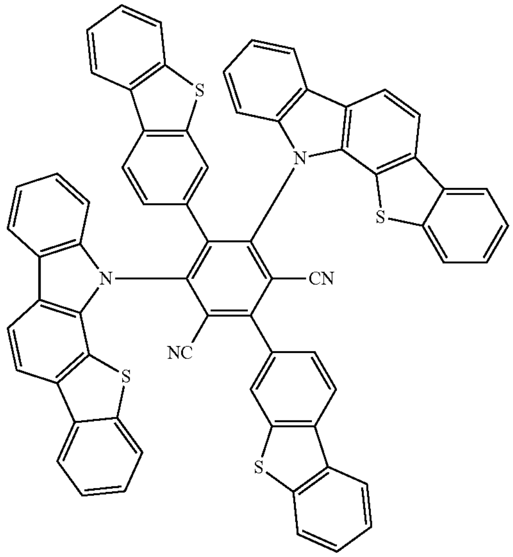
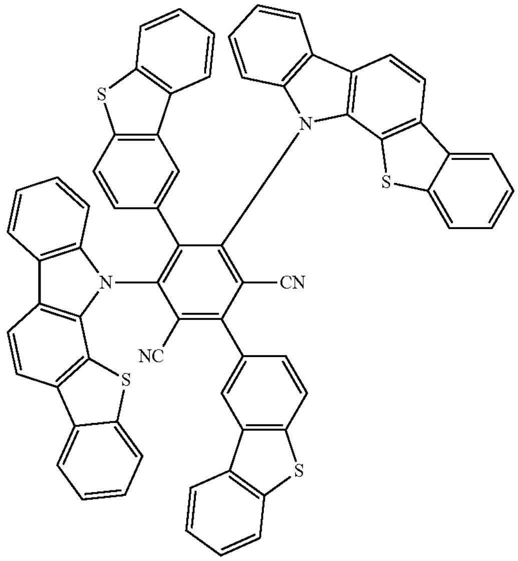

-continued
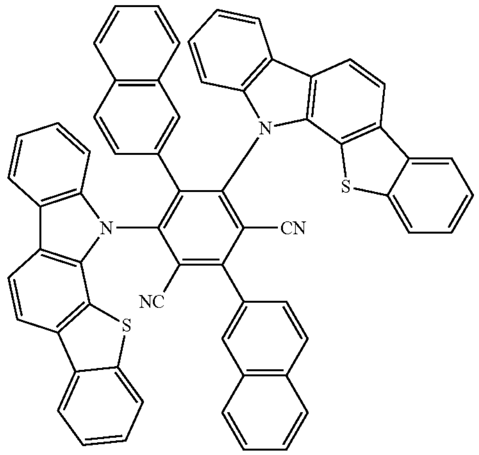
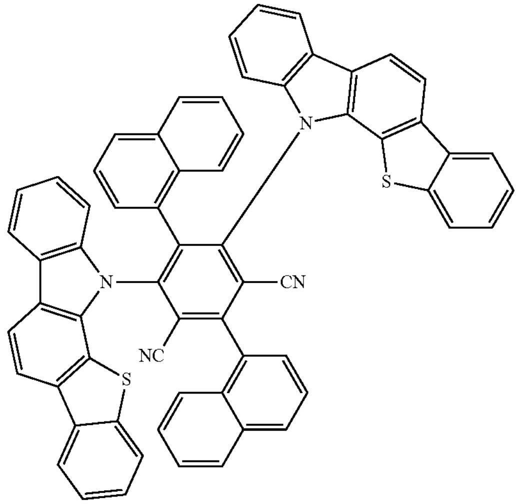
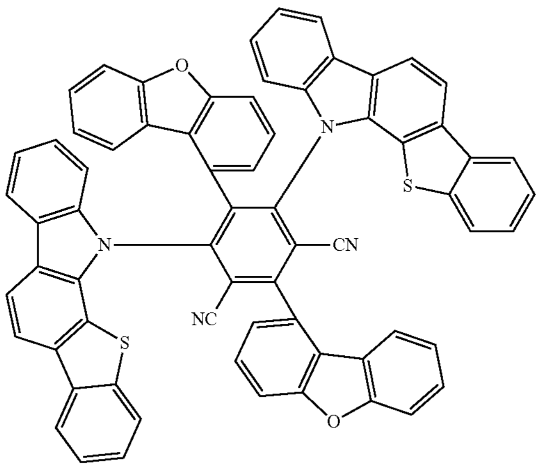
-continued
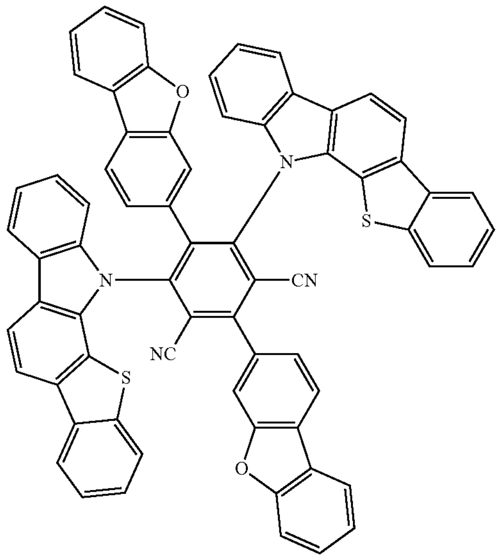
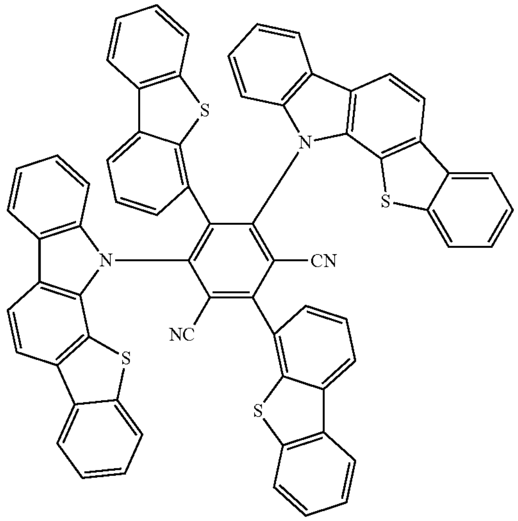
[Formula 70]
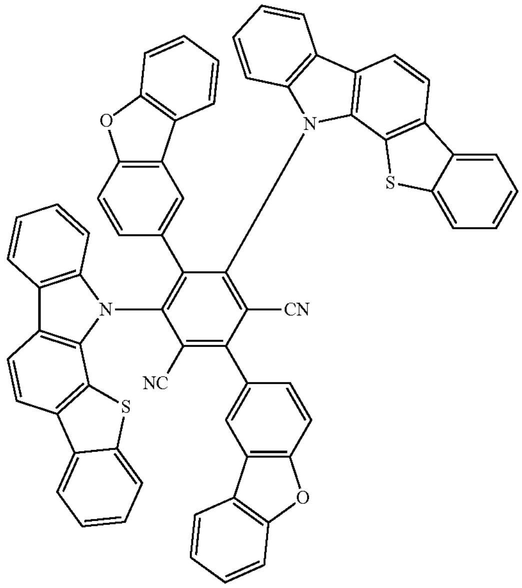

-continued
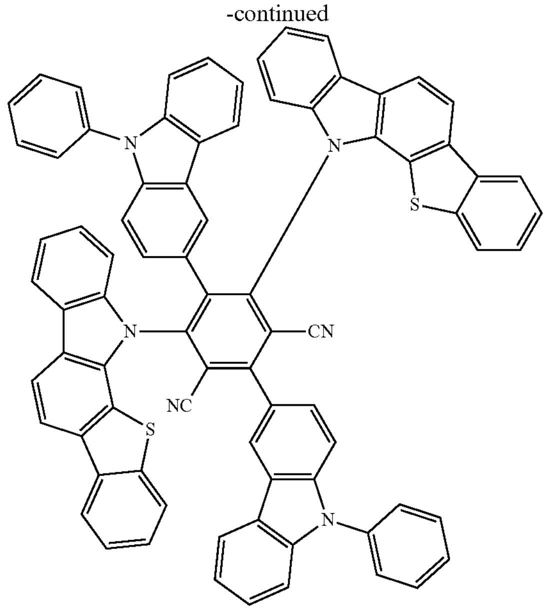
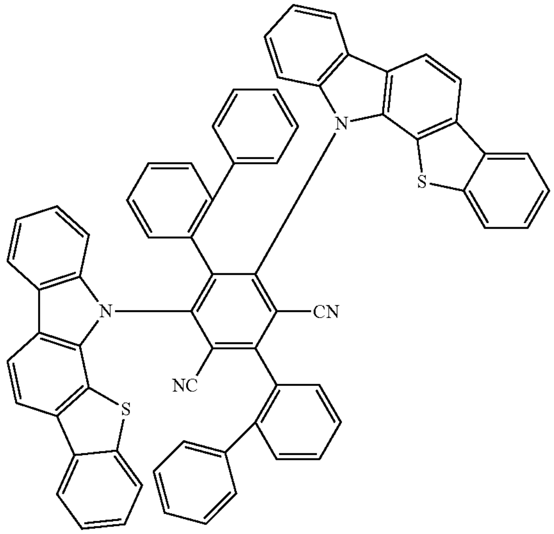
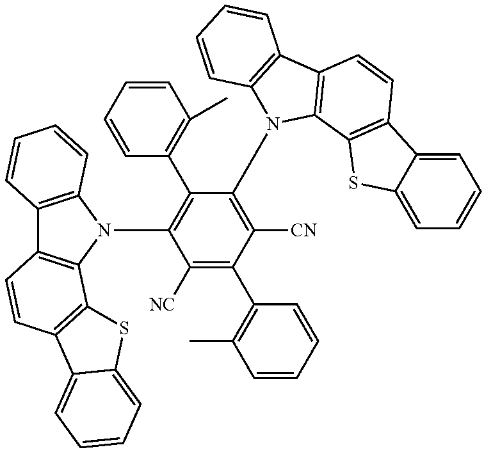
-continued
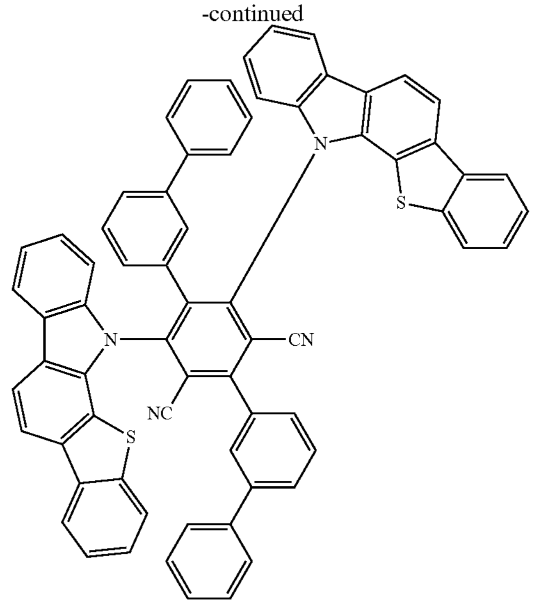
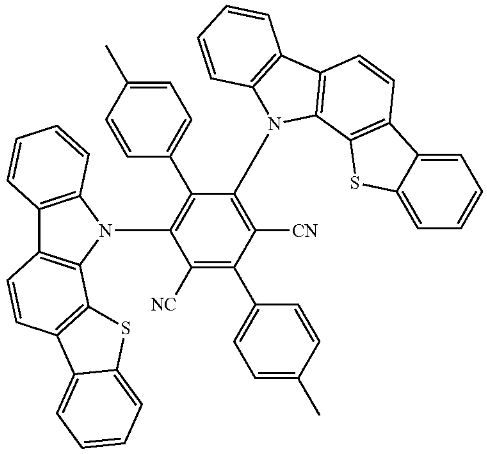
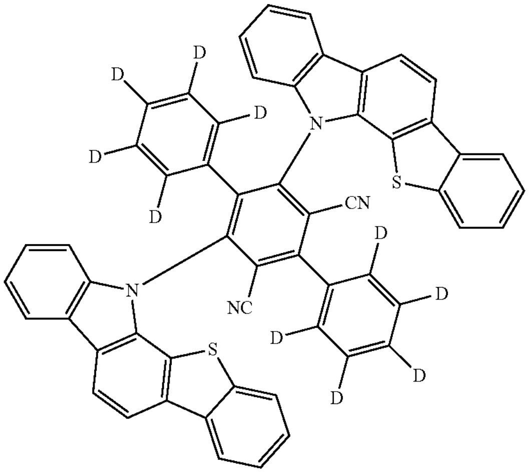

-continued
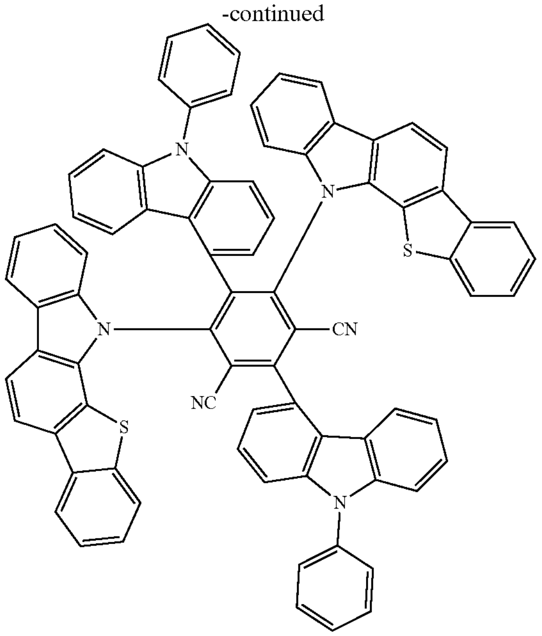
[Formula 71]
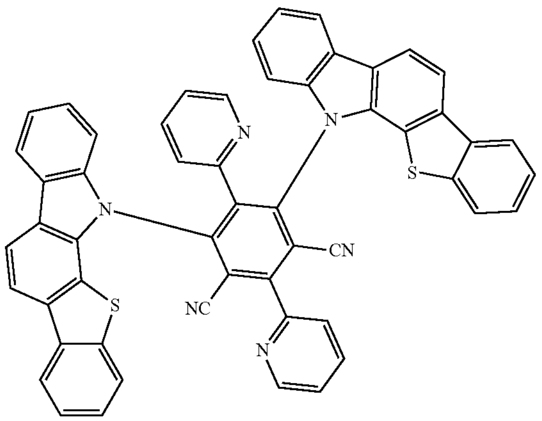
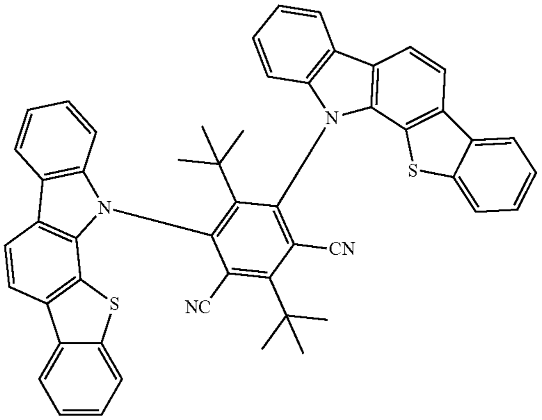
-continued
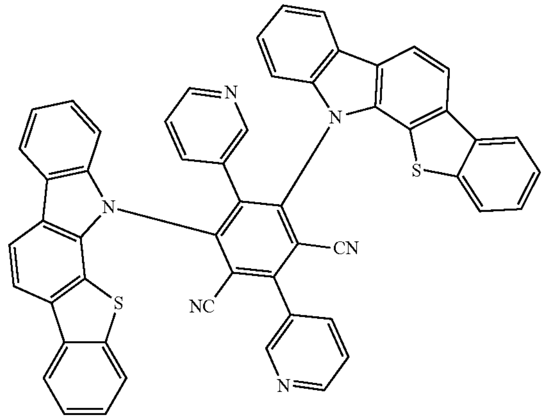
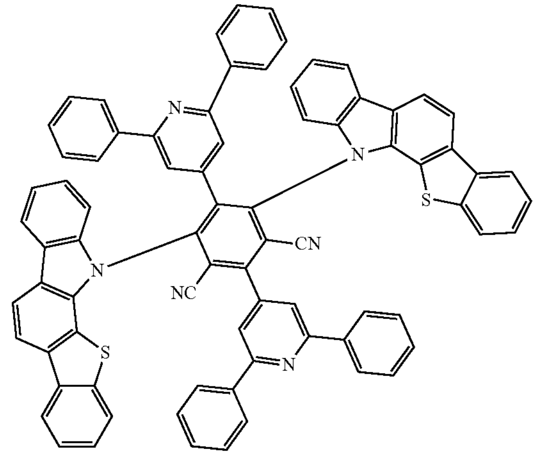
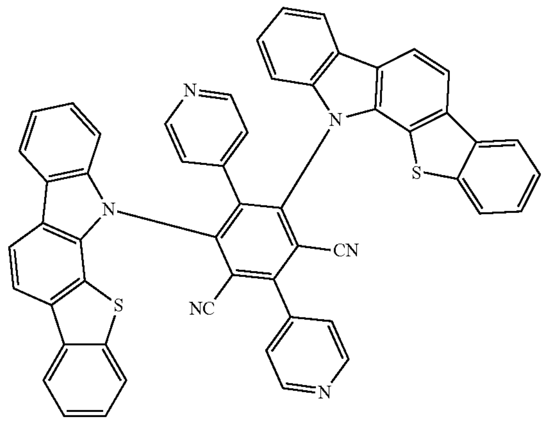

-continued
[Formula 72]
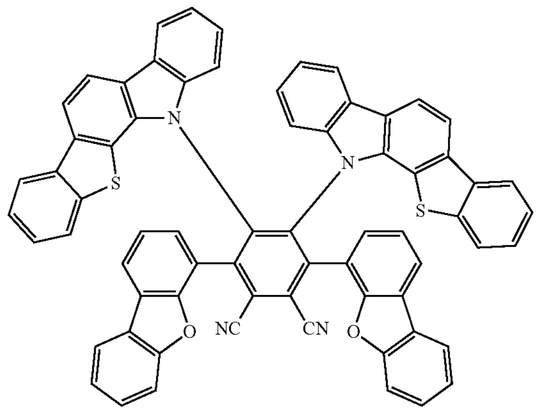
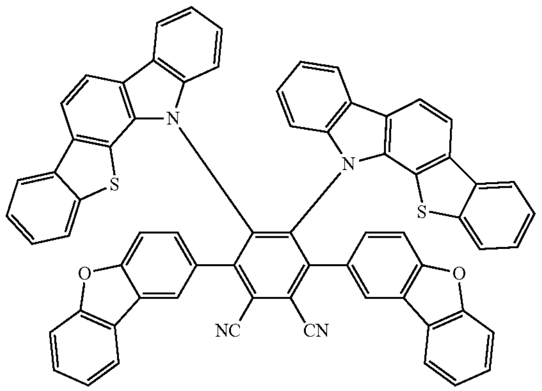
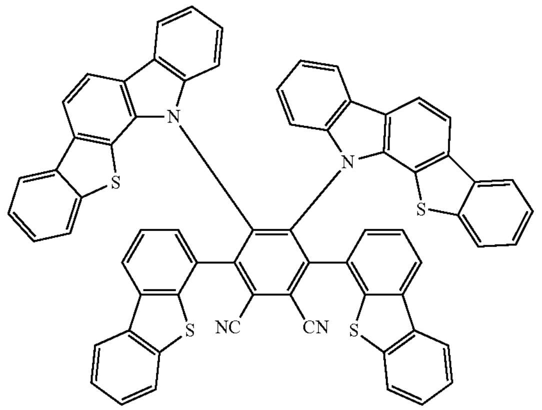
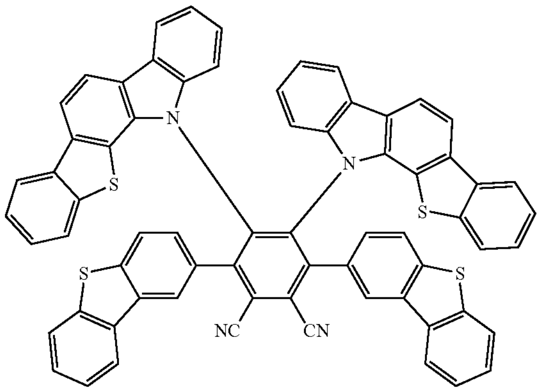
-continued
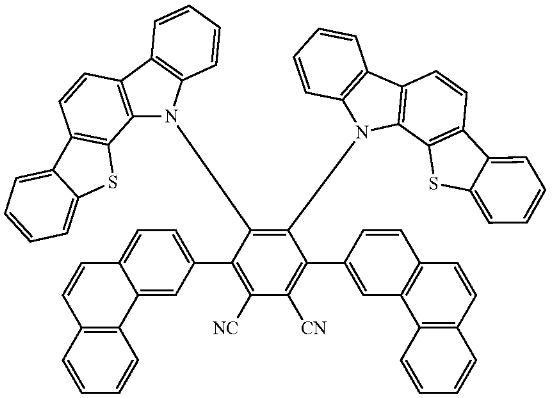
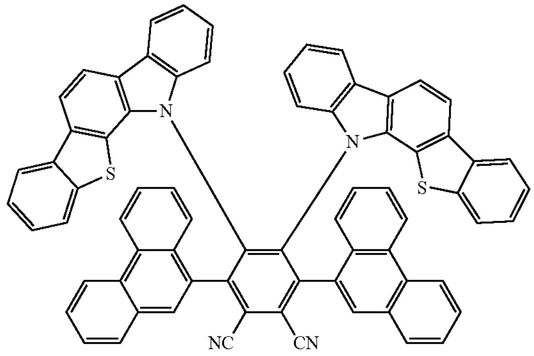
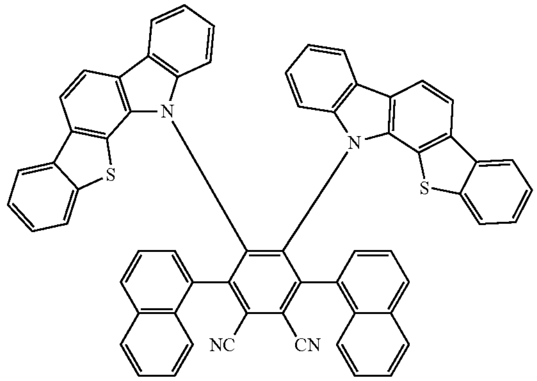
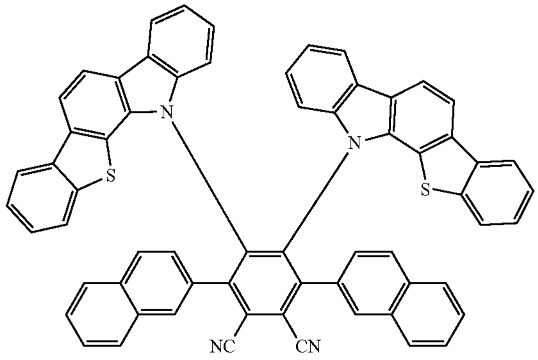

-continued
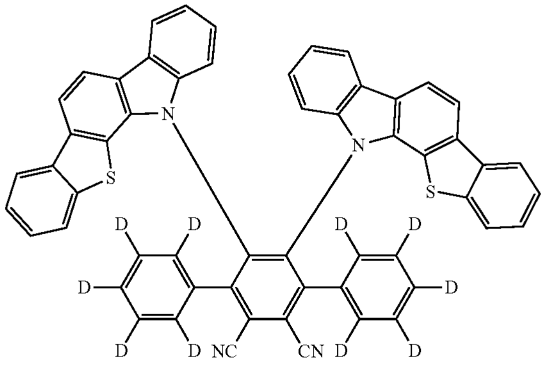
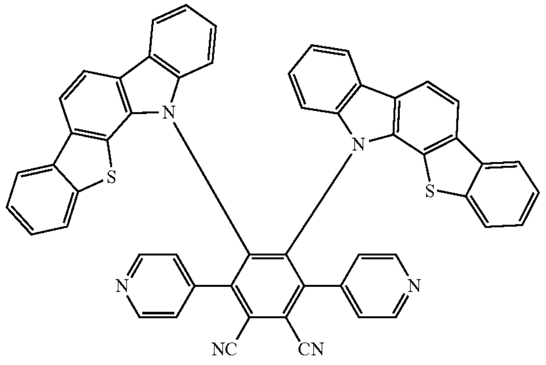
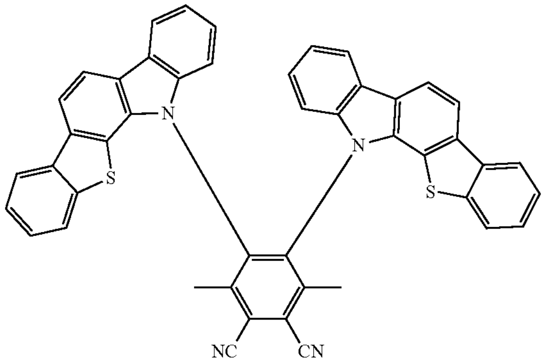
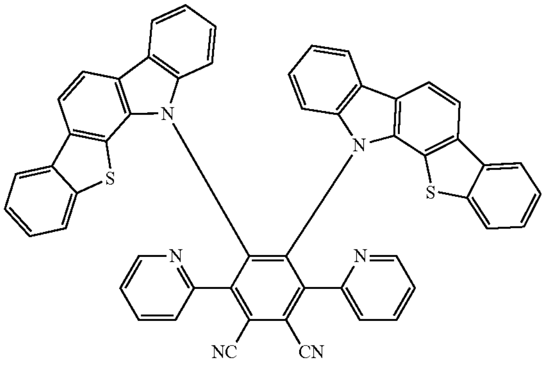
-continued
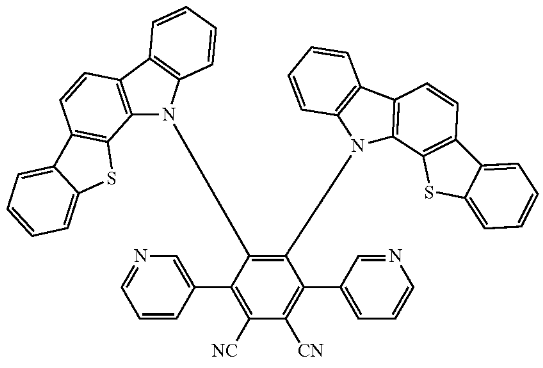
[Formula 73]
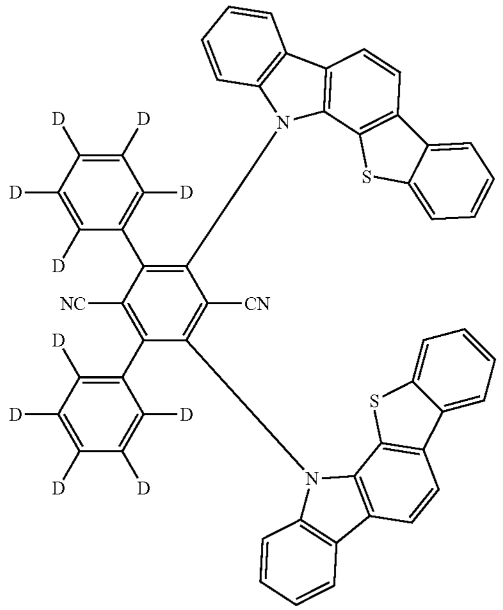
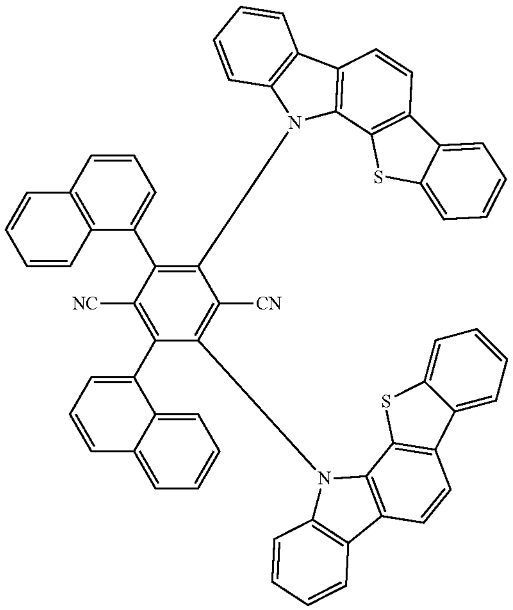

-continued
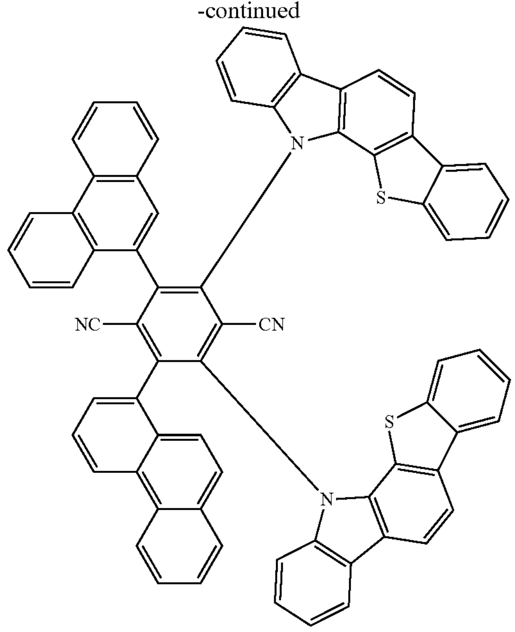
-continued
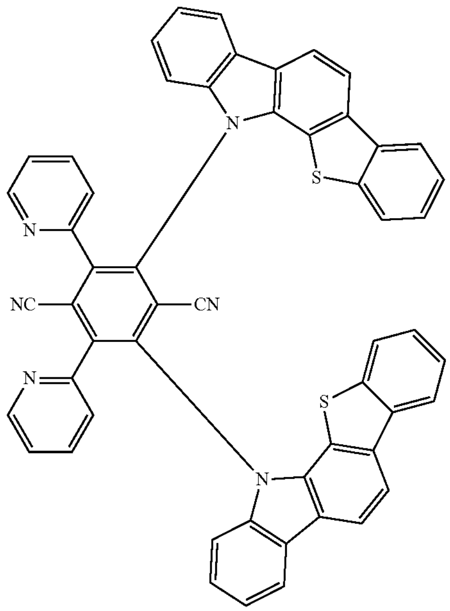
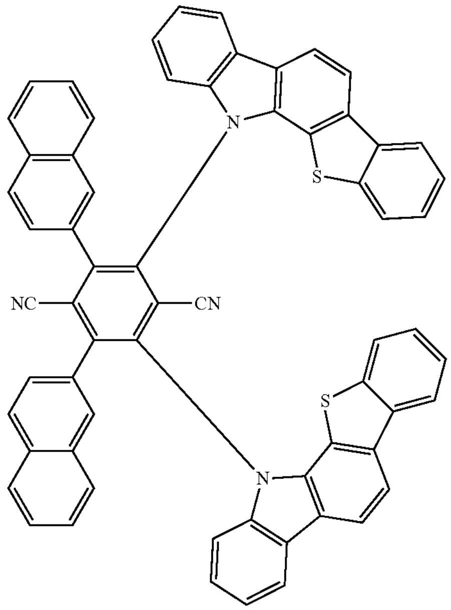
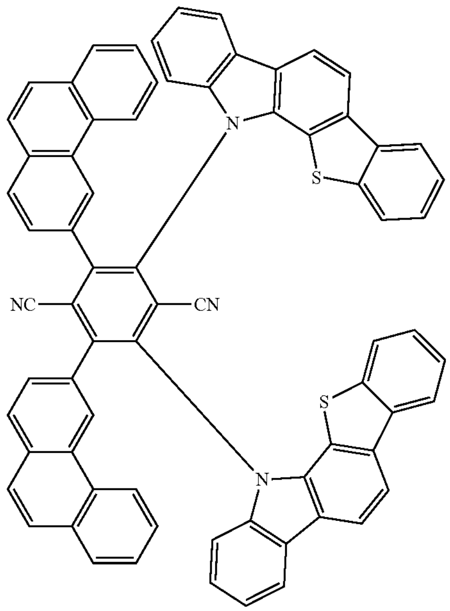

-continued
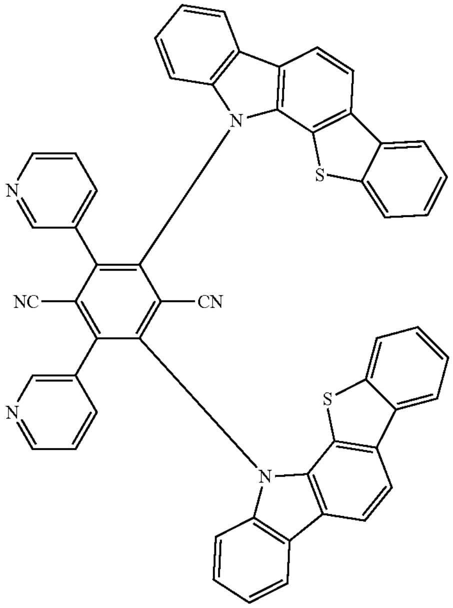
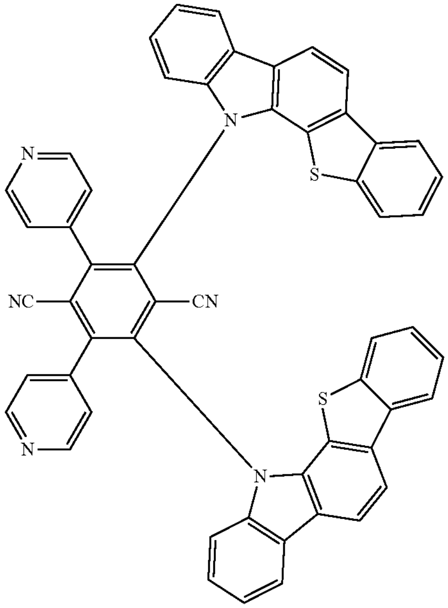
[Formula 74]
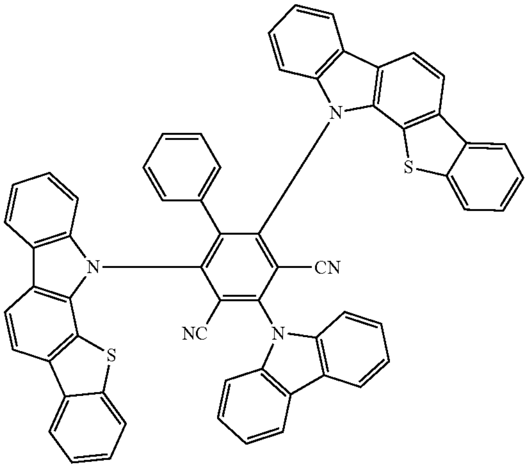
-continued
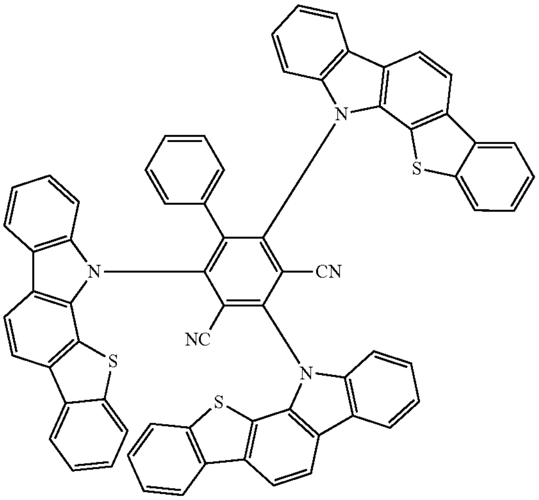
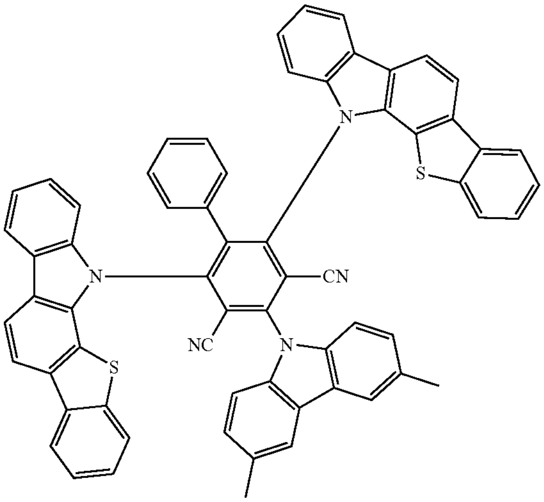
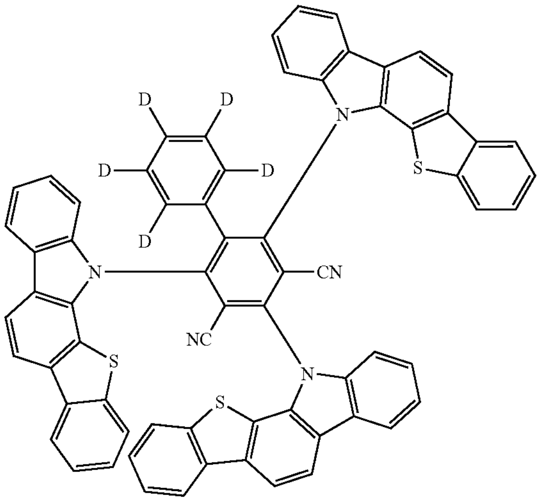

-continued
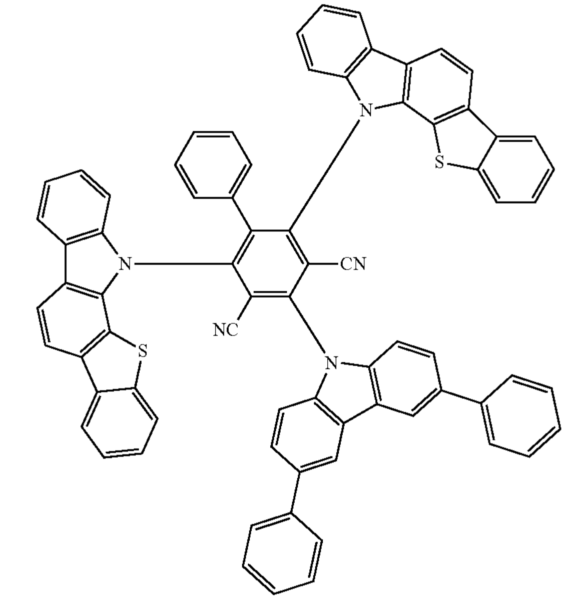
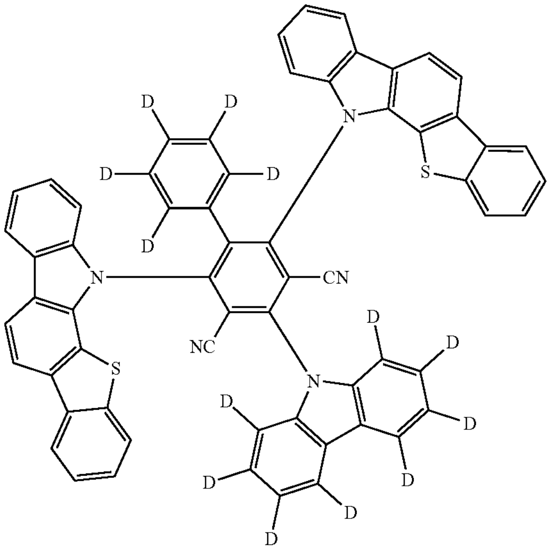
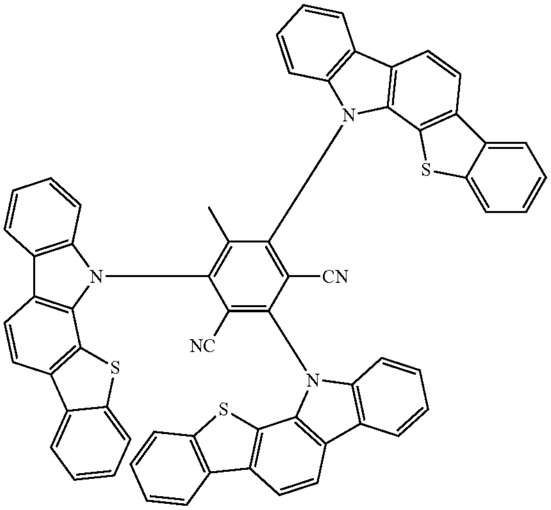
-continued
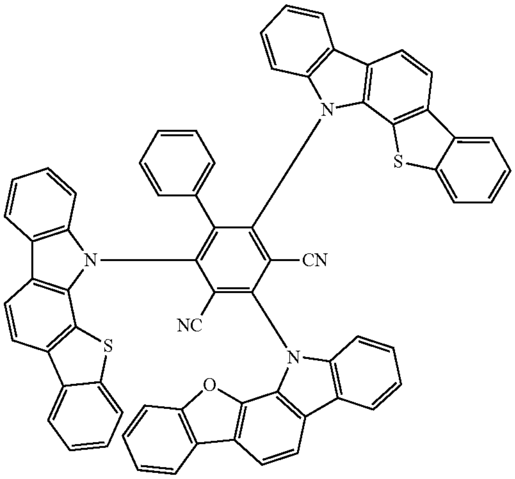
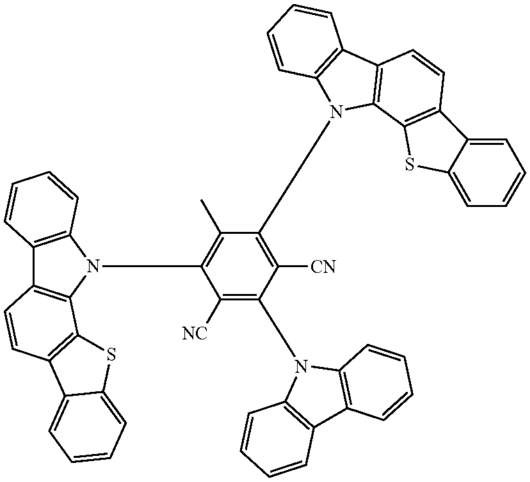
[Formula 75]
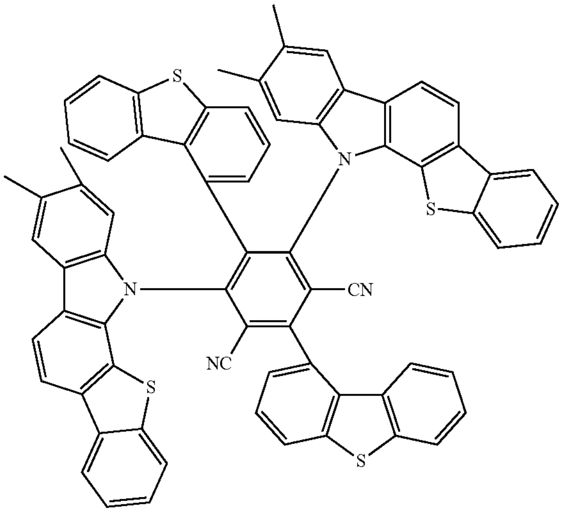

-continued
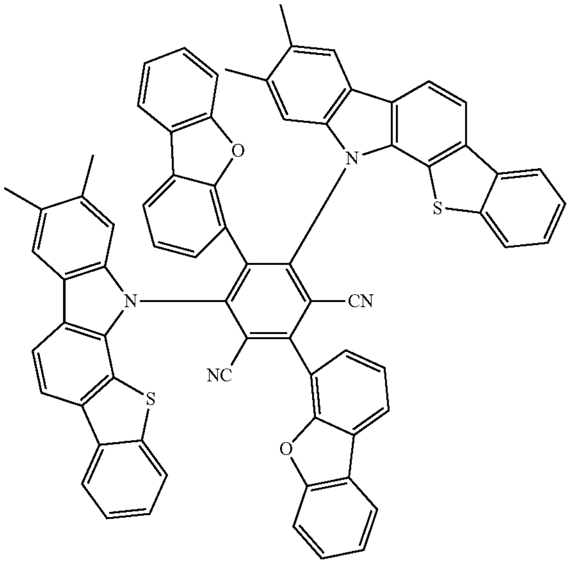
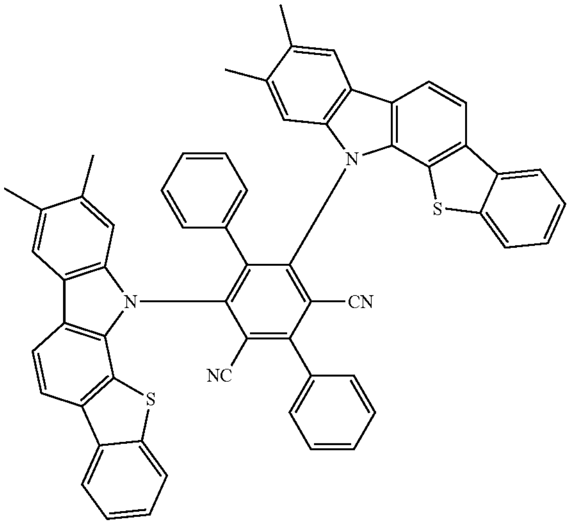
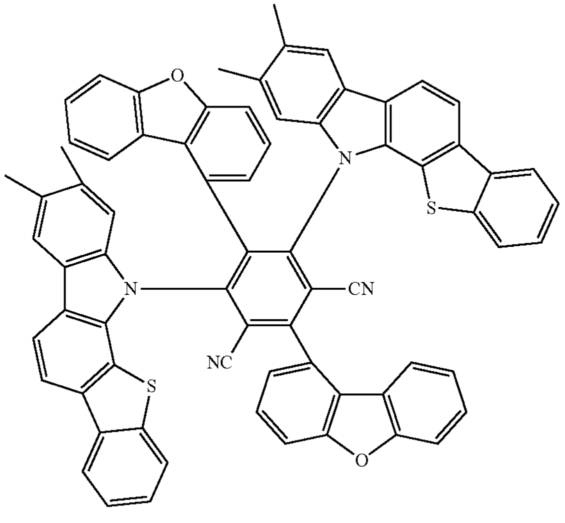
-continued
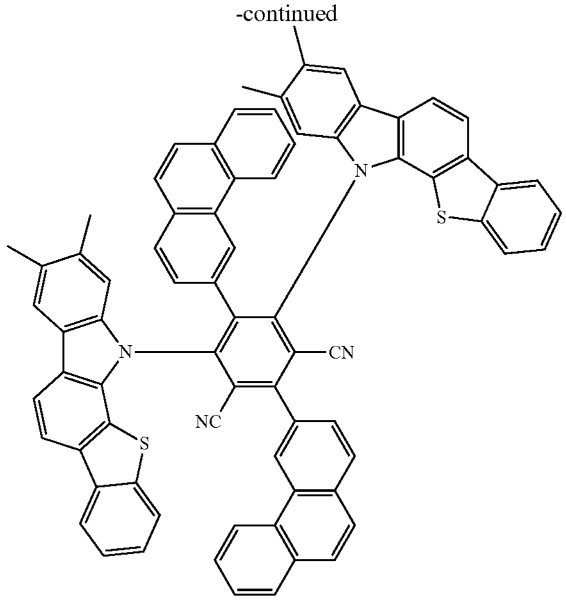
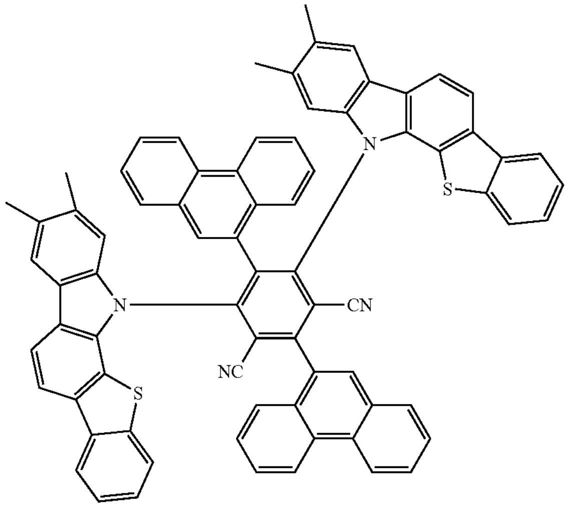
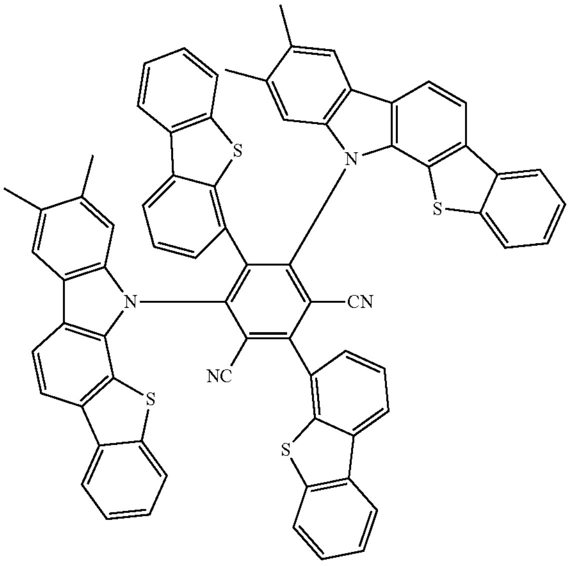

-continued
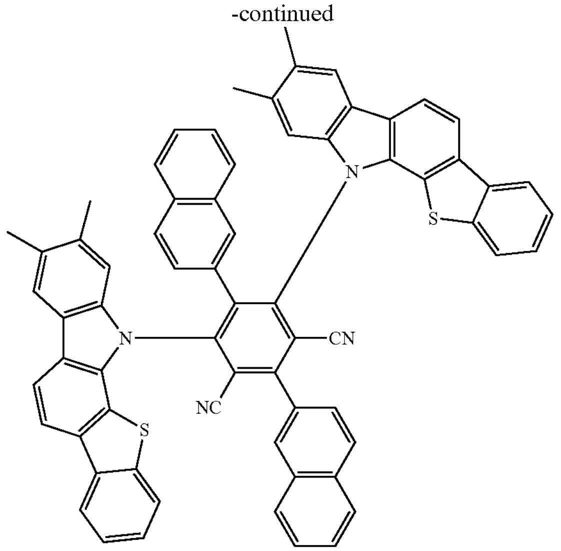
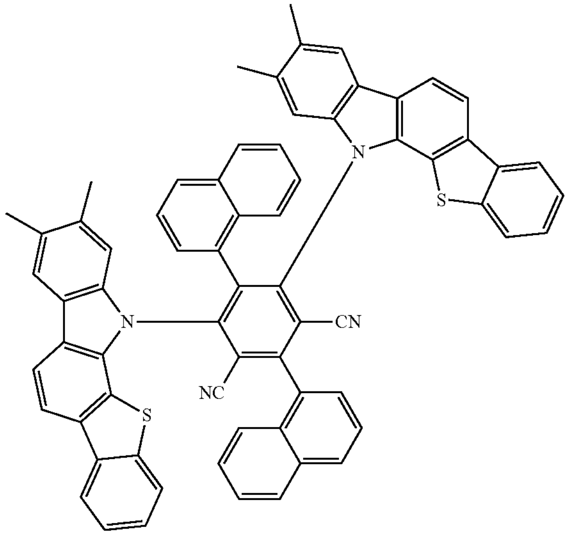
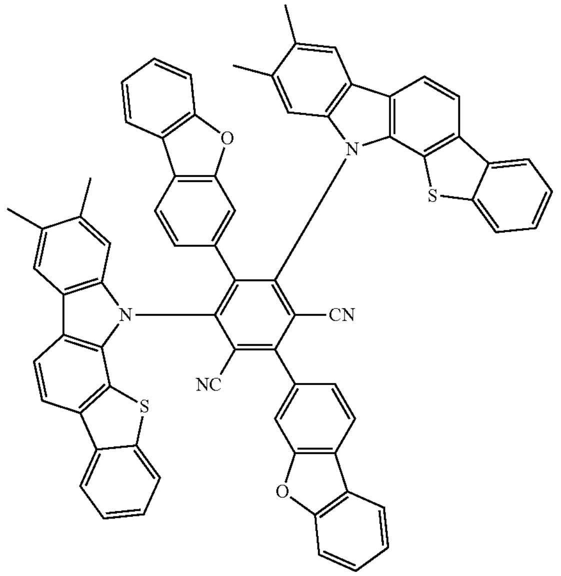
-continued
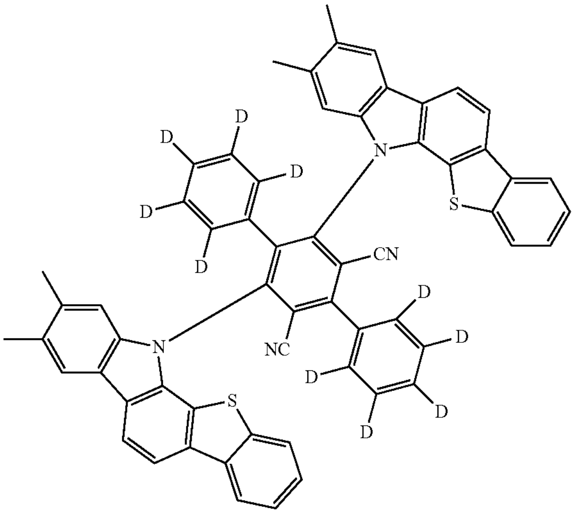
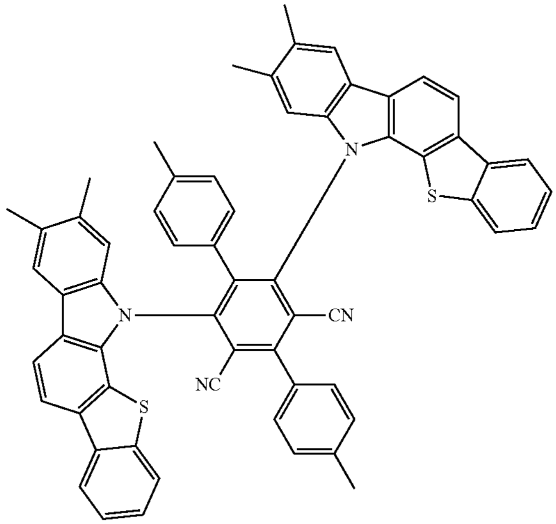
[Formula 76]
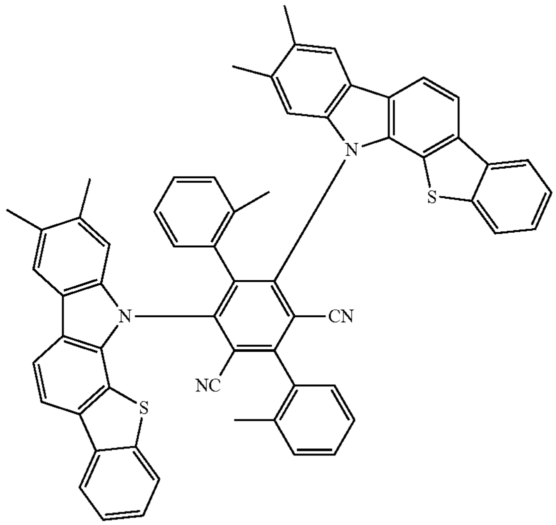

-continued
-continued
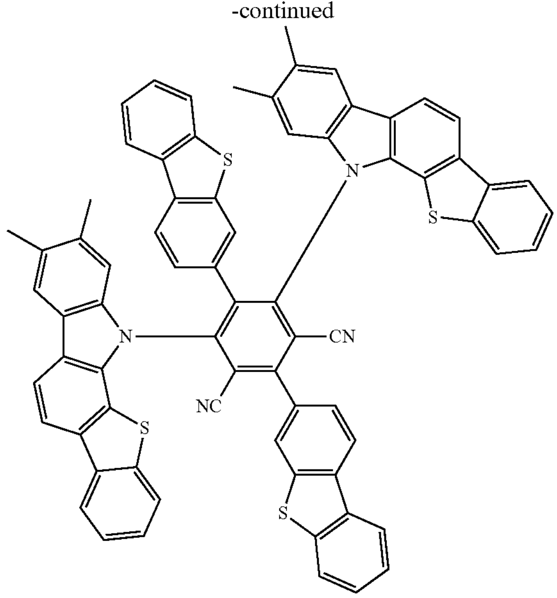
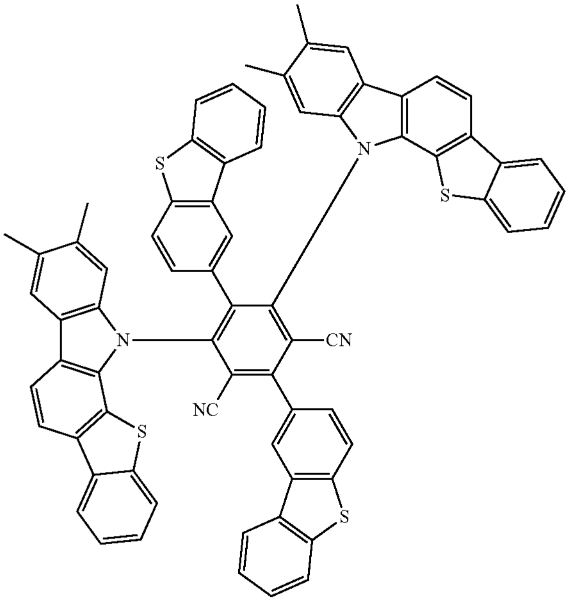
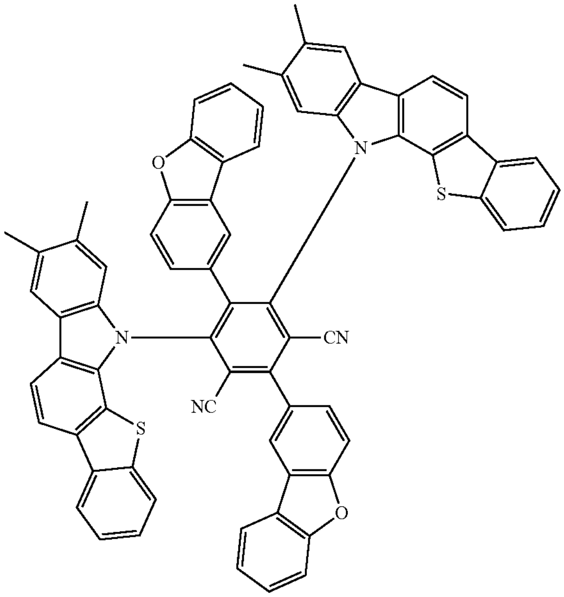
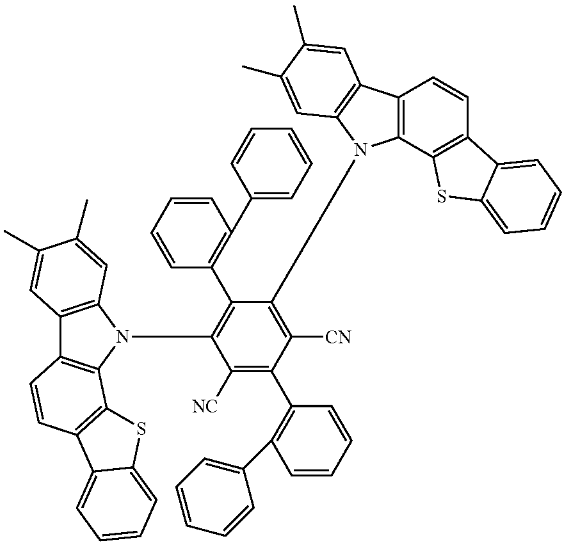
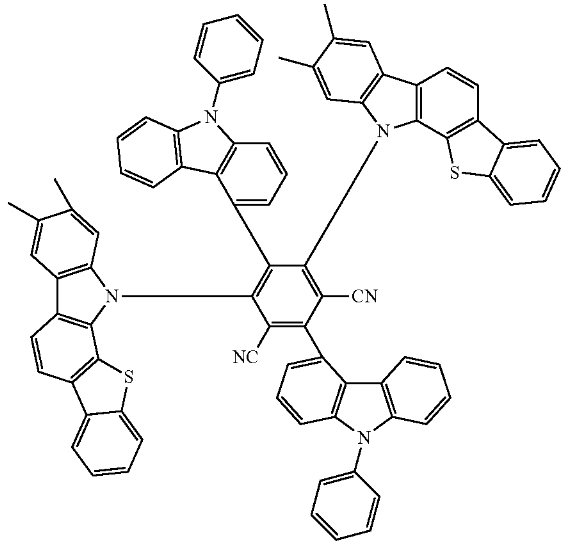

-continued
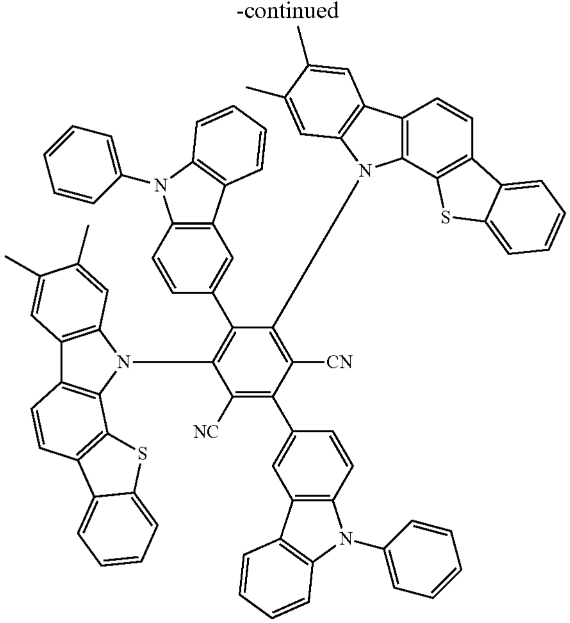
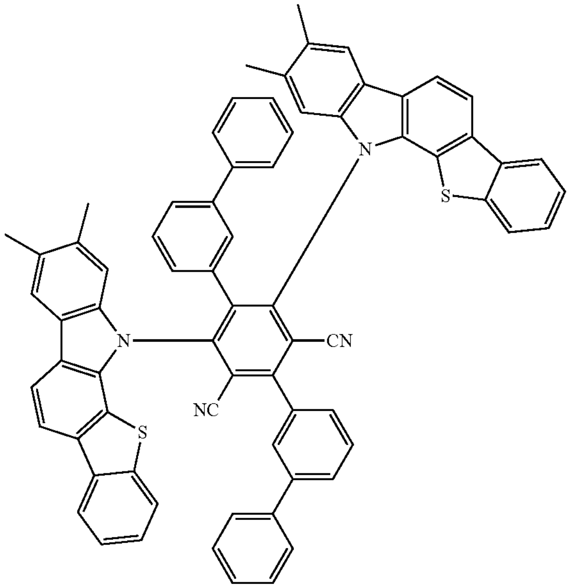
-continued
[Formula 77]
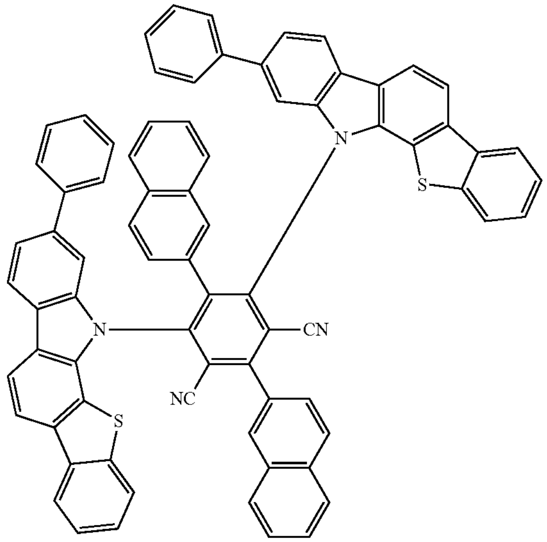
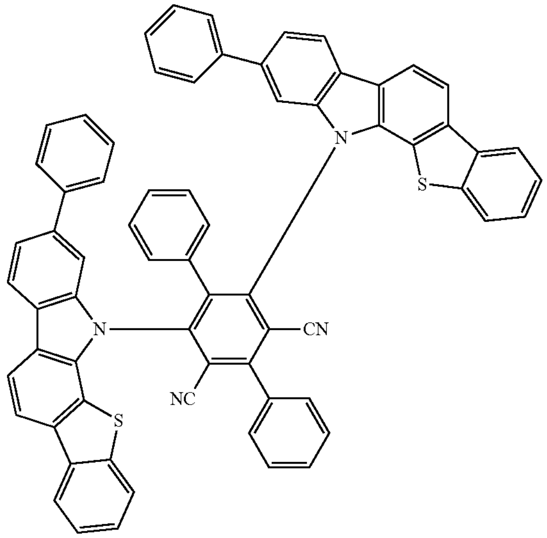
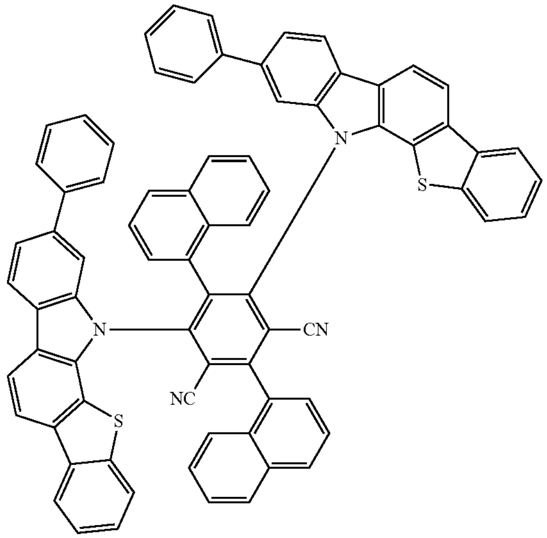

-continued
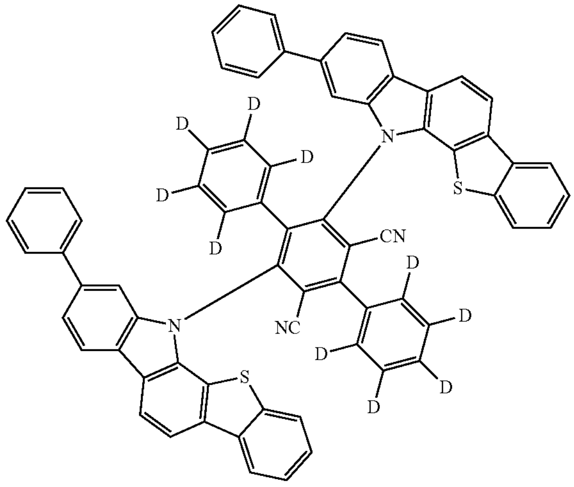
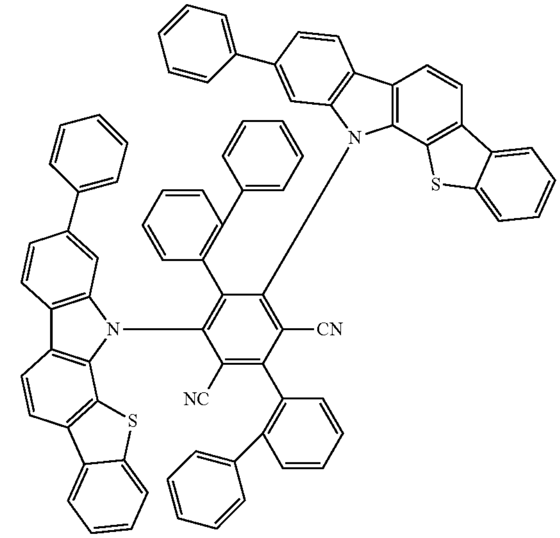
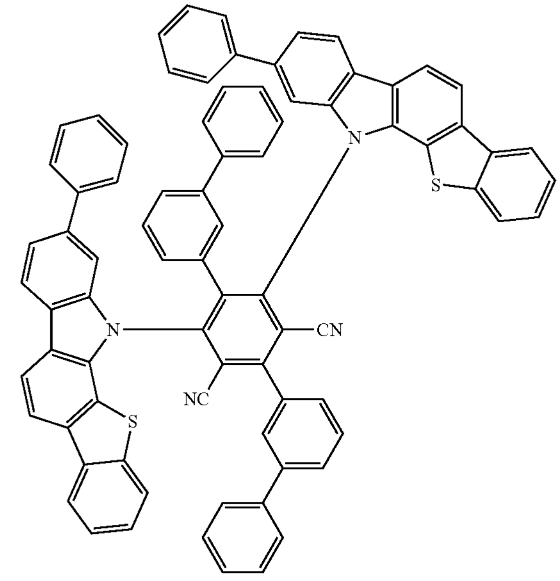
-continued
[Formula 78]
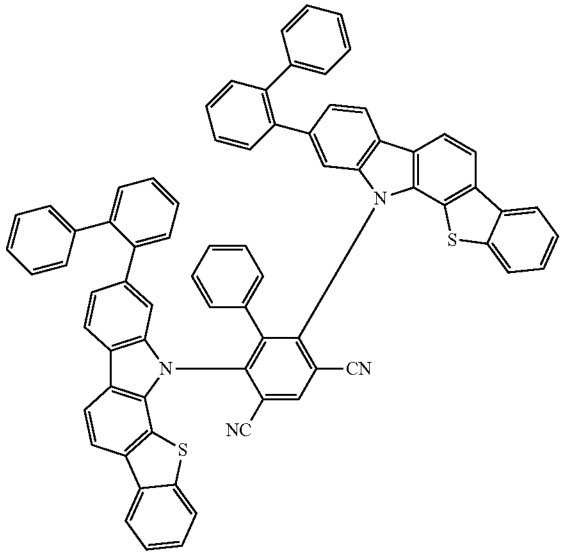
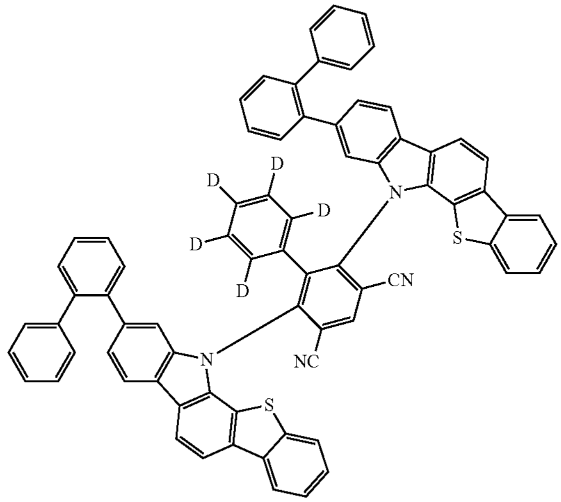
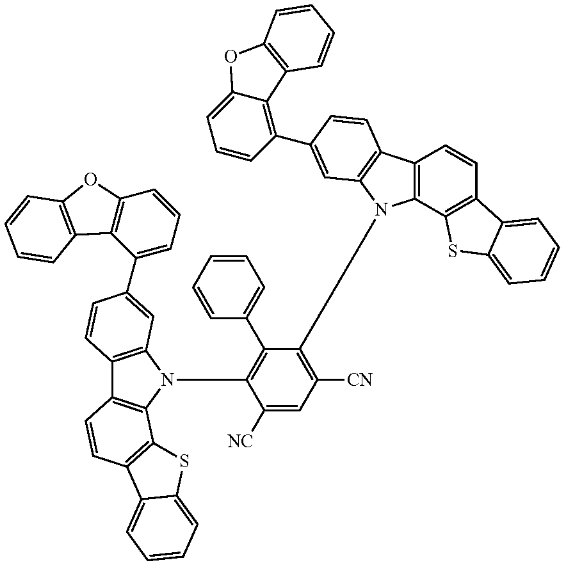

-continued
[Formula 79]
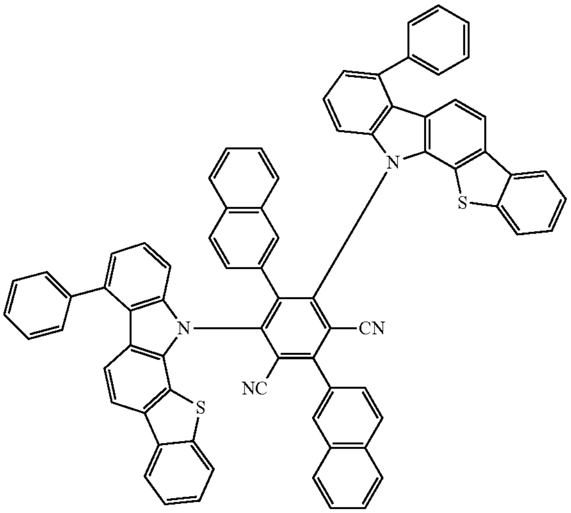
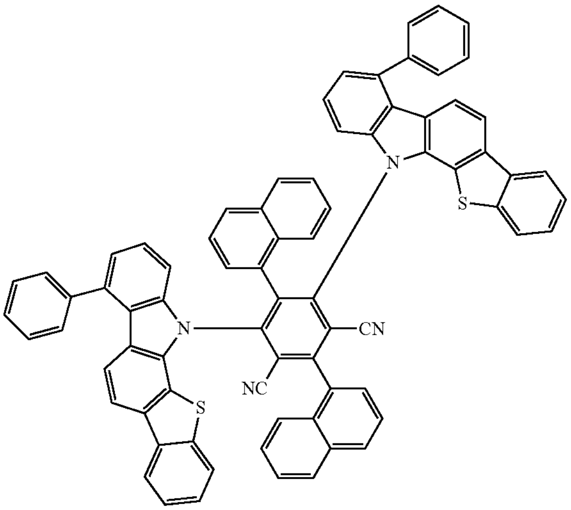
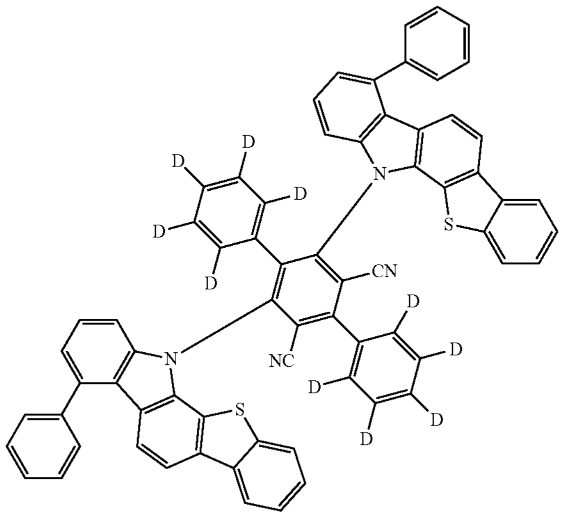
-continued
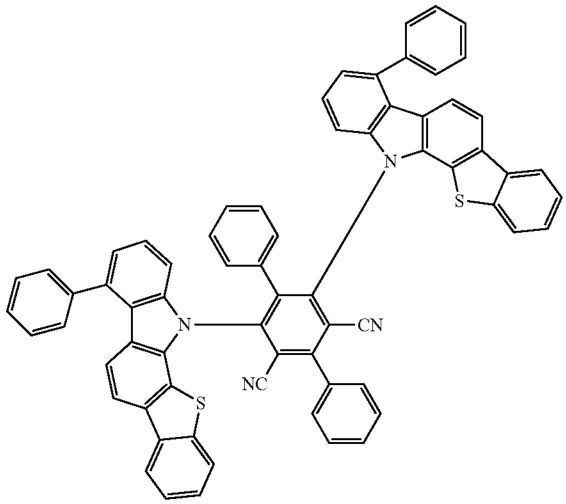
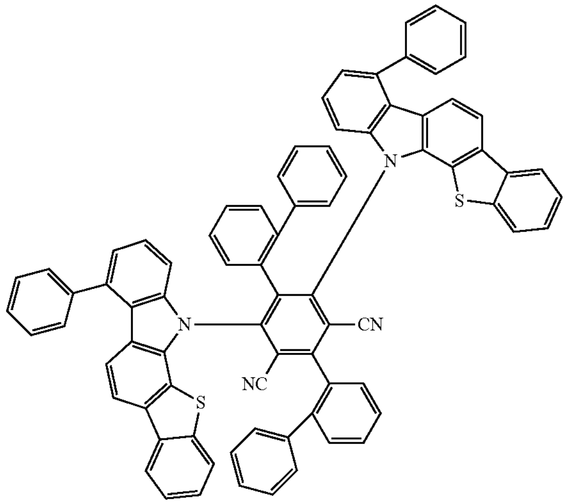
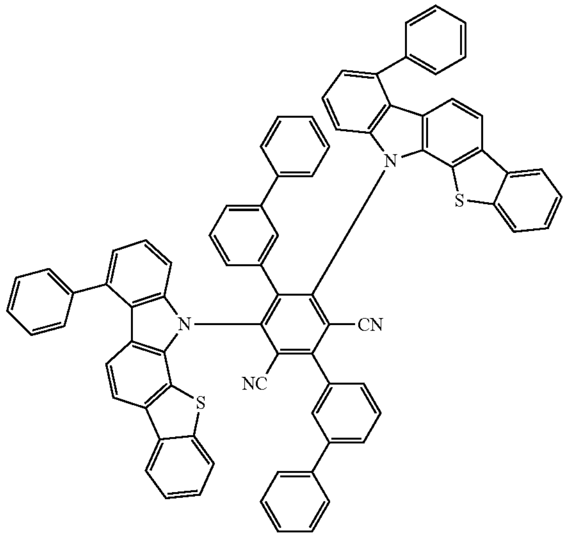

[Formula 80]
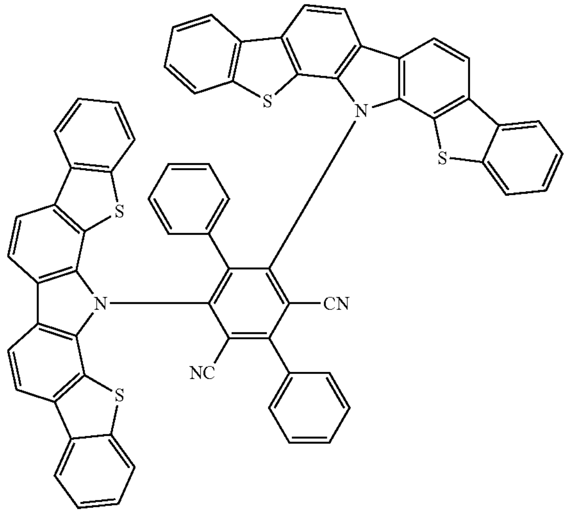
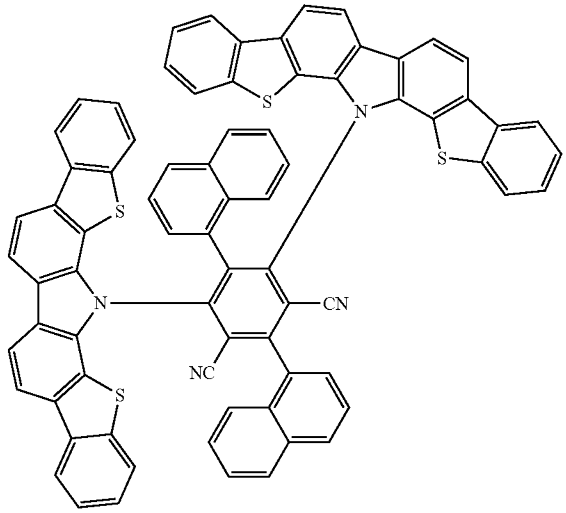
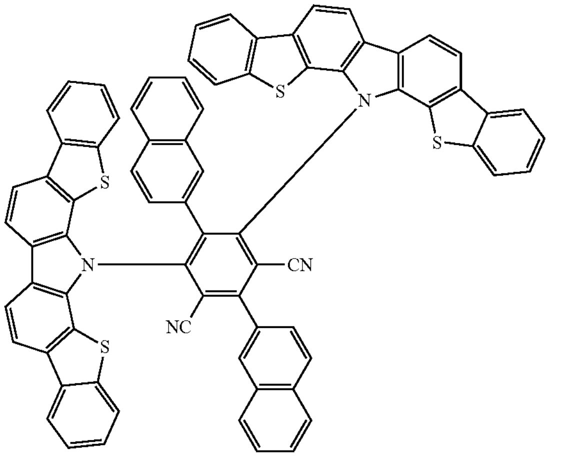
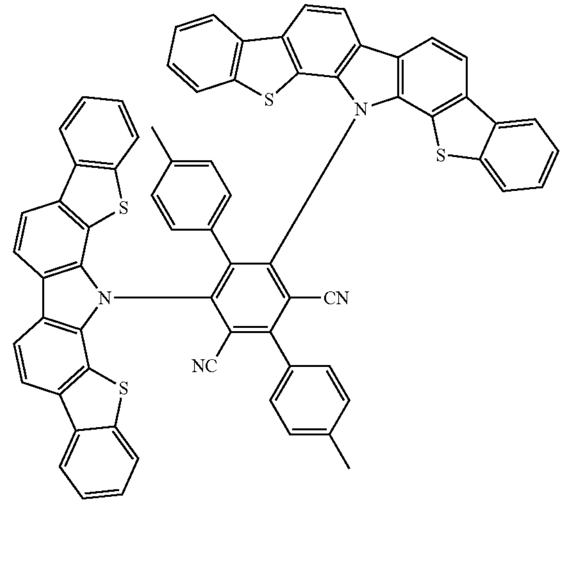
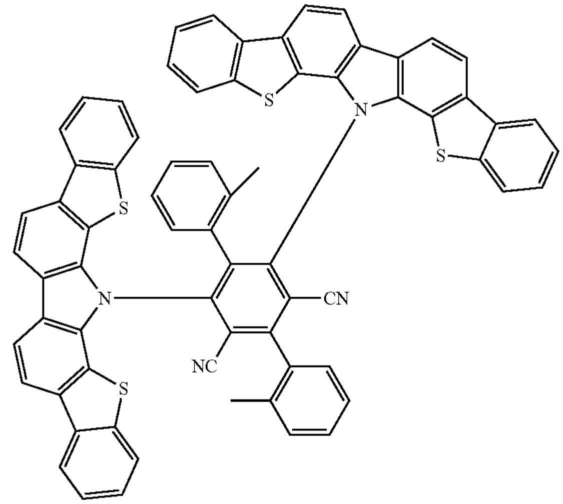
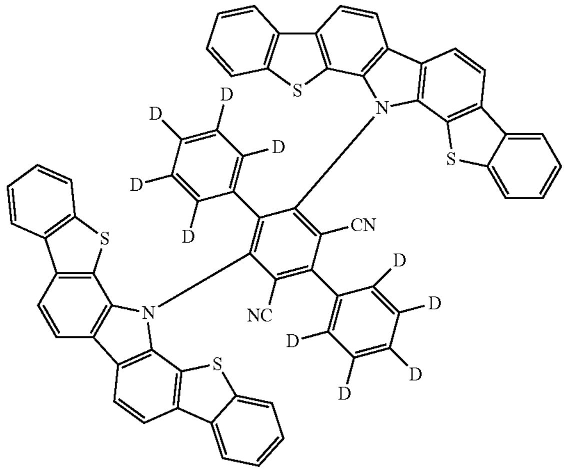

-continued
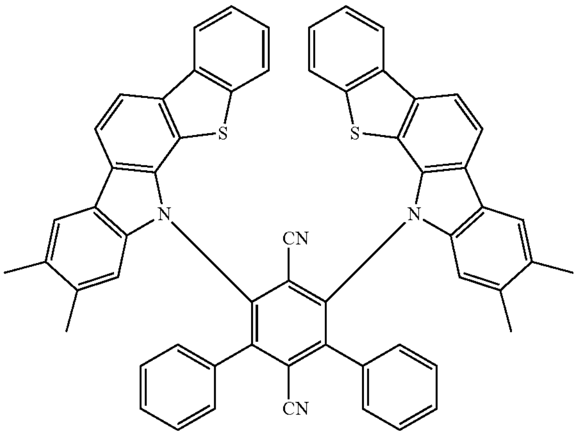
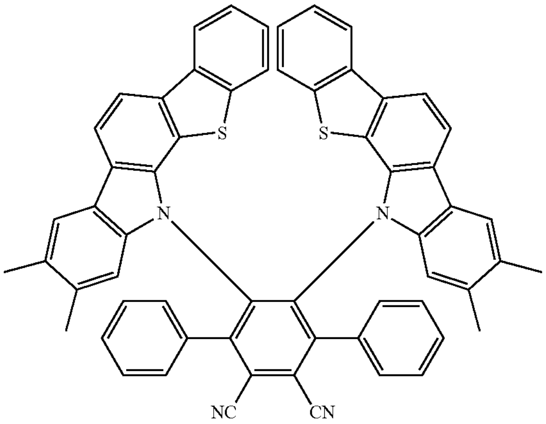
[Formula 81]
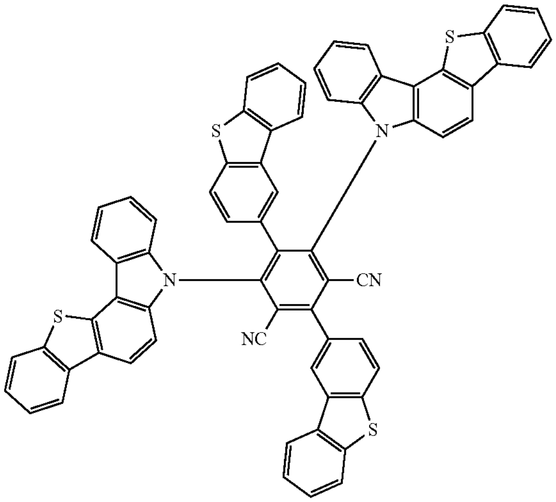
-continued
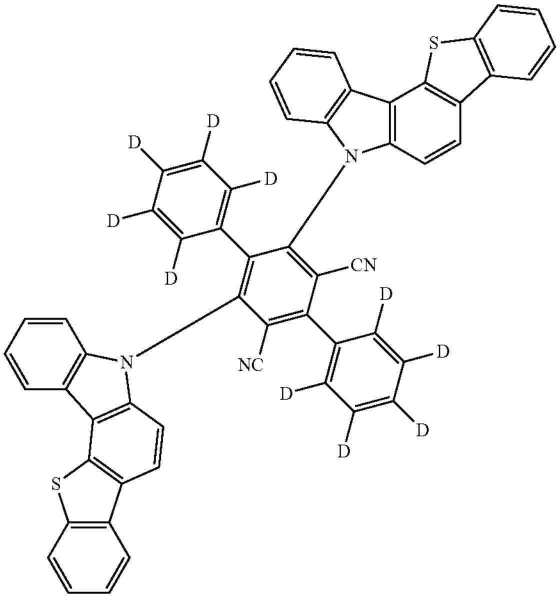
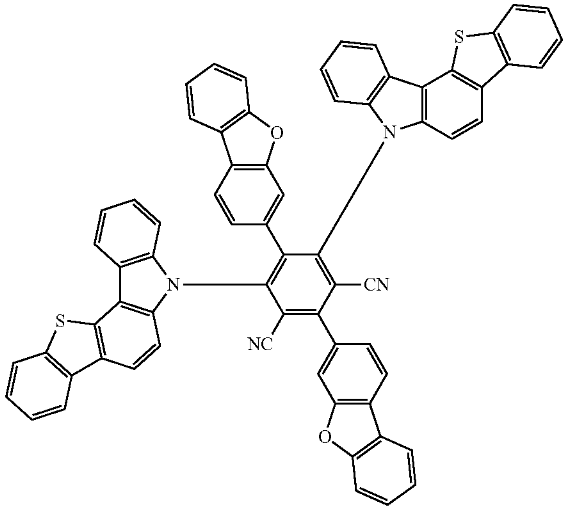
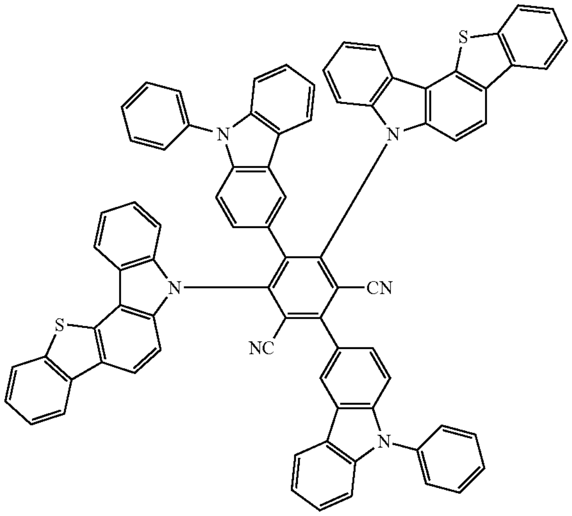

-continued
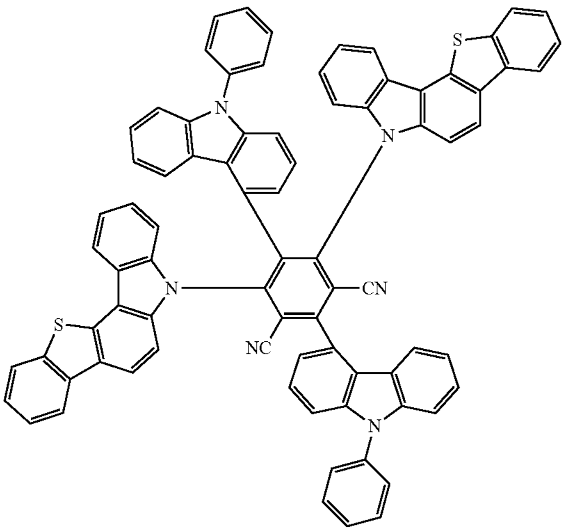
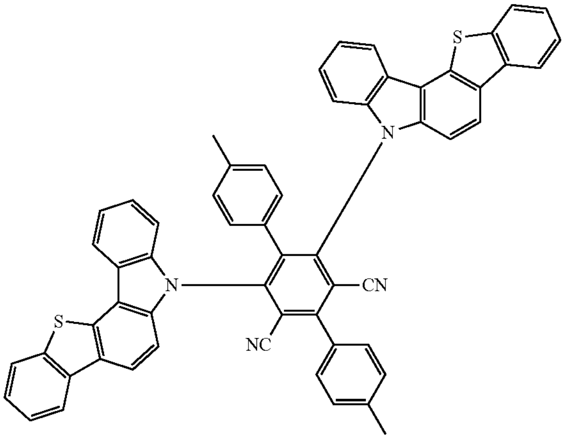
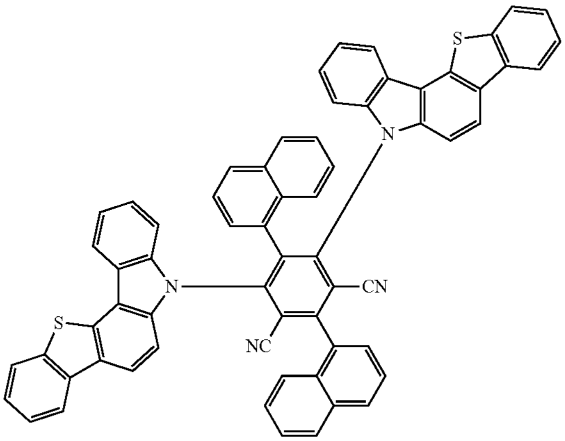
-continued
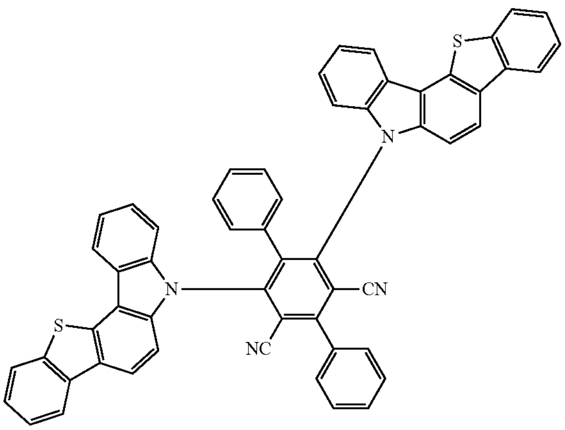
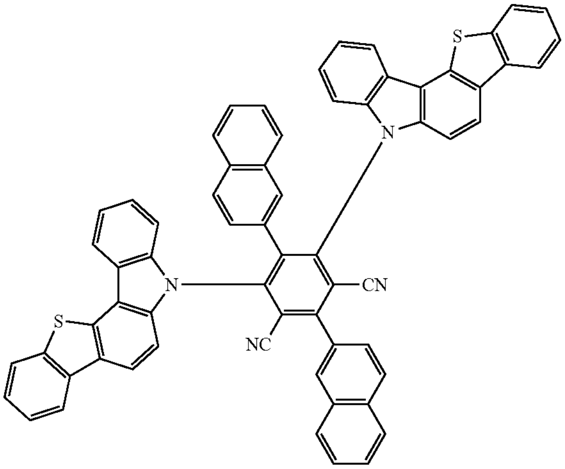
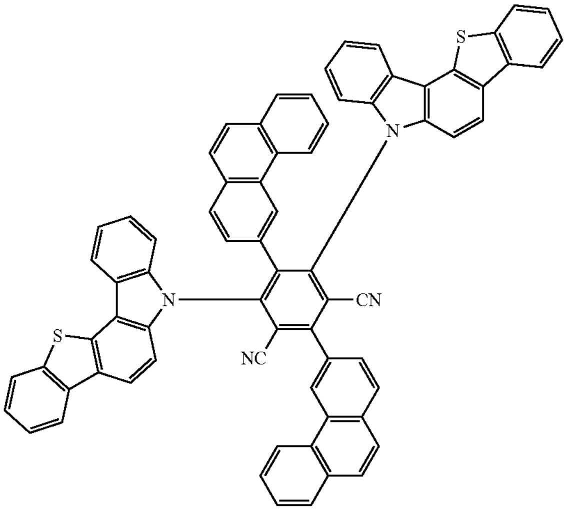

-continued
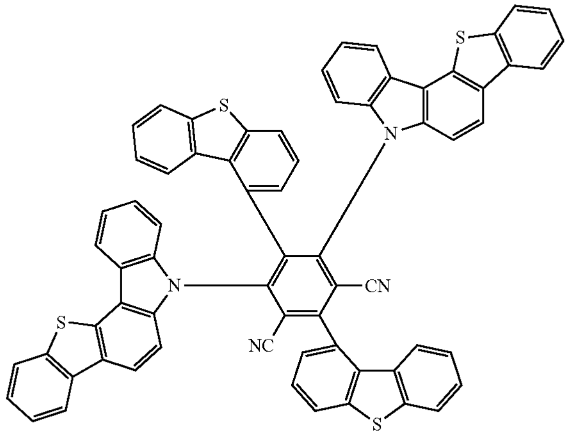
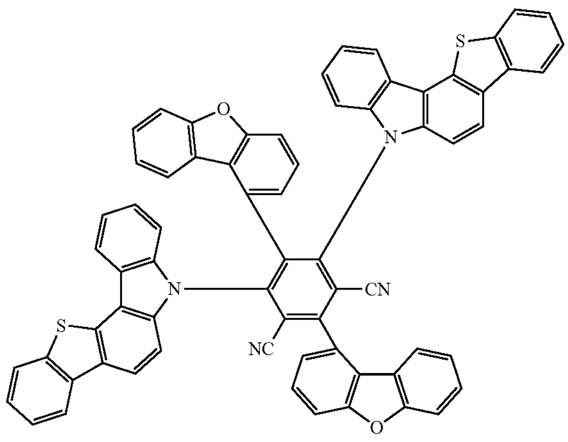
[Formula 82]
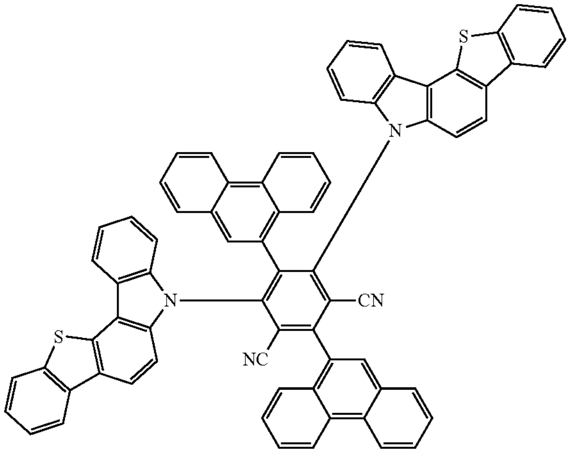
-continued
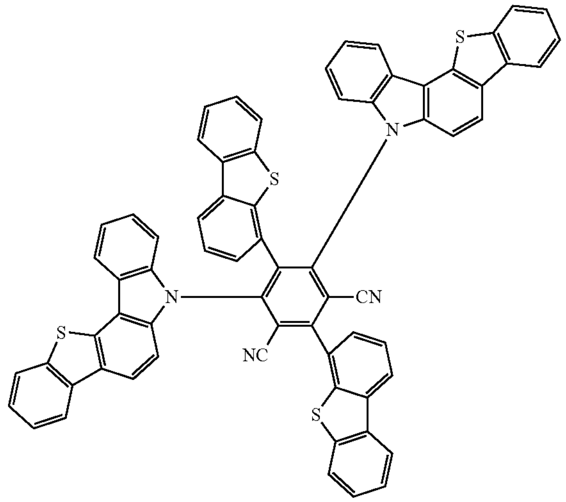
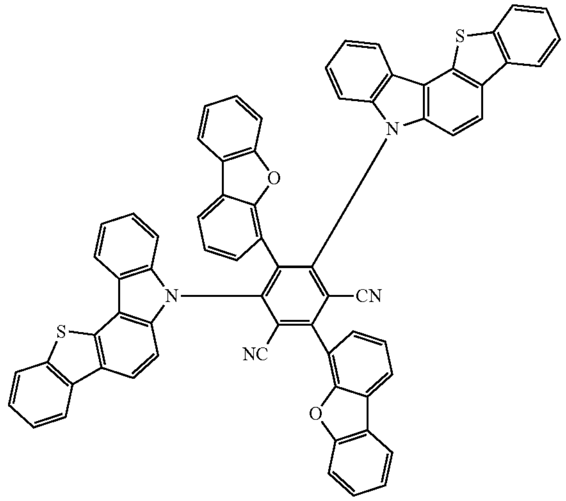
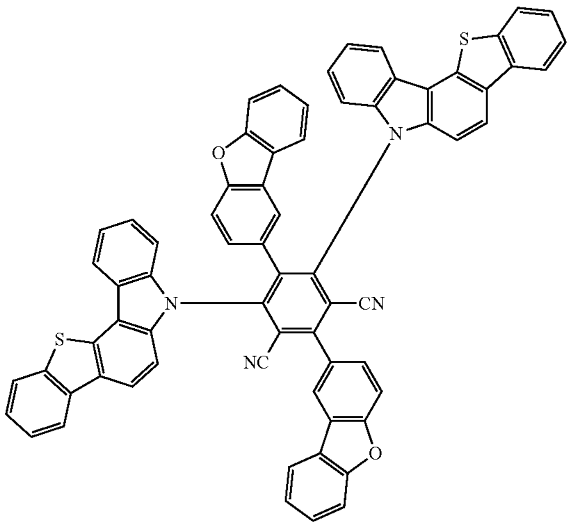

-continued
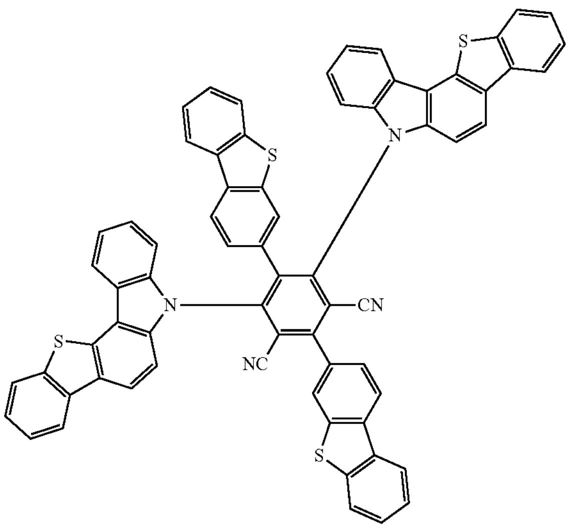
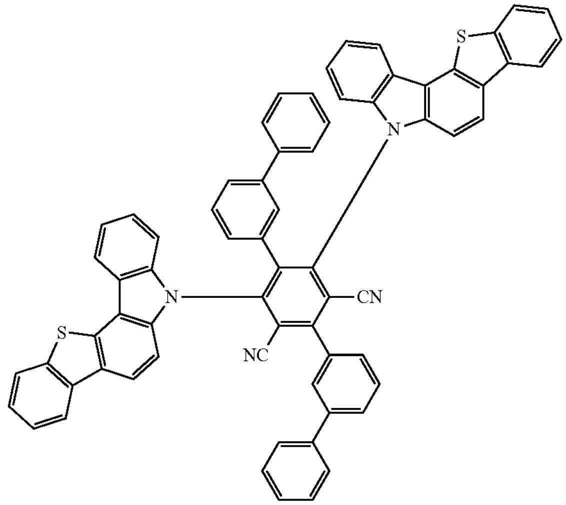
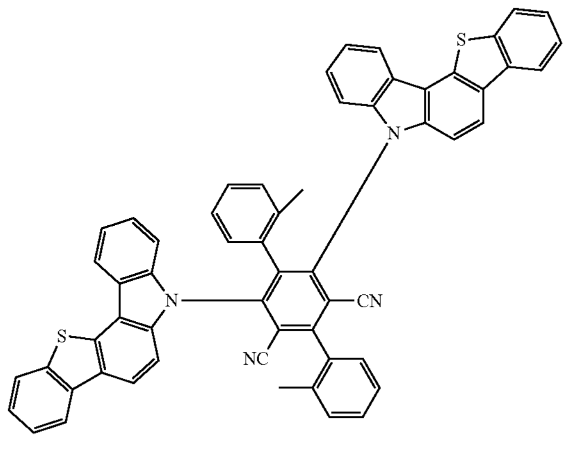
-continued
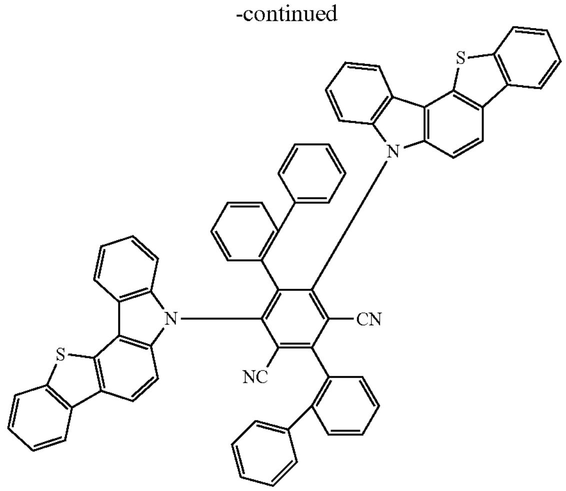
[Formula 83]
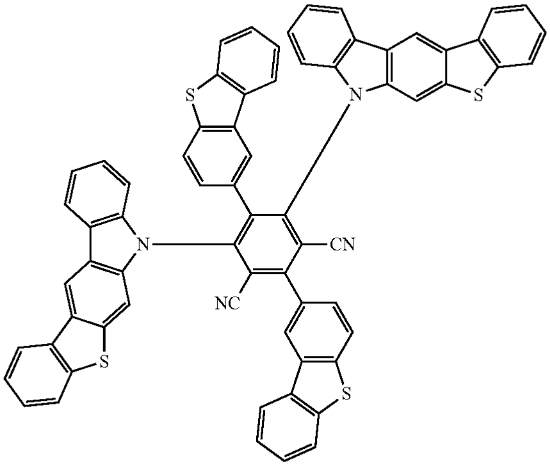
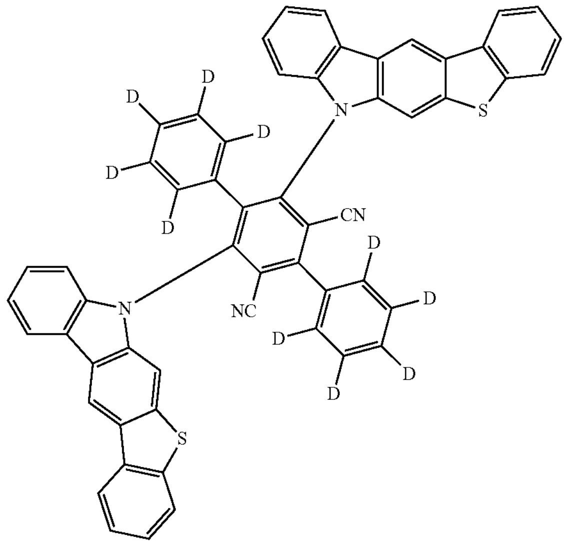

-continued
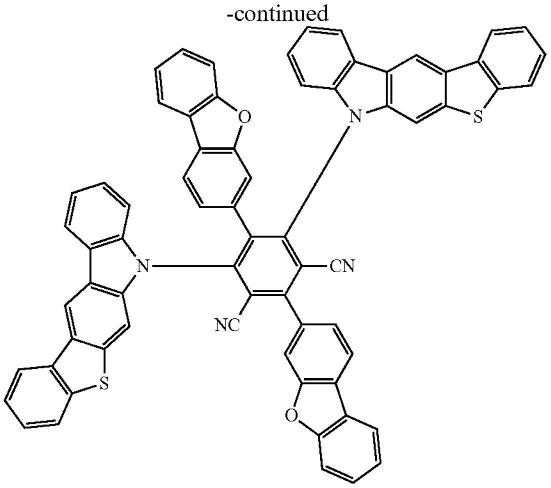
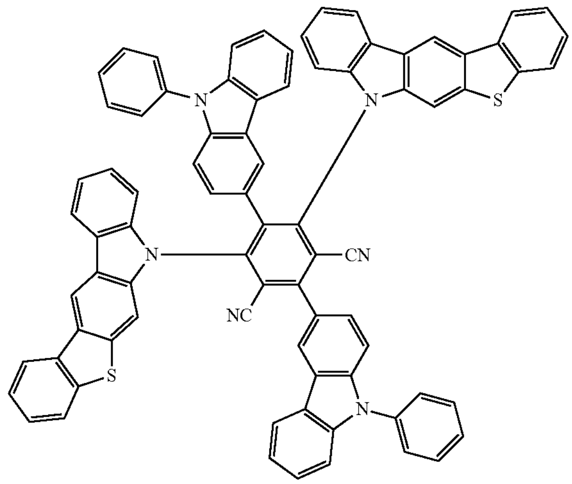
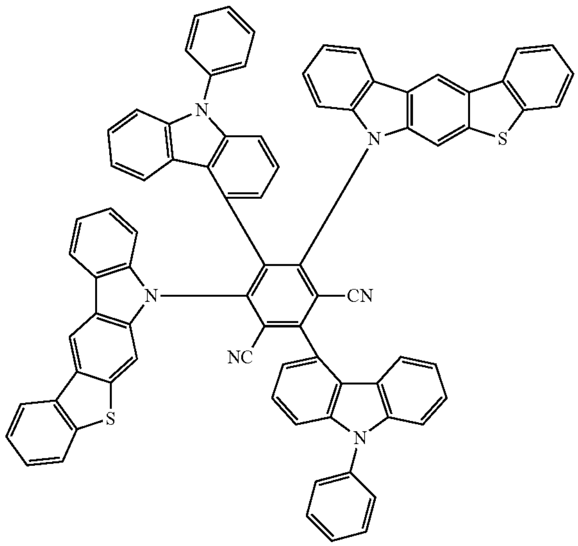
-continued
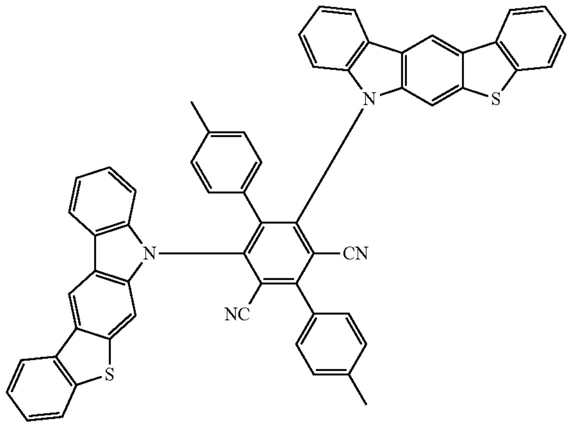
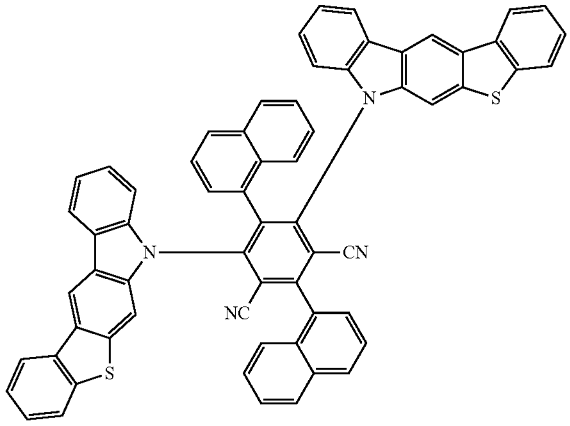
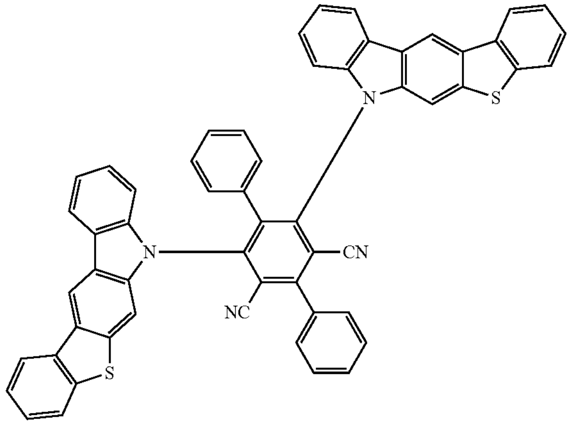
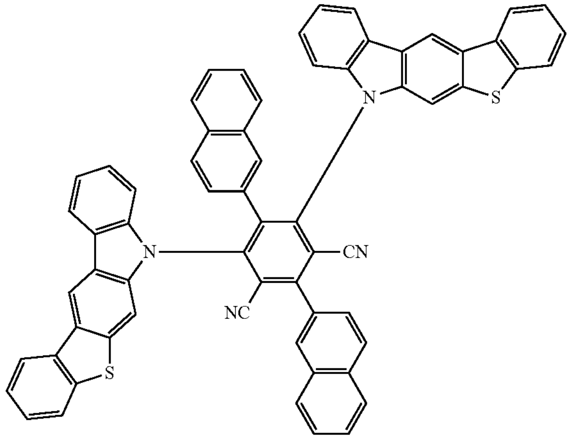

-continued
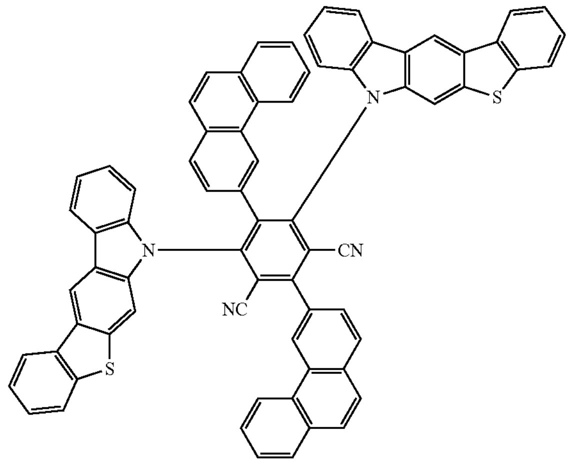
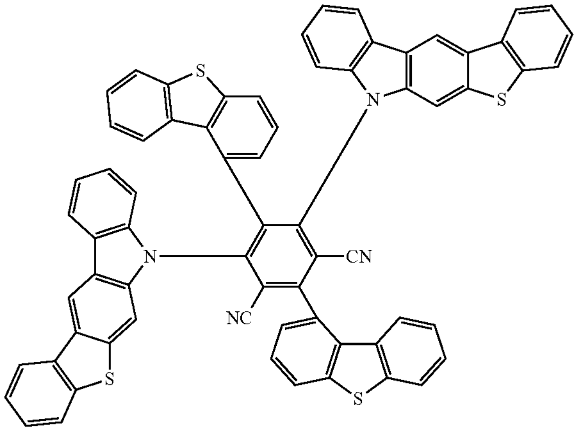
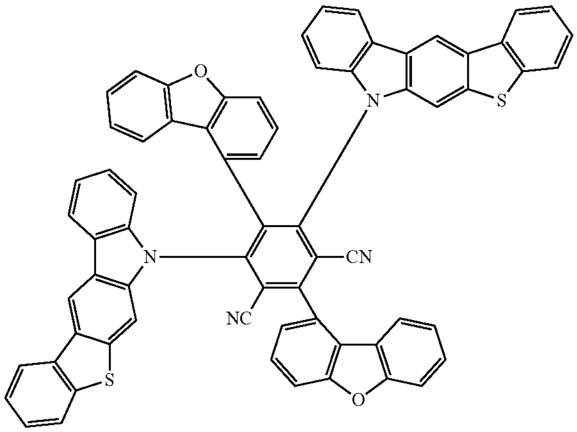
-continued
[Formula 84]
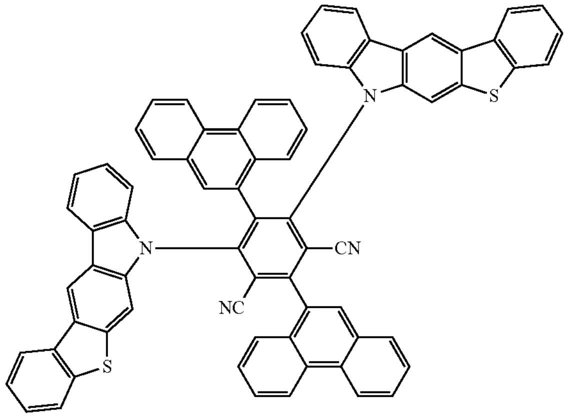
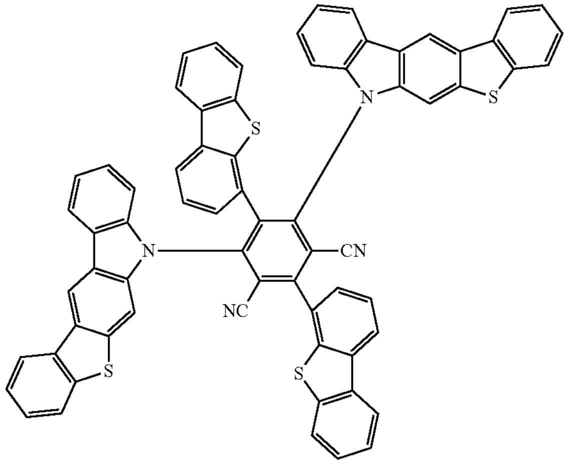
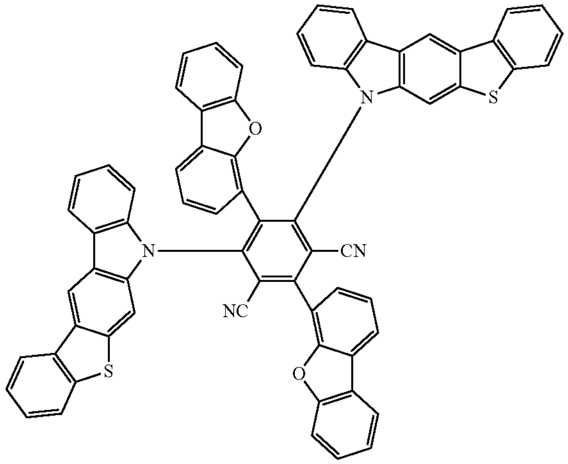

-continued
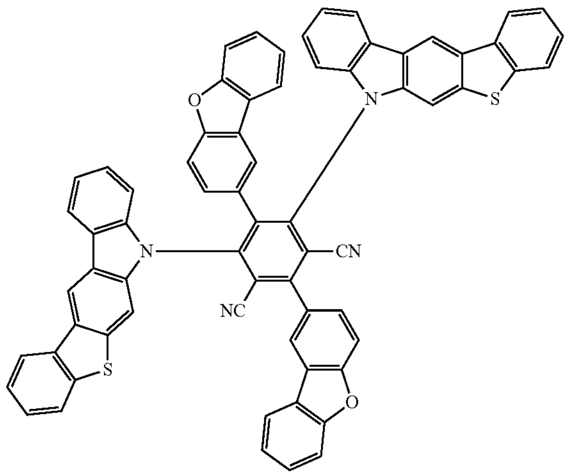
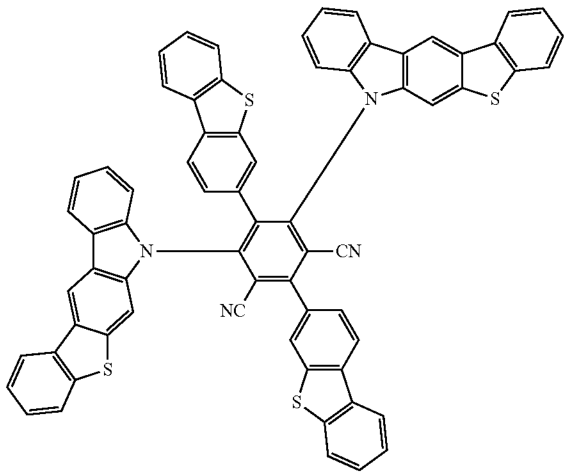
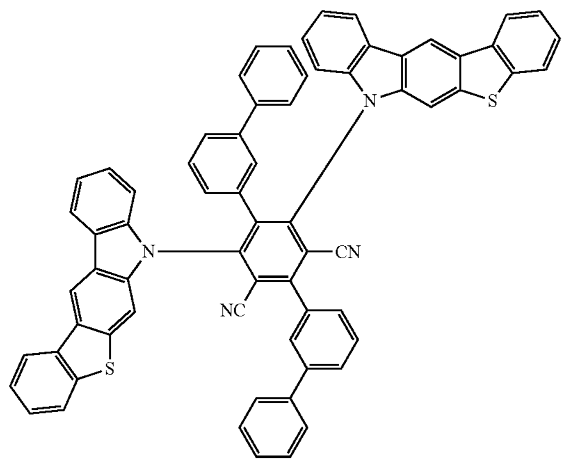
-continued
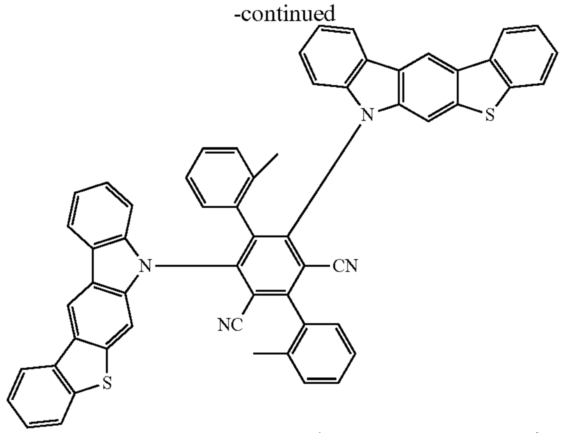
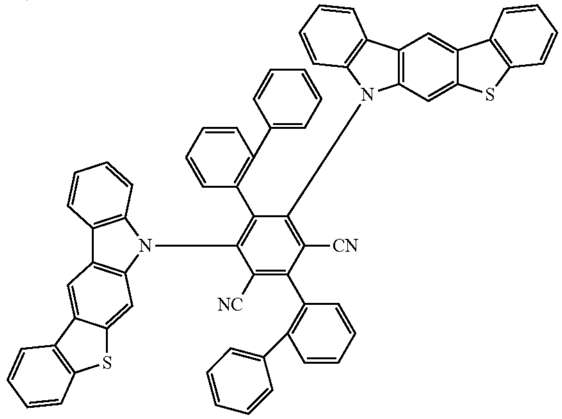
[Formula 85]
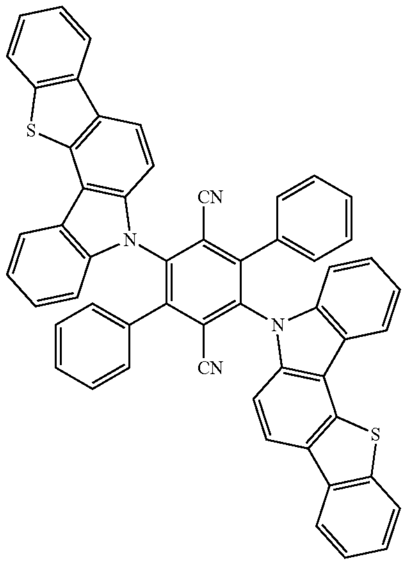
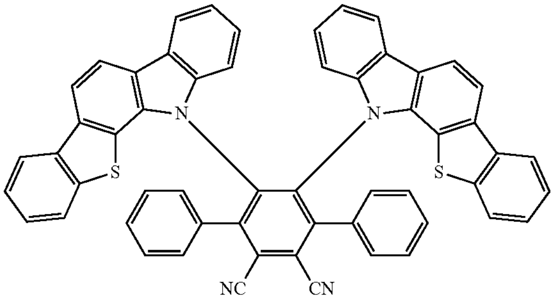

-continued

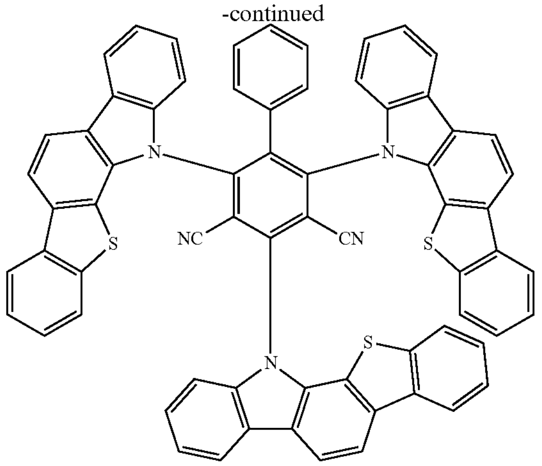

According to the exemplary embodiment, a compound having a high PLQY can be provided.

A measurement method of PLQY will be described below in Examples.

Second Exemplary Embodiment

Organic-Electroluminescence-Device Material

An organic-electroluminescence-device material according to a second exemplary embodiment contains the compound according to the first exemplary embodiment. An example of the organic-electroluminescence-device material contains only the compound according to the first exemplary embodiment. Another example of the organic-electroluminescence-device material contains the compound according to the first exemplary embodiment and another compound different from the compound according to the first exemplary embodiment.

In the organic-electroluminescence-device material according to the exemplary embodiment, the compound according to the first exemplary embodiment is preferably a host material. In this case, the organic-electroluminescence-device material may contain the compound according to the first exemplary embodiment serving as a host material and, for instance, an additional compound such as a dopant material.

Further, in the organic-electroluminescence-device material according to the exemplary embodiment, the compound according to the first exemplary embodiment is preferably a delayed fluorescent material.

Third Exemplary Embodiment

Organic Electroluminescence Device

An organic EL device according to a third exemplary embodiment will be described.

The organic EL device according to the exemplary embodiment includes an anode, a cathode, and at least one organic layer between the anode and the cathode. The organic layer includes at least one layer formed of an organic compound. Alternatively, the organic layer is provided by laminating a plurality of layers each formed of an organic compound. The organic layer may further contain an inorganic compound.

In the organic EL device according to the exemplary embodiment, the organic layer contains the compound according to the first exemplary embodiment.

The organic EL device according to the exemplary embodiment includes a first organic layer as the organic layer.

In the organic EL device according to the exemplary embodiment, at least one layer of the one or more organic layers is preferably an emitting layer. In the exemplary embodiment, the emitting layer preferably contains the compound according to the first exemplary embodiment.

For instance, the organic layer may be a single emitting layer or may further include at least one layer usable for the organic EL device. Examples of the layer usable in the organic EL device, which are not particularly limited, include at least one layer selected from the group consisting of a hole injecting layer, hole transporting layer, electron injecting layer, electron transporting layer, and blocking layer.

In an exemplary embodiment, the first organic layer as the emitting layer may contain a metal complex.

Alternatively, in an exemplary embodiment, the first organic layer as the emitting layer also preferably does not contain a metal complex.

Alternatively, in an exemplary embodiment, the emitting layer preferably does not contain a phosphorescent material (dopant material).

Alternatively, in an exemplary embodiment, the emitting layer preferably does not contain a heavy metal complex and phosphorescent rare earth metal complex. Examples of the heavy metal complex includes an iridium complex, osmium complex, and platinum complex.

Figure 3:
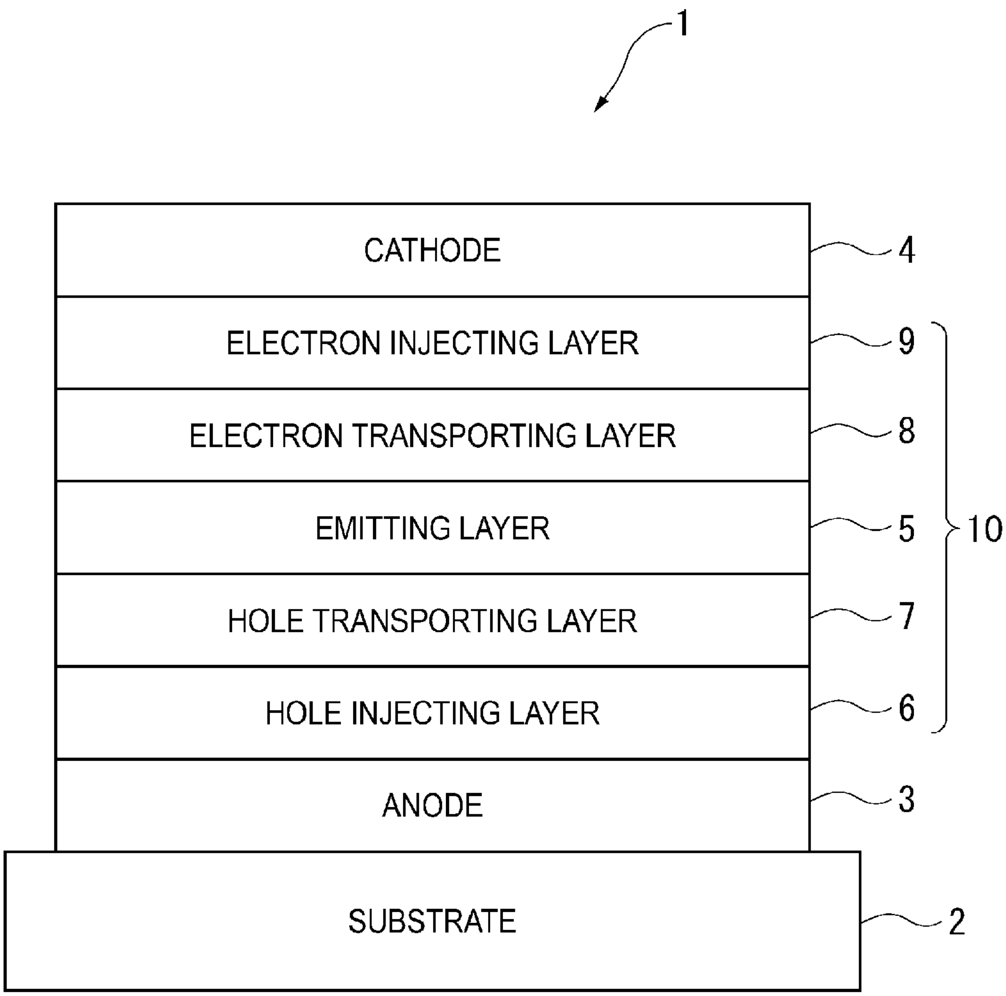

FIG. 3 schematically shows an exemplary arrangement of the organic EL device according to the exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5, an electron transporting layer 8, and an electron injecting layer 9, which are sequentially laminated on the anode 3.

Emitting Layer

In the exemplary embodiment, the first organic layer is the emitting layer. The first organic layer as the emitting layer contains a first compound and a second compound. The first compound in the first organic layer is preferably the compound according to the first exemplary embodiment.

In this arrangement, the first compound is preferably a host material (sometimes referred to as a matrix material), and the second compound is preferably a dopant material (sometimes referred to as a guest material, emitter or luminescent material).

In the exemplary embodiment, when the emitting layer contains the compound according to the first exemplary embodiment, the emitting layer preferably does not contain a phosphorescent metal complex and preferably does not contain a metal complex other than the phosphorescent metal complex.

First Compound

The first compound is according to the first exemplary embodiment.

The first compound is preferably a delayed fluorescent compound.

Second Compound

The second compound is preferably a fluorescent compound exhibiting no delayed fluorescence.

A fluorescent material is usable as the second compound in the exemplary embodiment. Specific examples of the fluorescent material include a bisarylam inonaphthalene derivative, aryl-substituted naphthalene derivative, bisarylam inoanthracene derivative, aryl-substituted anthracene derivative, bisarylaminopyrene derivative, aryl-substituted pyrene derivative, bisarylamino chrysene derivative, aryl-substituted chrysene derivative, bisarylaminofluoranthene derivative, aryl-substituted fluoranthene derivative, indenoperylene derivative, acenaphthofluoranthene derivative, pyromethene boron complex compound, compound having a pyromethene skeleton, metal complex of the compound having a pyrromethene skeleton, diketopyrrolopyrrole derivative, perylene derivative, and naphthacene derivative.

In the exemplary embodiment, the second compound is preferably a compound represented by a formula (2) below.

[Formula 86]

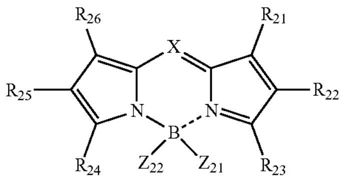

(2)

In the formula (2):

X is a nitrogen atom, or a carbon atom bonded to Y;

Y is a hydrogen atom or a substituent;

$R_{21}$ to $R_{26}$ are each independently a hydrogen atom or a substituent, or at least one of a combination of $R_{21}$ and $R_{22}$, a combination of $R_{22}$ and $R_{23}$, a combination of $R_{24}$ and $R_{25}$, or a combination of $R_{25}$ and $R_{26}$ are mutually bonded to form a ring;

Y and $R_{21}$ to $R_{26}$ serving as a substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, a substituted or unsubstituted alkylthio group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group, a cyano group, a substituted or unsubstituted silyl group, and a substituted or unsubstituted siloxanyl group;

$Z_{21}$ and $Z_{22}$ are each independently a substituent, or are mutually bonded to form a ring; and $Z_{21}$ and $Z_{22}$ serving as a substituent are each independently selected from the group consisting of a halogen atom, a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

When the second compound is a fluorescent compound, the second compound preferably emits light having a main peak wavelength in a range from 400 nm to 700 nm.

Herein, the main peak wavelength means a peak wavelength of a fluorescence spectrum exhibiting a maximum luminous intensity among fluorescence spectra measured in a toluene solution in which a measurement target compound is dissolved at a concentration ranging from $10^{-6}$ mol/l to $10^{-5}$ mol/l. A spectrophotofluorometer (F-7000 manufactured by Hitachi High-Tech Science Corporation) is used as a measurement device.

The second compound preferably exhibits red or green light emission.

Herein, the red light emission refers to light emission whose main peak wavelength of fluorescence spectrum is in a range from 600 nm to 660 nm.

When the second compound is a red fluorescent compound, the main peak wavelength of the second compound is preferably in a range from 600 nm to 660 nm, more preferably in a range from 600 nm to 640 nm, further preferably in a range from 610 nm to 630 nm.

Herein, the green light emission refers to light emission whose main peak wavelength of fluorescence spectrum is in a range from 500 nm to 560 nm.

When the second compound is a green fluorescent compound, the main peak wavelength of the second compound is preferably in a range from 500 nm to 560 nm, more preferably in a range from 500 nm to 540 nm, further preferably in a range from 510 nm to 530 nm.

Herein, the blue light emission refers to a light emission in which a main peak wavelength of fluorescence spectrum is in a range from 430 nm to 480 nm.

When the second compound is a blue fluorescent compound, the main peak wavelength of the second compound is preferably in a range from 430 nm to 480 nm, more preferably in a range from 445 nm to 480 nm.

Manufacturing Method of Second Compound

The second compound can be manufactured by a known method.

Specific Examples of Second Compound

Examples of the second compound according to the exemplary embodiment are shown below. It should be noted that the second compound of the invention is not limited to the specific examples.

A coordinate bond between a boron atom and a nitrogen atom in a pyrromethene skeleton is shown by various means such as a solid line, a broken line, an arrow, and omission. Herein, the coordinate bond is shown by a solid line or a broken line, or the description of the coordinate bond is omitted.

[Formula 87]
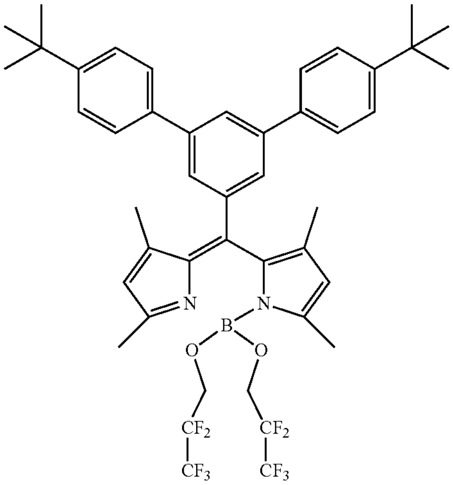
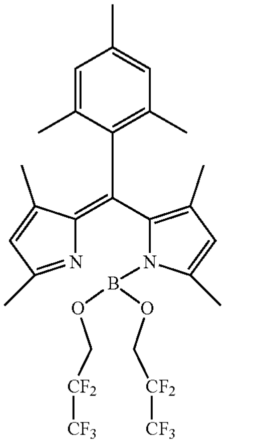
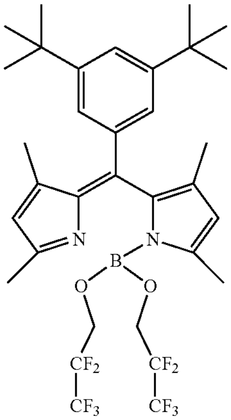
[Formula 88]
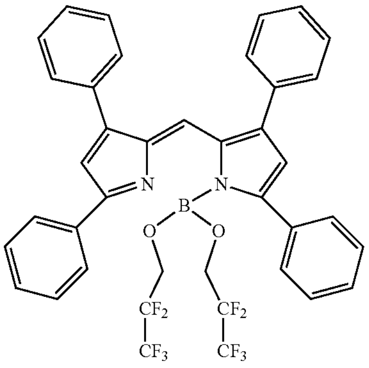
-continued
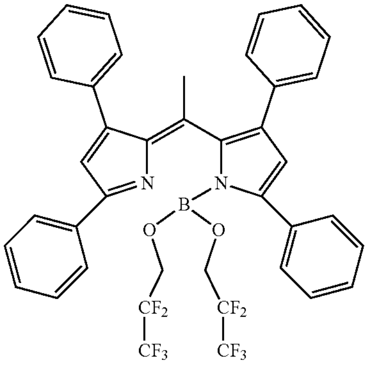
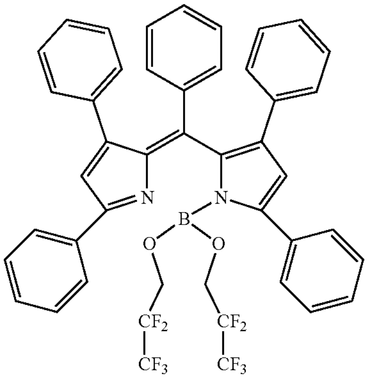
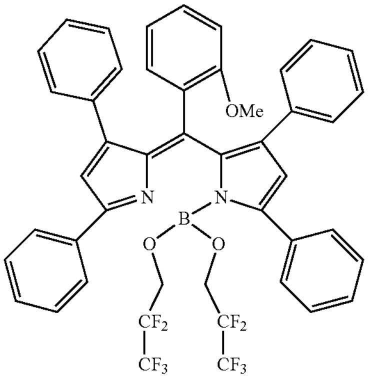
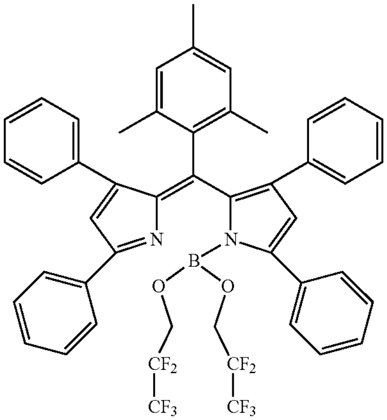

-continued
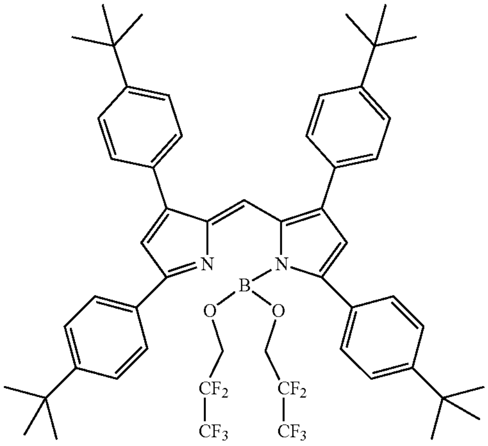
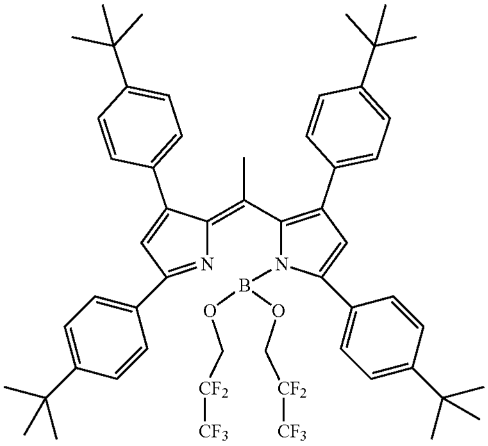
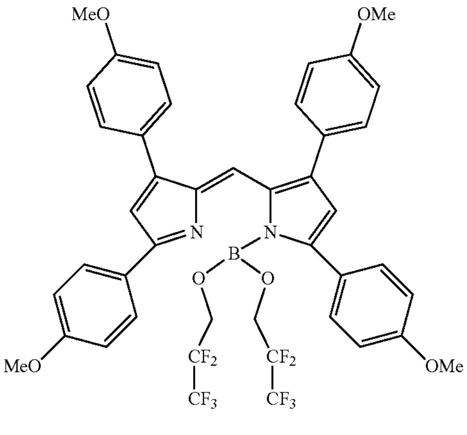
-continued
[Formula 89]
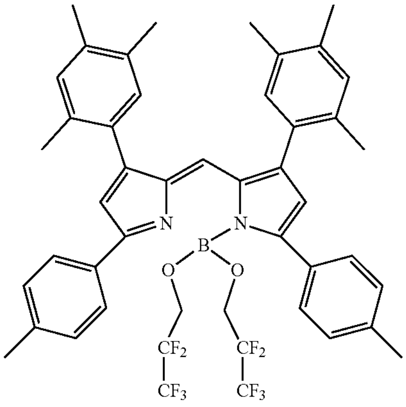
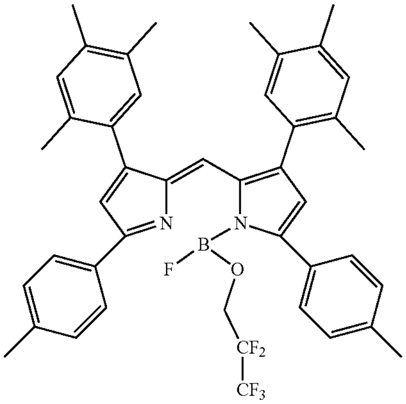
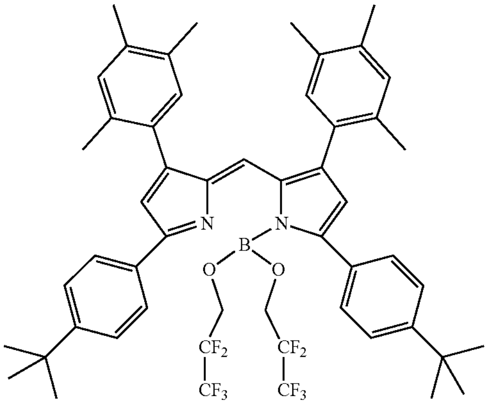

[Formula 90]
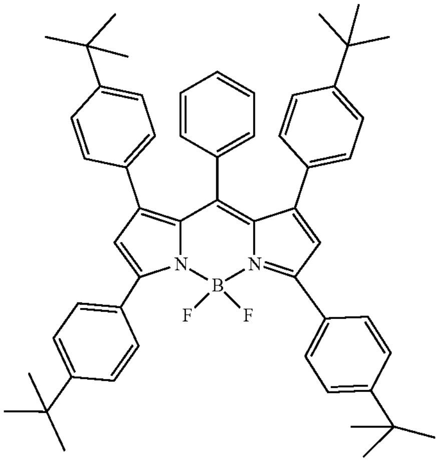
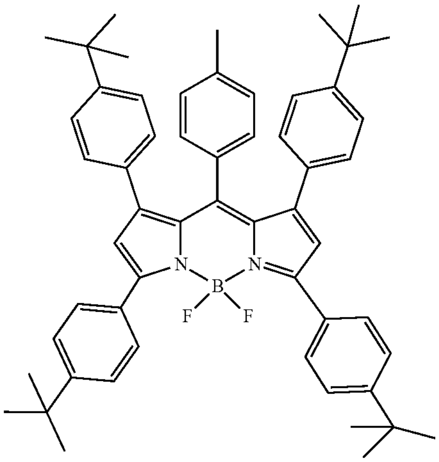
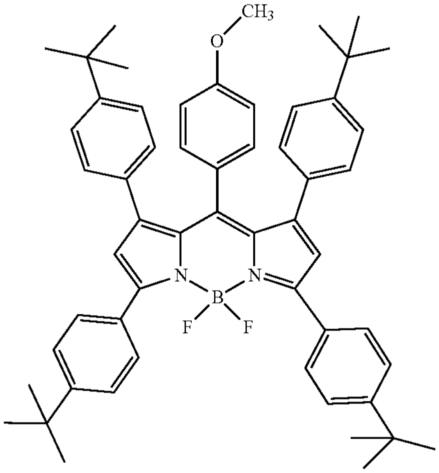
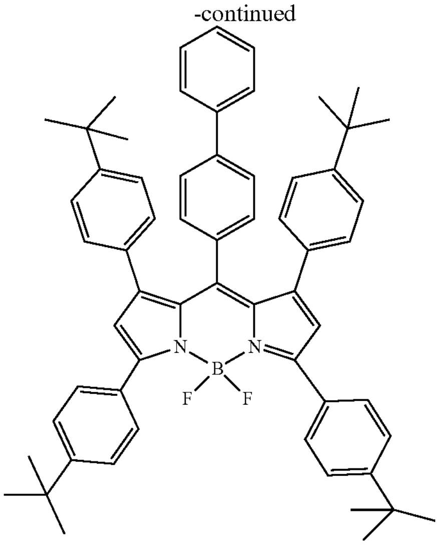
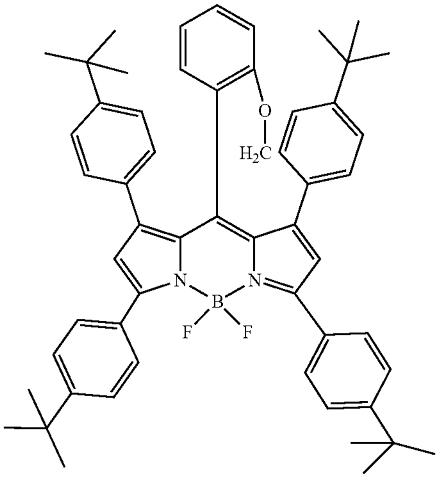
[Formula 91]
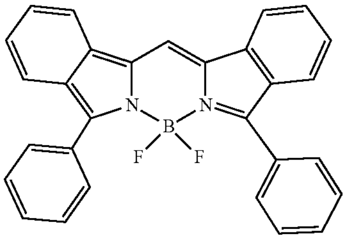
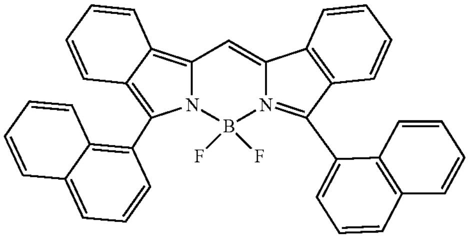

-continued
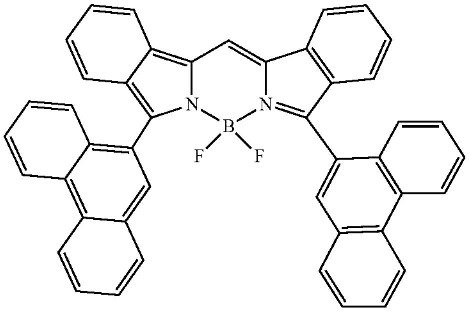
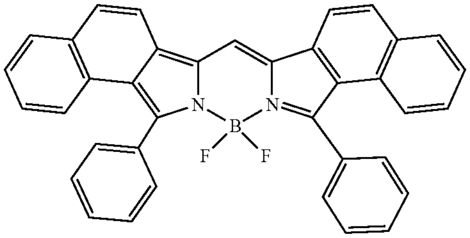
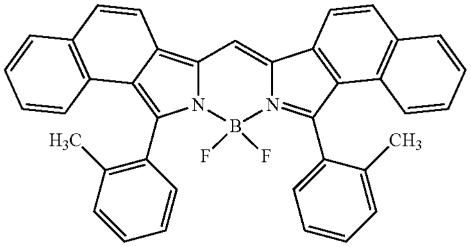
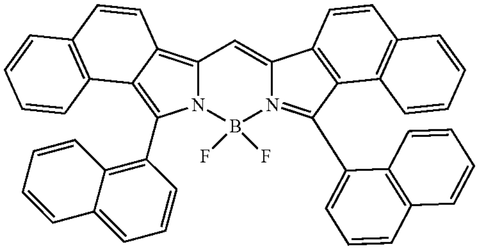
[Formula 92]
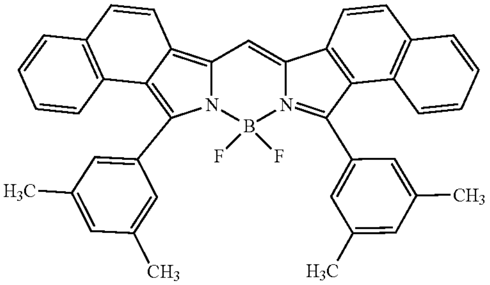
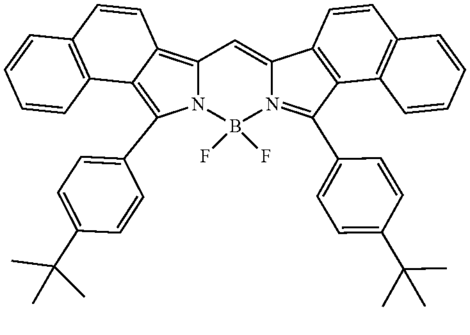
-continued
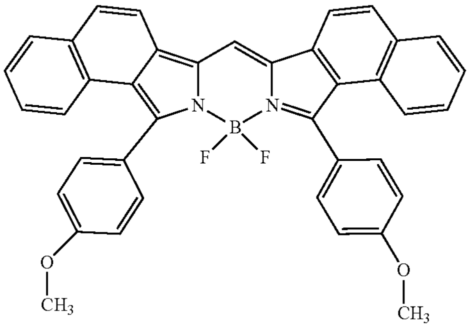
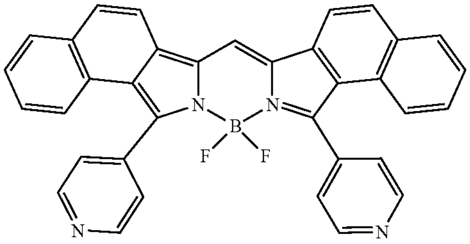
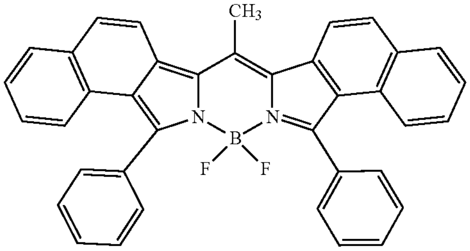
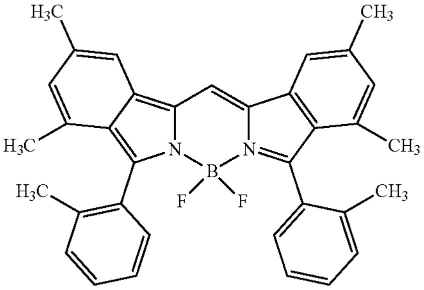
[Formula 93]
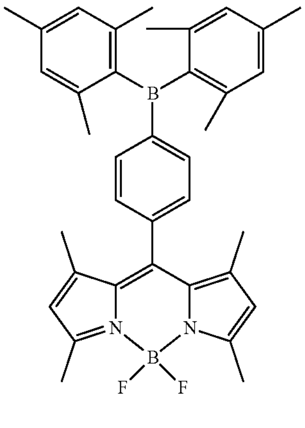

-continued

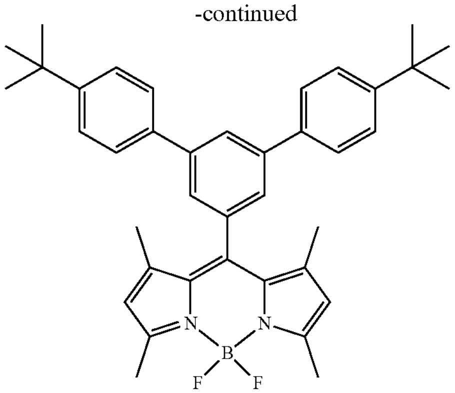

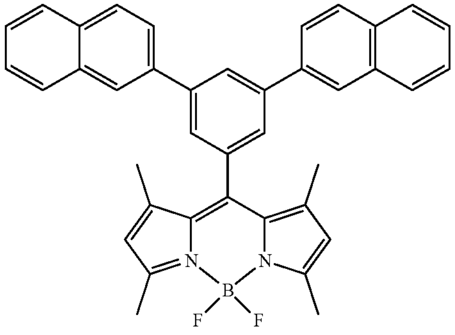

Relationship between First Compound and Second Compound in Emitting Layer

In the organic EL device of the third exemplary embodiment, a lowest singlet energy $S_1(M1)$ of the first compound and a lowest singlet energy $S_1(M2)$ of the second compound preferably satisfy a relationship of a numerical formula (Numerical Formula 3) below.

$$S_1(M1)>S_1(M2) \quad \text{(Numerical Formula 3)}$$

An energy gap $T_{77K}(M1)$ at 77K of the first compound is preferably larger than an energy gap $T_{77K}(M2)$ at 77K of the second compound. In other words, a relationship of the following numerical formula (Numerical Formula 5) is preferably satisfied.

$$T_{77K}(M1)>T_{77K}(M2) \quad \text{(Numerical Formula 5)}$$

When the organic EL device according to the exemplary embodiment emits light, it is preferable that the second compound mainly emits light in the emitting layer.

TADF Mechanism

Figure 4:
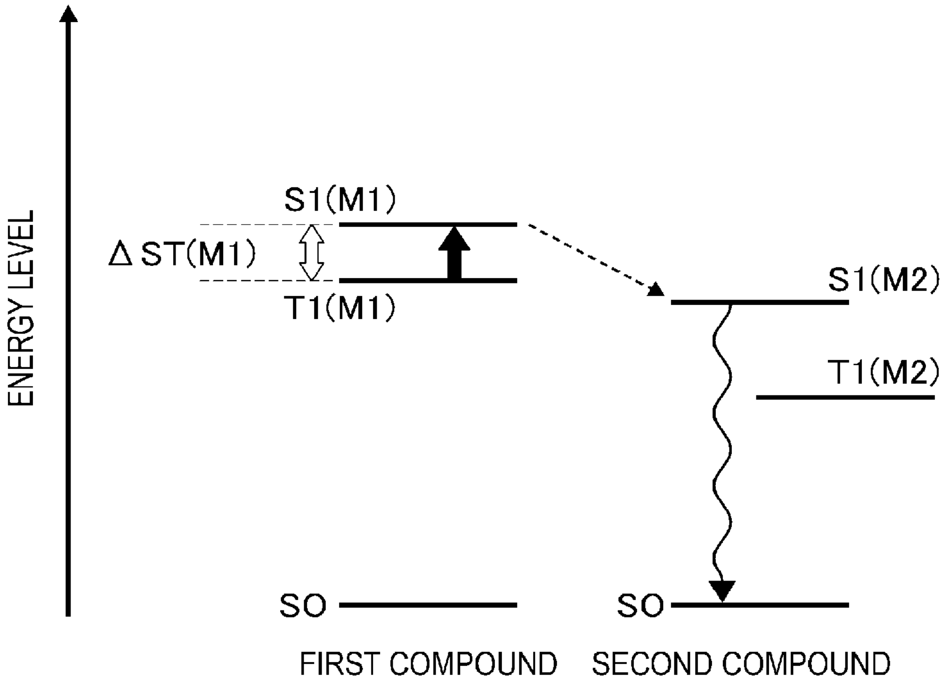
FIG. 4 shows a relationship in energy level and energy transfer between a first compound and a second compound in an emitting layer in the exemplary arrangement of the organic electroluminescence device according to the third exemplary embodiment of the invention.

FIG. 4 shows an example of a relationship between energy levels of the second compound M2 and the first compound M1 in the emitting layer. In FIG. 4, S0 represents a ground state. S1(M1) represents the lowest singlet state of the first compound M1. T1(M1) represents the lowest triplet state of the first compound M1. S1(M2) represents the lowest singlet state of the second compound M2. T1(M2) represents the lowest triplet state of the second compound M2.

A dashed arrow directed from S1(M1) to S1(M2) in FIG. 4 represents Förster energy transfer from the lowest singlet state of the first compound M1 to the lowest singlet state of the second compound M2.

As shown in FIG. 4, when a compound having a small ΔST(M1) is used as the first compound M1, inverse intersystem crossing from the lowest triplet state T1(M1) to the lowest singlet state S1(M1) can be caused by a heat energy. Subsequently, Fbrster energy transfer from the lowest singlet state S1(M1) of the first compound M1 to the second compound M2 occurs to generate the lowest singlet state S1(M2). Consequently, fluorescence from the lowest singlet state S1(M2) of the second compound M2 can be observed. It is inferred that the internal quantum efficiency can be theoretically raised up to 100% also by using delayed fluorescence by the TADF mechanism.

The organic EL device according to the exemplary embodiment preferably emits red light or green light.

When the organic EL device according to the exemplary embodiment emits green light, a main peak wavelength of the light emitted from the organic EL device is preferably in a range from 500 nm to 560 nm.

When the organic EL device according to the exemplary embodiment emits red light, a main peak wavelength of the light emitted from the organic EL device is preferably in a range from 600 nm to 660 nm.

When the organic EL device according to the exemplary embodiment emits blue light, a main peak wavelength of the light emitted from the organic EL device is preferably in a range from 430 nm to 480 nm.

A main peak wavelength of the light emitted from the organic EL device is measured as follows.

Voltage is applied on the organic EL devices such that a current density becomes 10 mA/$cm^2$, where spectral radiance spectrum is measured by a spectroradiometer CS-2000 (manufactured by Konica Minolta, Inc.).

A peak wavelength of an emission spectrum, at which the luminous intensity of the resultant spectral radiance spectrum is at the maximum, is measured and defined as the main peak wavelength (unit: nm).

Film Thickness of Emitting Layer

A film thickness of the emitting layer of the organic EL device in the exemplary embodiment is preferably in a range from 5 nm to 50 nm, more preferably in a range from 7 nm to 50 nm, most preferably in a range from 10 nm to 50 nm. When the film thickness of the emitting layer is 5 nm or more, the formation of the emitting layer and the adjustment of the chromaticity are easy. When the film thickness of the emitting layer is 50 nm or less, an increase in the drive voltage is likely to be reducible.

Content Ratios of Compounds in Emitting Layer

Content ratios of the first and second compounds contained in the emitting layer preferably fall, for instance, within a range below.

The content ratio of the first compound is preferably in a range from 10 mass % to 80 mass %, more preferably in a range from 10 mass % to 60 mass %, further preferably in a range from 20 mass % to 60 mass %. Further, the content ratio of the first compound may be in a range from 90 mass % to 99.9 mass %, from 95 mass % to 99.9 mass %, or from 99 mass % to 99.9 mass %.

The content ratio of the second compound is preferably in a range from 0.01 mass % to 10 mass %, more preferably in a range from 0.01 mass % to 5 mass %, further preferably in a range from 0.01 mass % to 1 mass %.

In the exemplary embodiment, it is not excluded that a material other than the first compound and the second compound is contained in the emitting layer.

The emitting layer may contain only one type of the first compound or contain two or more types thereof. The emitting layer may contain only one type of the second compound or contain two or more types thereof.

Substrate

The substrate is used as a support for the organic EL device. For instance, glass, quartz, plastics and the like are usable for the substrate. A flexible substrate is also usable.

The flexible substrate means a substrate that can be bent. Examples of the flexible substrate include a plastic substrate made using polycarbonate, polyarylate, polyethersulfone, polypropylene, polyester, polyvinyl fluoride, and polyvinyl chloride. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since a hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, a mixture thereof, or the like having a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide are usable for forming the cathode regardless of a magnitude of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of 10-6 cm2/Vs or more.

For the hole transporting layer, a carbazole derivative such as CBP, CzPA, and PCzPA and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. A layer containing the substance exhibiting a higher hole transportability may be provided in the form of a single layer or a laminated layer of two or more layers of the above substance(s).

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tent-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. The above-described substances mostly have an electron mobility of $10^{-6}$ $cm^2/Vs$ or more. It should be noted that any substance other than the above substance may be used for the electron transporting layer as long as the substance exhibits a higher electron transportability than the hole transportability. Moreover, the electron transporting layer may be provided in the form of a single layer or a laminated layer of two or more layers of the above substance(s).

Further, a high polymer compound is usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Film Thickness

A thickness of each of the organic layers in the organic EL device according to the exemplary embodiment is not limited except for the above particular description. In general, the thickness preferably ranges from several nanometers to 1 μm because excessively small film thickness is likely to cause defects (e.g. pin holes) and excessively large thickness leads to the necessity of applying high voltage and consequent reduction in efficiency.

The organic EL device according to the third exemplary embodiment contains the first compound that is the compound according to the first exemplary embodiment and the second compound having the lowest singlet energy smaller than that of the first compound in the emitting layer.

The organic EL device according to the third exemplary embodiment contains the compound according to the first exemplary embodiment (first compound) having a high PLQY. Thus, the third exemplary embodiment can provide a high-performance organic EL device. The performance of the organic EL device is evaluable in terms of, for instance, luminance, emission wavelength, chromaticity, emission efficiency, drive voltage, and lifetime.

The organic EL device according to the third exemplary embodiment is applicable to an electronic device such as a display device and a light-emitting device.

Fourth Exemplary Embodiment

An arrangement of an organic EL device according to a fourth exemplary embodiment will be described below. In the description of the fourth exemplary embodiment, the same components as those in the third exemplary embodiment are denoted by the same reference signs and names to simplify or omit an explanation of the components. In the fourth exemplary embodiment, any materials and compounds that are not specified may be the same as those in the third exemplary embodiment.

The organic EL device according to the fourth exemplary embodiment is different from the organic EL device according to the third exemplary embodiment in that the emitting layer further includes a third compound. The rest of the arrangement of the organic EL device according to the fourth exemplary embodiment is the same as in the third exemplary embodiment.

Specifically, in the fourth exemplary embodiment, the emitting layer as the first organic layer contains the first compound, the second compound and the third com pound.

In this arragement, the first compound is preferably a host material, and the second compound is preferably a dopant material.

Third Compound

The third compound may be a delayed fluorescent compound and a compound that does not exhibit delayed fluorescence.

The third compound is not particularly limited, but is preferably a compound other than an amine compound. Although the third compound may be a carbazole derivative, dibenzofuran derivative, or dibenzothiophene derivative, the third compound is not limited thereto.

The third compound is also preferably a compound containing, in a molecule, at least one of a partial structure represented by a formula (31) below, a partial structure represented by a formula (32) below, a partial structure represented by a formula (33A) below, or a partial structure represented by a formula (34B) below.

[Formula 94]

(31)

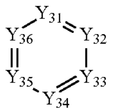

(32)

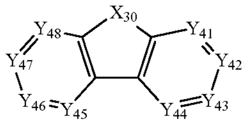

(33A)

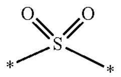

(34A)

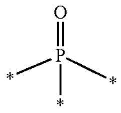

In the formula (31), $Y_{31}$ to $Y_{36}$ each independently represent a nitrogen atom or a carbon atom bonded to another atom in the molecule of the third compound.

At least one of $Y_{31}$ to $Y_{36}$ is a carbon atom bonded to another atom in the molecule of the third compound.

In the formula (32), $Y_{41}$ to $Y_{48}$ each independently represent a nitrogen atom or a carbon atom bonded to another atom in the molecule of the third compound.

At least one of $Y_{41}$ to $Y_{48}$ is a carbon atom bonded to another atom in the molecule of the third compound.

$X_{30}$ represents a nitrogen atom bonded to another atom in the molecule of the third compound, an oxygen atom, or a sulfur atom.

* in the formulae (33A) and (34A) each independently represents a bonding position to another atom or another structure in the molecule of the third compound.

In the formula (32), it is also preferable that at least two of $Y_{41}$ to $Y_{48}$ are carbon atoms bonded to other atoms in the molecule of the third compound to form a cyclic structure including the carbon atoms.

For instance, the partial structure represented by the formula (32) is preferably any one selected from the group consisting of partial structures represented by formulae (321), (322), (323), (324), (325) and (326).

[Formula 95]

(321)

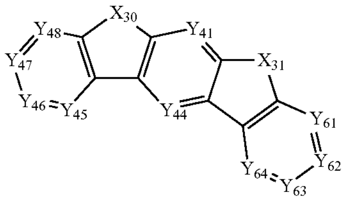

(322)

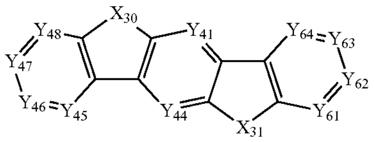

[Formula 96]

(323)

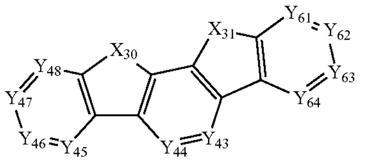

(324)

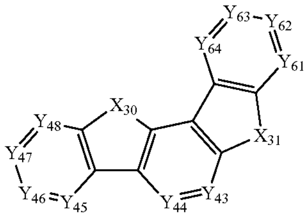

[Formula 97]

(325)

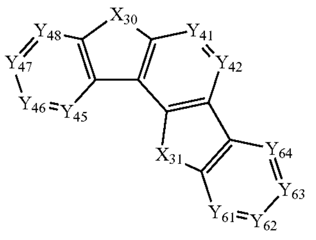

(326)

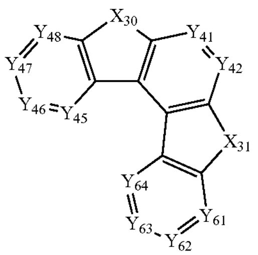

In the formulae (321) to (326), $X_{30}$ each independently represents a nitrogen atom bonded to another atom in the molecule of the third compound, an oxygen atom, ora sulfur atom.

$Y_{41}$ to $Y_{48}$ each independently represent a nitrogen atom or a carbon atom bonded to another atom in the molecule of the third compound.

$X_{31}$ each independently represents a nitrogen atom bonded to another atom in the molecule of the third compound, an oxygen atom, a sulfur atom, or a carbon atom bonded to another atom in the molecule of the third compound.

$Y_6$ to $Y_{64}$ each independently represent a nitrogen atom or a carbon atom bonded to another atom in the molecule of the third compound.

In the exemplary embodiment, the third compound preferably has the partial structure represented by the formula (323) among those represented by the formulae (323) to (326).

The partial structure represented by the formula (31) is preferably included in the third compound as at least one group selected from the group consisting of a group represented by a formula (33) and a group represented by a formula (34) below.

It is also preferable that the third compound has at least one of the partial structures represented by the formulae (33) and (34). Since bonding positions are situated in meta positions as shown in the partial structures represented by the formulae (33) and (34), an energy gap $T_{77K}$(M3) at 77 K of the third compound can be kept high.

[Formula 98]

(33)

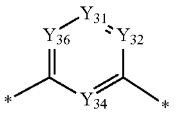

(34)

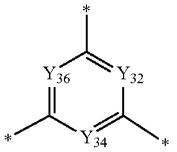

In the formula (33), $Y_{31}$, $Y_{32}$, $Y_{34}$ and $Y_{36}$ are each independently a nitrogen atom or $CR_{31}$.

In the formula (34), $Y_{32}$, $Y_{34}$ and $Y_{36}$ are each independently a nitrogen atom or $CR_{31}$.

In the formulae (33) and (34), $R_{31}$ each independently represents a hydrogen atom or a substituent.

$R_{31}$ as a substituent is each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

The substituted or unsubstituted aryl group having 6 to 30 ring carbon atoms for $R_{31}$ is preferably a non-fused ring.

* in the formulae (33) and (34) each independently represents a bonding position to another atom or another structure in the molecule of the third compound.

In the formula (33), $Y_{31}$, $Y_{32}$, $Y_{34}$ and $Y_{36}$ are each independently preferably $CR_{31}$, in which a plurality of $R_{31}$ are the same or different.

In the formula (34), $Y_{32}$, $Y_{34}$ and $Y_{36}$ are each independently preferably $CR_{31}$, in which a plurality of $R_{31}$ are the same or different.

The substituted germanium group is preferably represented by —Ge($R_{301}$)$_3$. $R_{301}$ is each independently a substituent. The substituent $R_{301}$ is preferably a substituted or unsubstituted alkyl group having 1 to 30 carbon atoms or a substituted or unsubstituted aryl group having 6 to 30 ring carbon atoms. A plurality of $R_{301}$ are mutually the same or different.

The partial structure represented by the formula (32) is preferably included in the third compound as at least one group selected from the group consisting of groups represented by formulae (35) to (39) and a group represented by a formula (30a).

[Formula 99]

(35)

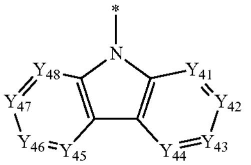

(36)

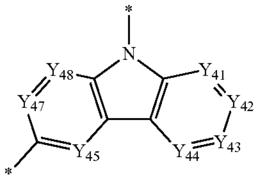

[Formula 100]

(37)

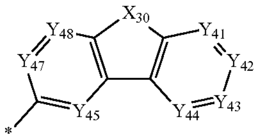

(38)

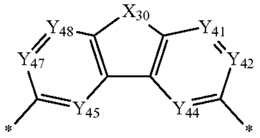

[Formula 101]

(39)

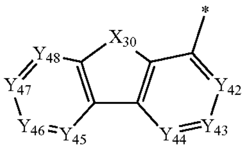

(30a)

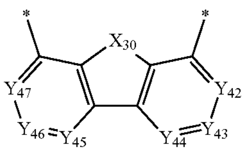

In the formula (35), $Y_{41}$ to $Y_{48}$ are each independently a nitrogen atom or $CR_{32}$.

In the formulae (36) and (37), $Y_{41}$ to $Y_{45}$, $Y_{47}$ and $Y_{48}$ are each independently a nitrogen atom or $CR_{32}$.

In the formula (38), $Y_{41}$, $Y_{42}$, $Y_{44}$, $Y_{45}$, $Y_{47}$ and $Y_{48}$ are each independently a nitrogen atom or $CR_{32}$.

In the formula (39), $Y_{42}$ to $Y_{48}$ are each independently a nitrogen atom or $CR_{32}$.

In the formula (30a), $Y_{42}$ to $Y_{47}$ are each independently a nitrogen atom or $CR_{32}$.

In the formulae (35) to (39) and (30a), $R_{32}$ each independently represents a hydrogen atom or a substituent.

$R_{32}$ as a substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

A plurality of $R_{32}$ are the same or different.

In the formulae (37) to (39) and (30a), $X_{30}$ is $NR_{33}$, an oxygen atom or a sulfur atom.

$R_{33}$ is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a fluorine atom, a cyano group, a nitro group, and a substituted or unsubstituted carboxy group.

A plurality of $R_{33}$ are the same or different.

The substituted or unsubstituted aryl group having 6 to 30 ring carbon atoms for $R_{33}$ is preferably a non-fused ring.

* in the formulae (35) to (39) and (30a) each independently represents a bonding position toanother atom or another structure in the molecule of the third com pound.

In the formula (35), $Y_{41}$ to $Y_{48}$ are each independently preferably $CR_{32}$. In the formulae (36) and (37), $Y_{41}$ to $Y_{45}$, $Y_{47}$ and $Y_{48}$ are each independently preferably $CR_{32}$. In the formula (38), $Y_{41}$, $Y_{42}$, $Y_{44}$, $Y_{45}$, $Y_{47}$ and $Y_{48}$ are each independently preferably $CR_{32}$. In the formula (39), $Y_{42}$ to $Y_{48}$ are each independently preferably $CR_{32}$. In the formula (30a), $Y_{42}$ to $Y_{47}$ are each independently preferably $CR_{32}$. A plurality of $R_{32}$ are the same or different.

In the third compound, $X_{30}$ is preferably an oxygen atom or a sulfur atom, more preferably an oxygen atom.

In the third compound, $R_{31}$ and $R_{32}$ each independently represent a hydrogen atom or a substituent. $R_{31}$ and $R_{32}$ as the substituents are preferably each independently a group selected from the group consisting of a fluorine atom, a cyano group, a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms. $R_{31}$ and $R_{32}$ are more preferably a hydrogen atom, a cyano group, a substituted or unsubstituted aryl group having 6 to 30 ring carbon atoms, or a substituted or unsubstituted heteroaryl group having 5 to 30 ring atoms. When $R_{31}$ and $R_{32}$ as the substituents are each a substituted or unsubstituted aryl group having 6 to 30 ring carbon atoms, the aryl group is preferably a non-fused ring.

It is also preferable that the third compound is an aromatic hydrocarbon compound or an aromatic heterocyclic compound.

Manufacturing Method of Third Compound

The third compound can be manufactured by methods disclosed in International Publication No. WO2012/153780, International Publication No. WO2013/038650, and the like. Furthermore, the second compound can be manufactured, for instance, by application of known substitution reactions and/or materials depending on a target compound.

Examples of the substituent in the third compound are shown below, but the invention is not limited thereto.

Specific examples of an aryl group (occasionally referred to as an aromatic hydrocarbon group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarter phenyl group, fluoranthenyl group, among which a phenyl group, biphenyl group, terphenyl group, quarter phenyl group, naphthyl group, triphenylenyl group, fluorenyl group and the like are preferable.

Specific examples of the aryl group having a substituent include a tolyl group, xylyl group and 9,9-dimethylfluorenyl group.

As is understood from the specific examples, the aryl group includes both fused aryl group and non-fused aryl group.

Preferable examples of the aryl group include a phenyl group, biphenyl group, terphenyl group, quarterphenyl group, naphthyl group, triphenylenyl group and fluorenyl group.

Specific examples of the heteroaryl group (occasionally referred to as a heterocyclic group, heteroaromatic ring group or aromatic heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothienyl group, dibenzothienyl group, azadibenzothienyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothienyl group, carbazolyl group, pyridyl group, pyrimidinyl group, triazinyl group, azadibenzofuranyl group, azadibenzothienyl group and the like are preferable.

The heteroaryl group is preferably a dibenzofuranyl group, dibenzothienyl group, carbazolyl group, pyridyl group, pyrimidinyl group, triazinyl group, azadibenzofuranyl group or azadibenzothienyl group, and more preferably a dibenzofuranyl group, dibenzothienyl group, azadibenzofuranyl group and azadibenzothienyl group.

In the third compound, it is also preferable that the substituted silyl group is selected from the group consisting of a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and triethylsilyl group.

Specific examples of the substituted or unsubstituted arylalkylsilyl group include diphenylmethylsilyl group, ditolylmethylsilyl group, and phenyldimethylsilyl group.

Specific examples of the substituted or unsubstituted triarylsilyl group include triphenylsilyl group and tritolylsilyl group.

In the third compound, it is also preferable that the substituted phosphine oxide group is a substituted or unsubstituted diaryl phosphine oxide group.

Specific examples of the substituted or unsubstituted diaryl phosphine oxide group include a diphenyl phosphine oxide group and ditolyl phosphine oxide group.

In the third compound, the substituted carboxy group is exemplified by a benzoyloxy group.

Specific Examples of Third Compound

Specific examples of the third compound in the exemplary embodiment are shown below. It should be noted that the third compound of the invention is not limited to the specific examples.

[Formula 102]

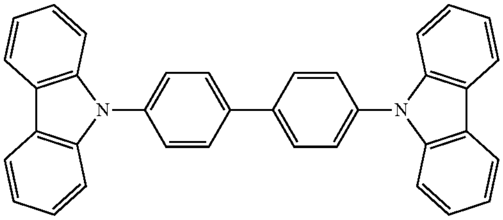

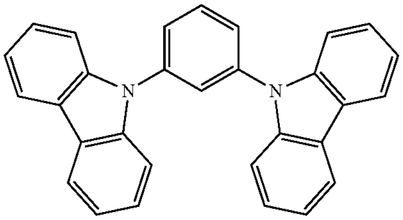

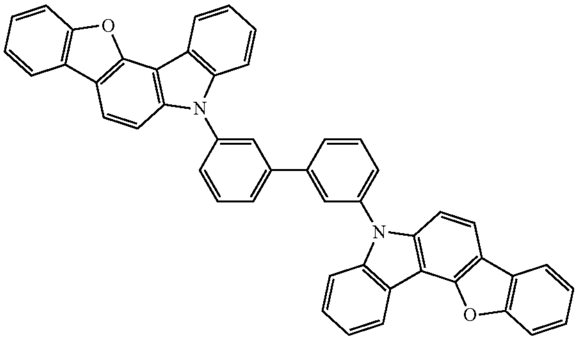

-continued

[Formula 103]

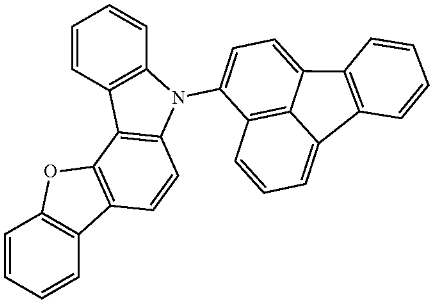

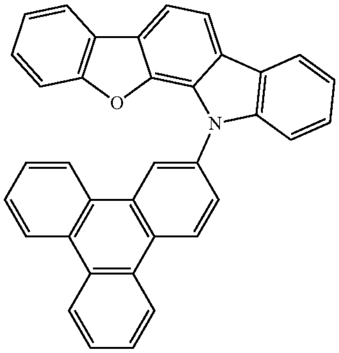

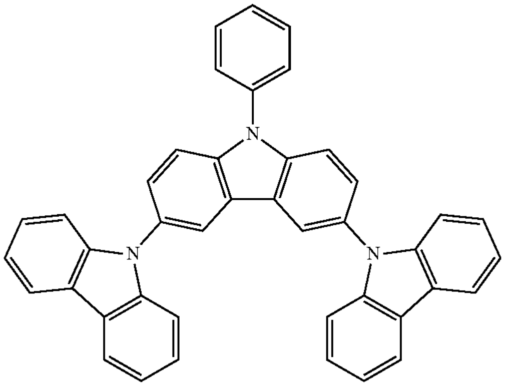

[Formula 104]

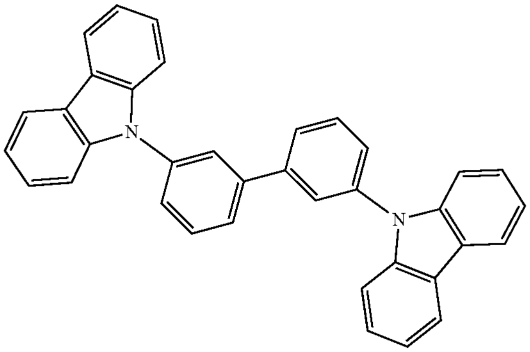

-continued

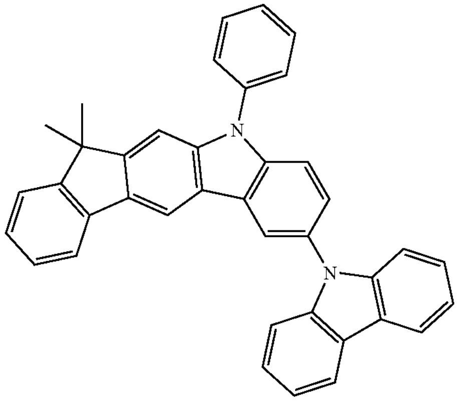

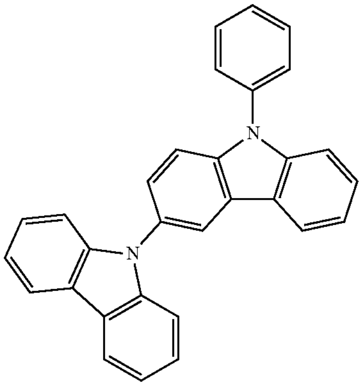

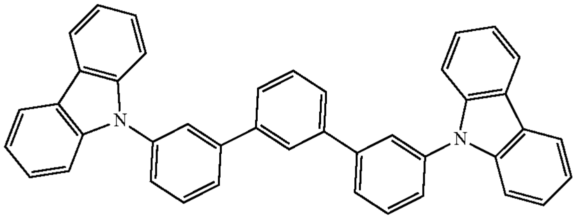

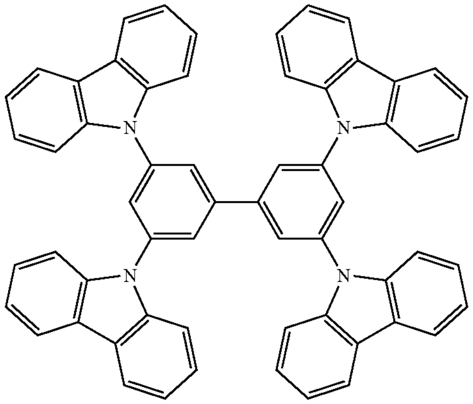

[Formula 105]

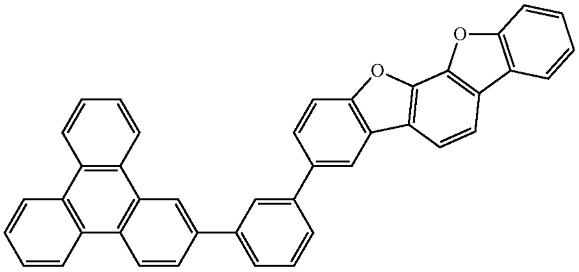

-continued

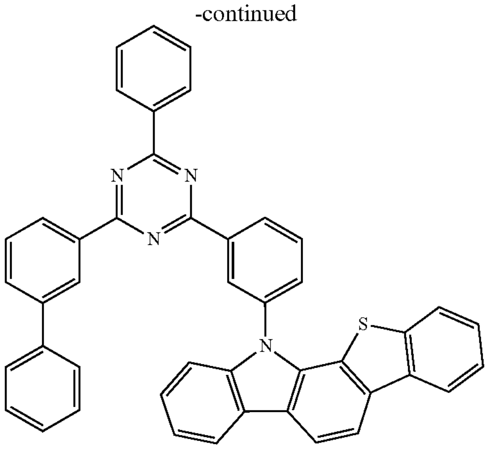

Relationship between First Compound, Second Compound and Third Compound in Emitting Layer In the organic EL device according to the exemplary embodiment, the lowest singlet energy $S_1(M1)$ of the first compound and a lowest singlet energy $S_1(M3)$ of the third compound preferably satisfy a relationship of a numerical formula (Numerical Formula 2) below.

$$S_1(M3)>S_1(M1) \quad \text{(Numerical Formula 2)}$$

An energy gap $T_{177K}(M3)$ at 77K of the third compound is preferably larger than an energy gap $T_{177K}(M1)$ at 77K of the first compound.

The energy gap $T_{77K}(M3)$ at 77K of the third compound is preferably larger than an energy gap $T_{77K}(M2)$ at 77K of the second compound.

A lowest singlet energy $S_1(M1)$ of the first compound, the lowest singlet energy $S_1(M2)$ of the second compound, and the lowest singlet energy $S_1(M3)$ of the third compound preferably satisfy a relationship of a numerical formula (Numerical Formula 2A) below.

$$S_1(M3)>S_1(M1)>S_1(M2) \quad \text{(Numerical Formula 2A)}$$

An energy gap $T_{177K}(M1)$ at 77K of the first compound, an energy gap $T_{77K}(M2)$ at 77K of the second compound, and an energy gap $T_{77K}(M3)$ at 77K of the third compound preferably satisfy a relationship of a numerical formula (Numerical Formula 2B) below.

$$T_{77K}(M3)>T_{77K}(M1)>T_{77K}(M2) \quad \text{(Numerical Formula 2B)}$$

When the organic EL device according to the exemplary embodiment emits light, it is preferable that the fluorescent compound in the emitting layer mainly emits light.

The organic EL device of the fourth exemplary embodiment preferably emits red light or green light in the same manner as the organic EL device of the third exemplary embodiment.

A main peak wavelength of the organic EL device can be measured by the same method as that for the organic EL device of the third exemplary embodiment.

Content Ratios of Compounds in Emitting Layer

Content ratios of the first, second and third compounds in the emitting layer preferably fall, for instance, within a range below.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

The content ratio of the third compound is preferably in a range from 10 mass % to 80 mass %.

An upper limit of the total of the respective content ratios of the first, second and third compounds in the emitting layer is 100 mass %. It should be noted that the emitting layer of the exemplary embodiment may further contain material(s) other than the first, second and third compounds.

The emitting layer may contain a single type of the first compound or may contain two or more types of the first compound. The emitting layer may contain a single type of the second compound or may contain two or more types of the second compound. The emitting layer may contain a single type of the third compound or may contain two or more types of the third compound.

Figure 5:
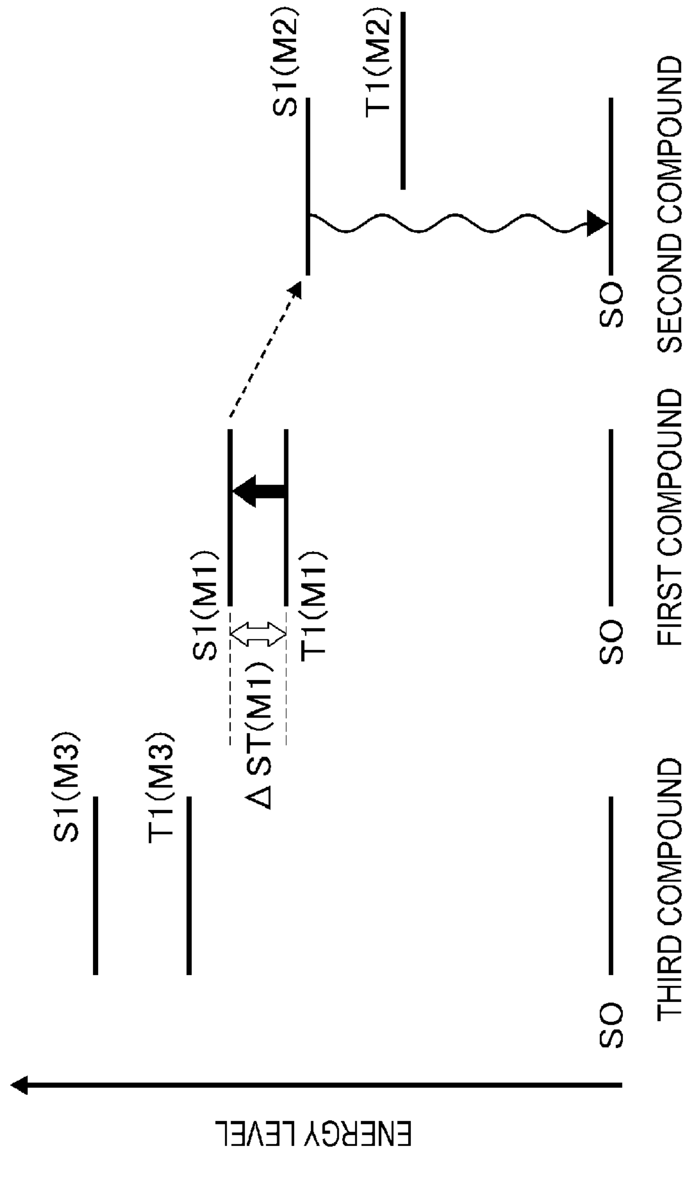
FIG. 5 shows a relationship in energy level and energy transfer between the first compound, the second compound and a third compound in an emitting layer in an exemplary arrangement of an organic electroluminescence device according to a fourth exemplary embodiment of the invention.

FIG. 5 shows an example of a relationship between energy levels of the first, second and third compounds in the emitting layer. In FIG. 5, S0 represents a ground state. S1(M1) represents the lowest singlet state of the first compound. T1(M1) represents the lowest triplet state of the first compound. S1(M2) represents the lowest singlet state of the second compound. T1(M2) represents the lowest triplet state of the second compound. S1(M3) represents the lowest singlet state of the third compound. T1(M3) represents the lowest triplet state of the third compound. A dashed arrow directed from S1(M1) to S1(M2) in FIG. 5 represents Förster energy transfer from the lowest singlet state of the first compound to the lowest singlet state of the second compound.

As shown in FIG. 5, when a compound having a small ΔST(M1) is used as the first compound, inverse intersystem crossing from the lowest triplet state T1(M1) to the lowest singlet state S1(M1) can be caused by a heat energy. Subsequently, Förster energy transfer from the lowest singlet state S1(M1) of the first compound to the second compound occurs to generate the lowest singlet state S1(M2). Consequently, fluorescence from the lowest singlet state S1(M2) of the second compound can be observed. It is inferred that the internal quantum efficiency can be theoretically raised up to 100% also by using delayed fluorescence by the TADF mechanism.

The organic EL device according to the fourth exemplary embodiment contains the first compound that is the compound according to the first exemplary embodiment, the second compound having the lowest singlet energy smaller than that of the first compound, and the third compound having the lowest singlet energy larger than that of the first compound in the emitting layer.

The organic EL device according to the fourth exemplary embodiment contains the compound according to the first exemplary embodiment (first compound) having a high PLQY. Thus, the fourth exemplary embodiment can provide a high-performance organic EL device.

The organic EL device according to the fourth exemplary embodiment is applicable to an electronic device such as a display device and a light-emitting device.

Fifth Exemplary Embodiment

An arrangement of an organic EL device according to a fifth exemplary embodiment will be described below. In the description of the fifth exemplary embodiment, the same components as those in the third or fourth exemplary embodiment are denoted by the same reference signs and names to simplify or omit an explanation of the components. In the fifth exemplary embodiment, any materials and compounds that are not specified may be the same as those in the third or fourth exemplary embodiment.

The organic EL device according to the fifth exemplary embodiment is different from the organic EL device according to the third or fourth exemplary embodiment in that the emitting layer contains the first compound and the third compound and does not contain the second compound. The organic EL device according to the fifth exemplary embodiment is otherwise the same as that in the third or fourth exemplary embodiment.

Specifically, in the fifth exemplary embodiment, the emitting layer as the first organic layer contains the first compound and the third compound.

In this arrangement, the third compound is preferably a host material, and the first compound is preferably a dopant material.

In the exemplary embodiment, when the emitting layer contains the compound according to the first exemplary embodiment, the emitting layer preferably does not contain a phosphorescent metal complex and preferably does not contain a metal complex other than the phosphorescent metal complex.

First Compound

The first compound is according to the first exemplary embodiment.

The first compound is preferably a delayed fluorescent compound.

Third Compound

The third compound is the same as the third compound described in the fourth exemplary embodiment.

Relationship between First Compound and Third Compound in Emitting Layer

In the organic EL device according to the exemplary embodiment, the lowest singlet energy $S_1$(M1) of the first compound and the lowest singlet energy $S_1$(M3) of the third compound preferably satisfy the relationship of the numerical formula (Numerical Formula 2) below.

$$S_1(M3)>S_1(M1) \quad \text{(Numerical Formula 2)}$$

The energy gap $T_{77K}$(M3) at 77K of the third compound is preferably larger than the energy gap $T_{177K}$(M1) at 77K of the first compound.

Figure 6:
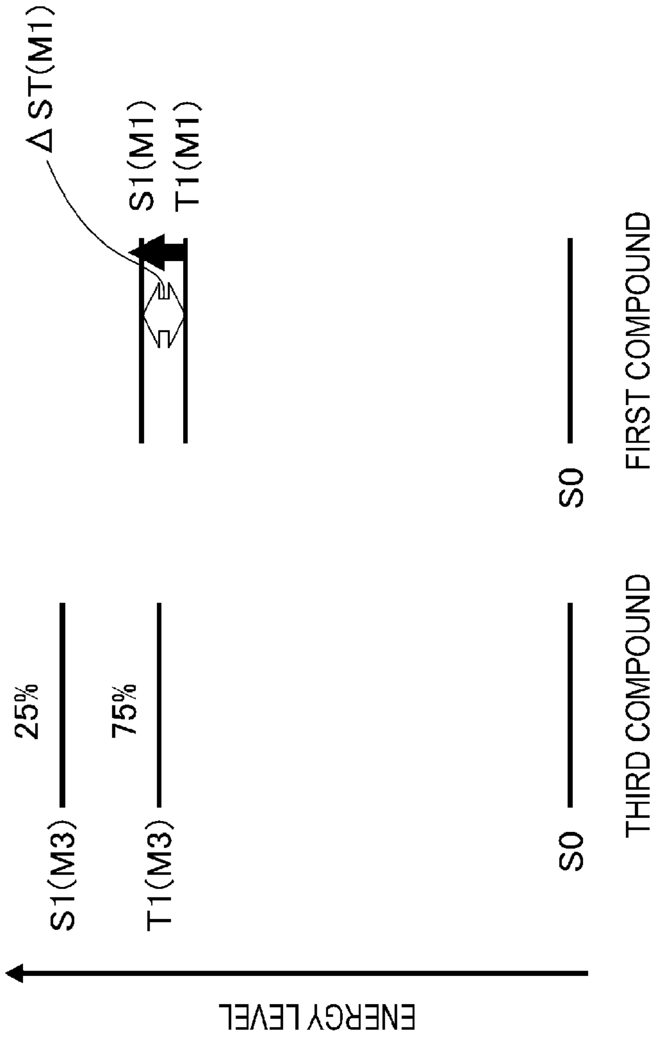
FIG. 6 shows a relationship in energy level and energy transfer between the first compound and the third compound in an emitting layer in an exemplary arrangement of an organic electroluminescence device according to a fifth exemplary embodiment of the invention.

FIG. 6 is an illustration for explaining a principle of light emission according to the exemplary embodiment of the invention.

In FIG. 6, S0 represents a ground state. S1(M1) represents the lowest singlet state of the first compound. T1(M1) represents the lowest triplet state of the first compound. S1(M3) represents the lowest singlet state of the third compound. T1(M3) represents the lowest triplet state of the third compound.

As shown in FIG. 6, when a compound having a small ΔST(M1) is used as the first compound, inverse intersystem crossing from the lowest triplet state T1(M1) of the first compound to the lowest singlet state S1(M1) can be caused by a heat energy.

The inverse intersystem crossing caused in the first compound enables, for instance, light emission shown in (i) or (ii) below to be observed.

(i) When the emitting layer does not contain a fluorescent dopant with the lowest singlet state S1 smaller than the lowest singlet state S1(M1) of the first compound, light emission from the lowest singlet state S1(M1) of the first compound can be observed.

(ii) When the emitting layer contains the fluorescent dopant with the lowest singlet state S1 (second compound that fluoresces in the third or fourth exemplary embodiment)

smaller than the lowest singlet state S1(M1) of the first compound, light emission from the fluorescent dopant can be observed.

It should be noted that in the organic EL device according to the exemplary embodiment, light emission shown in (i) can be observed. In the organic EL device according to the third or fourth exemplary embodiment, light emission shown in (ii) can be observed.

Content Ratios of Compounds in Emitting Layer

A content ratio of each of the first compound and the third compound in the emitting layer preferably falls, for instance, within a range below.

The content ratio of the first compound is preferably in a range from 10 mass % to 90 mass %, more preferably in a range from 10 mass % to 80 mass %, further preferably in a range from 10 mass % to 60 mass %, still further preferably in a range from 20 mass % to 60 mass %.

The content ratio of the third compound is preferably in a range from 10 mass % to 90 mass %.

The upper limit of the total of the content ratios of the first compound and the third compound in the emitting layer is 100 mass %.

The emitting layer may contain a single type of the first compound or may contain two or more types of the first compound. The emitting layer may contain a single type of the third compound or may contain two or more types of the third compound.

The organic EL device according to the fifth exemplary embodiment contains the compound according to the first exemplary embodiment (first compound) having a high PLQY. Thus, the fifth exemplary embodiment can provide a high-performance organic EL device.

The organic EL device according to the fifth exemplary embodiment is applicable to an electronic device such as a display device and a light-emitting device.

Sixth Exemplary Embodiment

Electronic Device

An electronic device according to a sixth exemplary embodiment is installed with any one of the organic EL devices according to the above exemplary embodiments. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Other Explanations

Herein, the phrase "Rx and Ry are mutually bonded to form a ring" means, for instance, that Rx and Ry include a carbon atom, a nitrogen atom, an oxygen atom, a sulfur atom or a silicon atom, the atom(s) contained in Rx (a carbon atom, a nitrogen atom, an oxygen atom, a sulfur atom or a silicon atom) and the atom(s) contained in Ry (a carbon atom, a nitrogen atom, an oxygen atom, a sulfur atom or a silicon atom) are bonded via a single bond(s), a double bond(s), a triple bond, and/or a divalent linking group(s) to form a ring having 5 or more ring atoms (specifically, a heterocycle or an aromatic hydrocarbon ring). x represents a number, a character or a combination of a number and a character. y represents a number, a character or a combination of a number and a character.

The divalent linking group is not limited. Examples of the divalent linking group include —O—, —CO—, $—CO_2—$, —S—, —SO—, $—SO_2—$, —NH—, —NRa—, and a group provided by a combination of two or more of these linking group.

Specific examples of the heterocyclic ring include a cyclic structure (heterocyclic ring) obtained by removing a bond from a "heteroaryl group $Sub_2$" exemplarily shown in the later-described "Description of Each Substituent in Formula." The heterocyclic ring may have a substituent.

Specific examples of the heterocyclic ring include a cyclic structure (heterocyclic ring) obtained by removing a bond from a "aryl group $Sub_1$" exemplarily shown in the later-described "Description of Each Substituent in Formula." The aromatic hydrocarbon ring may have a substituent.

Examples of Ra include a substituted or unsubstituted alkyl group $Sub_3$ having 1 to 30 carbon atoms, a substituted or unsubstituted aryl group $Sub_1$ having 6 to 30 ring carbon atoms, and a substituted or unsubstituted heteroaryl group $Sub_2$ having 5 to 30 ring atoms, which are exemplarily shown in the later-described "Description of Each Substituent in Formula."

Rx and Ry are mutually bonded to form a ring, which means, for instance, that: an atom contained in $Rx_1$ and an atom contained in $Ry_1$ in a molecular structure represented by a formula (E1) below form a ring (cyclic structure) E represented by a formula (E2); an atom contained in $Rx_1$ and an atom contained in $Ry_1$ in a molecular structure represented by a formula (F1) below form a ring F represented by a formula (F2); an atom contained in $Rx_1$ and an atom contained in $Ry_1$ in a molecular structure represented by a formula (G1) below form a ring G represented by a formula (G2); an atom contained in $Rx_1$ and an atom contained in $Ry_1$ in a molecular structure represented by a formula (H1) below form a ring H represented by a formula (H2); and an atom contained in $Rx_1$ and an atom contained in $Ry_1$ in a molecular structure represented by a formula (I1) below form a ring I represented by a formula (I2).

In the formulae (E1) to (I1), * each independently represent a bonding position to another atom in a molecule. The two * in the formulae (E1), (F1), (G1), (H1) and (I1) correspond to two * in the formulae (E2), (F2), (G2), (H2) and (I2), respectively.

[Formula 106]

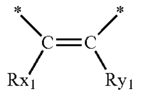
(E1)

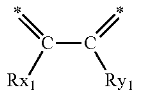
(F1)

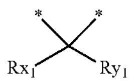
(G1)

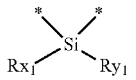
(H1)

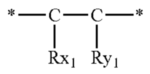
(I1)

[Formula 107]

-continued (E2)

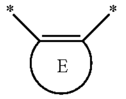

(F2)

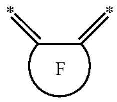

(G2)

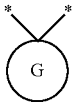

(H2)

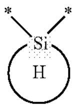

(I2)

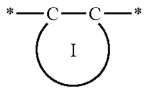

In the molecular structures represented by the formulae (E2) to (I2), E to I each represent a cyclic structure (the ring having 5 or more ring atoms). In the formulae (E2) to (I2), * each independently represent a bonding position to another atom in a molecule. The two * in the formula (E2) correspond to two * in the formula (E1). Similarly, two * in each of the formulae (F2) to (I2) correspond one-to-one to two * in in each of the formulae (F1) to (I1).

For instance, in the formula (E1), when $Rx_1$ and $Ry_1$ are mutually bonded to form the ring E in the formula (E2) and the ring E is an unsubstituted benzene ring, the molecular structure represented by the formula (E1) is a molecular structure represented by a formula (E3) below. Herein, two * in the formula (E3) correspond one-to-one to two * in each of the formulae (E2) and (E1).

For instance, in the formula (E1), when $Rx_1$ and $Ry_1$ are mutually bonded to form the ring E in the formula (E2) and the ring E is an unsubstituted pyrrole ring, the molecular structure represented by the formula (E1) is a molecular structure represented by a formula (E4) below. Herein, two * in the formula (E4) correspond one-to-one to two * in each of the formulae (E2) and (E1). In the formulae (E3) and (E4), * each independently represent a bonding position to another atom in a molecule.

[Formula 108]

(E3)

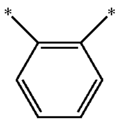

(E4)

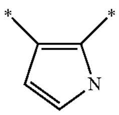

Herein, the ring carbon atoms refer to the number of carbon atoms among atoms forming a ring of a compound (e.g., a monocyclic compound, fused-ring compound, crosslinking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). Atom(s) not forming a ring and atom(s) included in a substituent when the ring is substituted by the substituent are not counted in the number of the ring atoms. Unless specifically described, the same applies to the "ring atoms" described later. For instance, a pyridine ring has six ring atoms, a quinazoline ring has ten ring atoms, and a furan ring has five ring atoms. A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Description of Each Substituent in Formulae

Next, each of substituents in formulae herein will be described.

The aryl group (occasionally referred to as an aromatic hydrocarbon group) herein is exemplified by an aryl group $Sub_1$. The aryl group $Sub_1$ preferably has 6 to 30 ring carbon atoms, more preferably 6 to 20 ring carbon atoms, further preferably 6 to 14 ring carbon atoms, still further preferably 6 to 12 ring carbon atoms.

The aryl group $Sub_1$ herein is at least one group selected from the group consisting of a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

Among the aryl group $Sub_1$, a phenyl group, biphenyl group, naphthyl group, phenanthryl group, terphenyl group and fluorenyl group are preferable. A carbon atom in a position 9 of each of 1-fluorenyl group, 2-fluorenyl group, 3-fluorenyl group and 4-fluorenyl group is preferably substituted by a substituted or unsubstituted alkyl group $Sub_3$ or a substituted or unsubstituted aryl group $Sub_1$ described later herein.

The heteroaryl group (occasionally referred to as a heterocyclic group, heteroaromatic cyclic group or aromatic heterocyclic group) herein is exemplified by a heterocyclic group $Sub_2$. The heterocyclic group $Sub_2$ is a group containing, as a hetero atom(s), at least one atom selected from the group consisting of nitrogen, sulfur, oxygen, silicon, selenium atom and germanium atom. The heterocyclic group $Sub_2$ preferably contains, as a hetero atom(s), at least one atom selected from the group consisting of nitrogen, sulfur and oxygen. The heterocyclic group $Sub_2$ preferably has 5 to 30 ring atoms, more preferably 5 to 20 ring atoms, further preferably 5 to 14 ring atoms.

The heterocyclic group $Sub_2$ herein are, for instance, at least one group selected from the group consisting of a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

Among the above heterocyclic group $Sub_2$, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are further more preferable. A nitrogen atom in position 9 of 1-carbazolyl group, 2-carbazolyl group, 3-carbazolyl group and 4-carbazolyl group is preferably substituted by the substituted or unsubstituted aryl group $Sub_1$ or the substituted or unsubstituted heterocyclic group $Sub_2$ described herein.

Herein, the heterocyclic group $Sub_2$ may be a group derived from any one of partial structures represented by formulae (XY-1) to (XY-18) below.

[Formula 109]

(XY-1)

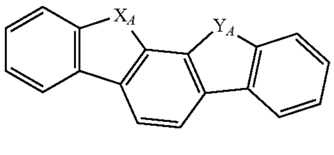

(XY-2)

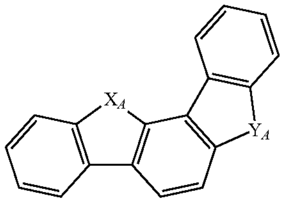

-continued (XY-3)

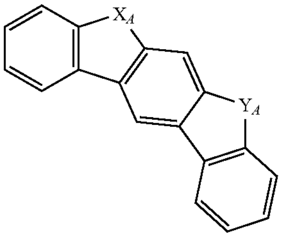

(XY-4)

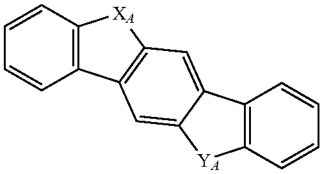

(XY-5)

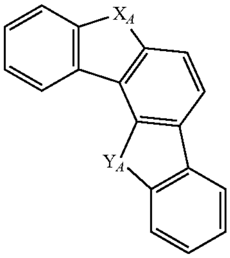

(XY-6)

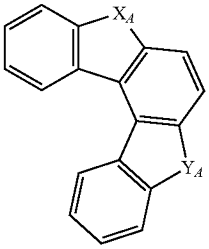

[Formula 110]

(XY-7)

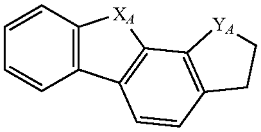

(XY-8)

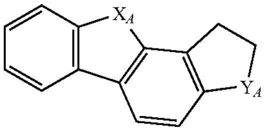

(XY-9)

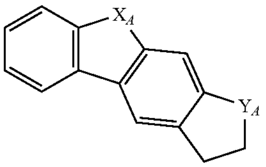

(XY-10)

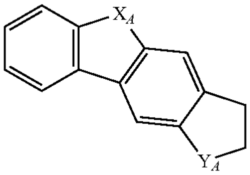

-continued (XY-11)

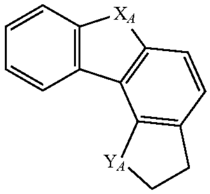

(XY-12)

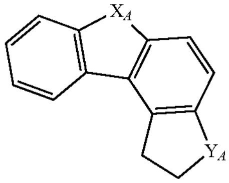

[Formula 111]

(XY-13)

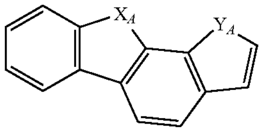

(XY-14)

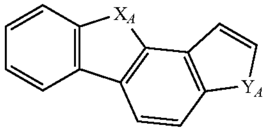

(XY-15)

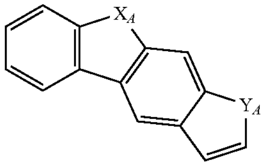

(XY-16)

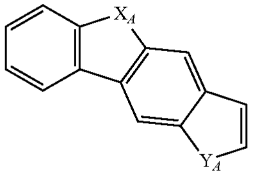

(XY-17)

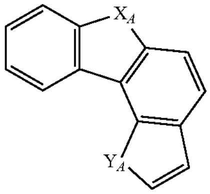

(XY-18)

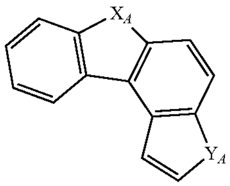

In the formulae (XY-1) to (XY-18), $X_A$ and $Y_A$ are each independently a hetero atom, preferably an oxygen atom, sulfur atom, selenium atom, silicon atom, or germanium atom. Each of the partial structures represented by the respective formulae (XY-1) to (XY-18) has a bond at any position to provide a heterocyclic group. The heterocyclic group may be substituted.

Herein, the heterocyclic group $Sub_2$ may be a group represented by one of formulae (XY-19) to (XY-22) below. Moreover, the position of the bond may be changed as needed.

[Formula 112]

(XY-19)

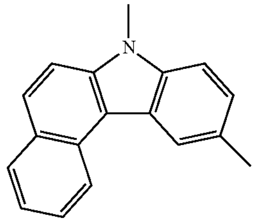

(XY-20)

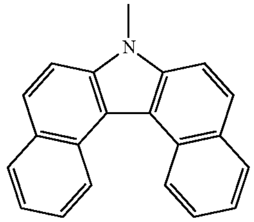

(XY-21)

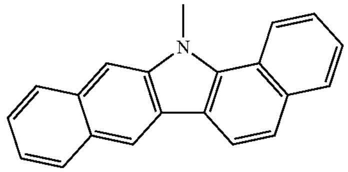

(XY-22)

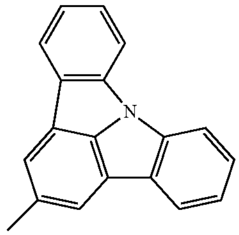

The alkyl group herein may be any one of a linear alkyl group, branched alkyl group and cyclic alkyl group.

The alkyl group herein is exemplified by an alkyl group $Sub_3$.

The linear alkyl group herein is exemplified by a linear alkyl group $Sub_{31}$.

The branched alkyl group herein is exemplified by a branched alkyl group $Sub_{32}$.

The cyclic alkyl group herein is exemplified by a cyclic alkyl group $Sub_{33}$ (sometimes referred to as a cycloalkyl group $Sub_{331}$).

For instance, the alkyl group $Sub_3$ is at least one group selected from the group consisting of the linear alkyl group $Sub_{31}$, branched alkyl group $Sub_{32}$, and cyclic alkyl group $Sub_{33}$.

Herein, the linear alkyl group $Sub_{31}$ or branched alkyl group $Sub_{32}$ preferably has 1 to 30 carbon atoms, more preferably 1 to 20 carbon atoms, further preferably 1 to 10 carbon atoms, further more preferably 1 to 6 carbon atoms.

Herein, the cycloalkyl group $Sub_{331}$ preferably has 3 to 30 ring carbon atoms, more preferably 3 to 20 ring carbon atoms, further preferably 3 to 10 ring carbon atoms, still further preferably 5 to 8 ring carbon atoms. The cycloalkyl group $Sub_{331}$ also preferably has 3 to 6 ring carbon atoms.

The linear alkyl group $Sub_{31}$ or branched alkyl group $Sub_{32}$ herein is exemplified by at least one group selected from the group consisting of a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear alkyl group $Sub_{31}$ or branched alkyl group $Sub_{32}$ is further more preferably a methyl group, ethyl group, propyl group, isopropyl group, n-butyl group, s-butyl group, isobutyl group, t-butyl group, n-pentyl group, n-hexyl group, amyl group, isoamyl group and neopentyl group.

Herein, the cyclic alkyl group $Sub_{33}$ is exemplified by a cycloalkyl group $Sub_{331}$.

The cycloalkyl group Sub331 herein is exemplified by at least one group selected from the group consisting of a cyclopropyl group, cyclobutyl group, cyclopentyl group, cyclohexyl group, 4-metylcyclohexyl group, adamantyl group and norbornyl group. Among the cycloalkyl group Sub331, a cyclopentyl group and a cyclohexyl group are still further preferable.

Herein, an alkyl halide group is exemplified by an alkyl halide group $Sub_4$.

The alkyl halide group $Sub_4$ is provided by substituting the alkyl group $Sub_3$ with at least one halogen atom, preferably at least one fluorine atom.

Herein, the alkyl halide group $Sub_4$ is exemplified by at least one group selected from the group consisting of a fluoromethyl group, difluoromethyl group, trifluoromethyl group, fluoroethyl group, trifluoromethylmethyl group, trifluoroethyl group, and pentafluoroethyl group.

Herein, a substituted silyl group is exemplified by a substituted silyl group $Sub_5$. The substituted silyl group $Sub_5$ is exemplified by at least one group selected from the group consisting of an alkylsilyl group $Sub_{51}$ and an arylsilyl group $Sub_{52}$.

Herein, the alkylsilyl group $Sub_{51}$ is exemplified by a trialkylsilyl group $Sub_{511}$ having the above-described alkyl group $Sub_3$.

The trialkylsilyl group $Sub_{511}$ is exemplified by at least one group selected from the group consisting of a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups $Sub_3$ in the trialkylsilyl group $Sub_{511}$ may be mutually the same or different.

Herein, the arylsilyl group $Sub_{52}$ is exemplified by at least one group selected from the group consisting of a dialkylarylsilyl group $Sub_{521}$, alkyldiarylsilyl group $Sub_{522}$ and triarylsilyl group $Sub_{523}$.

The dialkylarylsilyl group $Sub_{521}$ is exemplified by a dialkylarylsilyl group including two alkyl groups $Sub_3$ and one aryl group $Sub_1$. The dialkylarylsilyl group $Sub_{521}$ preferably has 8 to 30 carbon atoms.

The alkyldiarylsilyl group $Sub_{522}$ is exemplified by an alkyldiarylsilyl group including one alkyl group $Sub_3$ and two aryl groups $Sub_1$. The alkyldiarylsilyl group $Sub_{522}$ preferably has 13 to 30 carbon atoms.

The triarylsilyl group $Sub_{523}$ is exemplified by a triarylsilyl group including three aryl groups $Sub_1$. The triarylsilyl group $Sub_{523}$ preferably has 18 to 30 carbon atoms.

Herein, a substituted or unsubstituted alkyl sulfonyl group is exemplified by an alkyl sulfonyl group $Sub_6$. The alkyl sulfonyl group $Sub_6$ is represented by $—SO_2R_W$. $R_W$ in $—SO_2R_W$ represents a substituted or unsubstituted alkyl group $Sub_3$ described above.

Herein, an aralkyl group (occasionally referred to as an arylalkyl group) is exemplified by an aralkyl group $Sub_7$. An aryl group in the aralkyl group $Sub_7$ includes, for instance, at least one of the above-described aryl group $Sub_1$ or the above-described heteroaryl group $Sub_2$.

The aralkyl group $Sub_7$ herein is preferably a group having the aryl group $Sub_1$ and is represented by $—Z_3—Z_4$. $Z_3$ is exemplified by an alkylene group corresponding to the above alkyl group $Sub_3$. $Z_4$ is exemplified by the above aryl group $Sub_1$. In this aralkyl group $Sub_7$, an aryl moiety has 6 to 30 carbon atoms (preferably 6 to 20 carbon atoms, more preferably 6 to 12 carbon atoms) and an alkyl moiety has 1 to 30 carbon atoms (preferably 1 to 20 carbon atoms, more preferably 1 to 10 carbon atoms, further preferably 1 to 6 carbon atoms). The aralkyl group $Sub_7$ is exemplified by at least one group selected from the group consisting of a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

The alkoxy group herein is exemplified by an alkoxy group $Sub_8$. The alkoxy group $Sub_8$ is represented by $—OZ_1$. $Z_1$ is exemplified by the above alkyl group $Sub_3$.

The alkoxy group $Sub_8$ preferably has 1 to 30 carbon atoms, more preferably 1 to 20 carbon atoms.

The alkoxy group $Sub_8$ is exemplified by at least one group selected from the group consisting of a methoxy group, ethoxy group, propoxy group, butoxy group, pentyloxy group and hexyloxy group.

Herein, an alkoxy halide group is exemplified by an alkoxy halide group $Sub_9$. The alkoxy halide group $Sub_9$ is provided by substituting the alkoxy group $Sub_8$ with at least one halogen atom, preferably at least one fluorine atom.

Herein, an aryloxy group (occasionally referred to as an arylalkoxy group) is exemplified by an arylalkoxy group $Sub_{10}$. An aryl group in the arylalkoxy group $Sub_{10}$ includes at least one of the aryl group $Sub_1$ or the heteroaryl group $Sub_2$.

The arylalkoxy group $Sub_{10}$ herein is represented by $—OZ_2$. $Z_2$ is exemplified by the aryl group $Sub_1$ or the heteroaryl group $Sub_2$. The arylalkoxy group $Sub_{10}$ preferably has 6 to 30 ring carbon atoms, more preferably 6 to 20 ring carbon atoms. The arylalkoxy group $Sub_{10}$ is exemplified by a phenoxy group.

Herein, a substituted amino group is exemplified by a substituted amino group $Sub_{11}$. The substituted amino group $Sub_{11}$ is exemplified by at least one group selected from the group consisting of an arylamino group $Sub_{111}$ and an alkylamino group $Sub_{112}$.

An arylamino group $Sub_{111}$ is represented by —$NHR_{V1}$ or —$N(R_{V1})_2$. $R_{V1}$ is exemplified by the aryl group $Sub_1$. Two $R_{V1}$ in —$N(R_{V1})_2$ are mutually the same or different.

An alkylamino group $Sub_{112}$ is represented by —$NHR_{V2}$ or —$N(R_{V2})_2$. $R_{V2}$ is exemplified by the alkyl group $Sub_3$. Two $R_{V2}$ in —$N(R_{V2})_2$ are mutually the same or different.

Herein, the alkenyl group is exemplified by an alkenyl group $Sub_{12}$. The alkenyl group $Sub_{12}$, which is linear or branched, is exemplified by at least one group selected from the group consisting of a vinyl group, propenyl group, butenyl group, coleyl group, eicosapentaenyl group, docosahexaenyl group, styryl group, 2,2-diphenylvinyl group, 1,2,2-triphenylvinyl group, and 2-phenyl-2-propenyl group.

The alkynyl group herein is exemplified by an alkynyl group $Sub_{13}$. The alkynyl group $Sub_{13}$ may be linear or branched and is at least one group selected from the group consisting of an ethynyl group, a propynyl group and a 2-phenylethynyl group.

The alkylthio group herein is exemplified by an alkylthio group $Sub_{14}$.

The alkylthio group $Sub_{14}$ is represented by —$SR_{V3}$. $R_{V3}$ is exemplified by the alkyl group $Sub_3$. The alkylthio group $Sub_{14}$ preferably has 1 to 30 carbon atoms, more preferably 1 to 20 carbon atoms.

The arylthio group herein is exemplified by an arylthio group $Sub_{15}$.

The arylthio group $Sub_{15}$ is represented by —$SR_{V4}$. $R_{V4}$ is exemplified by the aryl group $Sub_1$. The arylthio group $Sub_{15}$ preferably has 6 to 30 ring carbon atoms, more preferably 6 to 20 ring carbon atoms.

Herein, examples of the halogen atom include a fluorine atom, a chlorine atom, a bromine atom and an iodine atom, among which a fluorine atom is preferable.

A substituted phosphino group herein is exemplified by a substituted phosphino group $Sub_{16}$. The substituted phosphino group $Sub_{16}$ is exemplified by a phenyl phosphanyl group.

An arylcarbonyl group herein is exemplified by an arylcarbonyl group $Sub_{17}$. The arylcarbonyl group $Sub_{17}$ is represented by —COY'. Y' is exemplified by the aryl group $Sub_1$. Herein, the arylcarbonyl group $Sub_{17}$ is exemplified by at least one group selected from the group consisting of a phenyl carbonyl group, diphenyl carbonyl group, naphthyl carbonyl group, and triphenyl carbonyl group.

An acyl group herein is exemplified by an acyl group $Sub_{18}$. The acyl group $Sub_{18}$ is represented by —COR'. R' is exemplified by the alkyl group $Sub_3$. The acyl group $Sub_{18}$ herein is exemplified by at least one group selected from the group consisting of an acetyl group and a propionyl group.

A substituted phosphoryl group herein is exemplified by a substituted phosphoryl group $Sub_{19}$. The substituted phosphoryl group $Sub_{19}$ is represented by a formula (P) below.

[Formula 113]

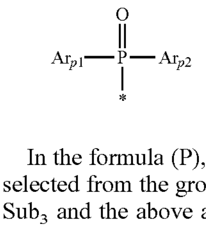

(P)

In the formula (P), $Ar_{P1}$ and $Ar_{P2}$ are any one substituent selected from the group consisting of the above alkyl group $Sub_3$ and the above aryl group $Sub_1$.

Herein, an ester group is exemplified by an ester group $Sub_{20}$. The ester group $Sub_{20}$ is exemplified by at least one group selected from the group consisting of an alkyl ester group and an aryl ester group.

An alkyl ester group herein is exemplified by an alkyl ester group $Sub_{201}$. The alkyl ester group $Sub_{201}$ is represented by —C(=O)$OR^E$. $R^E$ is exemplified by a substituted or unsubstituted alkyl group $Sub_3$ described above (preferably having 1 to 10 carbon atoms).

An aryl ester group herein is exemplified by an aryl ester group $Sub_{202}$. The aryl ester group $Sub_{202}$ is represented by —C(=O)$OR^{Ar}$. $R^{Ar}$ is exemplified by a substituted or unsubstituted aryl group $Sub_1$ described above.

A siloxanyl group herein is exemplified by a siloxanyl group $Sub_{21}$. The siloxanyl group $Sub_{21}$ is a silicon compound group through an ether bond. The siloxanyl group $Sub_{21}$ is exemplified by a trimethylsiloxanyl group.

A carbamoyl group herein is represented by —$CONH_2$.

A substituted carbamoyl group herein is exemplified by a carbamoyl group $Sub_{22}$. The carbamoyl group $Sub_{22}$ is represented by —CONH—$Ar^C$ or —CONH—$R^C$. $Ar^C$ is exemplified by at least one group selected from the group consisting of the above-described aryl group $Sub_1$ (preferably 6 to 10 ring carbon atoms) and the above-described heteroaryl group $Sub_2$ (preferably 5 to 14 ring atoms). $Ar^C$ may be a group formed by bonding the aryl group $Sub_1$ and the heteroaryl group $Sub_2$.

$R^C$ is exemplified by a substituted or unsubstituted alkyl group $Sub_3$ described above (preferably having 1 to 6 carbon atoms).

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

Herein, a "hydrogen atom" that is not specified as a "protium atom" or a "deuterium atom" includes isotope having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Hereinafter, an alkyl group $Sub_3$ means at least one group of a linear alkyl group $Sub_{31}$, a branched alkyl group $Sub_{32}$, or a cyclic alkyl group $Sub_{33}$ described in "Description of Each Substituent."

Similarly, a substituted silyl group $Sub_5$ means at least one group of an alkylsilyl group $Sub_{51}$ or an arylsilyl group $Sub_{52}$.

Similarly, a substituted amino group $Sub_{11}$ means at least one group of an arylamino group $Sub_{111}$ or an alkylamino group $Sub_{112}$.

Herein, a substituent for a "substituted or unsubstituted" group is exemplified by a substituent $R_{F1}$. The substituent $R_{F1}$ is at least one group selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxy group, thiol group, nitro group, and carboxy group.

Herein, the substituent $R_{F1}$ for a "substituted or unsubstituted" group may be a diaryl boron group ($Ar_{B1}Ar_{B2}B$—). $Ar_{B1}$ and $Ar_{B2}$ are exemplified by the above-described aryl group $Sub_1$. $Ar_{B1}$ and $Ar_{B2}$ in $Ar_{B1}Ar_{B2}B$— are the same or different.

Specific examples and preferable examples of the substituent $R_{F1}$ are the same as those of the substituents described in "Description of Each Substituent" (e.g., an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, and carbamoyl group $Sub_{22}$).

The substituent $R_{F1}$ for a "substituted or unsubstituted" group may be further substituted by at least one group (hereinafter, also referred to as a substitutent $R_{F2}$) selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxy group, thiol group, nitro group, and carboxy group. Moreover, a plurality of substituents $R_{F2}$ may be bonded to each other to form a ring.

"Unsubstituted" for a "substituted or unsubstituted" group means that a group is not substituted by the above-described substituent $R_{F1}$ but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of the substituent $R_{F1}$ of the substituted ZZ group.

Herein, "XX to YY atoms" in the description of "substituted or unsubstituted ZZ group having XX to YY atoms" represent atoms of an unsubstituted ZZ group and do not include atoms of the substituent $R_{F1}$ of the substituted ZZ group.

The same description as the above applies to "substituted or unsubstituted" in compounds or partial structures thereof described herein.

Herein, when substituents are bonded to each other to form a ring, the ring is structured to be a saturated ring, an unsaturated ring, an aromatic hydrocarbon ring or a hetero ring.

Herein, examples of the aromatic hydrocarbon group in the linking group include a divalent or multivalent group obtained by eliminating one or more atoms from the above monovalent aryl group $Sub_1$.

Herein, examples of the heterocyclic group in the linking group include a divalent or multivalent group obtained by eliminating one or more atoms from the above monovalent heteroaryl group $Sub_2$.

Herein, numerical ranges represented by "AA to BB" represent a range whose lower limit is the value (AA) recited before "to" and whose upper limit is the value (BB) recited after "to."

Modification of Embodiment(s)

The scope of the invention is not limited by the above-described exemplary embodiments but includes any modification and improvement as long as such modification and improvement are compatible with the invention.

For instance, the emitting layer is not limited to a single layer, but may be provided by laminating a plurality of emitting layers. When the organic EL device has the plurality of emitting layers, it is only required that at least one of the emitting layers satisfies the conditions described in the above exemplary embodiments. For instance, the rest of the emitting layers may be a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are layered via an intermediate layer.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, excitons or combinations thereof.

For instance, when the blocking layer is provided in contact with the side of the emitting layer close to the cathode, the blocking layer permits transport of electrons, and blocks holes from reaching a layer provided closer to the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably interposed between the emitting layer and the hole transporting layer.

Alternatively, the blocking layer may be provided adjacent to the emitting layer so that the excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

EXAMPLES

Example(s) of the invention will be described below. However, the invention is not limited to Example(s).

Compounds

Structures of compounds represented by the formula (1) in Examples 1 to 16 or Synthesis Examples 1 to 10 are shown below.

[Formula 114]
A1
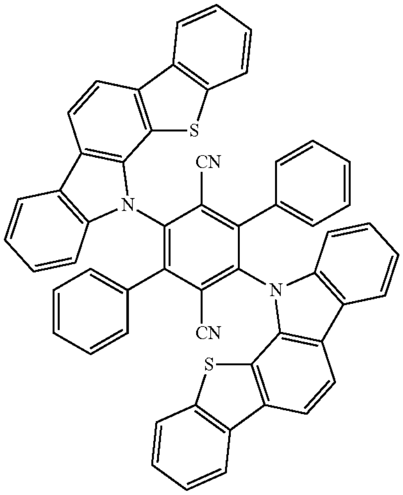
A2
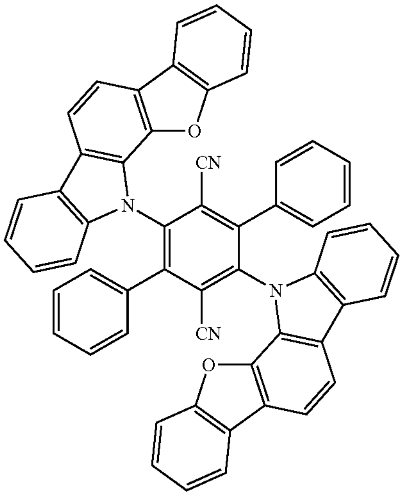
A3
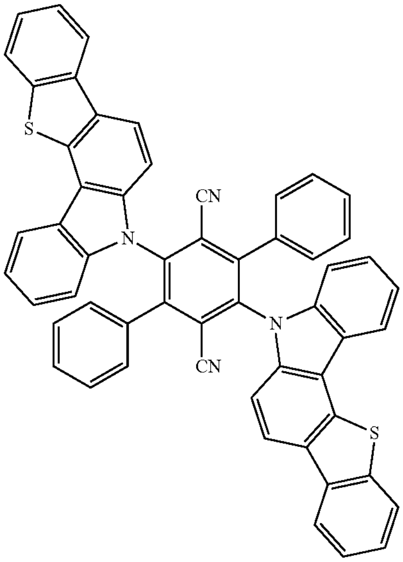
-continued
[Formula 115]
A4
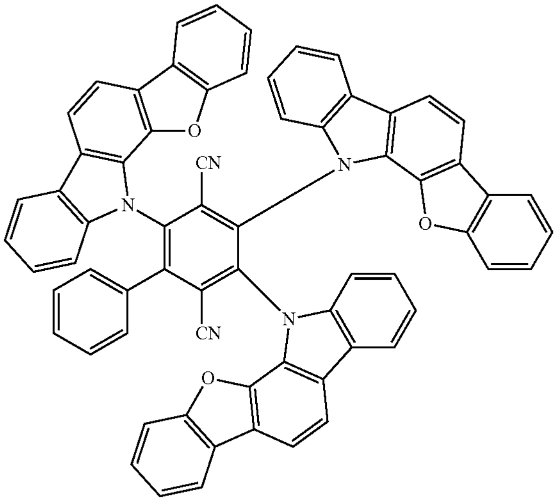
[Formula 116]
A5
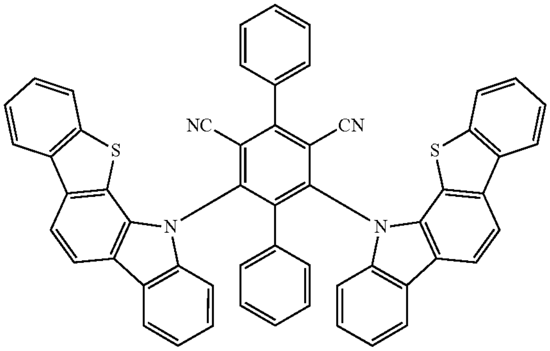
A6
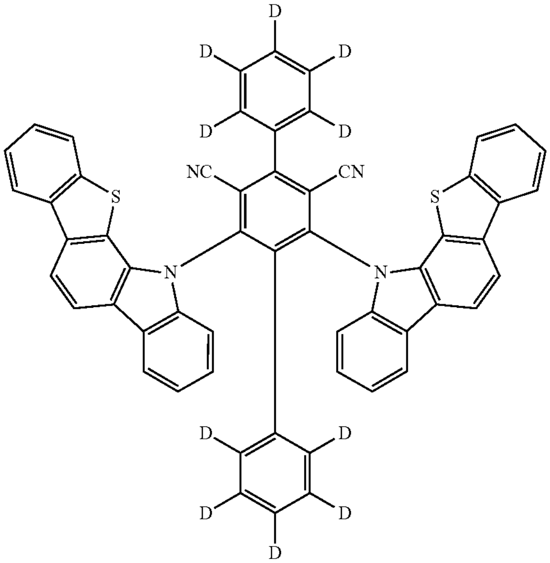

-continued
A7
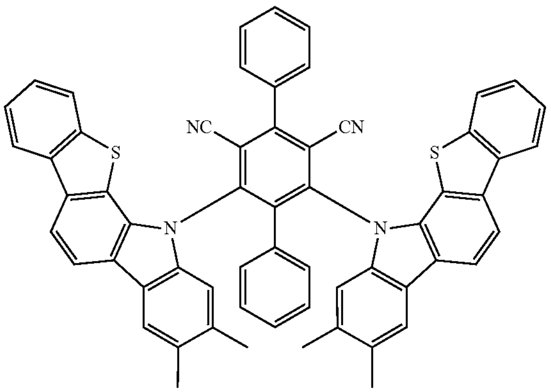
A8
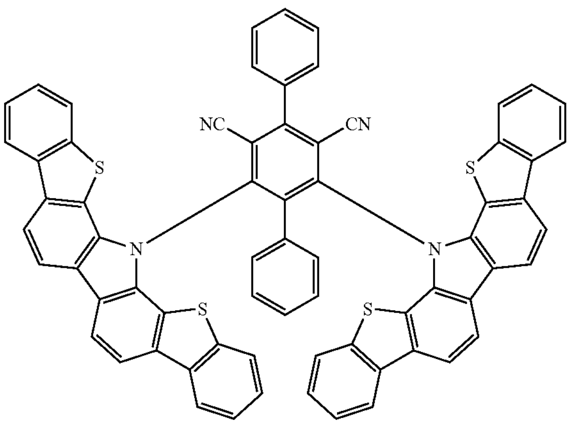
[Formula 117]
A9
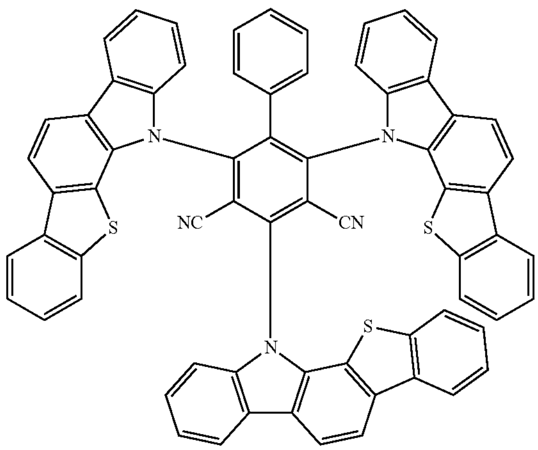
-continued
A10
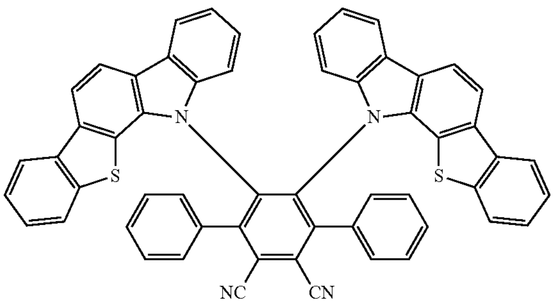
Structures of comparative compounds represented in Comparatives 1 to 4 are shown below.
[Formula 118]
Ref-1
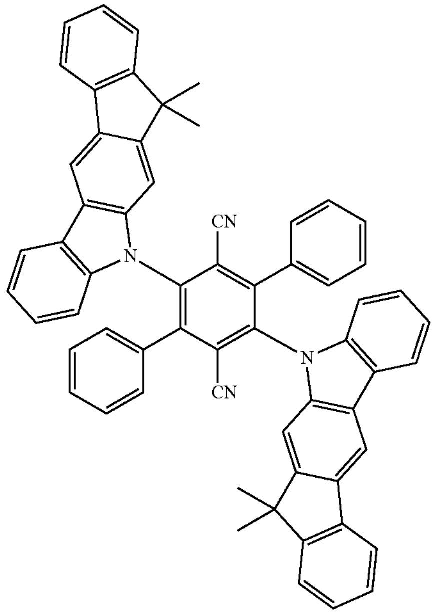
Ref-2
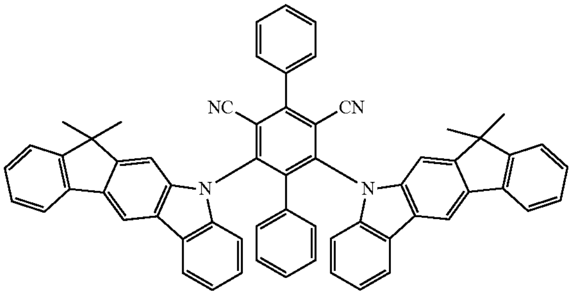
Structures of compounds used for manufacturing organic EL devices in Examples 10 to 16 and Comparatives 3 and 4 are shown below.

[Formula 119]
HA
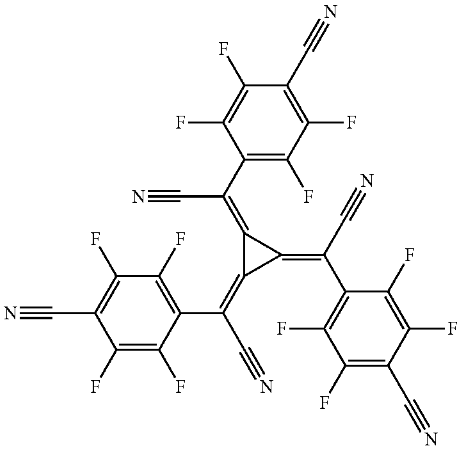
HT-1
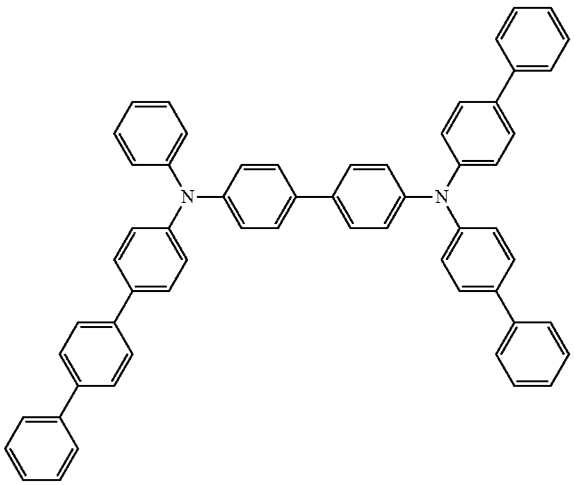
HT-2
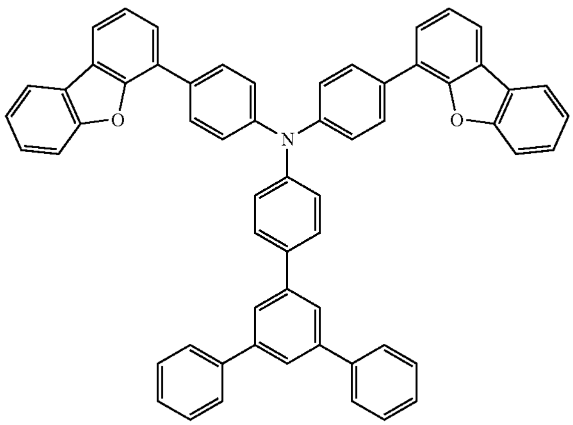
-continued
CBP
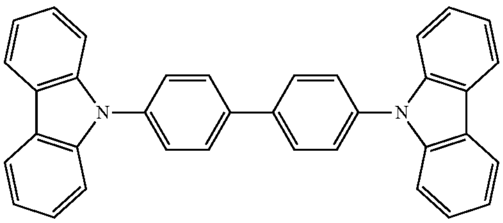
Formula 120]
Matrix-1
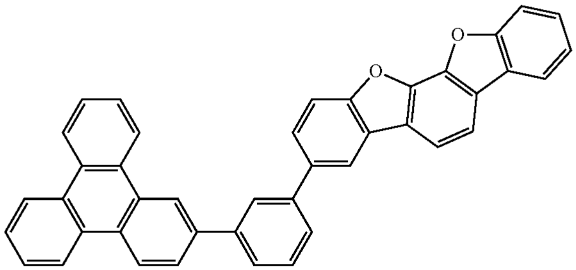
Matrix-2
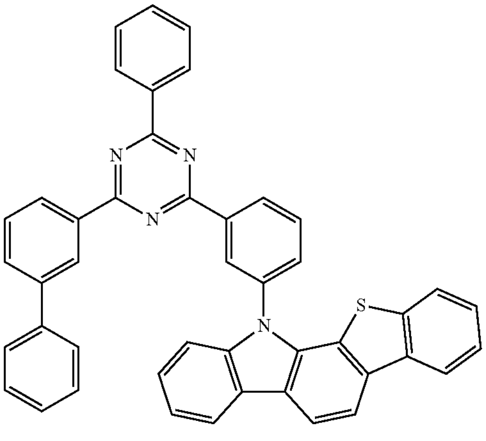
Formula 121]
GD
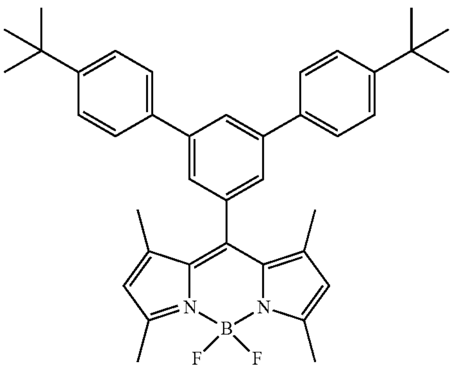

-continued

[Formula 122]

ET-1

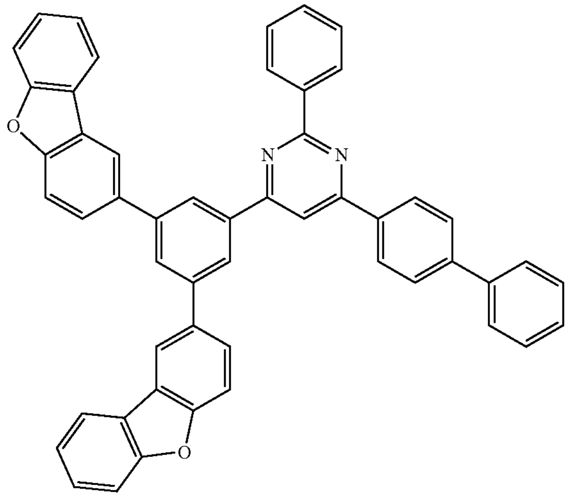

ET-2

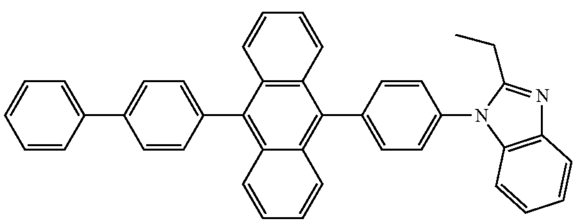

Evaluation of Compounds

Preparation of Toluene Solution

A compound A1 was dissolved in toluene at a concentration of 5 μmol/L to prepare a toluene solution of the compound A1. Subsequently, the prepared solution was subjected to nitrogen bubbling for five minutes and sealed to prevent inclusion of outside air.

A toluene solution of each of compounds A2, A3, A4, A5, A6, A7, A8, A9, Ref-1 and Ref-2 was prepared in the same manner as that of the compound A1. Subsequently, the prepared solution was subjected to nitrogen bubbling for five minutes and sealed to prevent inclusion of outside air.

Measurement of Photoluminescence Quantum Yield (PLQY)

PLQY of each of the prepared toluene solutions of the compounds A1, A2, A3, A4, A5, A6, A7, A8, A9, Ref-1 and Ref-2 was measured using an absolute PL (Photoluminescence) quantum yield measurement device Quantaurus-QY (manufactured by HAMAMATSU PHOTONICS K. K.).

Tables 1 and 2 show measurement results of values of PLQY of the compounds A1, A2, A3, A4, A5, A6, A7, A8, A9, Ref-1 and Ref-2. Table 1 shows PLQY relative values, assuming that PLQY of Comparative 1 is 100. Table 2 shows PLOY relative values, assuming that PLOY of Comparative 2 is 100. Specifically, the PLQY relative values are values calculated by any of the following formulae.

(PLQY relative value in Table 1)={(PLQY absolute value of compound of each Example or Comparative in Table 1)/(PLQY absolute value of comparative compound Ref-1)}×100

(PLQY relative value in Table 2)={(PLQY absolute value of compound of each Example or Comparative in Table 2)/(PLQY absolute value of comparative compound Ref-2)}×100

Main Peak Wavelength of Compounds

A toluene solutions of each of measurement target compounds at a concentration of 5 μmol/L was prepared and put in a quartz cell. A fluorescence spectrum (ordinate axis: fluorescence intensity, abscissa axis: wavelength) of each sample was measured at a normal temperature (300K). In Examples, the fluorescence spectrum was measured using a spectrophotometer (device name: F-7000) manufactured by Hitachi, Ltd. It should be noted that a measurement device of the fluorescence spectrum is not limited to the device used herein. A peak wavelength of the fluorescence spectrum exhibiting the maximum luminous intensity was defined as a main peak wavelength.

Tables 1 and 2 show measurement results of peak wavelengths of fluorescence spectra of the compounds A1, A2, A3, A4, A5, A6, A7, A8, A9, Ref-1 and Ref-2.

Thermally Activated Delayed Fluorescence

Delayed Fluorescence of Compound A1

Delayed fluorescence properties were checked by measuring transient PL using a device shown in FIG. 1. The compound A1 was dissolved in toluene to prepare a dilute solution with an absorbance of 0.05 or less at the excitation wavelength to eliminate the contribution of self-absorption. In order to prevent quenching due to oxygen, the sample solution was frozen and degassed and then sealed in a cell with a lid under an argon atmosphere to obtain an oxygen-free sample solution saturated with argon.

The fluorescence spectrum of the above sample solution was measured with a spectrofluorometer FP-8600 (manufactured by JASCO Corporation), and the fluorescence spectrum of a 9,10-diphenylanthracene ethanol solution was measured under the same conditions. Using the fluorescence area intensities of both spectra, the total fluorescence quantum yield was calculated by an equation (1) in Morris et al. J. Phys. Chem. 80 (1976) 969.

Prompt emission was observed immediately when the excited state was achieved by exciting the compound A1 with a pulse beam (i.e., a beam emitted from a pulse laser) having a wavelength to be absorbed by the compound A1, and Delay emission was observed not immediately when the excited state was achieved but after the excited state was achieved. The delayed fluorescence in Examples means that an amount of Delay Emission is 5% or more with respect to an amount of Prompt Emission. Specifically, provided that the amount of Prompt emission is denoted by $X_P$ and the amount of Delay emission is denoted by $X_D$, the delayed fluorescence means that a value of $X_D/X_P$ is 0.05 or more.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 1.

It was confirmed that the amount of Delay Emission was 5% or more with respect to the amount of Prompt Emission in the compound A1.

Specifically, it was found that the value of $X_D/X_P$ was 0.05 or more in the compound A1.

In Tables, the notation ">0.05" indicates that the value of $X_D/X_P$ exceeded 0.05.

Delayed Fluorescence of Compounds A2 to A9, Comparative Compound Ref-1 and Comparative Compound Ref-2

The compounds A2 to A9, the comparative compound Ref-1 and the comparative compound Ref-2 were checked in terms of delayed fluorescence in the same manner as above except that the compound A1 was replaced by the compounds A2 to A9, the comparative compound Ref-1 and the comparative compound Ref-2.

The value of $X_D/X_P$ was 0.05 or more in each of the compounds A2 to A9, the comparative compound Ref-1 and the comparative compound Ref-2.

Singlet Energy $S_1$

A singlet energy $S_1$ of each of the compounds A1 to A9, the comparative compound Ref-1 and the comparative compound Ref-2 was measured according to the above-described solution method. Tables 1 and 2 show measurement results.

ΔST $T_{77K}$ of each of the compounds A1 to A9, the comparative compound Ref-1 and the comparative compound Ref-2 was measured. $T_{77K}$ of each of the compounds A1 to A9, the comparative compound Ref-1 and the comparative compound Ref-2 was measured according to the measurement method of the energy gap $T_{77K}$ described in the above "Relationship between Triplet Energy and Energy Gap at 77K."

ΔST was checked from the values of the singlet energy $S_1$ described above and the values of $T_{77K}$. Tables 1 and 2 show values of ΔST of the respective compounds. In Tables, the notation "<0.01" indicates that ΔST was less than 0.01 eV.

TABLE 1

| | | Main Peak Wavelength [nm] | PLQY Relative Value | $S_1$ [eV] | ΔST [eV] | Delay/Prompt |
|---|---|---|---|---|---|---|
| Example 1 | Compound A1 | 513 | 320 | 2.52 | <0.01 | >0.05 |
| Example 2 | Compound A2 | 476 | 510 | 2.70 | <0.01 | >0.05 |
| Example 3 | Compound A3 | 514 | 350 | 2.54 | <0.01 | >0.05 |
| Example 4 | Compound A4 | 491 | 450 | 2.58 | <0.01 | >0.05 |
| Comparative 1 | Comparative Compound Ref-1 | 536 | 100 | 2.43 | <0.01 | >0.05 |

TABLE 2

| | | Main Peak Wavelength [nm] | PLQY Relative Value | $S_1$ [eV] | ΔST [eV] | Delay/Prompt |
|---|---|---|---|---|---|---|
| Example 5 | Compound A5 | 493 | 130 | 2.66 | <0.01 | >0.05 |
| Example 6 | Compound A6 | 493 | 120 | 2.66 | <0.01 | >0.05 |
| Example 7 | Compound A7 | 498 | 130 | 2.60 | <0.01 | >0.05 |
| Example 8 | Compound A8 | 504 | 130 | 2.52 | <0.01 | >0.05 |
| Example 9 | Compound A9 | 499 | 110 | 2.49 | <0.01 | >0.05 |
| Comparative 2 | Comparative Compound Ref-2 | 503 | 100 | 2.63 | <0.01 | >0.05 |

As shown in Table 1, the compounds A1 to A4 represented by the formula (1) had a higher PLQY than the comparative compound Ref-1 having the same para-dicyanobenzene skeleton.

As shown in Table 2, the compounds A5 to A9 represented by the formula (1) had a higher PLQY than the comparative compound Ref-2 having the same meta-dicyanobenzene skeleton.

Manufacture of Organic EL Device

The organic EL devices were manufactured and evaluated as follows.

Example 10

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV-ozone-cleaned for one minute. The film thickness of ITO was 130 nm After the glass substrate having the transparent electrode line was cleaned, the glass substrate was mounted on a substrate holder of a vacuum evaporation apparatus. Firstly, a compound HT-1 and a compound HA were co-deposited on a surface of the glass substrate where the transparent electrode line was provided in a manner to cover the transparent electrode, thereby forming a 10-nm-thick hole injecting layer. The concentrations of the compound HT-1 and the compound HA in the hole injecting layer were 97 mass % and 3 mass %, respectively.

Next, the compound HT-1 was vapor-deposited on the hole injecting layer to form a 110-nm-thick first hole transporting layer.

Next, a compound HT-2 was vapor-deposited on the first hole transporting layer to form a 5-nm-thick second hole transporting layer.

Next, a compound CBP was vapor-deposited on the second hole transporting layer to form a 5-nm-thick electron blocking layer.

Next, a compound Matrix-1 and a compound Matrix-2 (the third compounds) and a compound A5 (the first compound) were co-deposited on the electron blocking layer to form a 25-nm-thick emitting layer. The concentrations of the compound Matrix-1, the compound Matrix-2 and the compound A5 in the emitting layer were 25 mass %, 25 mass % and 50 mass %, respectively.

Next, a compound ET-1 was vapor-deposited on the emitting layer to form a 5-nm-thick hole blocking layer.

Next, a compound ET-2 was vapor-deposited on the hole blocking layer to form a 50-nm-thick electron transporting layer.

Next, lithium fluoride (LiF) was vapor-deposited on the electron transporting layer to form a 1-nm-thick electron injecting electrode (cathode).

Subsequently, metal aluminum (Al) was vapor-deposited on the electron injecting electrode to form an 80-nm-thick metal Al cathode.

A device arrangement of the organic EL device in Example 10 is roughly shown as follows.

ITO(130)/HT-1:HA(10.97%:3%)/HT-1(110)/HT-2(5)/CBP(5)/Matrix-1: Matrix-2:A5(25.25%:25%:50%)/ET-1(5)/ET-2(50)/LiF(1)/Al(80)

The numerals in parentheses represent film thickness (unit: nm).

The numerals (97%:3%) represented by percentage in the same parentheses indicate a ratio (mass %) between the compound HT-1 and the compound HA in the hole injecting layer, and the numerals (25%:25%:50%) represented by percentage in the same parentheses indicate a ratio (mass %) between the compound Matrix-1, the compound Matrix-2 and the compound A5 in the emitting layer. Similar notations apply to the description below.

Examples 11 to 13

The organic EL devices of Examples 11 to 13 were manufactured in the same manner as that of Example 10 except that the first compound in the emitting layer of Example 10 was replaced with the first compounds shown in Table 3.

Comparative 3

The organic EL device of Comparative 3 was manufactured in the same manner as that of Example 10 except that the first compound in the emitting layer of Example 10 was replaced with the first compound shown in Table 3.

Example 14

The organic EL device of Example 14 was manufactured in the same manner as that of Example 10 except that the emitting layer of Example 10 was changed as follows.

In the organic EL device of Example 14, the compound Matrix-1 and the compound Matrix-2 (the third compounds), the compound A5 (the first compound) and a compound GD (the second compound) were co-deposited to form a 25-nm-thick emitting layer as shown in Table 4. The concentrations of the compound Matrix-1, the compound Matrix-2, the compound A5 and the compound GD in the emitting layer were 24.5 mass %, 24.5 mass %, 50 mass % and 1 mass %, respectively.

Examples 15 and 16

The organic EL devices of Examples 15 and 16 were manufactured in the same manner as that of Example 14 except that the first compound in the emitting layer of Example 14 was replaced with the first compounds shown in Table 4.

Comparative 4

The organic EL device of Comparative 4 was manufactured in the same manner as that of Example 14 except that the first compound in the emitting layer of Example 14 was replaced with the first compound shown in Table 4.

Evaluation of Organic EL Device

Drive Voltage

A voltage (unit: V) was measured when current was applied between the anode and the cathode such that a current density was 10 $mA/cm^2$.

Table 3 shows relative values of drive voltages of the organic EL devices of Examples 10 to 13 or Comparative 3 relative to a drive voltage of the organic EL device of Comparative 3, assuming that the drive voltage of the organic EL device of Comparative 3 is 1.00.

Drive voltage (relative value)=[Drive voltage of organic EL device of each of Examples 10 to 13 or Comparative 3]/[Drive voltage of organic EL device of Comparative 3]

TABLE 3

| | Third Compound | | | | First Compound | | | Drive Voltage (Relative |
|---|---|---|---|---|---|---|---|---|
| | Name | $S_1$ [eV] | Name | $S_1$ [eV] | Name | $S_1$ [eV] | ΔST [eV] | Value) @10 $mA/cm^2$ |
| Example 10 | Matrix-1 | 3.68 | Matrix-2 | 3.08 | A5 | 2.66 | <0.01 | 0.91 |
| Example 11 | Matrix-1 | 3.68 | Matrix-2 | 3.08 | A6 | 2.66 | <0.01 | 0.91 |
| Example 12 | Matrix-1 | 3.68 | Matrix-2 | 3.08 | A8 | 2.52 | <0.01 | 0.85 |
| Example 13 | Matrix-1 | 3.68 | Matrix-2 | 3.08 | A9 | 2.49 | <0.01 | 0.88 |
| Comparative 3 | Matrix-1 | 3.68 | Matrix-2 | 3.08 | Ref-2 | 2.63 | <0.01 | 1.00 |

Table 4 shows relative values of drive voltages of the organic EL devices of Examples 14 to 16 or Comparative 4 relative to a drive voltage of the organic EL device of Comparative 4, assuming that the drive voltage of the organic EL device of Comparative 4 is 1.00.

Drive voltage (relative value)=[Drive voltage of organic EL device of each of Examples 14 to 16 or Comparative 4]/[Drive voltage of organic EL device of Comparative 4]

TABLE 4

| | Third Compound | | | | First Compound | | | Second Compound | | Drive Voltage (Relative |
|---|---|---|---|---|---|---|---|---|---|---|
| | Name | $S_1$ [eV] | Name | $S_1$ [eV] | Name | $S_1$ [eV] | ΔST [eV] | Name | $S_1$ [eV] | Value) @10 $mA/cm^2$ |
| Example 14 | Matrix-1 | 3.68 | Matrix-2 | 3.08 | A5 | 2.66 | <0.01 | GD | 2.39 | 0.91 |
| Example 15 | Matrix-1 | 3.68 | Matrix-2 | 3.08 | A6 | 2.66 | <0.01 | GD | 2.39 | 0.91 |

TABLE 4-continued

| | Third Compound | | | | First Compound | | | Second Compound | | Drive Voltage (Relative Value) @10 mA/$cm^2$ |
|---|---|---|---|---|---|---|---|---|---|---|
| | Name | $S_1$ [eV] | Name | $S_1$ [eV] | Name | $S_1$ [eV] | ΔST [eV] | Name | $S_1$ [eV] | |
| Example 16 | Matrix-1 | 3.68 | Matrix-2 | 3.08 | A9 | 2.49 | <0.01 | GD | 2.39 | 0.88 |
| Comparative 4 | Matrix-1 | 3.68 | Matrix-2 | 3.08 | Ref-2 | 2.63 | <0.01 | GD | 2.39 | 1.00 |

It is clear from Tables 3 and 4 that organic EL devices in which a compound represented by the formula (1) was used had a lower drive voltage than organic EL devices in which the comparative compound Ref-2 having the same meta-dicyanobenzene skeleton was used.

Modification of Examples

In Examples 10 to 13 shown in Table 3, two compounds, specifically, the compound Matrix-1 and the compound Matrix-2 are used as the third compounds. As modifications of these Examples, however, an organic EL device in which, for instance, only the compound Matrix-1 is used as the third compound can also be manufactured. Table 5 shows the compounds in the emitting layer when such modifications are made with respect to Examples 10 to 13.

TABLE 5

| | Third Compound | First Compound |
|---|---|---|
| Modification of Example 10 | Matrix-1 | A5 |
| Modification of Example 11 | Matrix-1 | A6 |
| Modification of Example 12 | Matrix-1 | A8 |
| Modification of Example 13 | Matrix-1 | A9 |

Synthesis of Compound

Synthesis Example 1

A synthesis method of the compound A1 is described below.

[Formula 123]

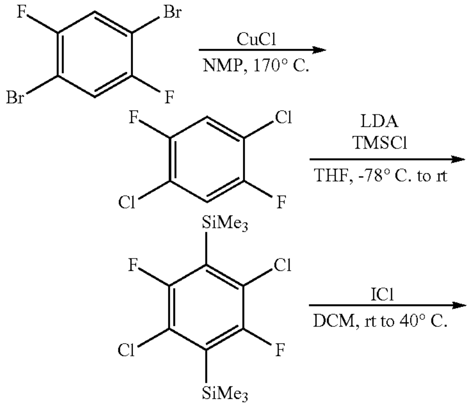

-continued

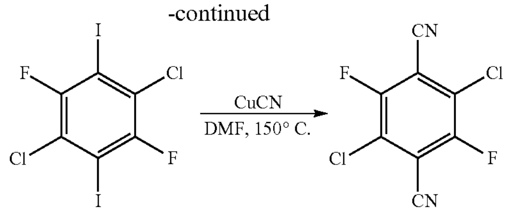

Under nitrogen atmosphere, 1,4-dibromo-2,5-difluorobenzene (15.2 g, 55.9 mmol), copper(I) chloride (13.8 g, 139 mmol) and NMP (200 mL) were put into a 500-mL eggplant flask, and heated at 170 degrees C. with stirring. After four-hour heating with stirring, the material in the eggplant flask was heated to 175 degrees C., further stirred for one hour, and then cooled to room temperature. After cooling, water (200 mL) was added into the eggplant flask. The deposited solid was removed by filtration through celite. The filtrate was extracted with acetic ether. Subsequently, the obtained organic layer was washed with water and a saturated saline solution. After the washed organic layer was dried with magnesium sulfate, a solvent was removed by a rotary evaporator under reduced pressure. The compound obtained through removal under reduced pressure was isolated and purified by silica-gel column chromatography to obtain 1,4-dichloro-2,5-difluorobenzene (4.11 g, 22.5 mmol). NMP is an abbreviation for N-methyl-2-pyrrolidone.

Under nitrogen atmosphere, 1,4-dichloro-2,5-difluorobenzene (4.11 g, 22.5 mmol), chlorotrimethylsilane (6.3 mL, 50 mmol) and THF (25 mL) were put into a 200-mL three-necked flask. The material in the three-necked flask was cooled to −78 degrees C. in a dry ice/acetone bath. Subsequently, LDA prepared was all dropped into the material. The solution obtained by dropping all LDA was stirred at room temperature for two hours. After stirring, water (10 mL) was added into the three-necked flask. Subsequently, an organic layer was extracted with acetic ether. The extracted organic layer was washed with water and a saline solution and dried with magnesium sulfate. Then, a solvent was removed by a rotary evaporator under reduced pressure. The obtained 2,5-dichloro-3,6-difluoro-1,4-phenylenebistrimethylsilane (6.61 g, 20.2 mmol) was not purified and used for the next reaction. Chlorotrimethylsilane is sometimes abbreviated as TMSCl. LDA is an abbreviation for lithium diisopropyl amide.

Under nitrogen atmosphere, 2,5-dichloro-3,6-difluoro-1,4-phenylenebistrimethylsilane (6.61 g, 20.2 mmol) and dichloromethane (100 mL) were put into a 500-mL eggplant flask. Iodine monochloride (2.5 mL) was dropped therein at room temperature. Subsequently, the mixture was stirred at 40 degrees C. Iodine monochloride (0.5 mL) was dropped into a reaction system every two hours, resulting in addition of the total amount of 4.5 mL of iodine monochloride. After all of the iodine monochloride was dropped into the reaction system, the reaction system was further stirred for one hour and 30 minutes and returned to room temperature. Next, a saturated aqueous solution of sodium thiosulfate (20 mL) was added into the eggplant flask. Then, an organic layer was extracted with dichloromethane. The extracted organic layer was washed with water and a saline solution. The washed organic layer was dried with magnesium sulfate. The dried organic layer was condensed by a rotary evaporator. The compound obtained through condensation was purified by silica-gel column chromatography to obtain 1,4-dichloro-2,5-difluoro-3,6-diiodobenzene (6.20 g, 14.3 mmol). DCM is an abbreviation for dichloromethane.

1,4-dichloro-2,5-difluoro-3,6-diiodobenzene (435 mg, 1.0 mmol), copper cyanide (360 mg, 4.0 mmol) and DMF (5 mL) were put into a 5-mL vial, and heated at 150 degrees C. with stirring. After one hour and 30 minutes, the reaction solution was cooled to room temperature and then poured into ammonia water (10 mL). Next, an organic layer was extracted with methylene chloride. The extracted organic layer was washed with water and a saline solution. The washed organic layer was dried with magnesium sulfate. After drying, a solvent was removed by a rotary evaporator under reduced pressure. The compound obtained through removal under reduced pressure was purified by silica-gel column chromatography to obtain 1,4-dicyano-2,5-dichloro-3,6-difluorobenzene (160 mg). DMF is an abbreviation for N,N-dimethylformamide.

[Formula 124]

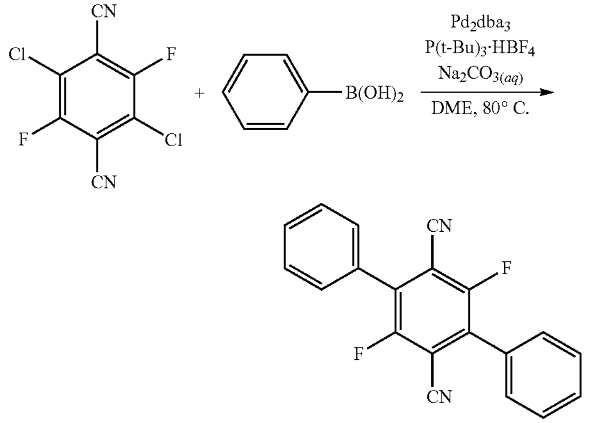

Under nitrogen atmosphere, 2,5-dichloro-3,6-difluoroterephthalonitrile (16.3 g, 70 mmol), phenylboronic acid (17.9 g, 147 mmol), $Pd_2dba_3$ (1.60 g, 1.75 mmol), $P(t\text{-}Bu)_3HBF_4$ (1.01 g, 3.5 mmol), DME (210 mL), sodium carbonate (5.6 g, 53 mmol) and water (105 mL) were put into a 500-mL three-necked flask, and stirred at 80 degrees C. for four hours. After stirring, the reaction solution was left to be cooled to room temperature. Subsequently, an organic layer was extracted with toluene. The extracted organic layer was washed with water and a saline solution. The washed organic layer was condensed by a rotary evaporator. The compound obtained through condensation was purified by silica-gel column chromatography to obtain 3',6'-difluoro-[1,1':4',1"-terphenyl]-2',5'-dicarbonitrile (18.8 g, 59.6 mmol). The structure of the purified compound was identified by ASAP-MS. ASAP/MS is an abbreviation for Atmospheric Pressure Solid Analysis Probe Mass Spectrometry.

[Formula 125]

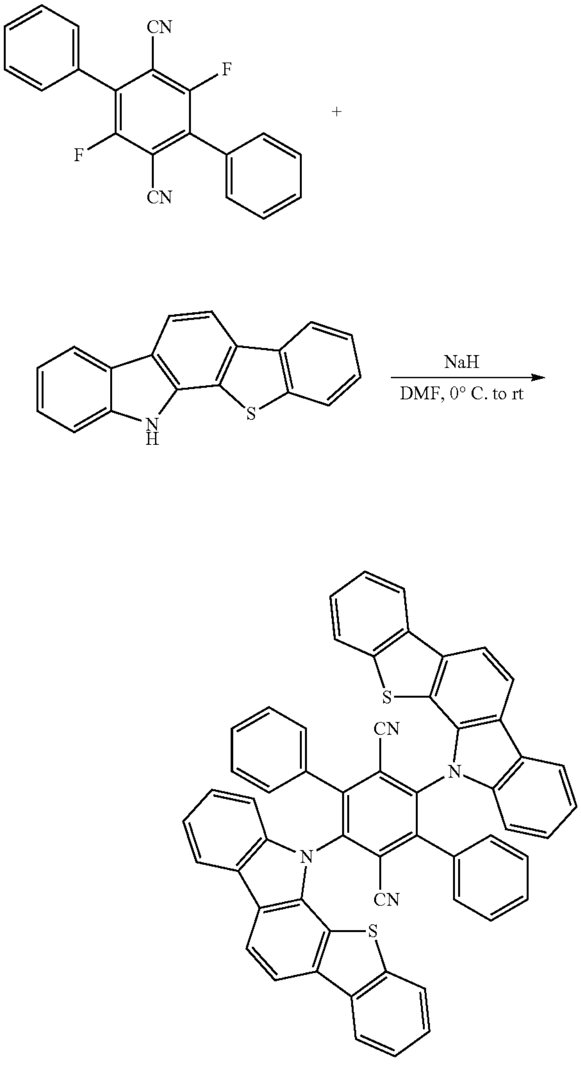

A1

Under nitrogen atmosphere, 12H-benzo[4,5]thieno[2,3-a]carbazole (2.87 g, 110.5 mmol) and DMF (30 mL) were put into a 200-mL flask. The mixture in the flask was cooled to 0 degrees C. Then, the mixture was added with sodium hydride (0.44 g, 10.5 mmol) and stirred for ten minutes. After stirring, 3',6'-difluoro-[1,1':4',1"-terphenyl]-2',5'-dicarbonitrile (1.58 g, 5.0 mmol) was added into the flask. Subsequently, the mixture was heated to room temperature and stirred for four hours. After stirring, water (10 mL) and methanol (10 mL) were added into the flask. The obtained solid was collected by filtration. The collected solid was purified by silica-gel column chromatography and then suspended in and washed with methanol and dimethoxyethane to obtain the target compound A1 (2.82 g, 3.43 mmol). The structure of the compound A1 was identified by LC/MS. LC/MS is an abbreviation for Liquid Chromatography-Mass Spectrometry.

Synthesis Example 2

A synthesis method of the compound A2 is described below.

[Formula 126]

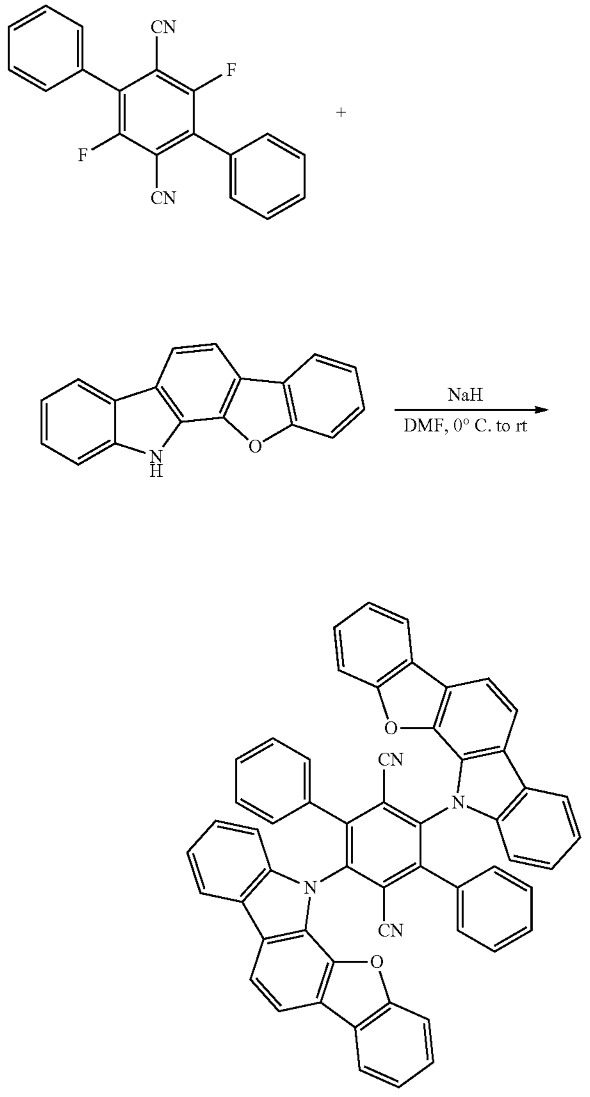

A2

Under nitrogen atmosphere, 12H-benzofluoro[2,3-a]carbazole (2.70 g, 10.5 mmol) and DMF (30 mL) were put into a 300-mL flask. The mixture in the flask was cooled to 0 degrees C. Then, the mixture was added with sodium hydride (0.44 g, 10.5 mmol) and stirred for ten minutes. After stirring, 3',6'-difluoro-[1,1':4',1"-terphenyl]-2',5'-dicarbonitrile (1.58 g, 5.0 mmol) was added into the flask. Subsequently, the mixture was heated to room temperature and stirred for two hours. After stirring, water (20 mL) and methanol (20 mL) were added into the flask. The obtained solid was collected by filtration. The collected solid was purified by silica-gel column chromatography and then suspended in and washed with methanol, dimethoxyethane and toluene to obtain the target compound A2 (2.42 g, 3.06 mmol). The structure of the compound A2 was identified by LC/MS.

Synthesis Example 3

A synthesis method of the compound A3 is described below.

[Formula 127]

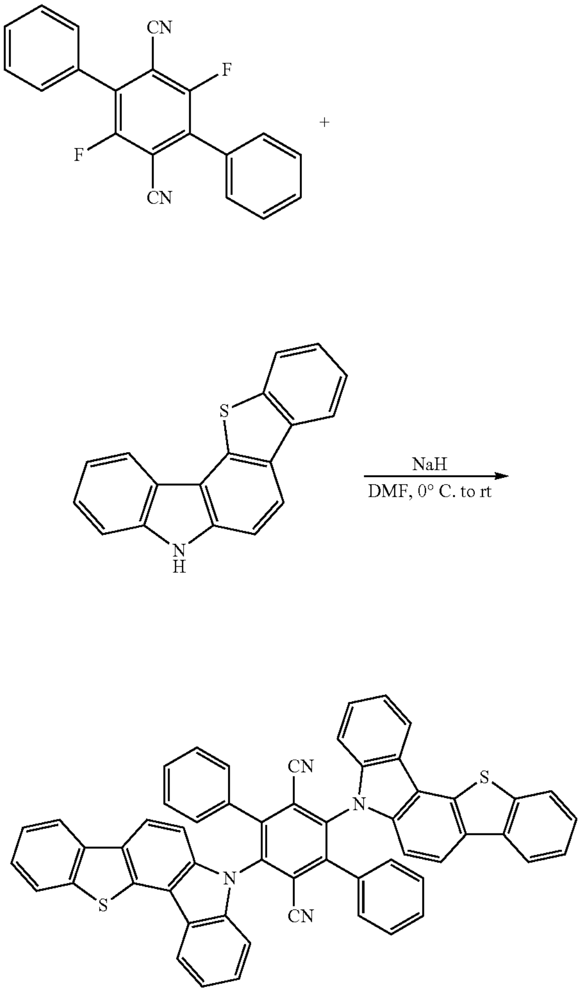

A3

Under nitrogen atmosphere, 5H-benzo[4,5]thieno[3,2-c]carbazole (2.87 g, 10.5 mmol) and DMF (52 mL) were put into a 300-mL flask. The mixture in the flask was cooled to 0 degrees C. Then, the mixture was added with sodium hydride (0.44 g, 10.5 mmol) and stirred for ten minutes. After stirring, 3',6'-difluoro-[1,1':4',1"-terphenyl]-2',5'-dicarbonitrile (1.58 g, 5.0 mmol) was added into the flask. Subsequently, the mixture was heated to room temperature and stirred for four hours. After stirring, water (40 mL) was added into the flask. The obtained solid was collected by filtration. The collected solid was purified by silica-gel column chromatography and then suspended in and washed with dimethoxyethane, acetic ether and toluene to obtain the target compound A3 (4.02 g, 4.9 mmol). The structure of the compound A3 was identified by LC/MS.

Synthesis Example 4

A synthesis method of the compound A4 is described below.

[Formula 128]

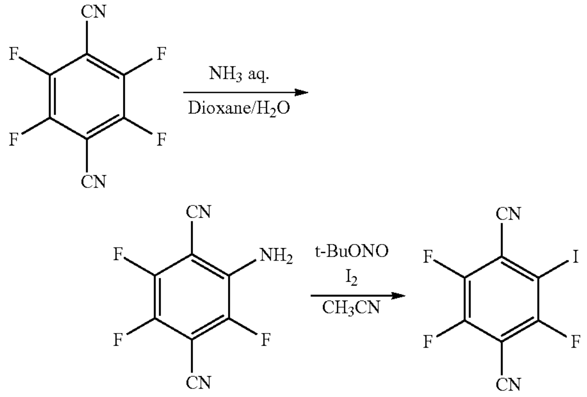

M41 M42

Under nitrogen atmosphere, tetrafluoroterephthalonitrile (25 g, 125 mmol), 1,4-dioxane (625 mL) and water (400 mL) were put into a 2000-mL three-necked flask. Next, 30 mass % ammonia water (13 mL) was put into the three-necked flask and heated at 80 degrees C. for ten hours with stirring. After heating with stirring, the mixture was returned to room temperature (25 degrees C.). A solvent was distilled off using an evaporator. The obtained solid was purified by silica-gel column chromatography to obtain a white solid (24 g). This white solid was analyzed by Gas Chromatograph Mass Spectrometer (GC-MS) and identified as a compound M41 (a yield of 98%).

Under nitrogen atmosphere, the compound M41 (10 g, 51 mmol), iodine (26 g, 102 mmol) and acetonitrile (100 mL) were put into a 200-mL three-necked flask. Next, tert-butyl nitrite (t-BuONO) (10 g, 102 mmol) was put into the three-necked flask and stirred at 25 degrees C. for eight hours. After stirring, the reaction solution was added with a saturated aqueous solution of sodium hydrogen sulfite (50 mL) to extract an organic layer. A solvent was removed from the obtained solution using a rotary evaporator. The obtained solid was purified by silica-gel column chromatography to obtain a white solid (8.4 g). This white solid was analyzed by GC-MS and identified as a compound M42 (a yield of 54%).

[Formula 129]

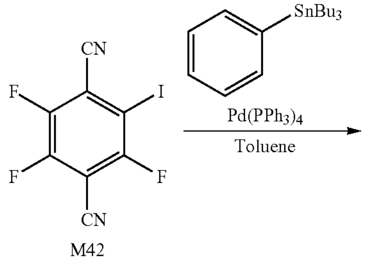

M42

-continued

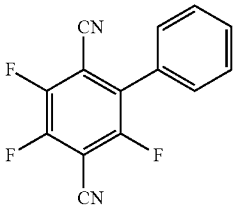

M43

Under nitrogen atmosphere, the compound M42 (8.4 g, 27 mmol) and tributylphenyltin (10 g, 27 mmol) were added with toluene (90 mL) and $Pd(PPh_3)_4$ (1.6 g, 1.4 mmol) and heated to reflux with stirring for eight hours. After the reaction, the reaction solution was purified by silica-gel column chromatography to obtain a white solid (5.2 g). This white solid was analyzed by GC-MS and identified as a compound M43 (a yield of 75%).

[Formula 130]

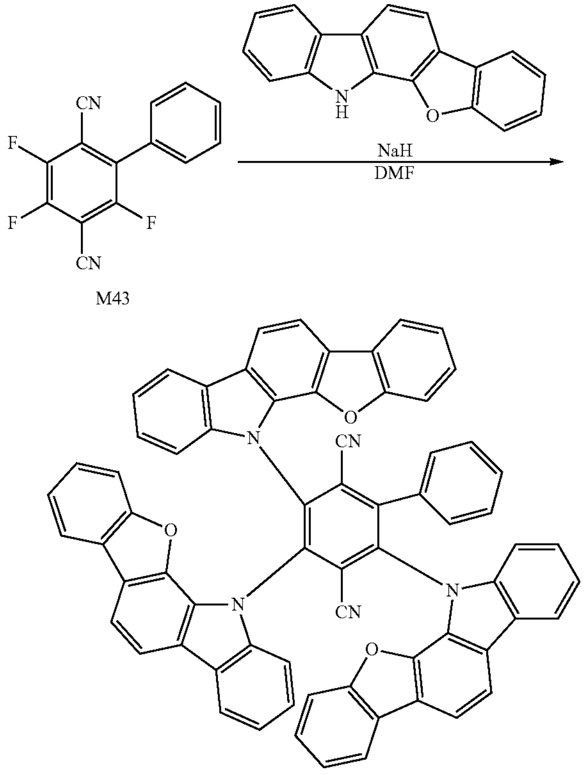

M43

A4

Under nitrogen atmosphere, 12H-Benzofuro[2,3-a]carbazole (1.74 g, 6.78 mmol), sodium hydride (0.27 g, 6.78 mmol) and DMF (30 mL) were put into a 200-mL three-necked flask, and stirred at room temperature (25 degrees C.) for 30 minutes. Next, the compound M43 (0.5 g, 1.94 mmol) was put into the three-necked flask and stirred at 80 degrees C. for four hours. Subsequently, the reaction mixture was added to a saturated aqueous solution of ammonium chloride (50 mL). The deposited solid was purified by silica-gel column chromatography to obtain a yellow solid (1.0 g). This yellow solid was analyzed by ASAP-MS and identified as the compound A4 (a yield of 55%). ASAP-MS is the same as ASAP/MS.

Synthesis Example 5

A synthesis method of the compound A5 is described below.

[Formula 131]

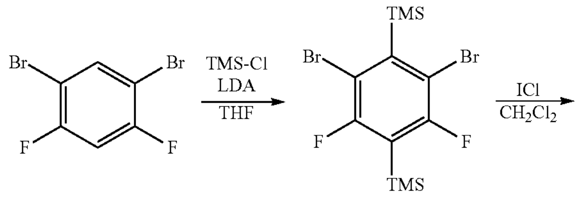

Intermediate a

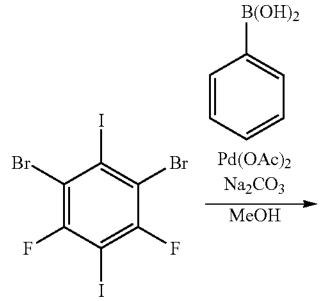

Intermediate b

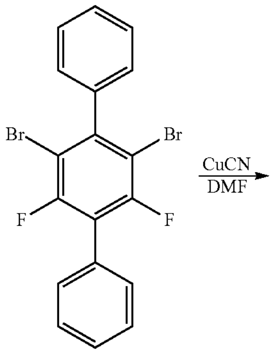

Intermediate c

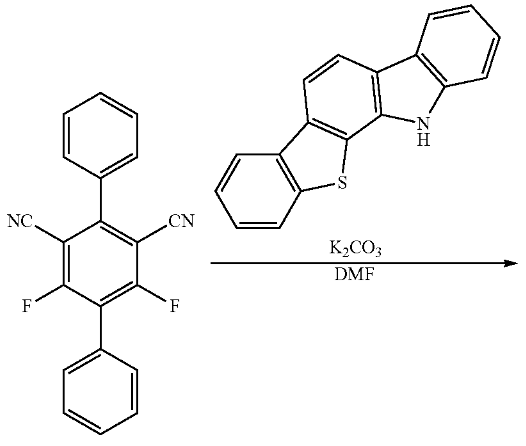

Intermediate d

-continued

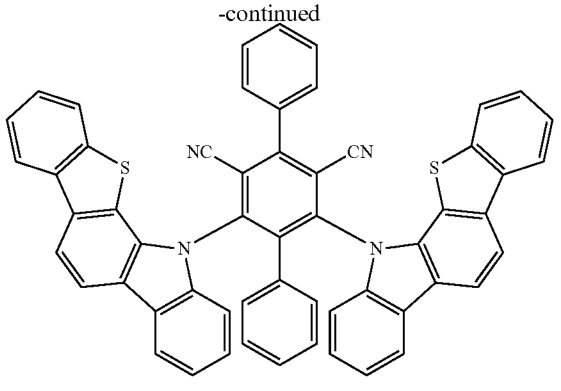

A5

Under nitrogen atmosphere, 1,5-dibromo-2,4-difluorobenzene (50 g, 184 mmol), chlorotrimethylsilane (60 g, 552 mmol) and THF (200 mL) were put into a 1000-mL three-necked flask. The material in the three-necked flask was cooled to −78 degrees C. in a dry ice/acetone bath. Subsequently, 230 ml of lithium diisopropyl amide (2M, THF solution) was dropped into the material. The material was stirred at −78 degrees C. for two hours, then returned to room temperature, and further stirred for two hours. After stirring, water (200 mL) was added into the three-necked flask. Subsequently, an organic layer was extracted with acetic ether. The extracted organic layer was washed with water and a saline solution and dried with magnesium sulfate. Then, a solvent was removed by a rotary evaporator under reduced pressure. The obtained intermediate a (73 g, 175 mmol, a yield of 95%) was not purified and used for the next reaction. Chlorotrimethylsilane is sometimes abbreviated as TMS-Cl. In the chemical formula of the intermediate a, TMS is a trimethylsilyl group. LDA is an abbreviation for lithium diisopropyl amide.

Under nitrogen atmosphere, the intermediate a (73 g, 175 mmol) and dichloromethane (200 mL) were put into a 1000-mL eggplant flask. Iodine monochloride (85 g, 525 mmol) was dissolved in dichloromethane (200 mL) and dropped therein at 0 degrees C. Subsequently, the mixture was stirred at 40 degrees C. for four hours. After stirring, the mixture was returned to room temperature and added with a saturated aqueous solution of sodium hydrogen sulfite (100 mL). Then, an organic layer was extracted with dichloromethane. The extracted organic layer was washed with water and a saline solution. The washed organic layer was dried with magnesium sulfate. The dried organic layer was condensed by a rotary evaporator. The compound obtained through condensation was purified by silica-gel column chromatography to obtain an intermediate b (65 g, 124 mmol, a yield of 71%).

Under nitrogen atmosphere, the intermediate b (22 g, 42 mmol), phenylboronic acid (12.8 g, 105 mmol), palladium acetate (0.47 g, 2.1 mmol), sodium carbonate (22 g, 210 mmol) and methanol (150 mL) were put into a 500-mL three-necked flask, and stirred at 80 degrees C. for four hours. After stirring, the reaction solution was left to be cooled to room temperature. Subsequently, an organic layer was extracted with acetic ether. The extracted organic layer was washed with water and a saline solution. The washed organic layer was condensed by a rotary evaporator. The compound obtained through condensation was purified by silica-gel column chromatography to obtain an intermediate c (10 g, 24 mmol, a yield of 56%). The structure of the purified compound was identified by ASAP/MS. ASAP/MS is an abbreviation for Atmospheric Pressure Solid Analysis Probe Mass Spectrometry.

Under nitrogen atmosphere, the intermediate c (10 g, 24 mmol), copper cyanide (10.6 g, 118 mmol) and DMF (15 mL) were put into a 200-mL three-necked flask, and heated at 150 degrees C. for eight hours with stirring. After stirring, the reaction solution was cooled to room temperature and then poured into ammonia water (10 mL). Next, an organic layer was extracted with methylene chloride. The extracted organic layer was washed with water and a saline solution. The washed organic layer was dried with magnesium sulfate. After drying, a solvent was removed by a rotary evaporator under reduced pressure. The compound obtained through removal under reduced pressure was purified by silica-gel column chromatography to obtain an intermediate d (5.8 g, 18.34 mmol, a yield of 78%). DMF is an abbreviation for N,N-dimethylformamide.

Under nitrogen atmosphere, the intermediate d (1.0 g, 3.2 mmol), 12H-[1]Benzothieno[2,3-a]carbazole (1.9 g, 7 mmol), potassium carbonate (1.3 g, 9.50 mmol) and DMF (30 mL) were put into a 100-mL three-necked flask, and stirred at 120 degrees C. for six hours. After stirring, the deposited solid was filtrated and purified by silica-gel column chromatography to obtain the compound A5 (1.8 g, 2.2 mmol, a yield of 69%). The obtained compound was identified as the compound A5 by ASAP-MS.

Synthesis Example 6

A synthesis method of the compound A6 is described below.

[Formula 132]

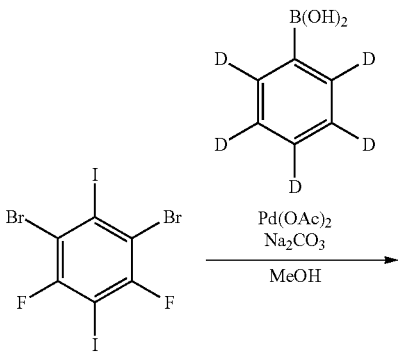

Intermediate b

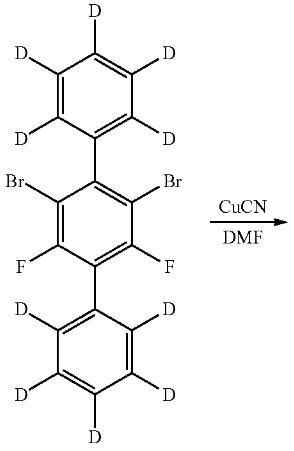

Intermediate e

-continued

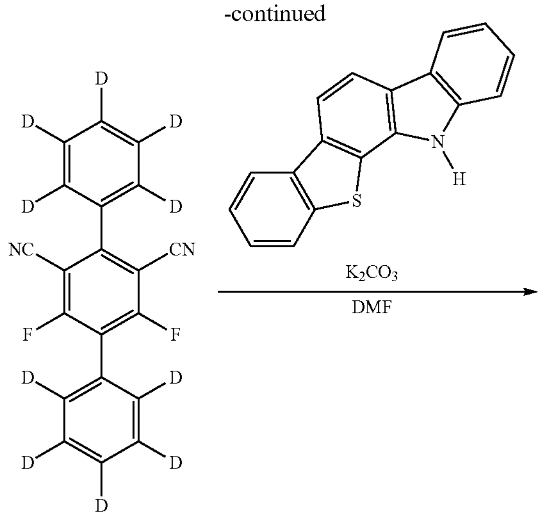

Intermediate f

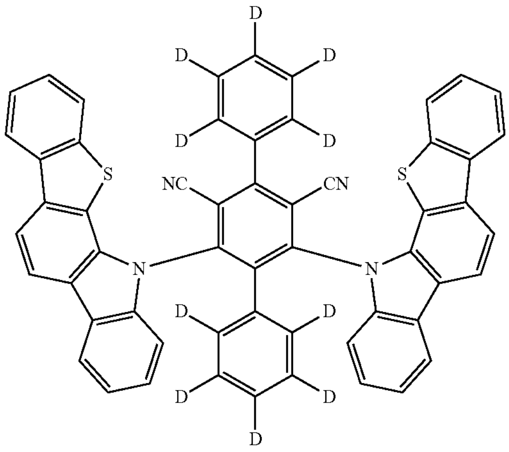

A6

Under nitrogen atmosphere, the intermediate b (30 g, 57 mmol), phenyl-d5-boronic acid (15.9 g, 125 mmol), palladium acetate (0.64 g, 2.9 mmol), sodium carbonate (27 g, 250 mmol) and methanol (150 mL) were put into a 500-mL three-necked flask, and stirred at 80 degrees C. for six hours. After stirring, the reaction solution was left to be cooled to room temperature. Subsequently, an organic layer was extracted with acetic ether. The extracted organic layer was washed with water and a saline solution. The washed organic layer was condensed by a rotary evaporator. The compound obtained through condensation was purified by silica-gel column chromatography to obtain an intermediate e (12.6 g, 29 mmol, a yield of 51%). The structure of the purified compound was identified by ASAP/MS.

Under nitrogen atmosphere, the intermediate e (12.6 g, 29 mmol), copper cyanide (13 g, 145 mmol) and DMF (20 mL) were put into a 200-mL three-necked flask, and heated at 150 degrees C. for eight hours with stirring. After stirring, the reaction solution was cooled to room temperature and then poured into ammonia water (10 mL). Next, an organic layer was extracted with methylene chloride. The extracted organic layer was washed with water and a saline solution. The washed organic layer was dried with magnesium sulfate. After drying, a solvent was removed by a rotary evaporator under reduced pressure. The compound obtained through removal under reduced pressure was purified by silica-gel column chromatography to obtain an intermediate f (6.2 g, 19.1 mmol, a yield of 66%).

Under nitrogen atmosphere, the intermediate f (1.5 g, 4.6 mmol), 12H-[1]Benzothieno[2,3-a]carbazole (2.8 g, 10.1 mmol), potassium carbonate (1.9 g, 13.8 mmol) and DMF (30 mL) were put into a 100-mL three-necked flask, and stirred at 120 degrees C. for six hours. After stirring, the deposited solid was filtrated and purified by silica-gel column chromatography to obtain the compound A6 (3.2 g, 3.82 mmol, a yield of 83%). The obtained compound was identified as the compound A6 by ASAP-MS.

Synthesis Example 7

A synthesis method of the compound A7 is described below.

[Formula 133]

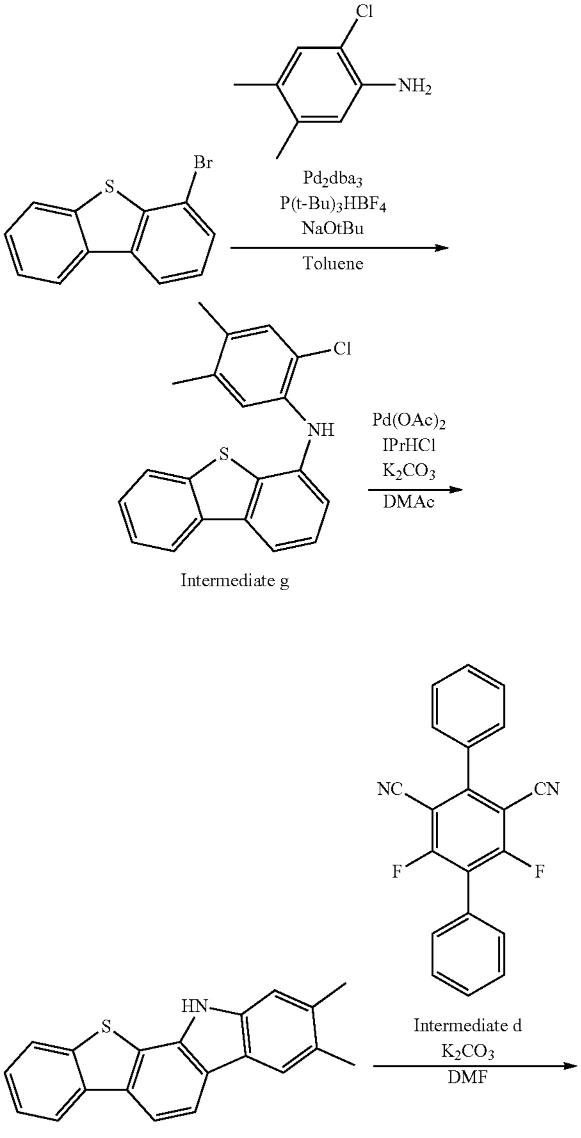

-continued

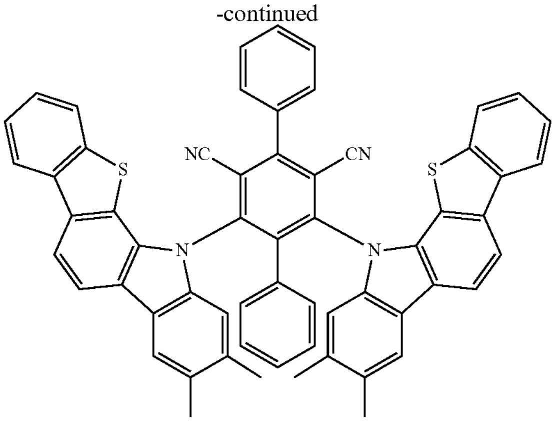

A7

Under nitrogen atmosphere, 4-bromodibenzothiophene (13.2 g, 50 mmol), 2-chloro-4,5-methylaniline (9.4 g, 60 mmol), tris(dibenzylideneacetone)dipalladium(0) (0.45 g, 0.5 mmol), tri-tert-butylphosphonium tetrafluoroborate (0.58 g, 2.0 mmol), sodium tert-butoxide (7.2 g, 75 mmol) and toluene (150 mL) were added into a 300-ml three-necked flask, and heated at 60 degrees C. for four hours with stirring. After stirring, the mixture was cooled to room temperature (25 degrees C.). The reaction solution was purified by silica-gel column chromatography to obtain an intermediate g (15 g, 44.5 mmol, a yield of 89%). The purified compound was identified as the intermediate g by GC-MS.

Under nitrogen atmosphere, the intermediate g (15 g, 44.5 mmol), 1,3-bis(2,6-diisopropylphenyl)imidazolium chloride (IPrHCl) (0.79 g, 1.78 mmol), palladium(II) acetate (0.2 g, 0.89 mmol), potassium carbonate (12.2 g, 89 mmol) and N,N-dimethylacetamide (DMAc) (120 mL) were added into a 300-ml three-necked flask, and stirred at 130 degrees C. for seven hours. After stirring, the mixture was cooled to room temperature (25 degrees C.). The reaction solution was purified by silica-gel column chromatography to obtain an intermediate h (12 g, 40.5 mmol, a yield of 91%). The purified compound was identified as the intermediate h by GC-MS.

Under nitrogen atmosphere, the intermediate d (1.0 g, 3.2 mmol), the intermediate h (2.1 g, 7 mmol), potassium carbonate (1.3 g, 9.50 mmol) and DMF (30 mL) were put into a 100-mL three-necked flask, and stirred at 120 degrees C. for four hours. The deposited solid was filtrated and purified by silica-gel column chromatography to obtain the compound A7 (1.5 g, 1.7 mmol, a yield of 54%). The obtained compound was identified as the compound A7 by ASAP-MS.

Synthesis Example 8

A synthesis method of the compound A8 is described below.

[Formula 134]

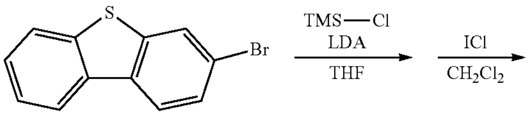

-continued

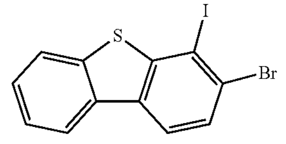

Intermediate i

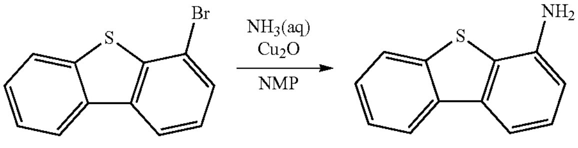

Intermediate j

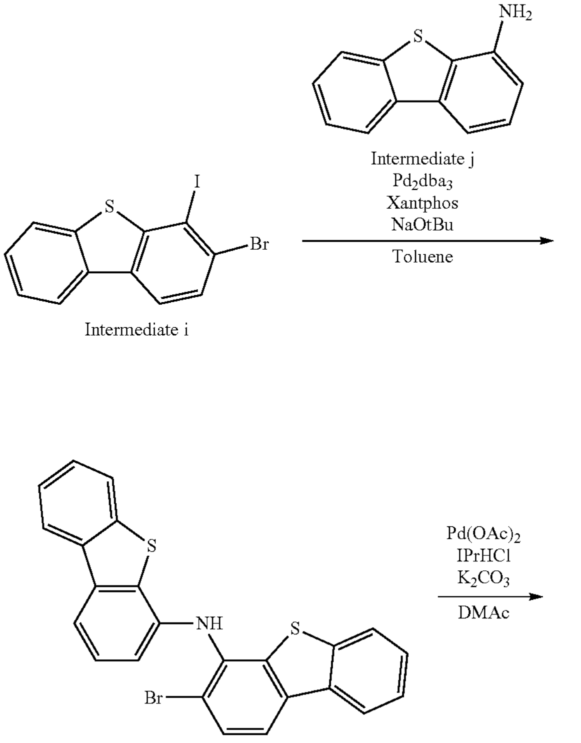

Intermediate i

Intermediate k

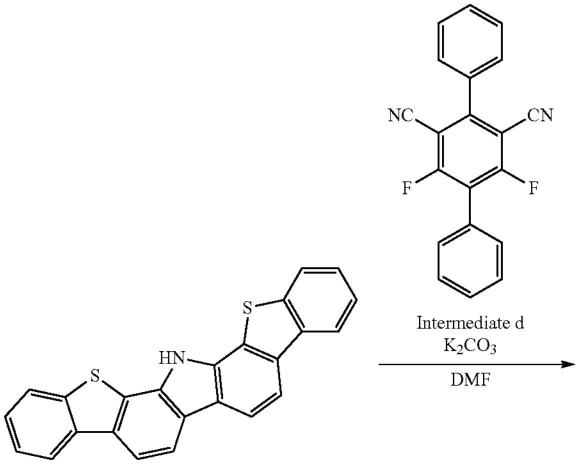

Intermediate L

-continued

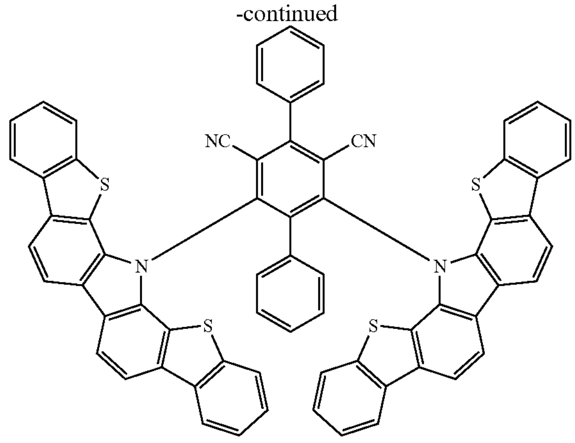

A8

Under nitrogen atmosphere, 3-bromodibenzothiophene (26.3 g, 100 mmol), chlorotrimethylsilane (33 g, 300 mmol) and THF (150 mL) were put into a 500-ml three-necked flask. The material in the three-necked flask was cooled to −78 degrees C. in a dry ice/acetone bath. Subsequently, 125 ml of lithium diisopropyl amide (2M, THF solution) was dropped into the material. The material was stirred at −78 degrees C. for two hours, then returned to room temperature, and further stirred for two hours. After stirring, water (100 mL) was added into the three-necked flask. Subsequently, an organic layer was extracted with acetic ether. The extracted organic layer was washed with water and a saline solution and dried with magnesium sulfate. Then, a solvent was removed by a rotary evaporator under reduced pressure. The obtained liquid was added with dichloromethane (200 ml). Then, iodine monochloride (49 g, 300 mmol) was dropped therein at 0 degrees C. Subsequently, the mixture was stirred at 40 degrees C. for six hours. After stirring, the mixture was returned to room temperature and added with a saturated aqueous solution of sodium hydrogen sulfite (100 mL). Then, an organic layer was extracted with dichloromethane. The extracted organic layer was washed with water and a saline solution. The washed organic layer was dried with magnesium sulfate. The dried organic layer was condensed by a rotary evaporator. The compound obtained through condensation was purified by silica-gel column chromatography to obtain an intermediate i (28 g, 72 mmol, a yield of 72%).

Under nitrogen atmosphere, 4-bromodibenzothiophene (13.2 g, 50 mmol), copper(I) oxide (0.1 g, 0.66 mmol), ammonia water (100 ml, 30%) and NMP (N-methylpyrrolidone) (100 mL) were put into a 500-ml three-necked flask, and stirred at 80 degrees C. for 12 hours. After stirring, the mixture was returned to room temperature. Then, an organic layer was extracted with ion exchange water (100 ml) and diethylether. The extracted organic layer was washed with water and a saline solution. The washed organic layer was dried with magnesium sulfate. The dried organic layer was condensed by a rotary evaporator. The compound obtained through condensation was purified by silica-gel column chromatography to obtain an intermediate j (9.0 g, 45 mmol, a yield of 90%).

Under nitrogen atmosphere, the intermediate i (17.5 g, 45 mmol), the intermediate j (9.0 g, 45 mmol), tris(dibenzylideneacetone)dipalladium(0) (0.8 g, 0.9 mmol), Xantphos (1.0 g, 1.8 mmol), sodium tert-butoxide (6.5 g, 68 mmol) and toluene (150 mL) were added into a 300-ml three-necked flask, and heated at 100 degrees C. for eight hours with stirring. After stirring, the mixture was cooled to room temperature (25 degrees C.). The reaction solution was purified by silica-gel column chromatography to obtain an intermediate k (9.5 g, 20.7 mmol, a yield of 46%). The purified compound was identified as the intermediate k by GC-MS.

Under nitrogen atmosphere, the intermediate k (9.5 g, 20.7 mmol), 1,3-bis(2,6-diisopropylphenyl)imidazolium chloride (IPrHCI) (0.36 g, 0.82 mmol), palladium(II) acetate (0.093 g, 0.41 mmol), potassium carbonate (5.8 g, 42 mmol) and N,N-dimethylacetamide (DMAc) (60 mL) were added into a 200-ml three-necked flask, and stirred at 160 degrees C. for ten hours. After stirring, the mixture was cooled to room temperature (25 degrees C.). The deposited solid was filtrated and washed with acetone to obtain an intermediate L (6.9 g, 18.2 mmol, a yield of 88%). The washed compound was identified as the intermediate L by GC-MS.

Under nitrogen atmosphere, the intermediate d (1.0 g, 3.2 mmol), the intermediate L (2.7 g, 7 mmol), potassium carbonate (1.3 g, 9.50 mmol) and DMF (30 mL) were put into a 100-mL three-necked flask, and stirred at 140 degrees C. for fou hours. After stirring, the deposited solid was filtrated and purified by silica-gel column chromatography to obtain the compound A8 (2.3 g, 2.2 mmol, a yield of 69%). The obtained compound was identified as the compound A8 by ASAP-MS.

Synthesis Example 9

A synthesis method of the compound A9 is described below.

[Formula 135]

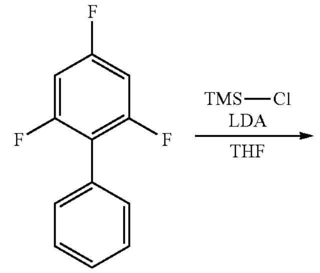

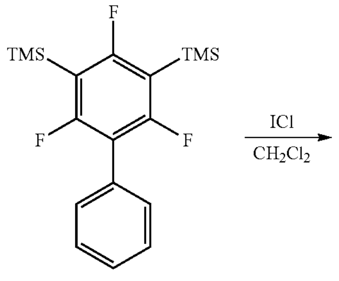

Intermediate n

-continued

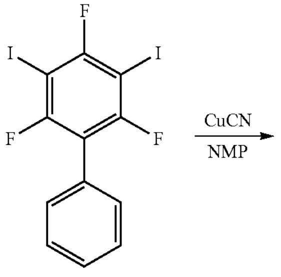

Intermediate o

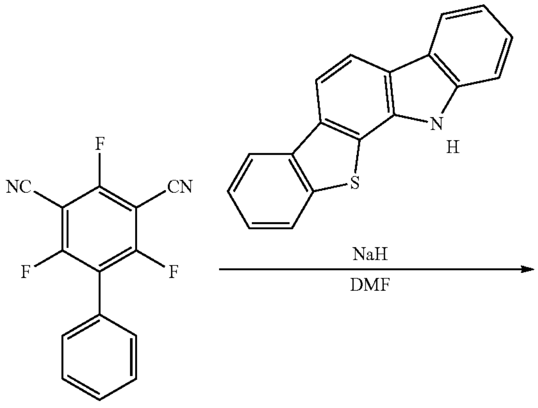

Intermediate p

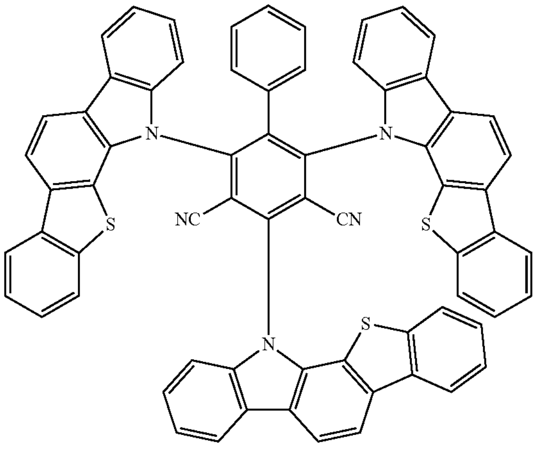

A9

Under nitrogen atmosphere, 2,4,6-trifluoro-1,1'-biphenyl (10 g, 48 mmol), chlorotrimethylsilane (17 g, 144 mmol) and THF (50 mL) were put into a 200-ml three-necked flask. The material in the three-necked flask was cooled to −78 degrees C. in a dry ice/acetone bath. Subsequently, 60 ml of lithium diisopropyl amide (2M, THF solution) was dropped into the material. The material was stirred at −78 degrees C. for two hours, then returned to room temperature, and further stirred for two hours. After stirring, water (50 mL) was added into the three-necked flask. Subsequently, an organic layer was extracted with acetic ether. The extracted organic layer was washed with water and a saline solution and dried with magnesium sulfate. Then, a solvent was removed by a rotary evaporator under reduced pressure. The obtained intermediate n (15 g, 44 mmol, a yield of 92%) was not purified and used for the next reaction. Chlorotrimethylsilane is sometimes abbreviated as TMS-Cl. In the chemical formula of the intermediate n, TMS is a trimethylsilyl group. LDA is an abbreviation for lithium diisopropyl amide.

Under nitrogen atmosphere, the intermediate n (15 g, 44 mmol) and dichloromethane (100 mL) were put into a 500-mL eggplant flask. Iodine monochloride (21 g, 132 mmol) was dissolved in dichloromethane (200 mL) and dropped therein at 0 degrees C. Subsequently, the mixture was stirred at 40 degrees C. for four hours. After stirring, the mixture was returned to room temperature and added with a saturated aqueous solution of sodium hydrogen sulfite (100 mL). Then, an organic layer was extracted with dichloromethane. The extracted organic layer was washed with water and a saline solution. The washed organic layer was dried with magnesium sulfate. The dried organic layer was condensed by a rotary evaporator. The compound obtained through condensation was purified by silica-gel column chromatography to obtain an intermediate o (10 g, 121 mmol, a yield of 48%).

Under nitrogen atmosphere, the intermediate o (10 g, 21 mmol), copper cyanide (4.1 g, 46 mmol) and NMP (N-methyl-2-pyrrolidone) (45 mL) were put into a 200-mL three-necked flask, and heated at 150 degrees C. for eight hours with stirring. After stirring, the reaction solution was cooled to room temperature and then poured into ammonia water (30 mL). Next, an organic layer was extracted with methylene chloride. The extracted organic layer was washed with water and a saline solution. The washed organic layer was dried with magnesium sulfate. After drying, a solvent was removed by a rotary evaporator under reduced pressure. The compound obtained through removal under reduced pressure was purified by silica-gel column chromatography to obtain an intermediate p (1.8 g, 7.1 mmol, a yield of 34%).

Under nitrogen atmosphere, 12H-[1]Benzothieno[2,3-a]carbazole (3.0 g, 11 mmol) and DMF (20 mL) were put into a 100-mL flask. The mixture in the flask was cooled to 0 degrees C. Then, the mixture was added with sodium hydride (0.44 g, 11 mmol) and stirred for 30 minutes. After stirring, the intermediate p (0.8 g, 3.2 mmol) was added into the flask. Subsequently, the mixture was heated to room temperature and stirred for two hours. After stirring, water (20 mL) and methanol (20 mL) were added into the flask. The obtained solid was collected by filtration. The collected solid was purified by silica-gel column chromatography to obtain the compound A9 (1.6 g, 1.60 mmol, a yield of 50%). The obtained compound was identified as the compound A9 by ASAP-MS.

Synthesis Example 10

A synthesis method of the compound A10 is described below.

[Formula 136]

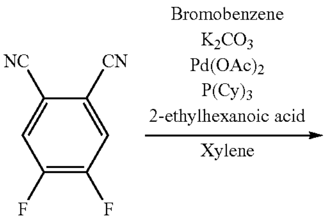

-continued

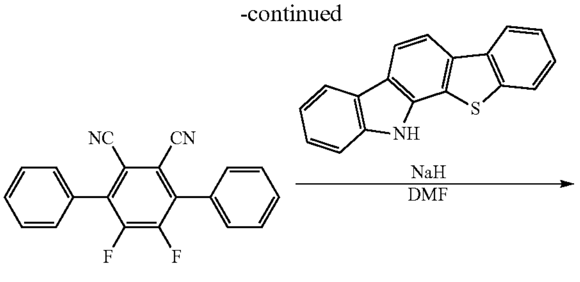

Intermediate m

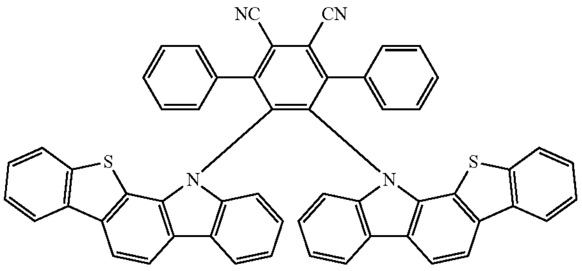

A10

Under nitrogen atmosphere, 4,5-difluorophthalonitrile (10 g, 61 mmol), bromobenzene (38 g, 244 mmol), potassium carbonate (13 g, 91 mmol), palladium acetate (0.4 g, 1.8 mmol), tricyclohexylphosphine (0.4 g, 1.8 mmol), palladium acetate (0.4 g, 1.8 mmol), 2-ethylhexanoic acid (2 ml, 12.2 mmol) and xylene (120 ml) were put into a 300-ml three-necked flask, and stirred at 150 degrees C. for ten hours. After stirring, the reaction solution was left to be cooled to room temperature. Subsequently, an organic layer was extracted with acetic ether. The extracted organic layer was washed with water and a saline solution. The washed organic layer was condensed by a rotary evaporator. The compound obtained through condensation was purified by silica-gel column chromatography to obtain an intermediate m (7.2 g, 23 mmol, a yield of 37%). The structure of the purified compound was identified as the intermediate m by ASAP/MS. ASAP/MS is an abbreviation for Atmospheric Pressure Solid Analysis Probe Mass Spectrometry. $P(Cy)_3$ is an abbreviation for tricyclohexylphosphine.

Under nitrogen atmosphere, 12H-[1]Benzothieno[2,3-a]carbazole (3.0 g, 11 mmol) and DMF (20 mL) were put into a 100-mL flask. The mixture in the flask was cooled to 0 degrees C. Then, the mixture was added with sodium hydride (0.44 g, 11 mmol) and stirred for 30 minutes. After stirring, the intermediate m (1.4 g, 4.4 mmol) was added into the flask. Subsequently, the mixture was heated to room temperature and stirred for two hours. After stirring, water (20 mL) and methanol (20 mL) were added into the flask. The obtained solid was collected by filtration. The collected solid was purified by silica-gel column chromatography to obtain the compound A10 (2.6 g, 3.16 mmol, a yield of 71%). The obtained compound was identified as the compound A10 by ASAP-MS.

Comparative Synthesis Example 1

A synthesis method of the comparative compound Ref-1 is described below.

[Formula 137]

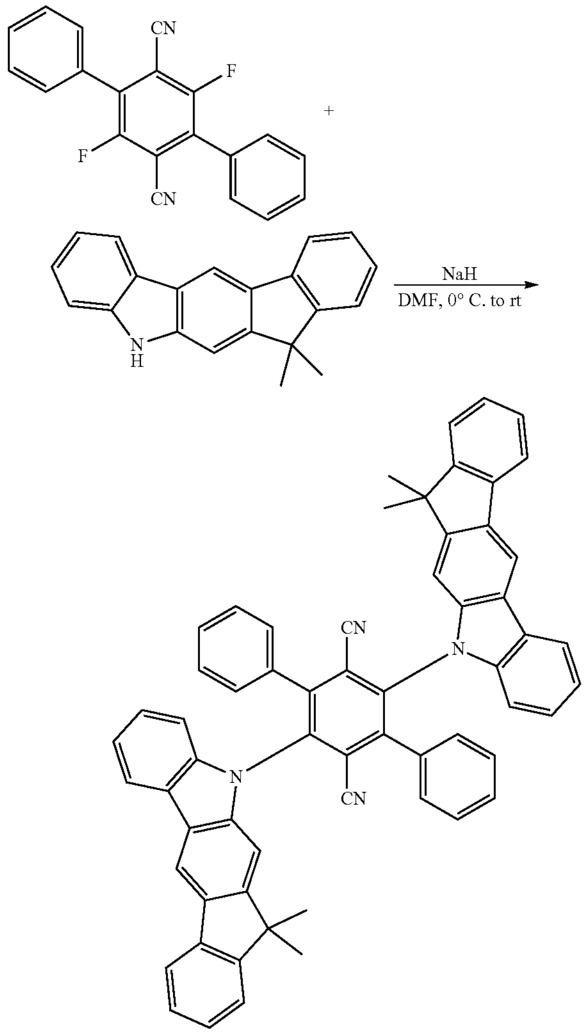

Ref-1

Under nitrogen atmosphere, 7,7-dimethyl-5,7-dihydroindeno[2,1-b]carbazole (2.97 g, 10.5 mmol) and DMF (30 mL) were put into a 300-mL flask. The mixture in the flask was cooled to 0 degrees C. Then, the mixture was added with sodium hydride (0.44 g, 10.5 mmol) and stirred for ten minutes. After stirring, 3',6'-difluoro-[1,1':4',1"-terphenyl]-2',5'-dicarbonitrile (1.58 g, 5.0 mmol) was added into the flask. Subsequently, the mixture was heated to room temperature and stirred for two hours. After stirring, water (20 mL) and methanol (20 mL) were added into the flask. The obtained solid was collected by filtration. The collected solid was purified by silica-gel column chromatography and then suspended in and washed with dimethoxyethane to obtain the target comparative compound Ref-1 (3.9 g, 4.6 mmol). The structure of the compound Ref-1 was identified by LC/MS.

Comparative Synthesis Example 2

A synthesis method of the comparative compound Ref-2 is described below.

[Formula 138]

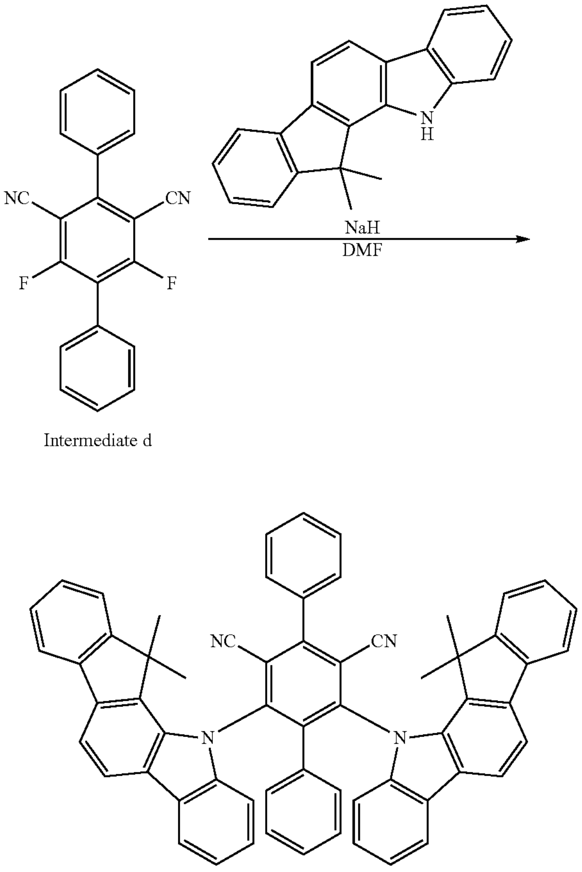

Intermediate d

Ref-2

Under nitrogen atmosphere, 7,7-dimethyl-5,7-dihydroindeno[2,1-b]carbazole (2.00 g, 7.1 mmol) and DMF (20 mL) were put into a 200-mL flask. The mixture in the flask was cooled to 0 degrees C. Then, the mixture was added with sodium hydride (0.28 g, 7.1 mmol) and stirred for 30 minutes. After stirring, the intermediate d (1.00 g, 3.2 mmol) was added into the flask. Subsequently, the mixture was heated to room temperature and stirred for two hours. After stirring, water (20 mL) and methanol (20 mL) were added into the flask. The obtained solid was collected by filtration. The collected solid was purified by silica-gel column chromatography to obtain the comparative compound Ref-2 (0.9 g, 1.00 mmol, a yield of 34%). The obtained compound was identified as the comparative compound Ref-2 by ASAP-MS.

EXPLANATION OF CODES

1 . . . organic EL device, 2 . . . substrate, 3 . . . anode, 4 . . . cathode, 5 . . . emitting layer, 6 . . . hole injecting layer, 7 . . . hole transporting layer, 8 . . . electron transporting layer, 9 . . . electron injecting layer

The invention claimed is:

1. A compound represented by a formula (1) below,

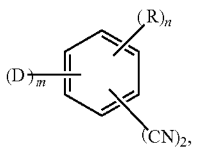

(1)

wherein:

D is a group represented by a formula (11), (12), or (13) below;

m is 1, 2, or 3;

when m is 2 or 3, a plurality of D are mutually the same or different;

R is each independently a hydrogen atom, a halogen atom, or a substituent;

R serving as a substituent is each independently a substituted or unsubstituted aryl group having 6 to 14 ring carbon atoms, a substituted or unsubstituted heteroaryl group having 5 to 14 ring atoms, a substituted or unsubstituted alkyl group having 1 to 6 carbon atoms, a substituted or unsubstituted cycloalkyl group having 3 to 6 ring carbon atoms, a substituted or unsubstituted alkylsilyl group having 3 to 6 carbon atoms, a substituted or unsubstituted arylsilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms;

a substituent of a substituted aryl group having 6 to 14 ring carbon atoms as R in the formula (1) is an aryl group, alkyl group, alkyl halide group, substituted silyl group, alkylsulfonyl group, aralkyl group, alkoxy group, alkoxy halide group, arylalkoxy group, alkenyl group, alkynyl group, alkylthio group, arylthio group, substituted phosphino group, arylcarbonyl group, acyl group, substituted phosphoryl group, ester group, siloxanyl group, carbamoyl group, unsubstituted silyl group, halogen atom, cyano group, hydroxy group, thiol group, nitro group, or carboxy group;

at least one R is a substituent;

the at least one R serving as a substituent is bonded by a carbon-carbon bond to a benzene ring in the formula (1);

n is 1, 2, or 3;

when n is 2 or 3, a plurality of R are mutually the same or different; and a sum of the number of R serving as a substituent and the number of a group represented by the formula (12) or (13) is 3 or 4, (11)

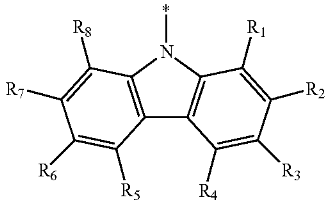

-continued (12)

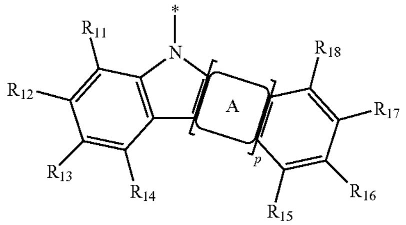

(13)

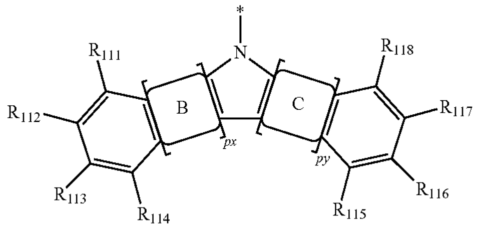

wherein:

$R_1$ to $R_8$ in the formula (11) are each independently a hydrogen atom, a halogen atom, or a substituent;

$R_{11}$ to $R_{18}$ in the formula (12) are each independently a hydrogen atom, a halogen atom, or a substituent, or at least one combination of a combination of $R_{15}$ and $R_{16}$, a combination of $R_{16}$ and $R_{17}$, or a combination of $R_{17}$ and $R_{18}$ are mutually bonded to form a ring, but each combination of a combination of $R_1$ and $R_{12}$, $R_{12}$ and $R_{13}$, and $R_{13}$ and $R_{14}$, are not mutually bonded;

$R_{111}$ to $R_{118}$ in the formula (13) are each independently a hydrogen atom, a halogen atom, or a substituent, or at least one combination of a combination of $R_{111}$ and $R_{112}$, a combination of $R_{112}$ and $R_{113}$, a combination of $R_{113}$ and $R_{114}$, a combination of $R_{115}$ and $R_{116}$, a combination of $R_{116}$ and $R_{117}$, or a combination of $R_{117}$ and $R_{118}$ are mutually bonded to form a ring;

$R_1$ to $R_8$ serving as a substituent, $R_{11}$ to $R_{18}$ serving as a substituent, and Rin to $R_{118}$ serving as a substituent are each independently a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted cycloalkyl group having 3 to 30 ring carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms, except that $R_{11}$ to $R_{18}$ serving as a substituent in the formula (12) are not a substituted or unsubstituted alkylamino group having 2 to 30 carbon atoms and not a substituted or unsubstituted arylamino group having 6 to 60 ring carbon atoms;

in the formulae (12) and (13):

A, B, and C are each independently a cyclic structure selected from the group consisting of cyclic structures represented by formulae (14), (15), and (16) below;

the cyclic structure A, the cyclic structure B and the cyclic structure C are each fused with adjacent ring(s) at any position(s);

p is 1, 2, 3, or 4;

px and py are each independently 2, 3, or 4;

when p is 2, 3, or 4, a plurality of cyclic structures A are mutually the same or different;

when px is 2, 3, or 4, a plurality of cyclic structures B are mutually the same or different;

when py is 2, 3, or 4, a plurality of cyclic structures C are mutually the same or different;

* in the formulae (11) to (13) represents a bonding position to a benzene ring in the formula (1), (14)

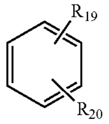

(15)

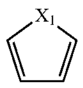

(16)

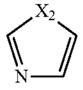
, where, in the formula (14):

$R_{19}$ and $R_{20}$ are each independently a hydrogen atom, a halogen atom, or a substituent, or a combination of $R_{19}$ and $R_{20}$ are mutually bonded to form a ring;

in the formulae (15) and (16):

X1 and X2 are each independently $NR_{120}$, a sulfur atom, or an oxygen atom;

$R_{120}$ is a hydrogen atom, a halogen atom, or a substituent; and $R_{19}$, $R_{20}$, and $R_{120}$ serving as a substituent each independently represent the same as $R_1$ to $R_8$ serving as a substituent; and at least one D is a group represented by the formula (13) satisfying that px and py are each 2 and comprising a first cyclic structure B represented by the formula (14), a second cyclic structure B represented by the formula (15), a first cyclic structure C represented by the formula (14), and a second cyclic structure C represented by the formula (15), X1 in the formula (15) being a sulfur atom or an oxygen atom.

2. The compound of claim 1, wherein the sum of the number of R serving as a substituent and the number of a group represented by the formula (12) or (13) is 4.

3. The compound of claim 1, wherein a compound represented by the formula (1) is represented by a formula (110), (120) or (130) below, (110)

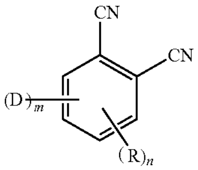

-continued (120)

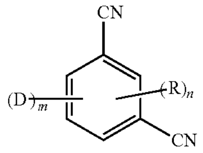

(130)

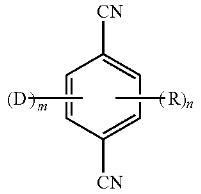

wherein:

D, m, R and n respectively represent the same as D, m, R and n in the formula (1).

4. The compound of claim 1, wherein a compound represented by the formula (1) is a compound selected from the group consisting of compounds represented by formulae (111) to (118) below, (111)

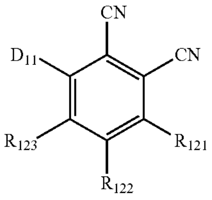

(112)

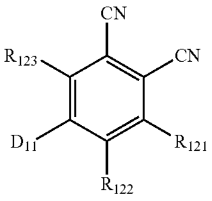

wherein:

$D_{11}$ is a group represented by the formula (13); and $R_{121}$ to $R_{123}$ each independently represent the same as R in the formula (1), at least one of $R_{121}$ to $R_{123}$ is a substituent, and $R_{121}$ to $R_{123}$ serving as a substituent represent the same as R serving as a substituent in the formula (1), (113)

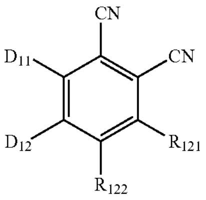

-continued (114)

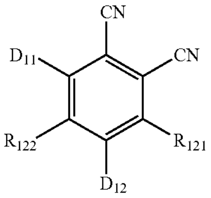

(115)

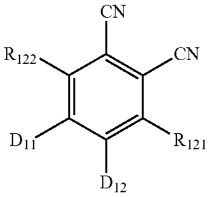

(116)

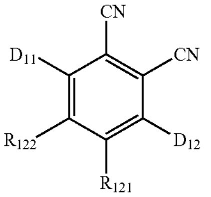

where:

$D_{11}$ and $D_{12}$ each independently represent the same as D in the formula (1), and at least one of $D_{11}$ or $D_{12}$ is a group represented by the formula (13); and $R_{121}$ and $R_{122}$ each independently represent the same as R in the formula (1), at least one of $R_{121}$ or $R_{122}$ is a substituent, and $R_{121}$ and $R_{122}$ serving as a substituent represent the same as R serving as a substituent in the formula (1), (117)

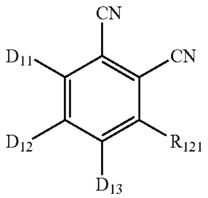

(118)

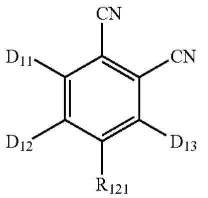

wherein:

$D_{11}$ to $D_{13}$ each independently represent the same as D in the formula (1), and at least one of $D_{11}$ to $D_{13}$ is a group represented by the formula (13); and $R_{121}$ is a substituent, and $R_{121}$ serving as a substituent represents the same as R serving as a substituent in the formula (1).

5. The compound of claim 1, wherein a compound represented by the formula (1) is a compound selected from the group consisting of compounds represented by formulae (121) to (129) below, (121)

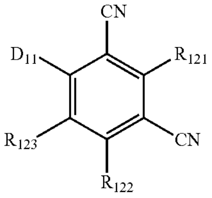

(122)

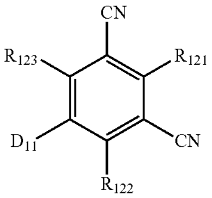

(123)

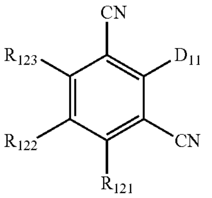

wherein:

$D_{11}$ is a group represented by the formula (13); and $R_{121}$ to $R_{123}$ each independently represent the same as R in the formula (1), at least one of $R_{121}$ to $R_{123}$ is a substituent, and $R_{121}$ to $R_{123}$ serving as a substituent represent the same as R serving as a substituent in the formula (1), (124)

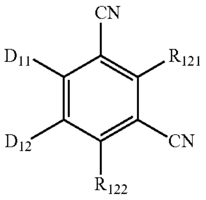

(125)

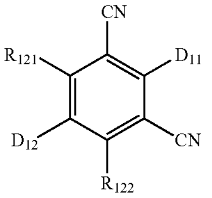

(126)

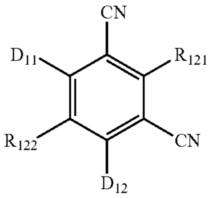

wherein:

$D_{11}$ and $D_{12}$ each independently represent the same as D in the formula (1), and at least one of $D_{11}$ or $D_{12}$ is a group represented by the formula (13); and $R_{121}$ and $R_{122}$ each independently represent the same as R in the formula (1), at least one of $R_{121}$ or $R_{122}$ is a substituent, and $R_{121}$ and $R_{122}$ serving as a substituent represent the same as R serving as a substituent in the formula (1), (127)

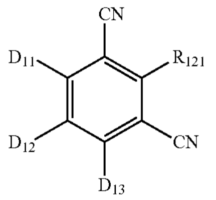

(128)

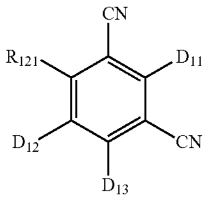

(129)

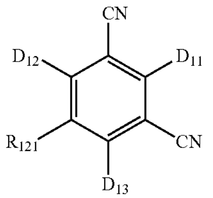

wherein:

$D_{11}$ to $D_{13}$ each independently represent the same as D in the formula (1), and at least one of $D_{11}$ to $D_{13}$ is a group represented by the formula (13); and $R_{121}$ is a substituent, and $R_{121}$ serving as a substituent represents the same as R serving as a substituent in the formula (1).

6. The compound of claim 1, wherein a compound represented by the formula (1) is a compound selected from the group consisting of compounds represented by formulae (131) to (135) below, (131)

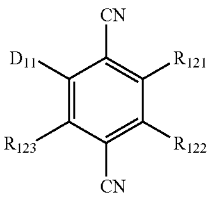

wherein:

$D_{11}$ is a group represented by the formula (13); and $R_{121}$ to $R_{123}$ each independently represent the same as R in the formula (1), at least one of $R_{121}$ to $R_{123}$ is a substituent, and $R_{121}$ to $R_{123}$ serving as a substituent represent the same as R serving as a substituent in the formula (1), (132)

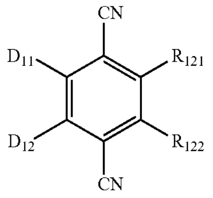

(133)

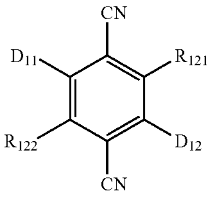

(134)

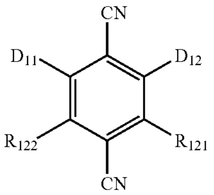

wherein:

$D_{11}$ and $D_{12}$ each independently represent the same as D in the formula (1), and at least one of $D_{11}$ or $D_{12}$ is a group represented by the formula (13); and $R_{121}$ and $R_{122}$ each independently represent the same as R in the formula (1), at least one of $R_{121}$ or $R_{122}$ is a substituent, and $R_{121}$ and $R_{122}$ serving as a substituent represent the same as R serving as a substituent in the formula (1), (135)

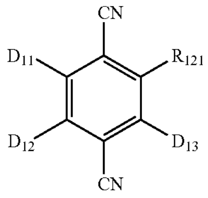

where:

$D_{11}$ to $D_{13}$ each independently represent the same as D in the formula (1), and at least one of $D_{11}$ to $D_{13}$ is a group represented by the formula (13); and $R_{121}$ is a substituent, and $R_{121}$ serving as a substituent represents the same as R serving as a substituent in the formula (1).

7. The compound of claim 1, wherein each of the combination of Ru and $R_{12}$, the combination of $R_{12}$ and $R_{13}$, the combination of $R_{13}$ and $R_{14}$, the combination of $R_{15}$ and $R_{16}$, the combination of $R_{16}$ and $R_{17}$, and the combination of $R_{17}$ and $R_{18}$ in the formula (12) are not mutually bonded, and each of the combination of $R_{111}$ and $R_{112}$, the combination of $R_{112}$ and $R_{113}$, the combination of $R_{113}$ and $R_{114}$, the combination of $R_{115}$ and $R_{116}$, the combination of $R_{116}$ and $R_{117}$, and the combination of $R_{117}$ and $R_{118}$ in the formula (13) are not mutually bonded.

8. The compound of claim 1, wherein the compound comprises at least one group represented by the formula (12).

9. The compound of claim 1, wherein a group represented by the formula (12) is a group selected from the group consisting of groups represented by formulae (12A), (12B), (12C), (12D), (12E), and (12F) below, (12A)

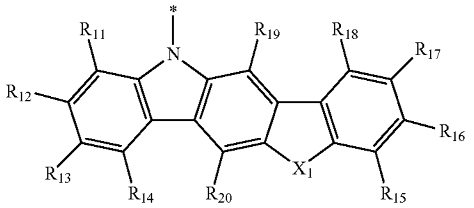

(12B)

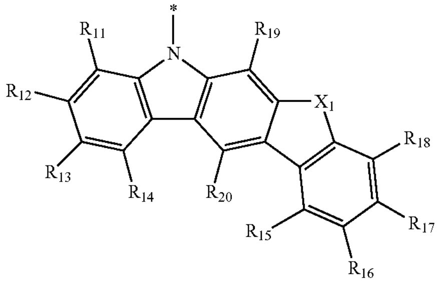

(12C)

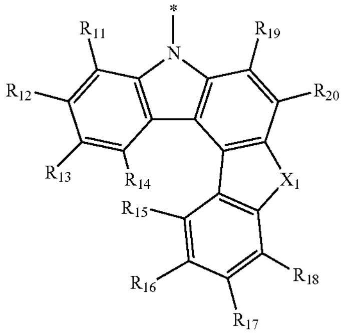

(12D)

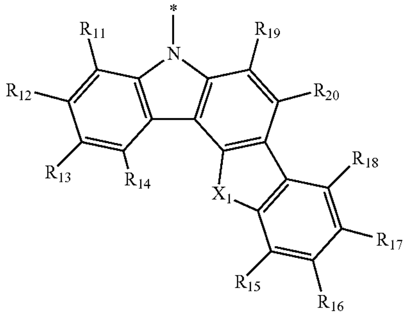

(12E)

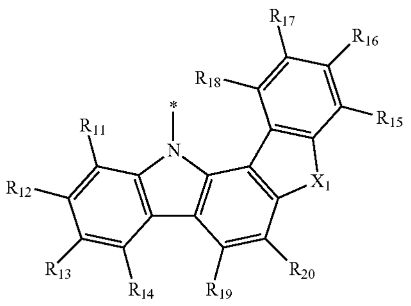

-continued (12F)

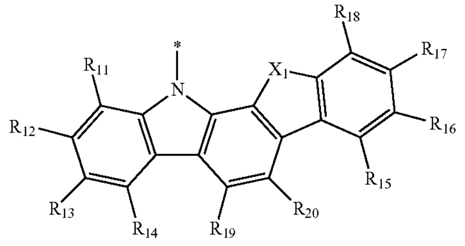

wherein:

$R_{11}$ to $R_{18}$ each independently represent the same as $R_{11}$ to $R_{18}$ in the formula (12);

$R_{19}$ and $R_{20}$ each independently represent the same as $R_{19}$ and $R_{20}$ in the formula (14);

X1 represents the same as X1 in the formula (15); and

* in the formulae (12A), (12B), (12C), (12D), (12E) and (12F) represents a bonding position to a benzene ring in the formula (1).

10. An organic-electroluminescence-device material, comprising:

the compound of claim 1.

11. An organic electroluminescence device comprising:

an anode;

a cathode; and an organic layer, wherein the organic layer comprises, as a first compound, the compound of claim 1.

12. An electronic device, comprising:

the organic electroluminescence device of claim 11.

13. The compound of claim 1, wherein R is independently an unsubstituted aryl group having 6 to 14 ring carbon atoms, wherein, when m is 1, n is 3, when m is 2, n is 2, and when m is 3, n is 1.

14. The compound of claim 13, wherein the group represented by the formula (12) is a group represented by a formula (12F) below, (12F)

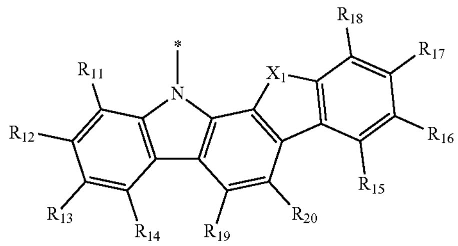

wherein:

$R_{11}$ to $R_{18}$ each independently represent the same as Ru to $R_{18}$ in the formula (12);

$R_{19}$ and $R_{20}$ each independently represent the same as $R_{19}$ and $R_{20}$ in the formula (14);

$X_1$ represents the same as $X_1$ in the formula (15); and

* in the formula (12F) represents a bonding position to a benzene ring in the formula (1).

15. The compound of claim 14, wherein px and py are each 2, wherein B and C are each independently a cyclic structure represented by the formula (14) or (15), and wherein, when two cyclic structures B are present, or when two cyclic structures C are present, one is a cyclic structure represented by the formula (14) and the other is a cyclic structure represented by the formula (15).

16. The compound of claim 1, wherein a compound represented by the formula (1) is a compound represented by a formula (126):

(126)

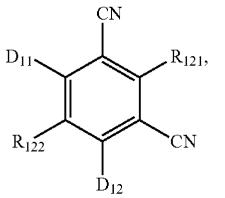

wherein $D_{11}$ and $D_{12}$ each independently represent the same as D in the formula (1), and at least one of $D_{11}$ or $D_{12}$ is a group represented by the formula (13), and wherein $R_{121}$ and $R_{122}$ are each a substituted or unsubstituted phenyl.

17. The compound of claim 16, wherein one of $D_{11}$ and $D_{12}$ is a group represented by the formula (12), and wherein the group represented by the formula (12) is a group represented by a formula (12F) below, (12F)

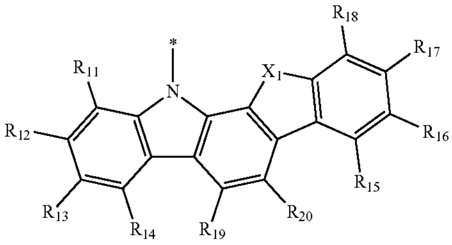

wherein:

$R_{11}$ to $R_{18}$ each independently represent the same as $R_{11}$ to $R_{18}$ in the formula (12);

$R_{19}$ and $R_{20}$ each independently represent the same as $R_{19}$ and $R_{20}$ in the formula (14);

$X_1$ represents the same as $X_1$ in the formula (15);

* in the formula (12F) represents a bonding position to a benzene ring in the formula (126).

18. The compound of claim 17, wherein $X_1$ is a sulfur atom or an oxygen atom.

19. The compound of claim 1, wherein R in the formula (1) is a hydrogen atom, a substituted or unsubstituted aryl group having 6 to 14 ring carbon atoms, or a substituted or unsubstituted heteroaryl group having 5 to 14 ring atoms, wherein, when R as a substituent is a substituted or unsubstituted heteroaryl group having 5 to 14 ring atoms, the heteroaryl group as R is a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, phenoxazinyl group, 1-carbazolyl group, 2-carbazolyl group, 3-carbazolyl group, or 4-carbazolyl group, and wherein $R_1$ to $R_8$ serving as a substituent, Ru to $R_{18}$ serving as a substituent, and $R_{111}$ to $R_{118}$ serving as a substituent are each independently limited to a substituted or unsubstituted aryl group having 6 to 30 ring carbon atoms, a substituted or unsubstituted alkyl group having 1 to 30 carbon atoms, or a substituted or unsubstituted cycloalkyl group having 3 to 30 ring carbon atoms.

20. The compound of claim 19, wherein a group represented by the formula (12) is a group selected from the group consisting of groups represented by formulae (12A), (12B), (12C), (12D), (12E), and (12F) below, (12A)

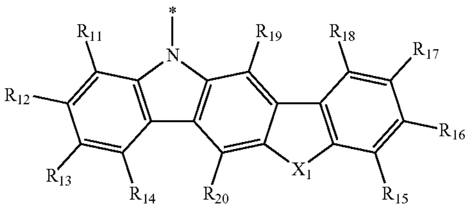

(12B)

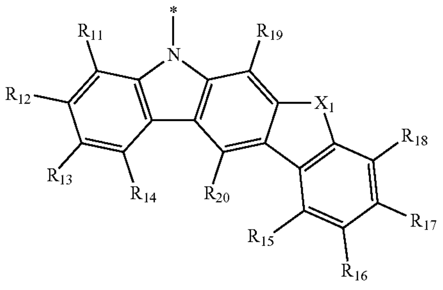

(12C)

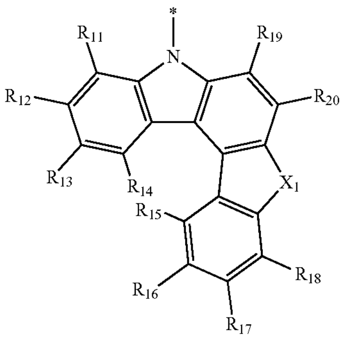

-continued (12D)

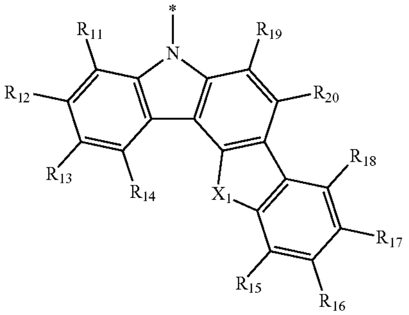

(12E)

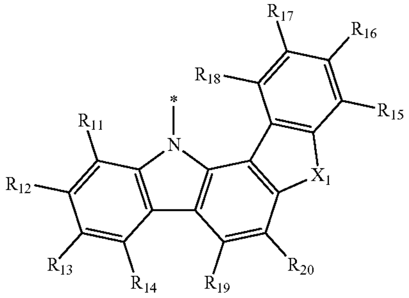

(12F)

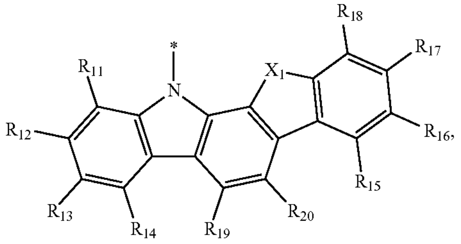

wherein:

$R_{11}$ to $R_{18}$ each independently represent the same as $R_{11}$ to $R_{18}$ in the formula (12);

$R_{19}$ and $R_{20}$ each independently represent the same as $R_{19}$ and $R_{20}$ in the formula (14);

$X_1$ represents the same as $X_1$ in the formula (15); and

* in the formulae (12A), (12B), (12C), (12D), (12E) and (12F) represents a bonding position to a benzene ring in the formula (1), wherein $R_{11}$ to $R_{18}$ in formulae (12A) to (12F) are not mutually bonded, $R_{19}$ to $R_{20}$ are not mutually bonded, and Rin to $R_{118}$ in formula (13) are not mutually bonded, wherein R serving as a substituent is an unsubstituted aryl group having 6 to 14 ring carbon atoms or an unsubstituted heteroaryl group having 5 to 14 ring atoms, wherein A, B, and C are each independently a cyclic structure selected from the group consisting of cyclic structures represented by the formulae (14) and (15), and wherein $R_1$ to $R_8$ serving as a substituent, $R_{11}$ to $R_{18}$ serving as a substituent, $R_{19}$ to $R_{20}$ serving as a substituent, and $R_{111}$ to $R_{118}$ serving as a substituent are each independently limited to a substituted or unsubstituted aryl group having 6 to 30 ring carbon atoms, a substituted or unsubstituted alkyl group having 1 to 30 carbon atoms, or a substituted or unsubstituted cycloalkyl group having 3 to 30 ring carbon atoms.

21. The compound of claim 20, wherein the compound represented by the formula (1) is represented by a formula (120) below, (120)

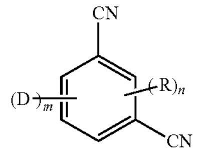

wherein:

D, m, and n respectively represent the same as D, m, and n in the formula (1), and R is an unsubstituted aryl group having 6 to 14 ring carbon atoms.

22. The compound of claim 21, wherein a compound represented by the formula (1) is a compound represented by formula (126) below, (126)

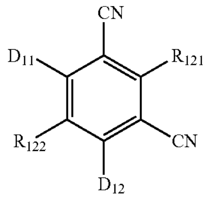

wherein:

$D_{11}$ and $D_{12}$ are each independently limited to a group represented by the formula (11), (12F), or (13), and at least one of $D_{11}$ or $D_{12}$ is a group represented by the formula (13):

(11)

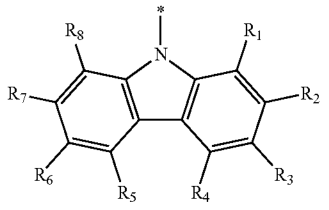

(12F)

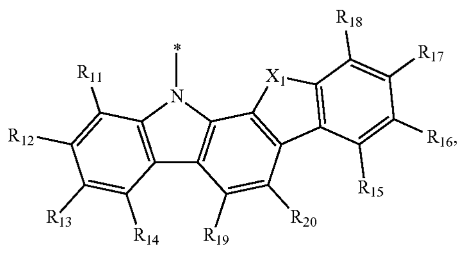

-continued
(13)
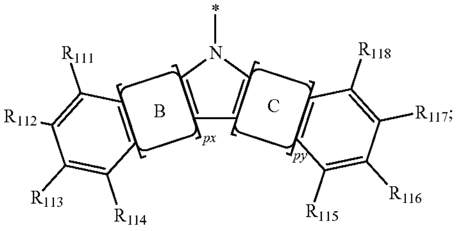
; and
$R_{121}$ and $R_{122}$ are each an unsubstituted phenyl group, wherein $R_1$ to $R_8$, $R_{11}$ to $R_{18}$, $R_{19}$ to $R_{20}$, and Rin to $R_{118}$ are not a halogen atom.
* * * * *